(12) United States Patent
Botta et al.

(10) Patent No.: US 12,358,880 B2
(45) Date of Patent: Jul. 15, 2025

(54) 1,4-BIS-(2-HYDROXY-BENZYL)-1,4,7-TRIAZACYCLONONANE DERIVATIVES AND SIMILAR COMPOUNDS AS LIGANDS IN IRON(III) COMPLEXES FOR USE AS MRI CONTRAST AGENTS

(71) Applicant: BRACCO IMAGING S.P.A., Milan (IT)

(72) Inventors: Mauro Botta, Turin (IT); Lorenzo Tei, Turin (IT); Fabio Carniato, Alessandria (IT); Zsolt Baranyai, Trieste (IT); Mariangela Boccalon, Terzo d'Aquileia (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 18/871,962

(22) PCT Filed: Jul. 28, 2023

(86) PCT No.: PCT/EP2023/071027
§ 371 (c)(1),
(2) Date: Dec. 5, 2024

(87) PCT Pub. No.: WO2024/023314
PCT Pub. Date: Feb. 1, 2024

(65) Prior Publication Data
US 2025/0163007 A1    May 22, 2025

(30) Foreign Application Priority Data
Jul. 28, 2022  (EP) .................................. 22187403

(51) Int. Cl.
*C07D 255/02* (2006.01)
*A61K 49/10* (2006.01)

(52) U.S. Cl.
CPC .......... *C07D 255/02* (2013.01); *A61K 49/106* (2013.01)

(58) Field of Classification Search
CPC ............................ A61K 49/106; C07D 255/02
See application file for complete search history.

(56) References Cited

FOREIGN PATENT DOCUMENTS

WO    2018213853 A1    11/2018
WO    2020099398 A1    5/2020

OTHER PUBLICATIONS

Alder, R.W., et al., "New synthetic routes to macrocyclic triamines," J. Chem. Soc. Chem. Commun., 507-508 (1992).
Atkins, T., "Tricyclic trisaminomethanes," J. Am. Chem. Soc., 102:6364-6365 (1980).
Auerbach, U., et al., "Synthesis and Coordination Chemistry of the Hexadentate Ligands 1,4,7-Tris(2-hydroxybenzyl)-1,4,7-triazacyclononane (H3L1) and 1,4,7-Tris(3-tert-butyl-2-hydroxybenzyl)-1,4,7-triazacyclononane (H3L2). Crystal Structures of [HL1CuII] and [L2FeIII]acacH," Inorganic Chem., 29:938-944 (1990).
Bales, B., et al., "Fe-HBED Analogs: A Promising Class of Iron-Chelate Contrast Agents for Magnetic Resonance Imaging," Contrast Media & Molecular Imaging, vol. 2019, Article ID 8356931 (2019).
Baranyai, Z. et al., "Defining the conditions for the development of the emerging class of FeIII-based MRI contrast agents," Chem. Sci., 12:11138-11145 (2021).
Baranyai, Z. et al., "Equilibrium, Kinetic and Structural Studies of AAZTA Complexes with Ga3+, In3+ and Cu2+," Eur. J. Inorg. Chem., 147-162 (2013).
Bates, G.W. et al., "The nonspecific binding of Fe3+ to transferrin in the absence of synergistic anions," J. Biol. Chem., 250:2177-2181 (1975).
Beck, M. T. et al., "Chemistry of Complex Equilibria," Akadémia Kiadó Budapest and Nostrand Reinhold Company Ltd., London, (1990).
Berge, S. M., et al., "Pharmaceutical Salts," J. Pharm. Sci., 66:1-19 (1977).
Boehm-Sturm, P., et al., "Low-Molecular-Weight Iron Chelates May be an Alternative to Gadolinium-based Contrast Agents for T1-weighted Contrast-enhanced MR Imaging," Radiology, 286:537-546 (2018).
Butler, S.J., et al., "Bright Mono-aqua Europium Complexes Based on Triazacyclononane That Bind Anions Reversibly and Permeate Cells Efficiently," Chem. Eur J., 19:9511-9517 (2013).
Clarke, E.T., et al., "Potentiometric and spectrophotometric determination of the stabilities of In(III), Ga(III) and Fe(III) complexes of N,N', N"-tris(3,5-dimethyl-2-hydroxybenzyl)-1,4,7-triazacyclononane," Inorganica Chimica Acta, 186:103-111 (1991).
Devreux, M., et al., "Bimodal Probe for Magnetic Resonance Imaging and Photoacoustic Imaging Based on a PCTA-Derived Gadolinium(III) Complex and ZW800-1," Eur. J. Inorg. Chem., 3354-3365 (2019).

(Continued)

*Primary Examiner* — James W Rogers
(74) *Attorney, Agent, or Firm* — VIVICAR Law, PLLC

(57) ABSTRACT

The invention relates to the novel compounds of formula (I) as well as ions, stereoisomers, tautomers, hydrates, solvates, pharmaceutically acceptable salts thereof, or mixtures of the same. The compounds of formula (I) are ligands that are able to chelate Fe(III) ions, thereby generating Fe(III) complexes, which are particularly suitable in diagnostic imaging, for example as contrast agents for magnetic resonance imaging (MRI), due to their high relaxivity, thermodynamic stability, kinetic inertness and redox stability.

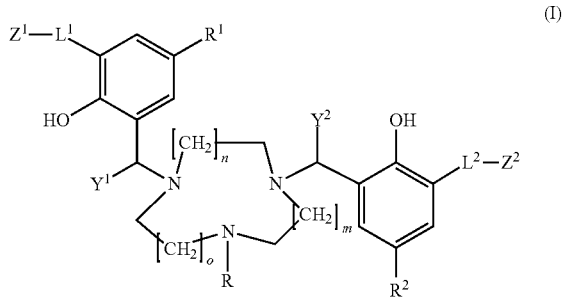

40 Claims, No Drawings

(56) References Cited

OTHER PUBLICATIONS

Greene, T.W. et al. (eds.), "Protection for the Amino Group," Chapter 7, pp. 494-653, In: Protective Groups in Organic Synthesis, John Wiley & Sons, Inc. (1999).

Hajela, S., et al., "A Tris-hydroxymethyl-Substituted Derivative of Gd-TREN-Me-3,2-HOPO: An MRI Relaxation Agent with Improved Efficiency," J. Am. Chem. Soc., 122:11228-11229 (2000).

Harris, W.R., et al., "Equilibrium Constants for the Binding of Indium(III) to Human Serum Transferrin," Inorg. Chem., 33:4991-4998 (1994).

International Search Report and Written Opinion for PCT/EP2023/071027, mailed Oct. 2, 2023.

Irving, H.M., et al., "A study of some problems in determining the stoicheiometric proton dissociation constants of complexes by potentiometric titrations using a glass electrode," Anal. Chim. Acta, 38:475-488 (1967).

May, P.M., et al., "Computer Simulation of Metal-ion Equilibria in Biofluids : Models for the Low-molecular-weight Complex Distribution of Calcium(II), Magnesium(II), Manganese(II), Iron(III), Copper(II), Zinc(II), and Lead(II) Ions in Human Blood Plasma," J. Chem. Soc. Dalton Trans., 588-595 (1977).

Pagano, J. M., et al., "A Thermodynamic Study of Homopiperazine, Piperazine and N-(2-Aminoethyl)-Piperazine and Their Complexes With Copper(II) Ion," J. Phys. Chem., 65:1062-1064 (1961).

Snyder, E., et al., "A Class of FeIII Macrocyclic Complexes with Alcohol Donor Groups as Effective T1 MRI Contrast Agents," Angew. Chem. Int. Ed., 59:2414-2419 (2020).

Wang, H. et al., "Molecular Magnetic Resonance Imaging Using a Redox-Active Iron Complex," J. Am. Chem. Soc., 141:5916-5925 (2019).

Zékány, L., et al., "PSEQUAD: A comprehensive program for the evaluation of potentiometric and/or spectrophotometric equilibrium data using analytical derivatives," Chapter 8, pp. 291-353, In: Computational Method for Determination of Formation Constants, Leggett, D.J. (Ed.), Plenum Press, New York (1985).

1,4-BIS-(2-HYDROXY-BENZYL)-1,4,7-TRIAZACYCLONONANE DERIVATIVES AND SIMILAR COMPOUNDS AS LIGANDS IN IRON(III) COMPLEXES FOR USE AS MRI CONTRAST AGENTS

TECHNICAL FIELD

The invention relates to novel compounds able to complex Fe(III), and to the complexes with Fe(III) thereof. These complexes are particularly suitable as contrast agents for magnetic resonance imaging (MRI).

BACKGROUND OF THE INVENTION

Magnetic resonance imaging (MRI) contrast agents currently used in clinical practice are small and hydrophilic paramagnetic Gd(III) complexes, or chelates, that accelerate the relaxation rates ($R_1$ and $R_2$) of proximate tissue water protons in regions of agent accumulation. Despite the fact that these clinically used Gd(III) complexes are generally very safe and very well tolerated by patients, there has been recently some concerns related to contraindications in patients with severely compromised kidney function (nephrogenic systemic fibrosis), to the retention of small amounts of Gd(III) in the tissues of patients exposed to multiple MRI scans (although without any evidence that this is associated with clinical harm), and possibly to the environment (due to difficulties in the removal of gadolinium-based contrast agents, or GBCAs, in wastewater treatment plants). Therefore, alternative contrast agents based on chemical species different than Gd(III) have been sought.

Among these alternatives, complexes chelating endogenous paramagnetic metals, such as iron, are possible candidates. Indeed, iron complexes, and in particular Fe(III) complexes, have been studied for their use in MRI. Fe(II) complexes are generally less suitable for providing MRI contrast, as they are characterized by lower relaxivity compared to Fe(III) complexes.

For a clinical use in MRI, the ideal Fe(III) complex possesses high relaxivity to obtain high contrast in vivo, high thermodynamic stability and kinetic inertness to minimalize and possibly to avoid the hydrolyzation, transmetallation and transchelation reactions with the challenging endogenous metal ions and ligands, and stability to reduction to avoid triggering the Fenton reaction, that is the reduction of Fe(III) to Fe(II) (Baranyai et al. (*Chem. Sci.* 2021, 12, 11138)) triggered in vivo e.g. by anti-oxidants such as ascorbic acid. This reduction would indeed lower the relaxivity of the administered iron complex (due to the generation of the Fe(II)-complex) and might generate in vivo OH· radicals, which are toxic.

Schellenberger et al. (*Radiology*, 2018, 286, 537) discloses low molecular weight Fe(III) complexes such as the Fe(III) chelates of pentetic acid (Fe(DTPA)) and of trans-cyclohexane diamine tetraacetic acid (Fe(CDTA)), which provide image contrast in vivo and exhibit enhancement kinetics very similar to that of Gd(DTPA)$^{2-}$ (Magnevist®), a clinically used GBCA. These complexes are however characterized by unsatisfying redox stability and relaxivity (as reported in Baranyai et al., Chem. Sci. 2021, 12, 11138)).

Gale et al. (*J. Am. Chem. Soc.,* 2019, 141, 5916) discloses the redox-active iron complex Fe-PyC3A, characterized by relatively high relaxivity at the imaging fields and by Fe$^{3+/2+}$ interchange (mediated by biochemical processes; e.g. Fe$^{3+}$ is rapidly reduced to Fe$^{2+}$ by L-cysteine). Accordingly, this complex is purposely characterized by very low redox stability to allow the Fe$^{3+/2+}$ interchange, which is a very specific application for imaging of acute inflammations and is not ideal for a wide range of MRI applications.

Morrow et al. (*Angew. Chem. Int. Ed.,* 2020, 59, 2414 and WO 2018/213853) discloses a series of substituted macrocyclic ligands used for Fe(III) complexation and their use as MRI contrast agents.

In view of the above, there is a lack of Fe(III)-complexes for use in magnetic resonance imaging that exhibit high relaxivity, kinetic inertness, thermodynamic stability and stability to reduction.

It has now been found that the ligands of the invention, when complexed to Fe(III) ions, thus forming the complexes of the invention, have surprisingly and advantageous properties. In particular, said ligands have been found to possess a balanced profile of high relaxivity, kinetic inertness, thermodynamic stability and stability to reduction. Accordingly, the complexes of the invention can be advantageously used as contrast agents for MRI.

SUMMARY OF THE INVENTION

The present invention relates to a compound of formula (I), or an ion, a stereoisomer, a tautomer, a hydrate, a solvate, or a salt thereof, or a mixture of same, as set out in the claims. The compound of formula (I) is a ligand that, when complexed to Fe(III) ions, forms a Fe(III) complex (also object of the present invention, as set out in the claims) that possess a balanced profile of high relaxivity, kinetic inertness, thermodynamic stability and stability to reduction.

The present invention further relates to the methods of preparation of the compound and of the complex of the invention, as well as their use as MRI contrast agents and in diagnostic (MRI) imaging, as set out in the claims.

DETAILED DESCRIPTION OF THE INVENTION

According to a first aspect, the present invention relates to a compound of Formula (I):

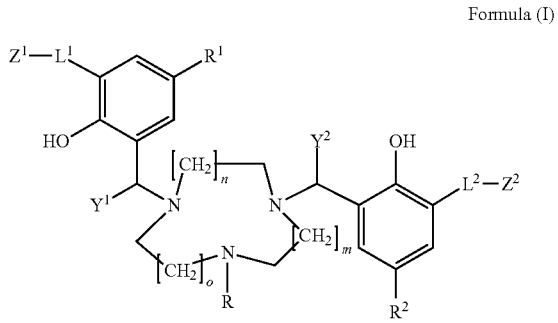

Formula (I)

wherein: n, m, and o are integer numbers independently selected between 1 and 2;
$Y^1$ and $Y^2$ are independently selected from the group consisting of hydrogen and a $C_1$-$C_4$-alkyl;
$R^1$ and $R^2$ are independently selected from the group consisting of hydrogen and $C_1$-$C_4$-alkyl;
$L^1$ and $L^2$ are independently selected from the group consisting of $C_1$-$C_4$-alkylaminyl, $C_1$-$C_4$-alkylamidyl, and $C_1$-$C_4$-alkylether; preferably of $C_1$-$C_4$-alkylaminyl, and $C_1$-$C_4$-alkylamidyl;
$Z^1$ and $Z^2$ are independently selected from the group consisting of hydrogen and a $C_1$-$C_6$-alkyl, preferably a $C_1$-$C_4$-alkyl, said $C_1$-$C_6$-alkyl (preferably $C_1$-$C_4$-alkyl) being optionally substituted by one or more groups selected from the group consisting of hydroxyl (—OH), carboxyl (—COOH), and phosphonate (—PO$_3$H$_2$);

R is selected from the group consisting of hydrogen, $C_1$-$C_4$ alkyl optionally substituted by an aryl (such as a substituted or unsubstituted aryl), and the moiety of Formula (IA):

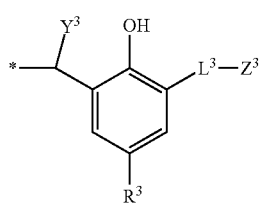

Formula (IA)

wherein: the asterisk (*) indicates the point of attachment of said moiety of Formula (IA) to the nitrogen bearing the R group;

$Y^3$ has the same meaning provided above for $Y^1$ and $Y^2$;

$R^3$ has the same meaning provided above for $R^1$ and $R^2$;

$L^3$ has the same meaning provided above for $L^1$ and $L^2$; and $Z^3$ has the same meaning provided above for $Z^1$ and $Z^2$;

or an ion, or a stereoisomer, or a tautomer, or a hydrate, or a solvate, or a pharmaceutically acceptable salt thereof, or a mixture of the same.

According to the present invention, the term "alkyl" refers to any linear or branched hydrocarbon chain. In particular "$C_1$-$C_4$-alkyl" comprises within its meaning a linear or branched chain comprising from 1 to 4 carbon atoms such as: methyl, ethyl, propyl, iso-propyl, butyl, iso-butyl, tert-butyl, and the like. Similarly, the term "$C_1$-$C_3$-alkyl" refers to a linear or branched chain comprising from 1 to 3 carbon atoms such as, for instance, methyl, ethyl, propyl and iso-propyl; the term "$C_1$-$C_2$-alkyl" refers to a linear or branched chain comprising from 1 to 2 carbon atoms such as methyl and ethyl; the term "$C_1$-alkyl" refers to a methyl (—CH$_3$) group; and the term "$C_1$-$C_6$-alkyl" refers to methyl, ethyl, propyl, iso-propyl, butyl, iso-butyl, tert-butyl, and the like, as well as n-penthyl and isomers thereof (such as isopentane, neopentane, and the like), and n-hexyl and isomers thereof (such as 2-methylpentane, 3-methylpentane, 2,3-dimethylbutane, and the like).

According to the present invention, the term "alkylaminyl" refers to an alkyl as above defined wherein one of the hydrogen atoms is substituted by an amine group, said alkylaminyl being attached to both (i) the phenolic moiety of the compound of the invention and (ii) the $Z^1$, $Z^2$, or $Z^3$ group (as the case may be). The term "$C_x$-$C_y$-alkylaminyl", wherein x and y denote two integer numbers, refers to an alkylaminyl as above defined with a number of carbons comprised between x and y.

According to the present invention, the term "alkylamidyl" refers to an alkyl as above defined wherein one the carbon atoms is a carbonyl group (C═O) directly bonded to a nitrogen atom, said alkylamidyl being attached to both (i) the phenolic moiety of the compound of the invention and (ii) the $Z^1$, $Z^2$, or $Z^3$ group (as the case may be). The term "$C_x$-$C_y$-alkylamidyl", wherein x and y denote two integer numbers, refers to an alkylamidyl as above defined with a number of carbons comprised between x and y.

According to the present invention, the term "alkylether" refers to an alkyl as above defined wherein one of the hydrogen atoms is substituted by an ether group (—O—), said alkylether being attached to both (i) the phenolic moiety of the compound of the invention and (ii) the $Z^1$, $Z^2$, or $Z^3$ group (as the case may be). The term "$C_x$-$C_y$-alkylether", wherein x and y denote two integer numbers, refers to an alkylether as above defined with a number of carbons comprised between x and y.

According to the present invention, the term "aryl" refers to an aromatic hydrocarbon and, preferably, to a phenyl ring. Unless otherwise specifically provided, aryls according to the invention can be either unsubstituted or substituted with one or more substituent groups that, simultaneously with or independently of each other, are selected from hydroxyl (—OH), halogen, and $C_1$-$C_4$-alkyl optionally substituted by one or more hydroxyl (—OH); preferably, the term "aryl" refers to unsubstituted aromatic hydrocarbons, such as unsubstituted phenyl.

According to the present invention, the term "L-Z" when referring to substituent groups generally refers to any or all of the $L^1$-$Z^1$, $L^2$-$Z^2$, and $L^3$-$Z^3$ (if present) substituent groups.

In the present description, the term macrocycle or macrocyclic cage when referring to triazacyclononane (or [9]-membered cycle), triazacyclodecane (or [10]-membered cycle), triazacycloundecane (or [11]-membered cycle), or triazacyclododecane (or [12]-membered cycle), refers to the macrocycles having the following structures:

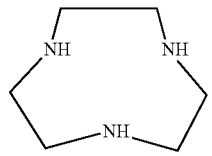 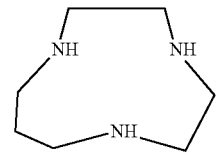

Triazacyclononane (TACN)    Triazacyclodecane (TACD)

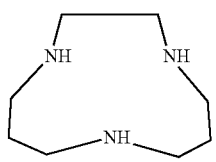 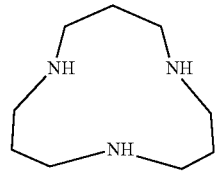

Triazacycloundecane (TACUD)    Triazacyclododecane (TADD)

In the present description, the term "protecting group" designates a protective group adapted for preserving the function of the group and/or atom to which it is bonded. Specifically, protective groups can be used to preserve amino, hydroxyl or carboxyl functions. Appropriate carboxyl protective groups may thus include, for example, benzyl, alkyl e.g. tert-butyl or benzyl esters, or other substituents commonly used for the protection of such functions, which are all well known to those skilled in the art (e.g. from T. W. Greene and P. G. M. Wuts; "Protective Groups in Organic Synthesis", Wiley, N.Y. 1999, third edition).

The compounds of the above formula (I) may have one or more asymmetric carbon atom, otherwise referred to as a chiral carbon atom, and may thus give rise to diastereomers, optical isomers and enantiomers. The present invention further includes all such possible diastereomers, optical isomers and enantiomers, as well as their racemic mixtures, their substantially pure resolved enantiomers. All possible geometric isomers are included as well. The individual stereoisomer of a compound of formula (I), e.g. a particular diastereomer, may be isolated by any conventional means, such as for example chromatography, possibly chiral chromatography.

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable, for example as disclosed in S. M. Berge. et al., J. Pharm. Sci. 1977, 66, 1-19.

According to an embodiment, $Y^1$ and $Y^2$, and $Y^3$ if present, are independently selected from the group consisting of hydrogen and a $C_1$-$C_3$-alkyl, preferably of hydrogen and a $C_1$-$C_2$-alkyl, and more preferably of hydrogen and a $C_1$-alkyl (that is, methyl). Preferably, $Y^1$ and $Y^2$, and $Y^3$ if present, are simultaneously the same group, most preferably hydrogen.

According to an embodiment, $R^1$, $R^2$, and $R^3$ if present, are independently selected from the group consisting of hydrogen and $C_1$-$C_3$-alkyl, preferably of hydrogen and $C_1$-$C_2$-alkyl, more preferably of hydrogen and $C_1$-alkyl, and even more preferably $C_1$-alkyl (that is, methyl (—$CH_3$)). According to a preferred embodiment, $R^1$, $R^2$, and $R^3$ if present, are simultaneously the same group.

According to an embodiment, $L^1$, $L^2$, and $L^3$ if present, are independently selected from the group consisting of $C_1$-$C_3$-alkylaminyl, $C_1$-$C_3$-alkylamidyl, and $C_1$-$C_3$-alkylether; preferably of $C_1$-$C_2$-alkylaminyl, $C_1$-$C_2$-alkylamidyl, and $C_1$-$C_2$-alkylether; and more preferably of $C_1$-alkylaminyl, $C_1$-alkylamidyl, and $C_1$-alkylether; according to this latter more preferred embodiment, $L^1$, $L^2$, and $L^3$ if present, are independently selected from *—$CH_2$—NH—•, *—C(O)—NH—•, *—NHC(O)—•, and *—$CH_2$—O—•, preferably from *—$CH_2$—NH—•, *—C(O)—NH—•, and *—$CH_2$—O—•, and more preferably from *—$CH_2$—NH—•, and *—C(O)—NH—•, with the asterisk (*) representing the phenolic moiety and the middle dot (•) representing the $Z^1$, $Z^2$, or $Z^3$ group (if present) (as the case might be). According to a preferred embodiment, $L^1$, $L^2$, and $L^3$ if present, are simultaneously the same group.

The nitrogen atoms of the alkylaminyl and of the alkylamidyl groups $L^1$, $L^2$, and $L^3$ if present, preferably bear at least one hydrogen; in other words, the amines of the alkylaminyl groups and/or the amides of the alkylamidyl groups $L^1$, $L^2$, and $L^3$ if present, are preferably primary or secondary; more preferably secondary.

According to a preferred embodiment, $Z^1$, $Z^2$, and $Z^3$ if present, are directly bonded to the nitrogen of the alkylaminyl or of the alkylamidyl group, to the carbonylic (C═O) portion of the alkylamidyl group, or to the oxygen of the alkylether group of (respectively) $L^1$, $L^2$, and $L^3$.

According to a preferred embodiment, $Z^1$, $Z^2$, and $Z^3$ if present, are independently selected from the group consisting of hydrogen, $C_4$-$C_6$-alkyl substituted by two or more hydroxyl (—OH) groups, and $C_1$-$C_3$-alkyl substituted by at least one group selected from the group consisting of hydroxyl (—OH), carboxyl (—COOH), and phosphonate (—$PO_3H_2$). According to a more preferred embodiment, $Z^1$, $Z^2$, and $Z^3$ if present, are independently selected from the group consisting of hydrogen, $C_6$-alkyl substituted by two or more, such as two to five (preferably five), hydroxyl (—OH) group, $C_1$-$C_3$-alkyl substituted by at least one, such as two, hydroxyl (—OH) groups, and $C_1$-alkyl substituted by carboxyl (—COOH) or phosphonate (—$PO_3H_2$).

According to an embodiment, when R is $C_1$-$C_4$ alkyl optionally substituted by an aryl (such as a substituted or unsubstituted aryl), R is preferably a $C_1$-$C_3$-alkyl or a $C_1$-$C_3$-alkyl substituted by an aryl (such as a substituted or unsubstituted aryl), preferably phenyl, more preferably $C_1$-$C_2$-alkyl or a $C_1$-$C_2$-alkyl substituted by an aryl (such as a substituted or unsubstituted aryl), preferably phenyl, and even more preferably a $C_1$-alkyl or a $C_1$-alkyl substituted by an aryl (such as a substituted or unsubstituted aryl), preferably phenyl (thereby providing the benzyl group —$CH_2$—$C_6H_5$).

According to a preferred embodiment, R is selected from the group consisting of hydrogen, $C_1$-alkyl, $C_1$-alkyl substituted by an aryl (such as a substituted or unsubstituted aryl), preferably phenyl (thereby providing the benzyl group —$CH_2$—$C_6H_5$), and the moiety of Formula (IA), wherein $Y^3$, $R^3$, $L^3$, and $Z^3$ have the same meanings provided above for, respectively, $Y^1$, $R^1$, $L^1$, and $Z^1$ of formula (I) and any embodiments thereof.

According to an embodiment, n, m, and o of formula (I) are 1, whereby the compound of the invention has a triazacyclononane macrocyclic cage and has the following formula (II)

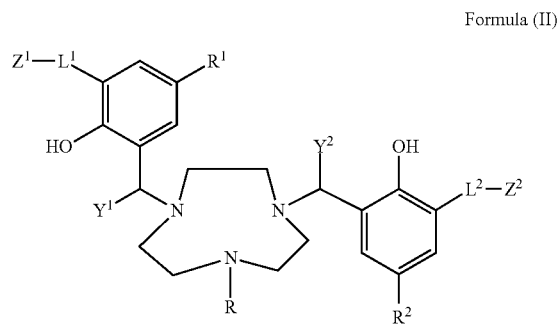

Formula (II)

wherein R, $R^1$, $R^2$, $Y^1$, $Y^2$, $L^1$, $L^2$, $Z^1$, and $Z^2$ are as above defined for formula (I) or for any embodiment thereof.

According to another embodiment, only one between n, m, and o of formula (I) is 2, and the other two are 1, whereby the compound of the invention has a triazacyclodecane macrocyclic cage and has one of the formulae (IIIA), (IIIB) or (IIIC)

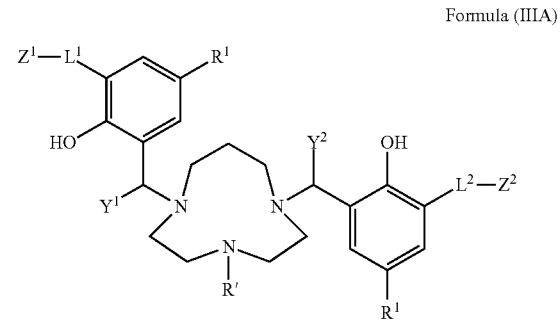

Formula (IIIA)

Formula (IIIB)

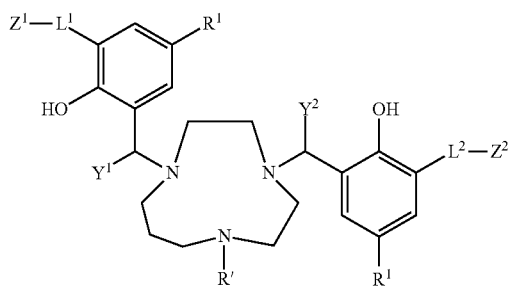

Formula (IIIC)

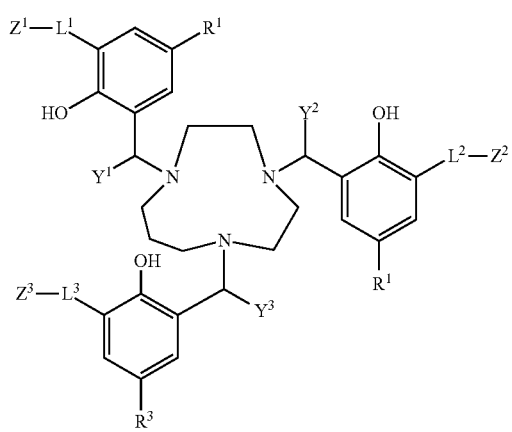

wherein, for formulae (IIIA), (IIIB), and (IIIC), $R^1$, $R^2$, $R^3$, $Y^1$, $Y^2$, $Y^3$, $L^1$, $L^2$, $L^3$, $Z^1$, $Z^2$, and $Z^3$ are as above defined for formula (I) or for any embodiment thereof, and R' is hydrogen or $C_1$-$C_4$-alkyl optionally substituted by an aryl (such as a substituted or unsubstituted aryl), preferably is hydrogen or $C_1$-$C_3$-alkyl optionally substituted by an aryl (such as a substituted or unsubstituted aryl), more preferably is hydrogen or $C_1$-$C_2$-alkyl optionally substituted by an aryl (such as a substituted or unsubstituted aryl), and even more preferably is hydrogen or $C_1$-alkyl optionally substituted by an aryl (such as a substituted or unsubstituted aryl).

According to a further embodiment, only one between n, m, and o of formula (I) is 1, and the other two are 2, whereby the compound of the invention has a triazacycloundecane macrocyclic cage and has one of the formulae (IVA), (IVB), or (IVC)

Formula (IVA)

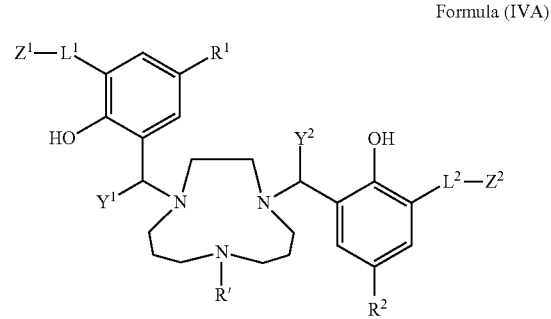

Formula (IVB)

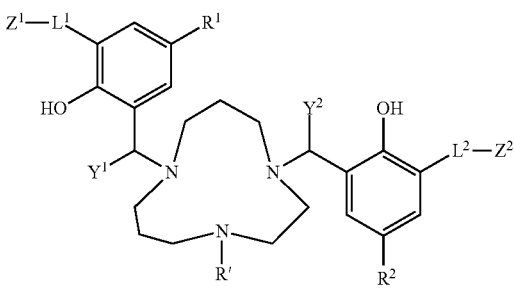

Formula (IVC)

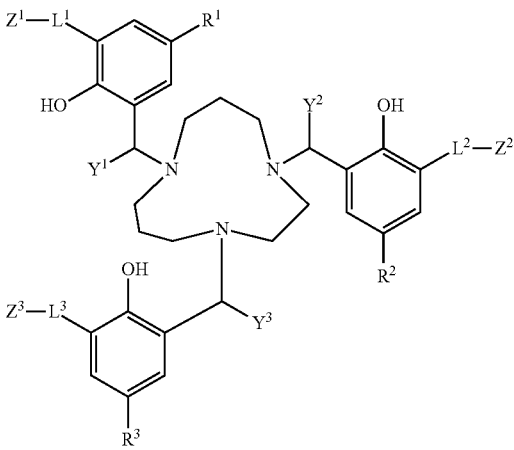

wherein, for formulae (IVA), (IVB), and (IVC), $R^1$, $R^2$, $R^3$, $Y^1$, $Y^2$, $Y^3$, $L^1$, $L^2$, $L^3$, $Z^1$, $Z^2$, and $Z^3$ are as above defined for formula (I) or for any embodiment thereof, and R' is hydrogen or $C_1$-$C_4$-alkyl optionally substituted by an aryl (such as a substituted or unsubstituted aryl), preferably is hydrogen or $C_1$-$C_3$-alkyl optionally substituted by an aryl (such as a substituted or unsubstituted aryl), more preferably is hydrogen or $C_1$-$C_2$-alkyl optionally substituted by an aryl (such as a substituted or unsubstituted aryl), and even more preferably is hydrogen or $C_1$-alkyl optionally substituted by an aryl (such as a substituted or unsubstituted aryl).

According to a fourth embodiment, n, m, and o of formula (I) are 2, whereby the compound of the invention has a triazacyclododecane macrocyclic cage and has the following formula (V)

Formula (V)

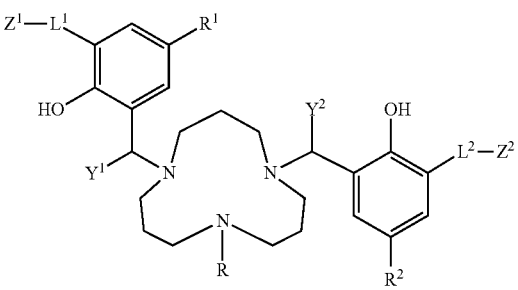

wherein R, $R^1$, $R^2$, $Y^2$, $Y^1$, $L^1$, $L^2$, $Z^1$, and $Z^2$ are as above defined for formula (I) or for any embodiment thereof.

According to a preferred embodiment, the compound of the invention is selected from the group consisting of:

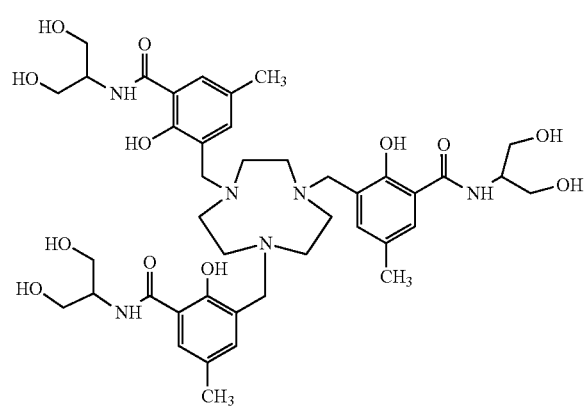 [SMILES: Cc1cc(CN2CCN(Cc3cc(C)cc(C(=O)NC(CO)CO)c3O)CCN(Cc3cc(C)cc(C(=O)NC(CO)CO)c3O)CC2)c(O)c(C(=O)NC(CO)CO)c1]

Compound 1 (3,3',3''-[1,4,7-triazonane-1,4,7-triyltris(methylene)]tris[N-(1,3-dihydroxypropan-2-yl)-2-hydroxy-5-methylbenzamide])

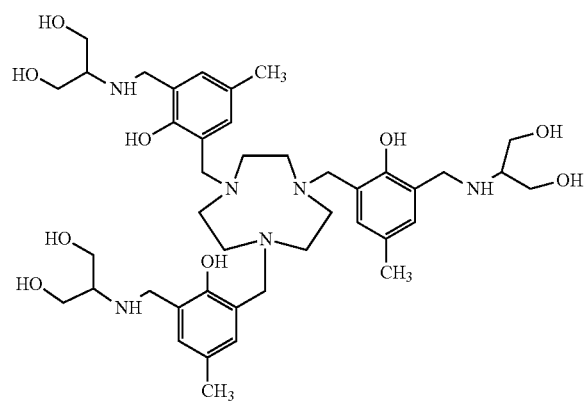 [SMILES: Cc1cc(CNC(CO)CO)c(O)c(CN2CCN(Cc3cc(C)cc(CNC(CO)CO)c3O)CCN(Cc3cc(C)cc(CNC(CO)CO)c3O)CC2)c1]

Compound 2 (2,2',2''-{1,4,7-triazonane-1,4,7-triyl-tris[methylene(2-hydroxy-5-methyl-3,1-phenylene)methyleneazanediyl]}tri(propane-1,3-diol))

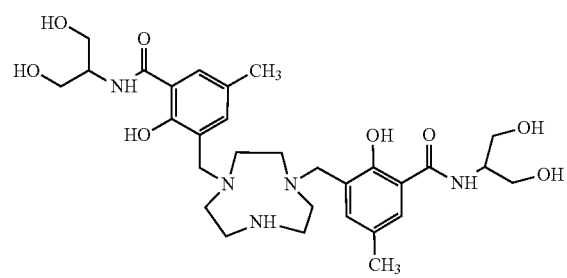 [SMILES: Cc1cc(CN2CCNCCN(Cc3cc(C)cc(C(=O)NC(CO)CO)c3O)CC2)c(O)c(C(=O)NC(CO)CO)c1]

Compound 3 (3,3'-[1,4,7-triazonane-1,4-diylbis(methylene)]bis[N-(1,3-dihydroxypropan-2-yl)-2-hydroxy-5-methylbenzamide])

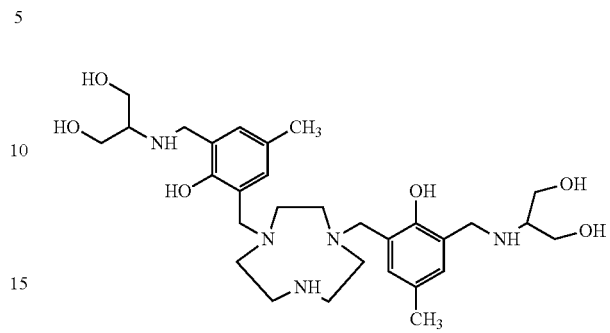

Compound 4 (2,2'-{1,4,7-triazonane-1,4-diylbis[methylene(2-hydroxy-5-methyl-3,1-phenylene)methyleneazanediyl]}di(propane-1,3-diol))

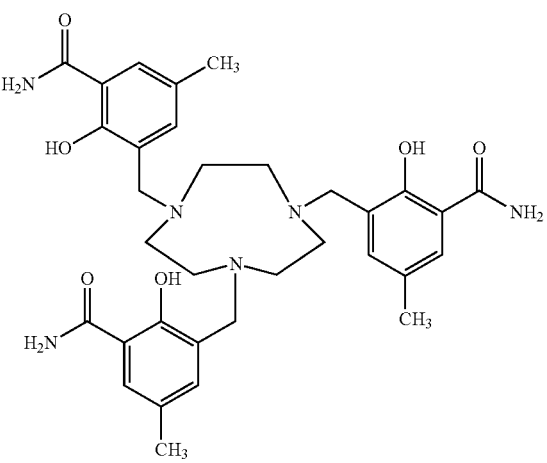 [SMILES: Cc1cc(CN2CCN(Cc3cc(C)cc(C(N)=O)c3O)CCN(Cc3cc(C)cc(C(N)=O)c3O)CC2)c(O)c(C(N)=O)c1]

Compound 5 (3,3',3''-[1,4,7-triazonane-1,4,7-triyltris(methylene)]tris(2-hydroxy-5-methylbenzamide))

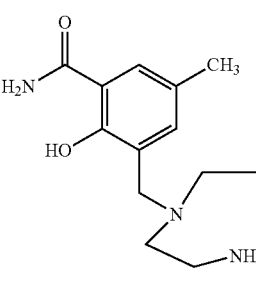

Compound 6 (3,3'-[1,4,7-triazonane-1,4-diylbis(methylene)]bis(2-hydroxy-5-methylbenzamide))

Compound 9 ({1,4,7-triazonane-1,4,7-triyltris[methylene(2-hydroxy-5-methyl-3,1-phenylene)carbonylazanediyimethylene]}tris(phosphonic acid))

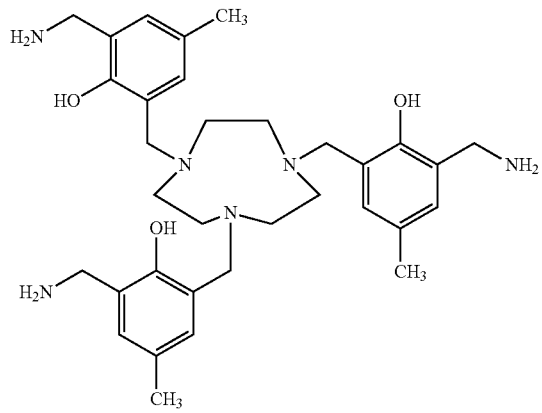 [SMILES: Cc1cc(CN)c(O)c(CN2CCN(Cc3cc(C)cc(CN)c3O)CCN(Cc3cc(C)cc(CN)c3O)CC2)c1]

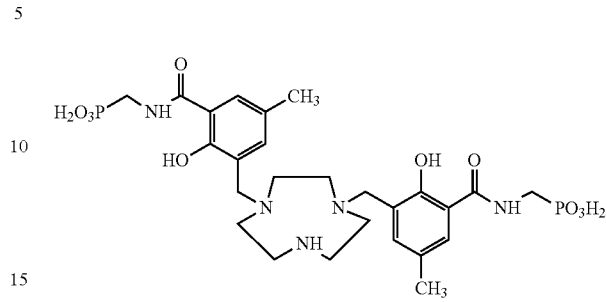

Compound 10 ({1,4,7-triazonane-1,4-diylbis[methylene(2-hydroxy-5-methyl-3,1-phenylene)carbonylazanediyimethylene]}bis(phosphonic acid))

Compound 7 (2,2',2''-[1,4,7-triazonane-1,4,7-triyltris(methylene)]tris[6-(aminomethyl)-methylphenol])

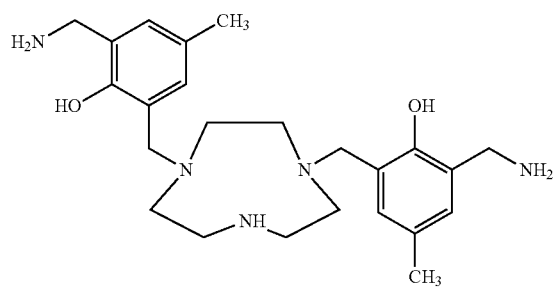 [SMILES: Cc1cc(CN)c(O)c(CN2CCNCCN(Cc3cc(C)cc(CN)c3O)CC2)c1]

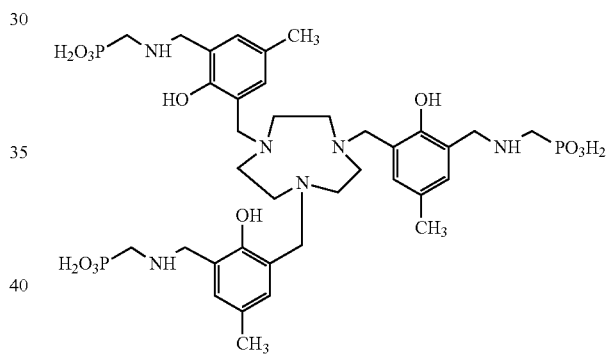

Compound 8 (2,2'-[1,4,7-triazonane-1,4-diylbis(methylene)]bis[6-(aminomethyl)-methylphenol])

Compound 11 ({1,4,7-triazonane-1,4,7-triyltris[methylene(2-hydroxy-5-methyl-3,1-phenylene)methyleneazanediylmethylene]}tris(phosphonic acid))

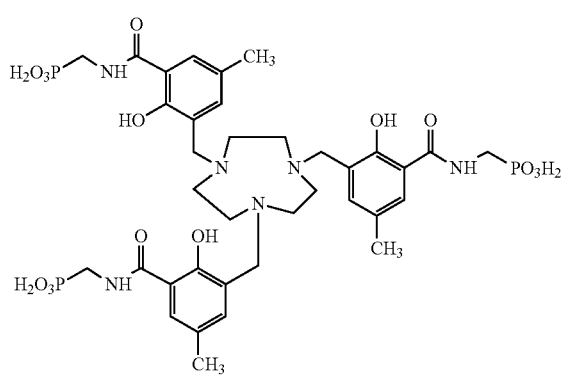

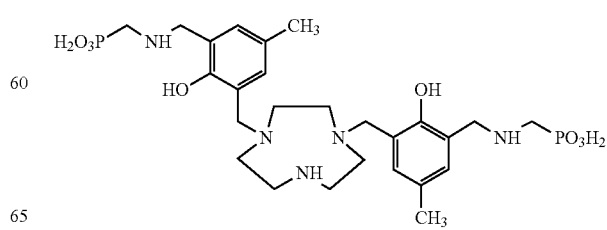

Compound 12 ({1,4,7-triazonane-1,4-diylbis[methylene(2-hydroxy-5-methyl-3,1-phenylene)methyleneazanediylmethylene]}bis(phosphonic acid))

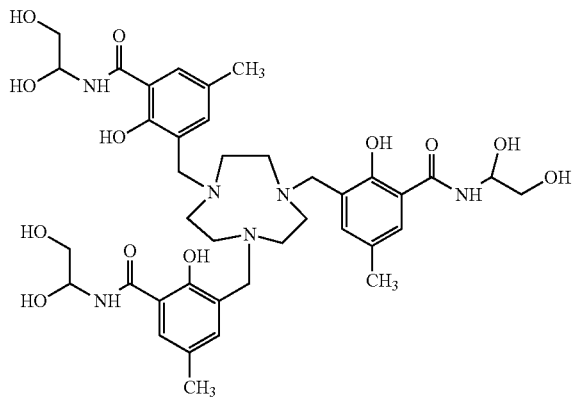 [SMILES: Cc1cc(CN2CCN(Cc3cc(C)cc(C(=O)NC(O)CO)c3O)CCN(Cc3cc(C)cc(C(=O)NC(O)CO)c3O)CC2)c(O)c(C(=O)NC(O)CO)c1]

Compound 13 (3,3',3''-[1,4,7-triazonane-1,4,7-triyltris(methylene)]tris[N-(1,2-dihydroxyethyl)-2-hydroxy-5-methylbenzamide])

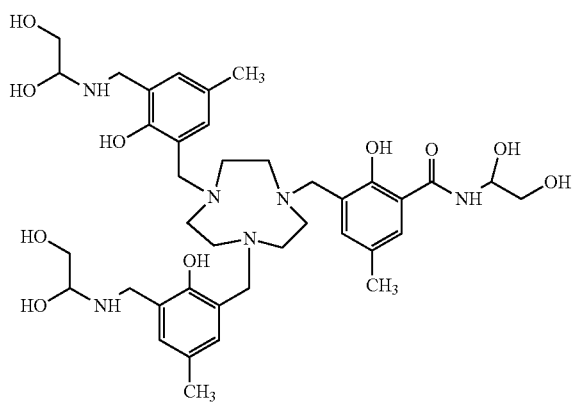 [SMILES: Cc1cc(CNC(O)CO)c(O)c(CN2CCN(Cc3cc(C)cc(CNC(O)CO)c3O)CCN(Cc3cc(C)cc(C(=O)NC(O)CO)c3O)CC2)c1]

Compound 14 (1,1',1''-{1,4,7-triazonane-1,4,7-triyltris[methylene(2-hydroxy-5-methyl-3,1-phenylene)methyleneazanediyl]}tri(ethane-1,2-diol))

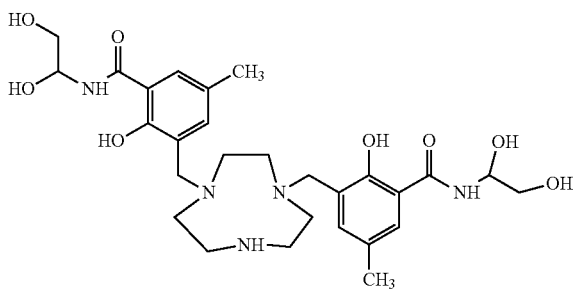 [SMILES: Cc1cc(CN2CCNCCN(Cc3cc(C)cc(C(=O)NC(O)CO)c3O)CC2)c(O)c(C(=O)NC(O)CO)c1]

Compound 15 (3,3'-[1,4,7-triazonane-1,4-diylbis(methylene)]bis[N-(1,2-dihydroxyethyl)-2-hydroxy-5-methylbenzamide])

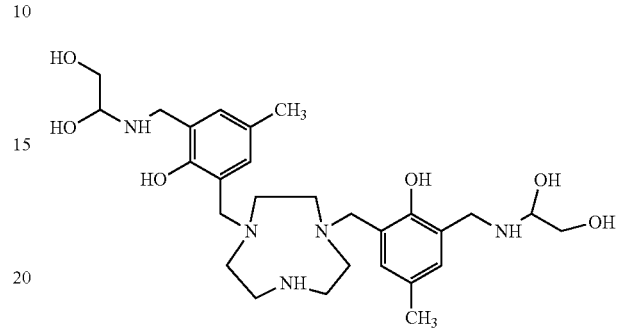

Compound 16 (1,1'-{1,4,7-triazonane-1,4-diylbis[methylene(2-hydroxy-5-methyl-3,1-phenylene)methyleneazanediyl]}di(ethane-1,2-diol))

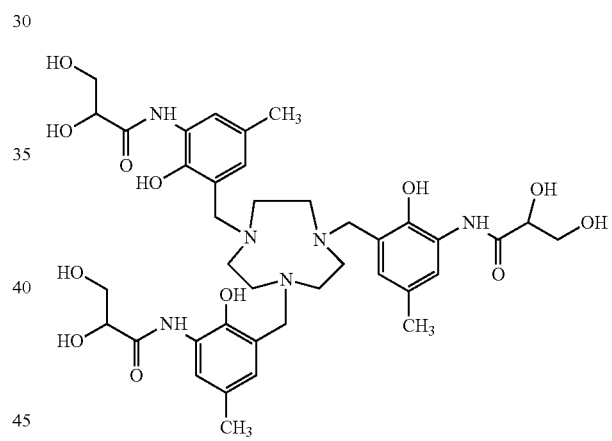

Compound 17 (N,N',N''-{1,4,7-triazonane-1,4,7-triyltris[methylene(2-hydroxy-5-methyl-3,1-phenylene)]}tris(2,3-dihydroxypropanamide))

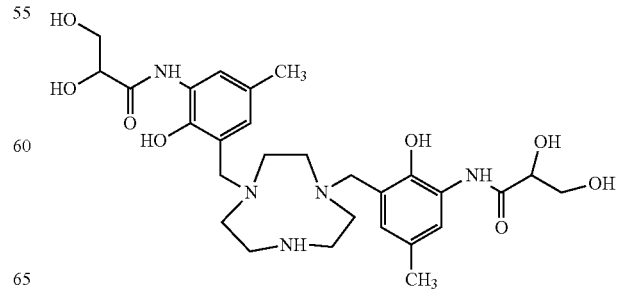

Compound 18 (N,N'-{1,4,7-triazonane-1,4-diylbis[methylene(2-hydroxy-5-methyl-3,1-phenylene)]}bis(2,3-dihydroxypropanamide))

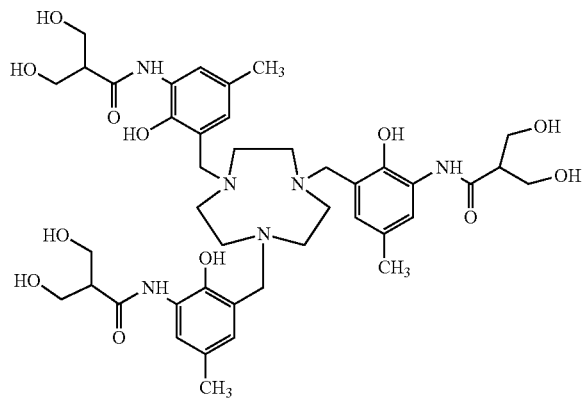 [SMILES: Cc1cc(CN2CCN(Cc3cc(C)cc(NC(=O)C(CO)CO)c3O)CCN(Cc3cc(C)cc(NC(=O)C(CO)CO)c3O)CC2)c(O)c(NC(=O)C(CO)CO)c1]

Compound 19 (N,N',N''-{1,4,7-triazonane-1,4,7-triyltris[methylene(2-hydroxy-5-methyl-3,1-phenylene)]}tris[3-hydroxy-2-(hydroxymethyl)propanamide])

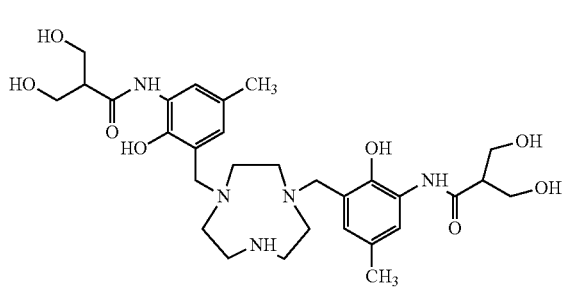 [SMILES: Cc1cc(CN2CCNCCN(Cc3cc(C)cc(NC(=O)C(CO)CO)c3O)CC2)c(O)c(NC(=O)C(CO)CO)c1]

Compound 20 (N,N'-{1,4,7-triazonane-1,4-diylbis[methylene(2-hydroxy-5-methyl-3,1-phenylene)]}bis[3-hydroxy-2-(hydroxymethyl)propanamide])

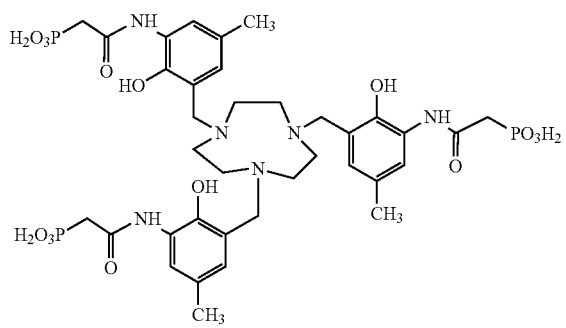

Compound 21 ({1,4,7-triazonane-1,4,7-triyltris[methylene(2-hydroxy-5-methyl-3,1-phenylene)azanediyl(2-oxoethane-2,1-diyl)]}tris(phosphonic acid))

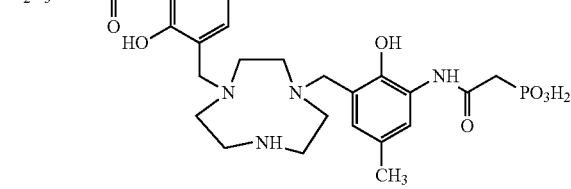

Compound 22 ({1,4,7-triazonane-1,4-diylbis[methylene(2-hydroxy-5-methyl-3,1-phenylene)azanediyl(2-oxoethane-2,1-diyl)]}bis(phosphonic acid))

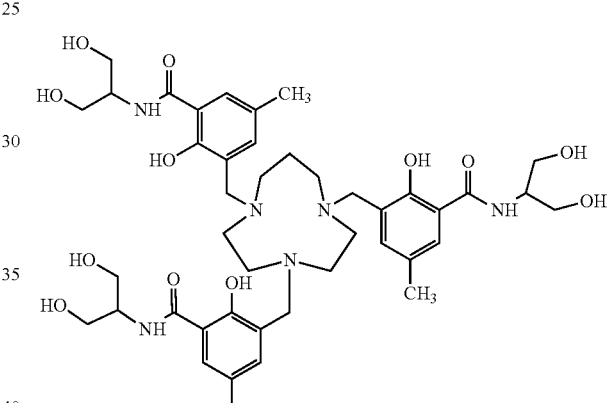

Compound 23 (3,3',3''-[1,4,7-triazecane-1,4,7-triyltris(methylene)]tris[N-(1,3-dihydroxypropan-2-yl)-2-hydroxy-5-methylbenzamide])

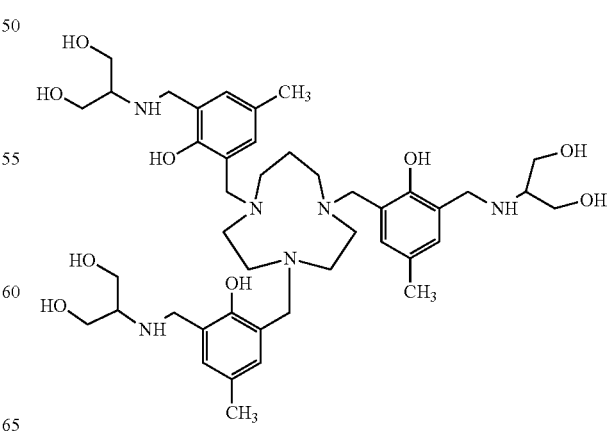

Compound 24 (2,2',2''-{1,4,7-triazecane-1,4,7-triyl-tris[methylene(2-hydroxy-5-methyl-3,1-phenylene)methyleneazanediyl]}tri(propane-1,3-diol))

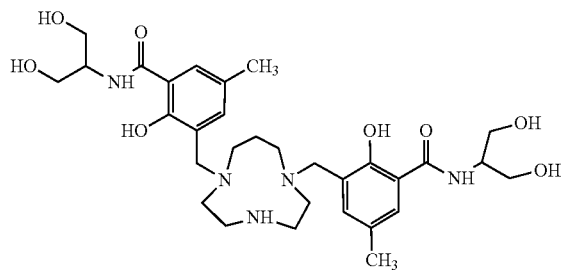 [SMILES: Cc1cc(CN2CCCN(Cc3cc(C)cc(C(=O)NC(CO)CO)c3O)CCNCC2)c(O)c(C(=O)NC(CO)CO)c1]

Compound 27 (2,2'-{1,4,7-triazecane-1,7-diylbis[methylene(2-hydroxy-5-methyl-3,1-phenylene)methyleneazanediyl]}di(propane-1,3-diol))

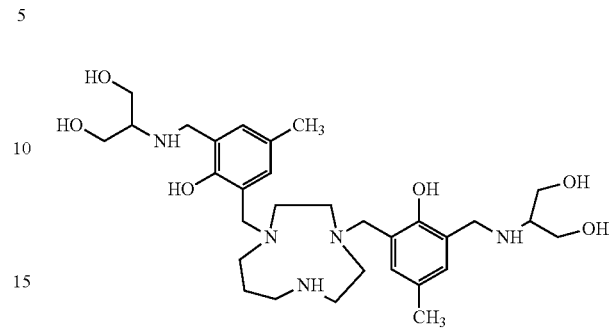

Compound 28 (2,2'-{1,4,7-triazecane-1,4-diylbis[methylene(2-hydroxy-5-methyl-3,1-phenylene)methyleneazanediyl]}di(propane-1,3-diol))

Compound 25 (3,3'-[1,4,7-triazecane-1,7-diylbis(methylene)]bis[N-(1,3-dihydroxypropan-2-yl)-2-hydroxy-5-methylbenzamide])

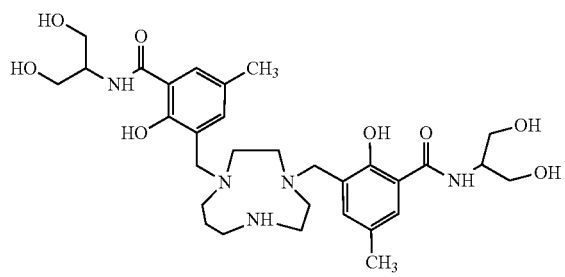 [SMILES: Cc1cc(CN2CCCNCCN(Cc3cc(C)cc(C(=O)NC(CO)CO)c3O)CC2)c(O)c(C(=O)NC(CO)CO)c1]

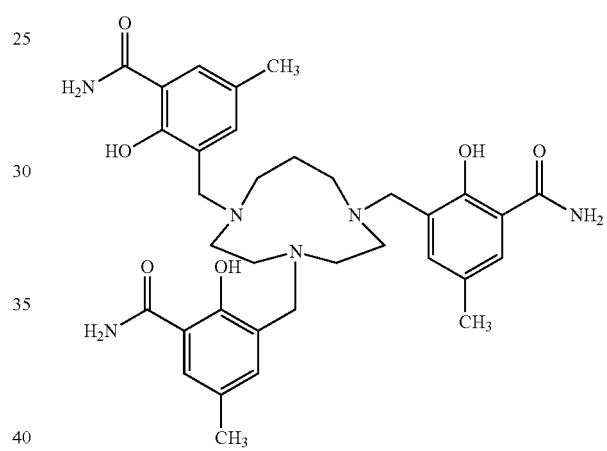

Compound 26 (3,3'-[1,4,7-triazecane-1,4-diylbis(methylene)]bis[N-(1,3-dihydroxypropan-2-yl)-2-hydroxy-5-methylbenzamide])

Compound 29 (3,3',3''-[1,4,7-triazecane-1,4,7-triyl-tris(methylene)]tris(2-hydroxy-5-methylbenzamide))

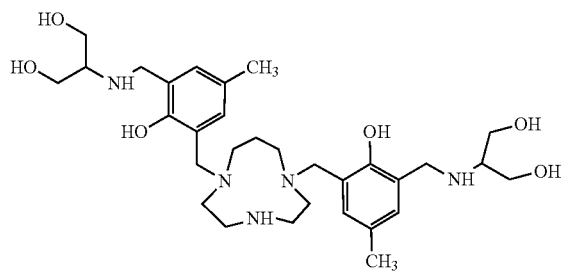 [SMILES: Cc1cc(CNC(CO)CO)c(O)c(CN2CCCN(Cc3cc(C)cc(CNC(CO)CO)c3O)CCNCC2)c1]

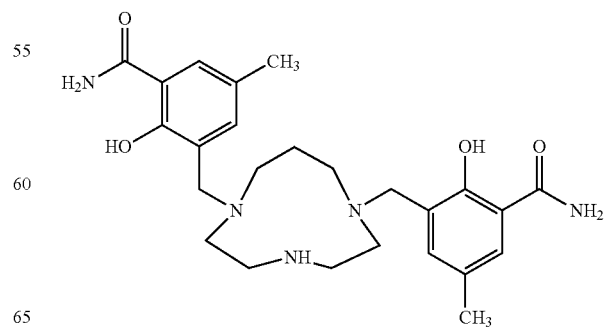

Compound 30 (3,3'-[1,4,7-triazecane-1,7-diylbis(methylene)]bis(2-hydroxy-5-methylbenzamide))

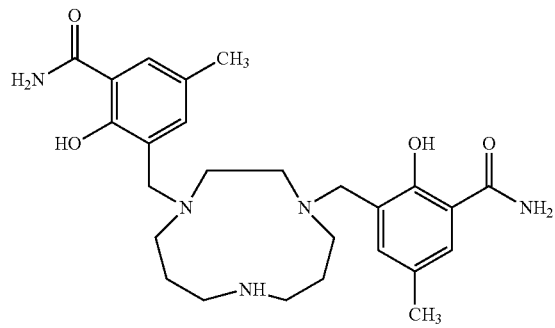 [SMILES: Cc1cc(CN2CCCNCCCN(Cc3cc(C)cc(C(N)=O)c3O)CC2)c(O)c(C(N)=O)c1]

Compound 31 (3,3'-[1,4,7-triazecane-1,4-diylbis(methylene)]bis(2-hydroxy-5-methylbenzamide))

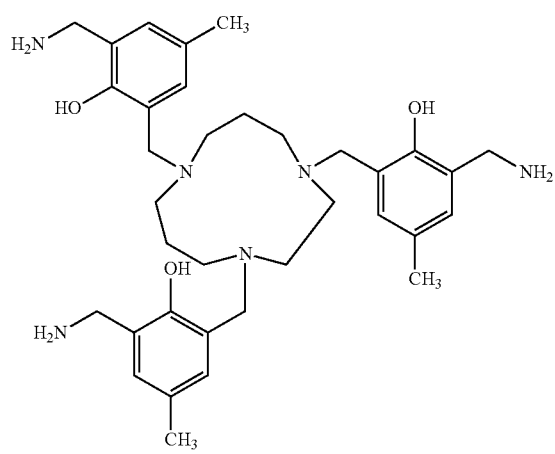 [SMILES: Cc1cc(CN)c(O)c(CN2CCCN(Cc3cc(C)cc(CN)c3O)CCN(Cc3cc(C)cc(CN)c3O)CCC2)c1]

Compound 32 (2,2',2''-[1,4,7-triazecane-1,4,7-triyl-tris(methylene)]tris[6-(aminomethyl)-methylphenol])

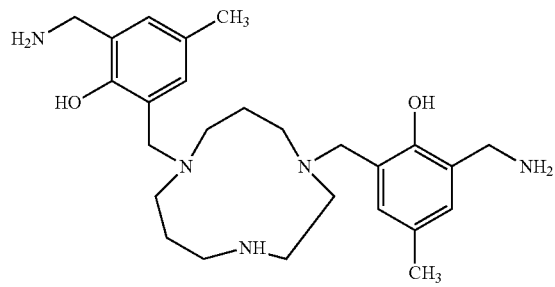 [SMILES: Cc1cc(CN)c(O)c(CN2CCCNCCN(Cc3cc(C)cc(CN)c3O)CCC2)c1]

Compound 33 (2,2'-[1,4,7-triazecane-1,7-diylbis(methylene)]bis[6-(aminomethyl)-4-methylphenol])

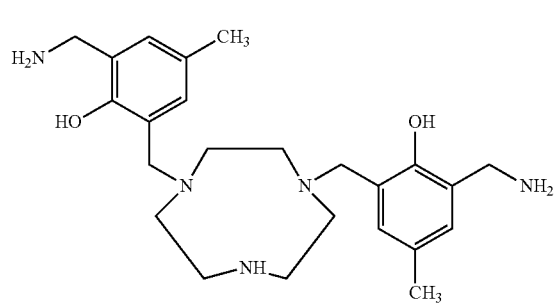 [SMILES: Cc1cc(CN)c(O)c(CN2CCNCCN(Cc3cc(C)cc(CN)c3O)CC2)c1]

Compound 34 (2,2'-[1,4,7-triazecane-1,4-diylbis(methylene)]bis[6-(aminomethyl)-4-methylphenol])

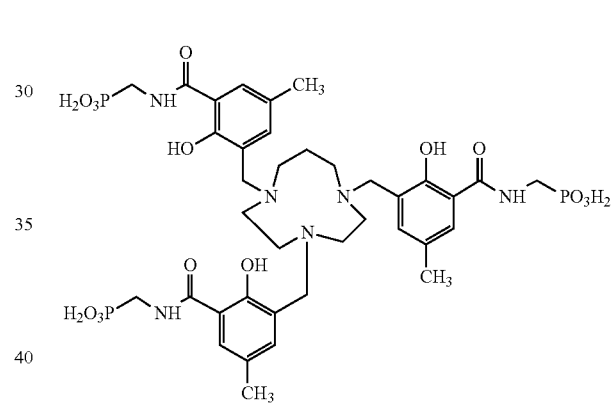

Compound 35 ({1,4,7-triazecane-1,4,7-triyltris[methylene(2-hydroxy-5-methyl-3,1-phenylene)carbonylazanediyimethylene]}tris(phosphonic acid))

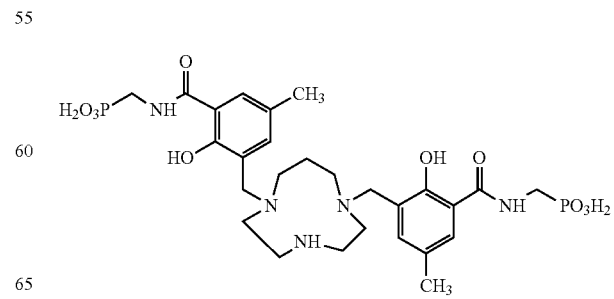

Compound 36 ({1,4,7-triazecane-1,7-diylbis[methylene(2-hydroxy-5-methyl-3,1-phenylene)carbonylazanediyimethylene]}bis(phosphonic acid)

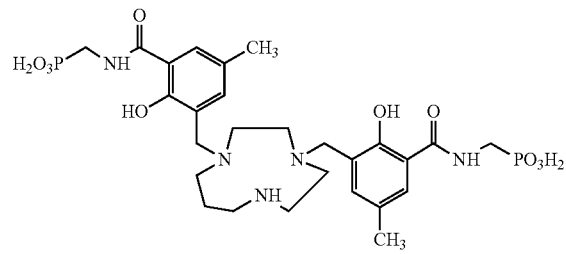

Compound 37 ({1,4,7-triazecane-1,4-diylbis[methylene(2-hydroxy-5-methyl-3,1-phenylene)carbonylazanediyimethylene]}bis(phosphonic acid))

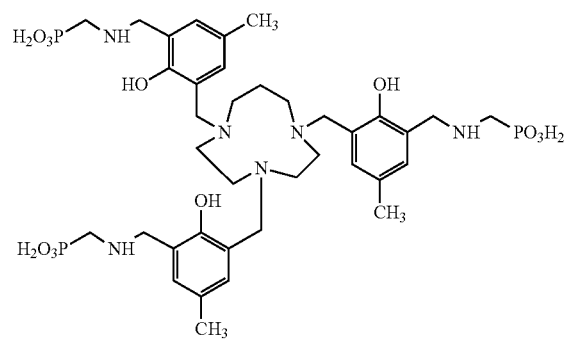

Compound 38 ({1,4,7-triazecane-1,4,7-triyltris[methylene(2-hydroxy-5-methyl-3,1-phenylene)methyleneazanediylmethylene]}tris(phosphonic acid))

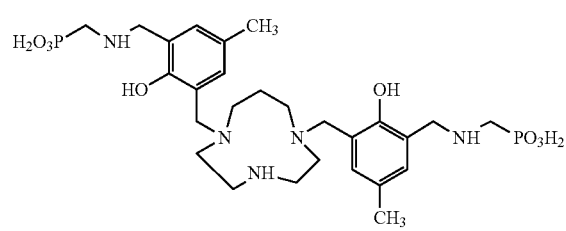

Compound 39 ({1,4,7-triazecane-1,7-diylbis[methylene(2-hydroxy-5-methyl-3,1-phenylene)methyleneazanediylmethylene]}bis(phosphonic acid))

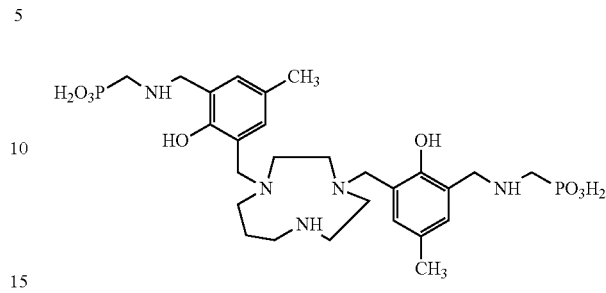

Compound 40 ({1,4,7-triazecane-1,4-diylbis[methylene(2-hydroxy-5-methyl-3,1-phenylene)methyleneazanediylmethylene]}bis(phosphonic acid))

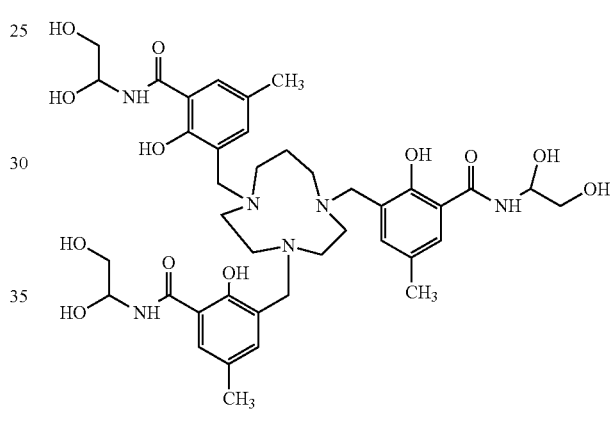

Compound 41 (3,3',3''-[1,4,7-triazecane-1,4,7-triyltris(methylene)]tris[N-(1,2-dihydroxyethyl)-2-hydroxy-5-methylbenzamide])

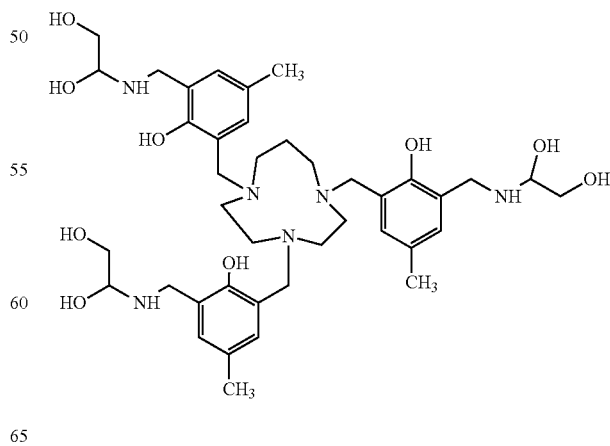

Compound 42 (1,1',1''-{1,4,7-triazecane-1,4,7-triyl-tris[methylene(2-hydroxy-5-methyl-3,1-phenylene)methyleneazanediyl]}tri(ethane-1,2-diol))

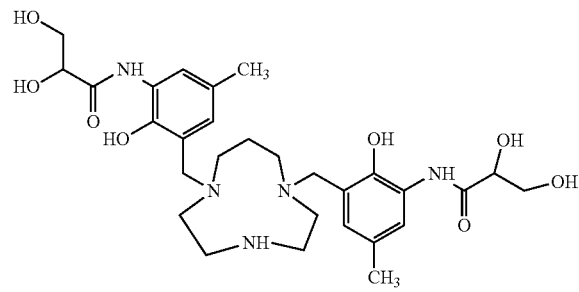 [SMILES: Cc1cc(CN2CCCN(Cc3cc(C)cc(NC(=O)C(O)CO)c3O)CCNCC2)c(O)c(NC(=O)C(O)CO)c1]

Compound 43 (3,3'-[1,4,7-triazecane-1,7-diylbis(methylene)]bis[N-(1,2-dihydroxyethyl)-2-hydroxy-5-methylbenzamide])

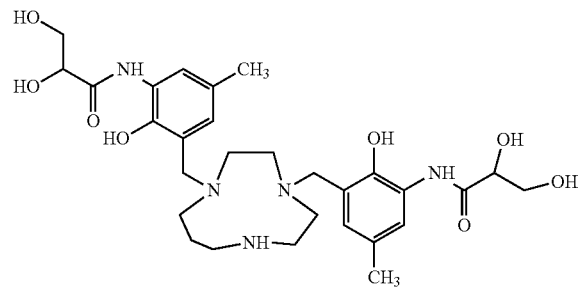 [SMILES: Cc1cc(CN2CCCNCCN(Cc3cc(C)cc(NC(=O)C(O)CO)c3O)CC2)c(O)c(NC(=O)C(O)CO)c1]

Compound 44 (3,3'-[1,4,7-triazecane-1,4-diylbis(methylene)]bis[N-(1,2-dihydroxyethyl)-2-hydroxy-5-methylbenzamide])

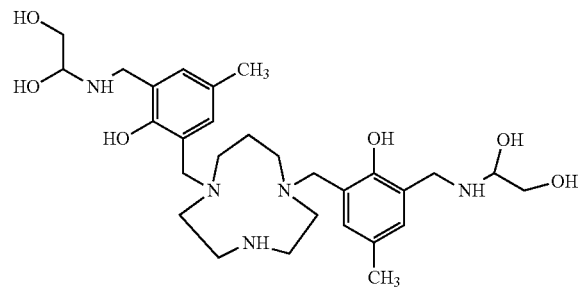 [SMILES: Cc1cc(CNC(O)CO)c(O)c(CN2CCCN(Cc3cc(C)cc(CNC(O)CO)c3O)CCNCC2)c1]

Compound 45 (1,1'-{1,4,7-triazecane-1,7-diylbis[methylene(2-hydroxy-5-methyl-3,1-phenylene)methyleneazanediyl]}di(ethane-1,2-diol))

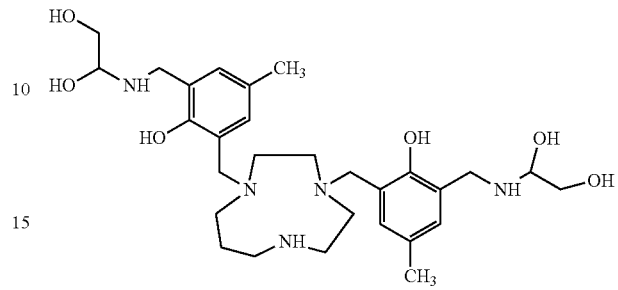

Compound 46 (1,1'-{1,4,7-triazecane-1,4-diylbis[methylene(2-hydroxy-5-methyl-3,1-phenylene)methyleneazanediyl]}di(ethane-1,2-diol))

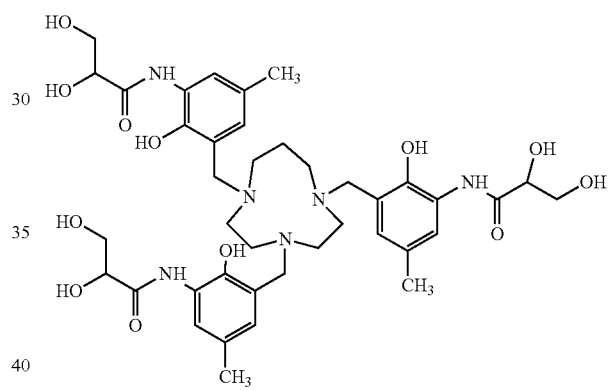

Compound 47 (N,N',N''-{1,4,7-triazecane-1,4,7-triyltris[methylene(2-hydroxy-5-methyl-3,1-phenylene)]}tris(2,3-dihydroxypropanamide))

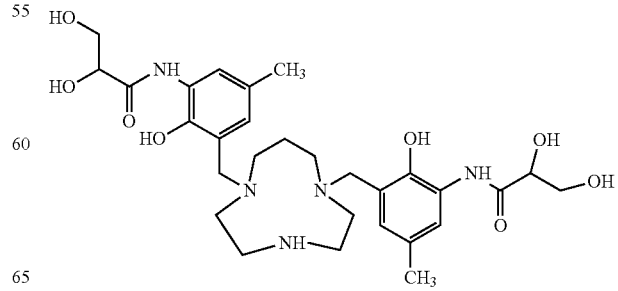

Compound 48 (N,N'-{1,4,7-triazecane-1,7-diylbis[methylene(2-hydroxy-5-methyl-3,1-phenylene)]}bis(2,3-dihydroxypropanamide))

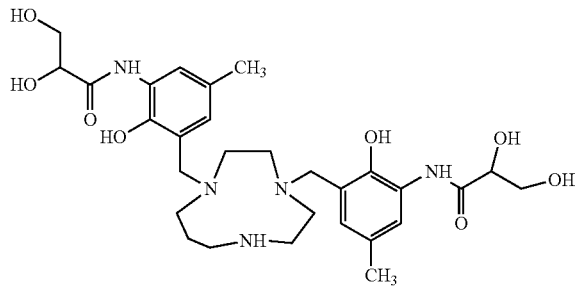 [SMILES: Cc1cc(CN2CCCNCCN(Cc3cc(C)cc(NC(=O)C(O)CO)c3O)CC2)c(O)c(NC(=O)C(O)CO)c1]

Compound 49 (N,N'-{1,4,7-triazecane-1,4-diylbis[methylene(2-hydroxy-5-methyl-3,1-phenylene)]}bis(2,3-dihydroxypropanamide))

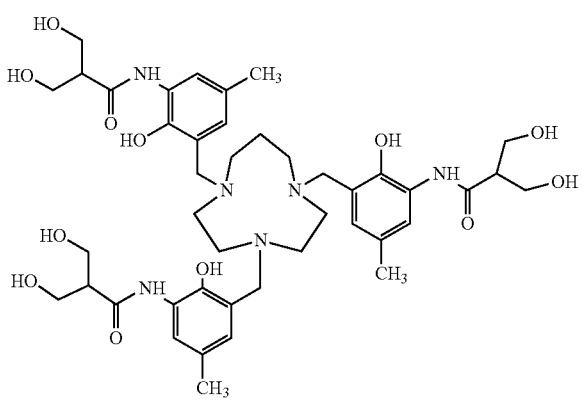 [SMILES: Cc1cc(CN2CCCN(Cc3cc(C)cc(NC(=O)C(CO)CO)c3O)CCN(Cc3cc(C)cc(NC(=O)C(CO)CO)c3O)CC2)c(O)c(NC(=O)C(CO)CO)c1]

Compound 50 (N,N',N''-{1,4,7-triazecane-1,4,7-triyltris[methylene(2-hydroxy-5-methyl-3,1-phenylene)]}tris[3-hydroxy-2-(hydroxymethyl)propanamide])

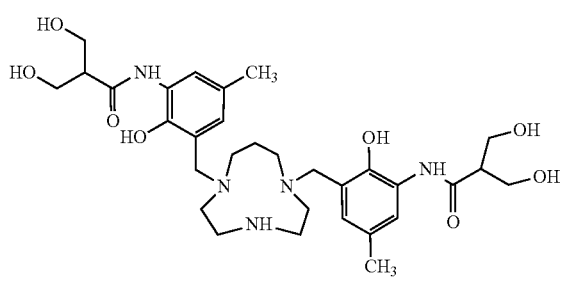 [SMILES: Cc1cc(CN2CCCN(Cc3cc(C)cc(NC(=O)C(CO)CO)c3O)CCNCC2)c(O)c(NC(=O)C(CO)CO)c1]

Compound 51 (N,N-{1,4,7-triazecane-1,7-diylbis[methylene(2-hydroxy-5-methyl-3,1-phenylene)]}bis[3-hydroxy-2-(hydroxymethyl)propanamide])

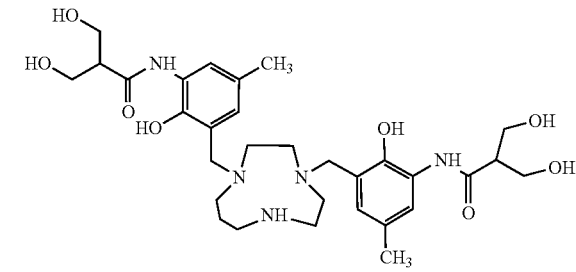 [SMILES: Cc1cc(CN2CCCNCCN(Cc3cc(C)cc(NC(=O)C(CO)CO)c3O)CC2)c(O)c(NC(=O)C(CO)CO)c1]

Compound 52 (N,N'-{1,4,7-triazecane-1,4-diylbis[methylene(2-hydroxy-5-methyl-3,1-phenylene)]}bis[3-hydroxy-2-(hydroxymethyl)propanamide])

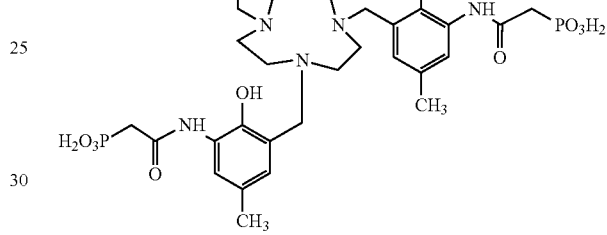

Compound 53 ({1,4,7-triazecane-1,4,7-triyltris[methylene(2-hydroxy-5-methyl-3,1-phenylene)azanediyl(2-oxoethane-2,1-diyl)]}tris(phosphonic acid))

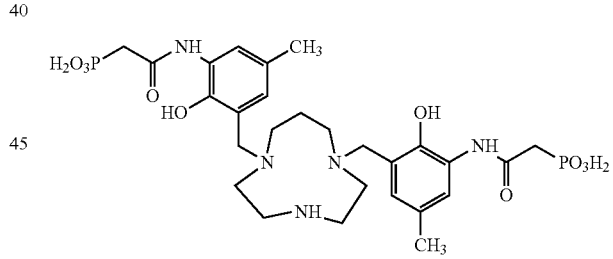

Compound 54 ({1,4,7-triazecane-1,7-diylbis[methylene(2-hydroxy-5-methyl-3,1-phenylene)azanediyl(2-oxoethane-2,1-diyl)]}bis(phosphonic acid))

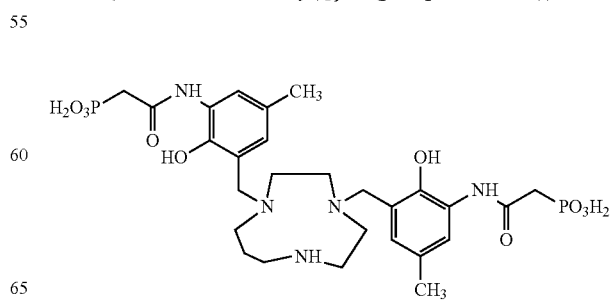

Compound 55 ({1,4,7-triazecane-1,4-diylbis[methylene(2-hydroxy-5-methyl-3,1-phenylene)azanediyl(2-oxoethane-2,1-diyl)]}bis(phosphonic acid))

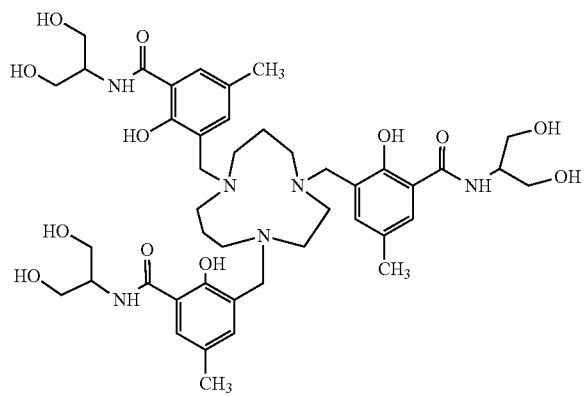 [SMILES: Cc1cc(CN2CCCN(Cc3cc(C)cc(C(=O)NC(CO)CO)c3O)CCN(Cc3cc(C)cc(C(=O)NC(CO)CO)c3O)CCC2)c(O)c(C(=O)NC(CO)CO)c1]

Compound 56 (3,3',3''-[1,4,8-triazacycloundecane-1,4,8-triyltris(methylene)]tris[N-(1,3-dihydroxypropan-2-yl)-2-hydroxy-5-methylbenzamide])

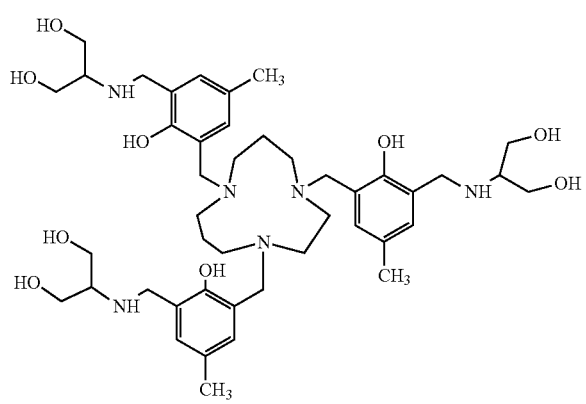 [SMILES: Cc1cc(CNC(CO)CO)c(O)c(CN2CCCN(Cc3cc(C)cc(CNC(CO)CO)c3O)CCN(Cc3cc(C)cc(CNC(CO)CO)c3O)CCC2)c1]

Compound 57 (2,2',2''-{1,4,8-triazacycloundecane-1,4,8-triyltris[methylene(2-hydroxy-5-methyl-3,1-phenylene)methyleneazanediyl]}tri(propane-1,3-diol))

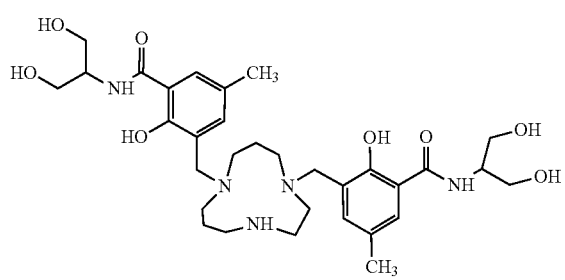

Compound 58 (3,3'-[1,4,8-triazacycloundecane-1,8-diylbis(methylene)]bis[N-(1,3-dihydroxypropan-2-yl)-2-hydroxy-5-methylbenzamide])

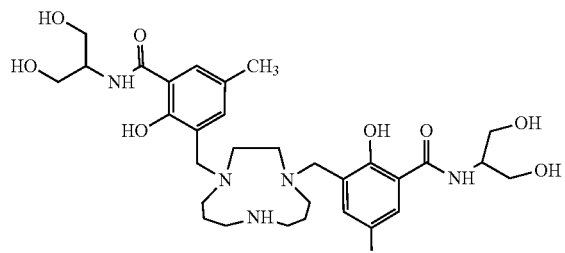

Compound 59 (3,3'-[1,4,8-triazacycloundecane-1,4-diylbis(methylene)]bis[N-(1,3-dihydroxypropan-2-yl)-2-hydroxy-5-methylbenzamide])

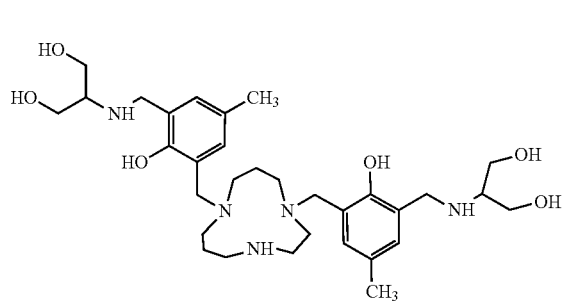

Compound 60 (2,2'-{1,4,8-triazacycloundecane-1,8-diylbis[methylene(2-hydroxy-5-methyl-3,1-phenylene)methyleneazanediyl]}di(propane-1,3-diol))

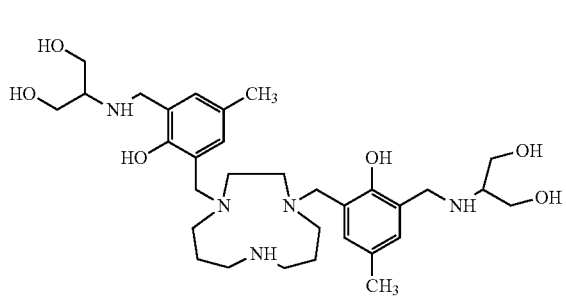 [SMILES: Cc1cc(CNC(CO)CO)c(O)c(CN2CCCNCCCN(Cc3cc(C)cc(CNC(CO)CO)c3O)CC2)c1]

Compound 61 (2,2'-{1,4,8-triazacycloundecane-1,4-diylbis[methylene(2-hydroxy-5-methyl-3,1-phenylene)methyleneazanediyl]}di(propane-1,3-diol))

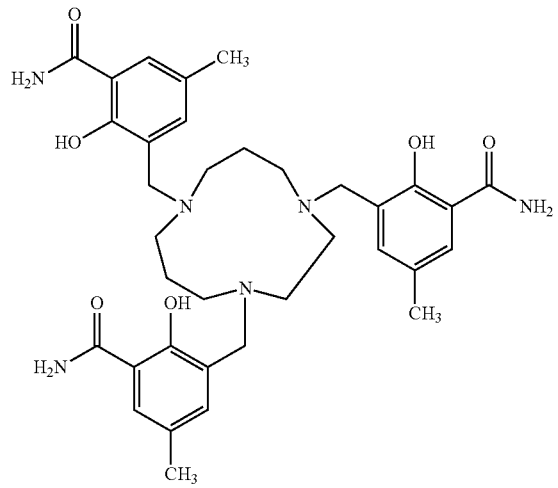 [SMILES: Cc1cc(CN2CCCN(Cc3cc(C)cc(C(N)=O)c3O)CCN(Cc3cc(C)cc(C(N)=O)c3O)CCC2)c(O)c(C(N)=O)c1]

Compound 62 (3,3',3''-[1,4,8-triazacycloundecane-1,4,8-triyltris(methylene)]tris(2-hydroxy-5-methylbenzamide))

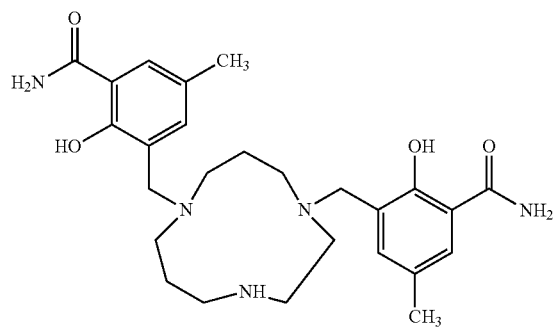 [SMILES: Cc1cc(CN2CCCNCCN(Cc3cc(C)cc(C(N)=O)c3O)CCC2)c(O)c(C(N)=O)c1]

Compound 63 (3,3'-[1,4,8-triazacycloundecane-1,8-diylbis(methylene)]bis(2-hydroxy-5-methylbenzamide))

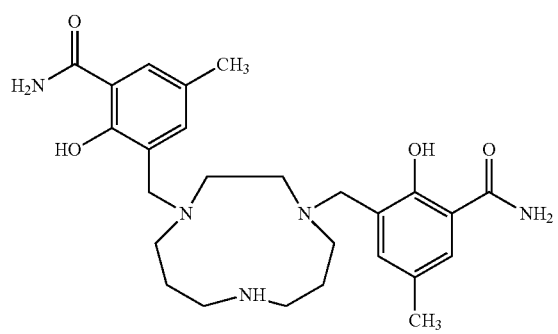 [SMILES: Cc1cc(CN2CCCNCCCN(Cc3cc(C)cc(C(N)=O)c3O)CC2)c(O)c(C(N)=O)c1]

Compound 64 (3,3'-[1,4,8-triazacycloundecane-1,4-diylbis(methylene)]bis(2-hydroxy-5-methylbenzamide))

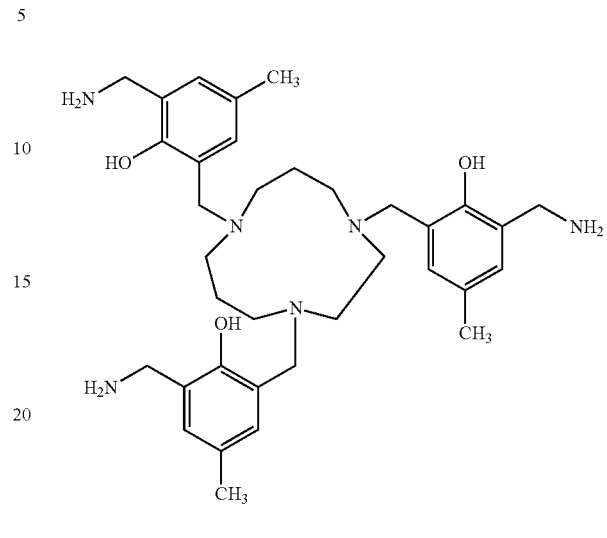

Compound 65 (2,2',2''-[1,4,8-triazacycloundecane-1,4,8-triyltris(methylene)]tris[6-(aminomethyl)-4-methylphenol])

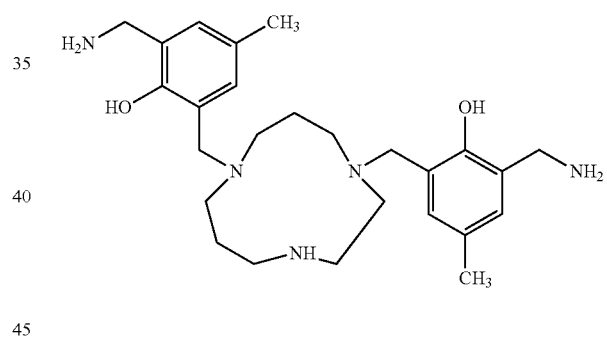

Compound 66 (2,2'-[1,4,8-triazacycloundecane-1,8-diylbis(methylene)]bis[6-(aminomethyl)-4-methylphenol])

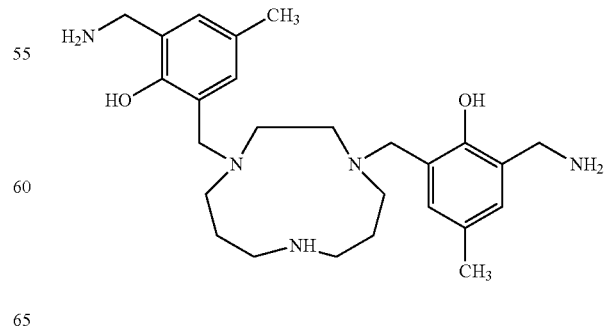

Compound 67 (2,2'-[1,4,8-triazacycloundecane-1,4-diylbis(methylene)]bis[6-(aminomethyl)-4-methylphenol])

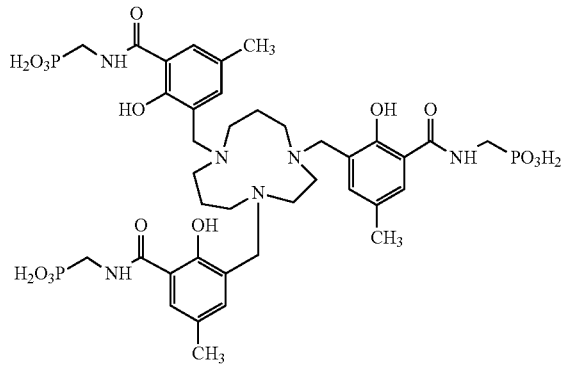

Compound 68 ({1,4,8-triazacycloundecane-1,4,8-triyltris[methylene(2-hydroxy-5-methyl-3,1-phenylene)carbonylazanediyimethylene]}tris(phosphonic acid))

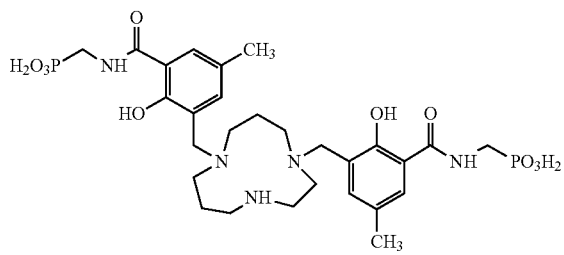

Compound 69 ({1,4,8-triazacycloundecane-1,8-diyl-bis[methylene(2-hydroxy-5-methyl-3,1-phenylene)carbonylazanediyimethylene]}bis(phosphonic acid))

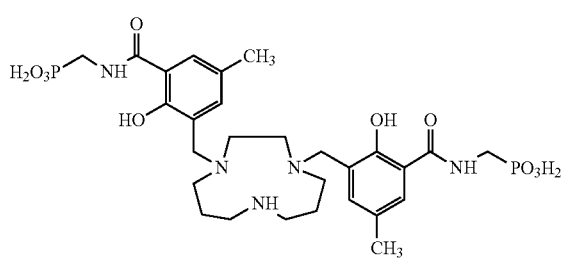

Compound 70 ({1,4,8-triazacycloundecane-1,4-diyl-bis[methylene(2-hydroxy-5-methyl-3,1-phenylene)carbonylazanediyimethylene]}bis(phosphonic acid))

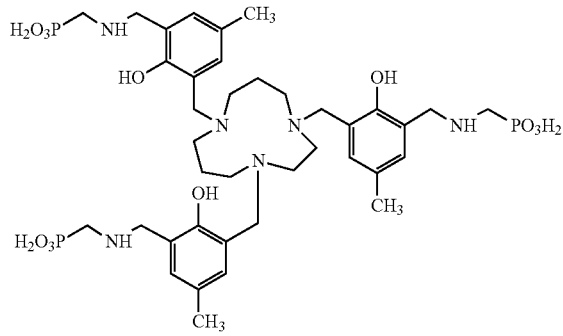

Compound 71 ({1,4,8-triazacycloundecane-1,4,8-triyltris[methylene(2-hydroxy-5-methyl-3,1-phenylene)methyleneazanediylmethylene]}tris(phosphonic acid))

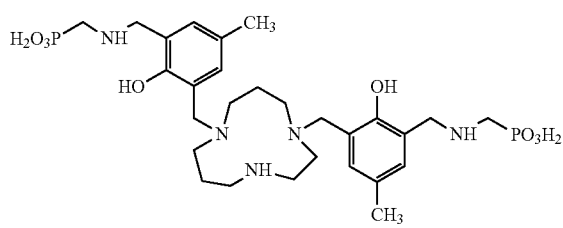

Compound 72 ({1,4,8-triazacycloundecane-1,8-diyl-bis[methylene(2-hydroxy-5-methyl-3,1-phenylene)methyleneazanediylmethylene]}bis(phosphonic acid))

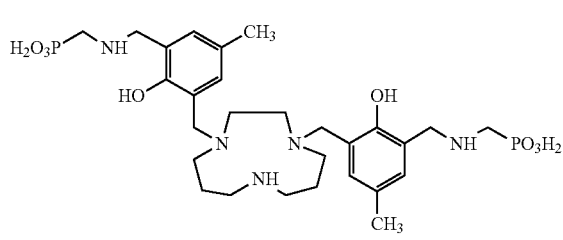

Compound 73 ({1,4,8-triazacycloundecane-1,4-diyl-bis[methylene(2-hydroxy-5-methyl-3,1-phenylene)methyleneazanediylmethylene]}bis(phosphonic acid))

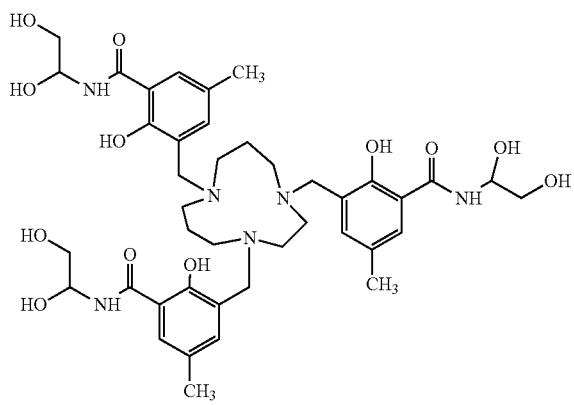 [SMILES: Cc1cc(CN2CCCN(Cc3cc(C)cc(C(=O)NC(O)CO)c3O)CCN(Cc3cc(C)cc(C(=O)NC(O)CO)c3O)CCC2)c(O)c(C(=O)NC(O)CO)c1]

Compound 74 (3,3',3''-[1,4,8-triazacycloundecane-1,4,8-triyltris(methylene)]tris[N-(1,2-dihydroxyethyl)-2-hydroxy-5-methylbenzamide])

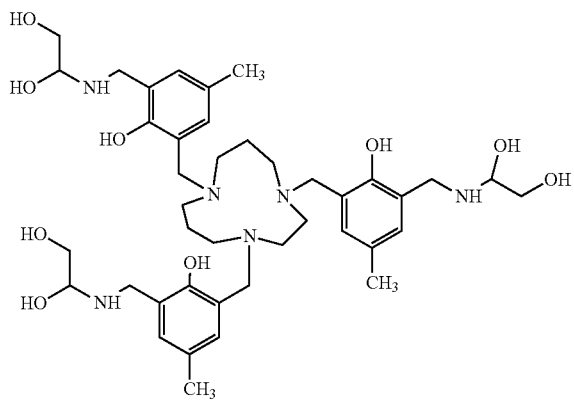 [SMILES: Cc1cc(CNC(O)CO)c(O)c(CN2CCCN(Cc3cc(C)cc(CNC(O)CO)c3O)CCN(Cc3cc(C)cc(CNC(O)CO)c3O)CCC2)c1]

Compound 75 (1,1',1''-{1,4,8-triazacycloundecane-1,4,8-triyltris[methylene(2-hydroxy-5-methyl-3,1-phenylene)methyleneazanediyl]}tri(ethane-1,2-diol))

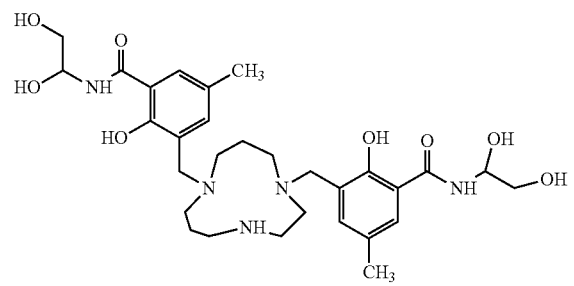 [SMILES: Cc1cc(CN2CCCNCCN(Cc3cc(C)cc(C(=O)NC(O)CO)c3O)CCC2)c(O)c(C(=O)NC(O)CO)c1]

Compound 76 (3,3'-[1,4,8-triazacycloundecane-1,8-diylbis(methylene)]bis[N-(1,2-dihydroxyethyl)-2-hydroxy-5-methylbenzamide])

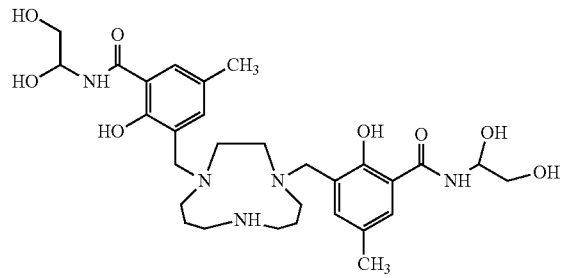 [SMILES: Cc1cc(CN2CCCNCCCN(Cc3cc(C)cc(C(=O)NC(O)CO)c3O)CC2)c(O)c(C(=O)NC(O)CO)c1]

Compound 77 (3,3'-[1,4,8-triazacycloundecane-1,4-diylbis(methylene)]bis[N-(1,2-dihydroxyethyl)-2-hydroxy-5-methylbenzamide])

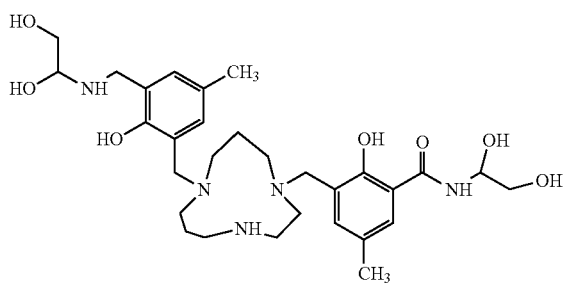 [SMILES: Cc1cc(CNC(O)CO)c(O)c(CN2CCCNCCN(Cc3cc(C)cc(C(=O)NC(O)CO)c3O)CCC2)c1]

Compound 78 (1,1'-{1,4,8-triazacycloundecane-1,8-diylbis[methylene(2-hydroxy-5-methyl-3,1-phenylene)methyleneazanediyl]}di(ethane-1,2-diol))

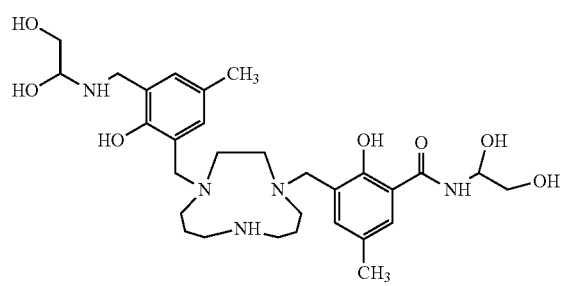 [SMILES: Cc1cc(CNC(O)CO)c(O)c(CN2CCCNCCCN(Cc3cc(C)cc(C(=O)NC(O)CO)c3O)CC2)c1]

Compound 79 (1,1'-{1,4,8-triazacycloundecane-1,4-diylbis[methylene(2-hydroxy-5-methyl-3,1-phenylene)methyleneazanediyl]}di(ethane-1,2-diol))

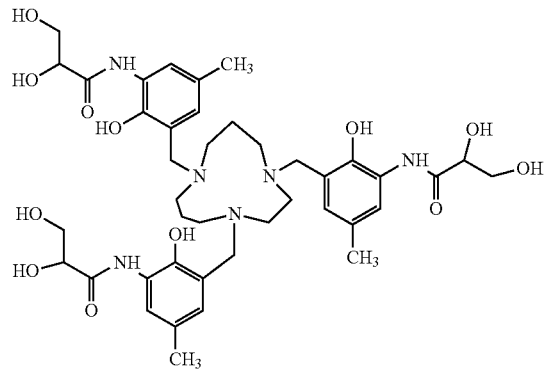 [SMILES: Cc1cc(CN2CCCN(Cc3cc(C)cc(NC(=O)C(O)CO)c3O)CCN(Cc3cc(C)cc(NC(=O)C(O)CO)c3O)CCC2)c(O)c(NC(=O)C(O)CO)c1]

Compound 82 (N,N'-{1,4,8-triazacycloundecane-1,4-diylbis[methylene(2-hydroxy-5-methyl-3,1-phenylene)]}bis(2,3-dihydroxypropanamide))

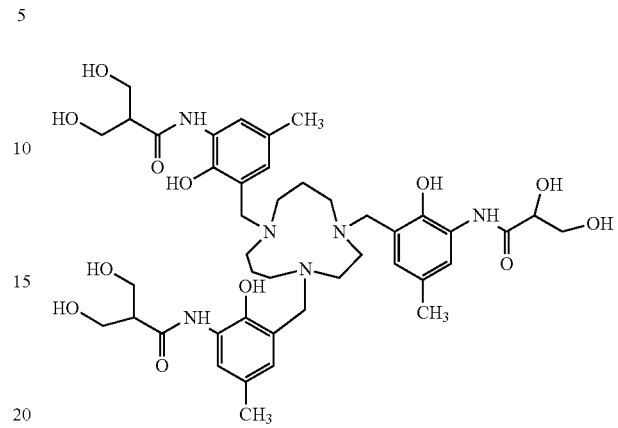

Compound 80 (N,N',N''-{1,4,8-triazacycloundecane-1,4,8-triyltris[methylene(2-hydroxy-5-methyl-3,1-phenylene)]}tris(2,3-dihydroxypropanamide))

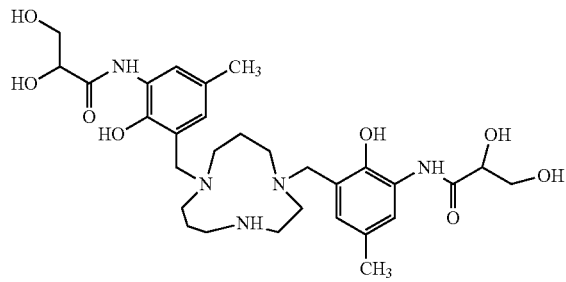 [SMILES: Cc1cc(CN2CCCNCCN(Cc3cc(C)cc(NC(=O)C(O)CO)c3O)CCC2)c(O)c(NC(=O)C(O)CO)c1]

Compound 83 (N,N',N''-{1,4,8-triazacycloundecane-1,4,8-triyltris[methylene(2-hydroxy-5-methyl-3,1-phenylene)]}tris[3-hydroxy-2-(hydroxymethyl)propanamide])

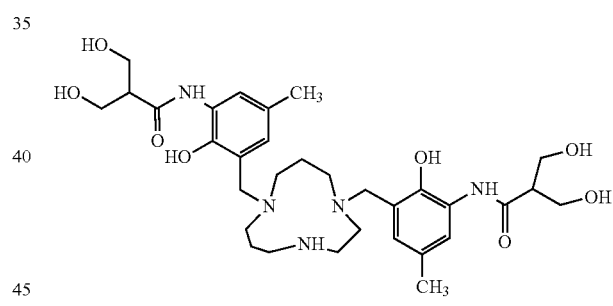

Compound 81 (N,N-{1,4,8-triazacycloundecane-1,8-diylbis[methylene(2-hydroxy-5-methyl-3,1-phenylene)]}bis(2,3-dihydroxypropanamide))

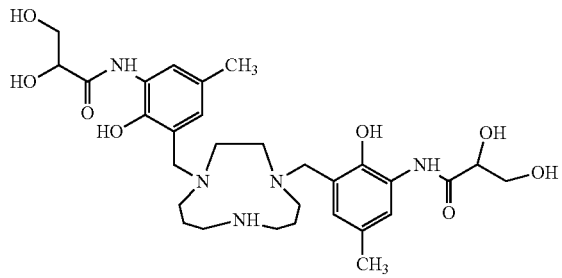 [SMILES: Cc1cc(CN2CCCNCCCN(Cc3cc(C)cc(NC(=O)C(O)CO)c3O)CC2)c(O)c(NC(=O)C(O)CO)c1]

Compound 84 (N,N'-{1,4,8-triazacycloundecane-1,8-diylbis[methylene(2-hydroxy-5-methyl-3,1-phenylene)]}bis[3-hydroxy-2-(hydroxymethyl)propanamide])

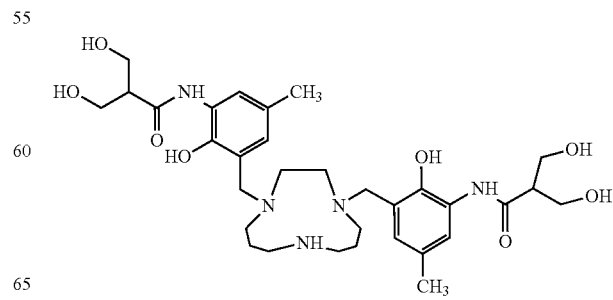

Compound 85 (N,N'-{1,4,8-triazacycloundecane-1,4-diylbis[methylene(2-hydroxy-5-methyl-3,1-phenylene)]}bis[3-hydroxy-2-(hydroxymethyl)propanamide])

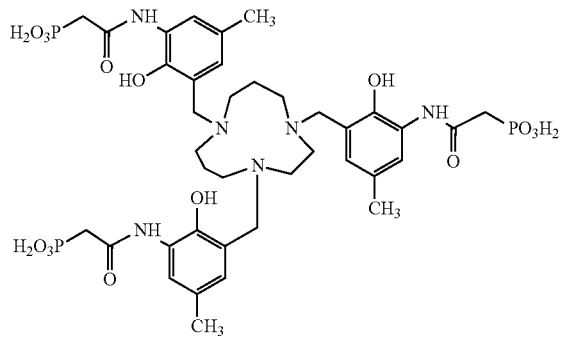

Compound 86 ({1,4,8-triazacycloundecane-1,4,8-triyltris[methylene(2-hydroxy-5-methyl-3,1-phenylene)azanediyl(2-oxoethane-2,1-diyl)]}tris(phosphonic acid))

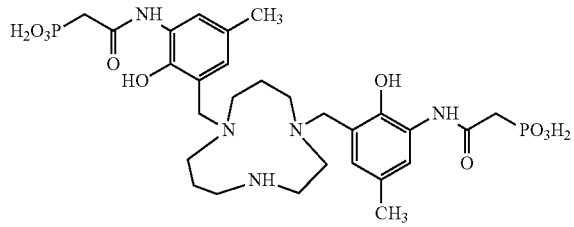

Compound 87 ({1,4,8-triazacycloundecane-1,8-diylbis[methylene(2-hydroxy-5-methyl-3,1-phenylene)azanediyl(2-oxoethane-2,1-diyl)]}bis(phosphonic acid))

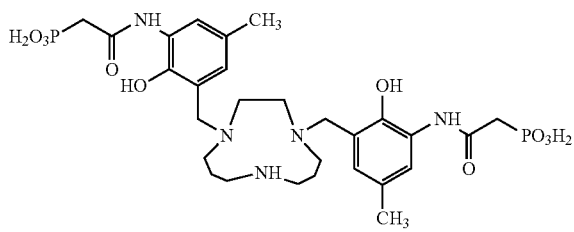

Compound 88 ({1,4,8-triazacycloundecane-1,4-diylbis[methylene(2-hydroxy-5-methyl-3,1-phenylene)azanediyl(2-oxoethane-2,1-diyl)]}bis(phosphonic acid))

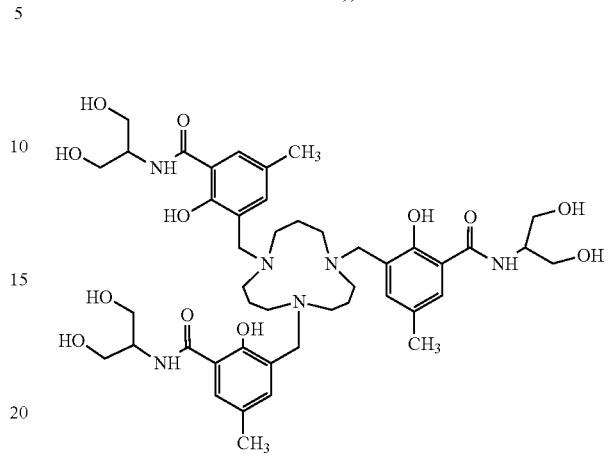

Compound 89 (3,3',3''-[1,5,9-triazacyclododecane-1,5,9-triyltris(methylene)]tris[N-(1,3-dihydroxypropan-2-yl)-2-hydroxy-5-methylbenzamide])

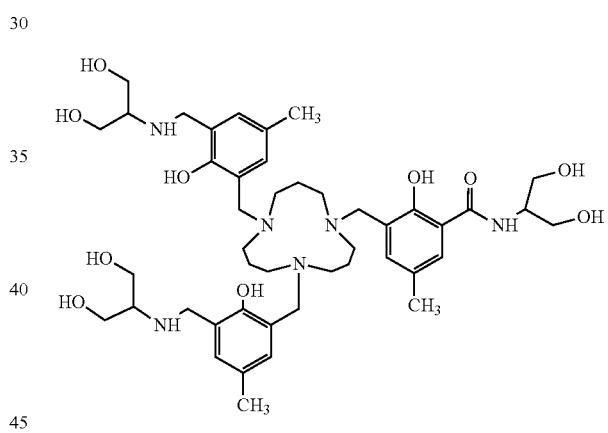

Compound 90 (2,2',2''-{1,5,9-triazacyclododecane-1,5,9-triyltris[methylene(2-hydroxy-5-methyl-3,1-phenylene)methyleneazanediyl]}tri(propane-1,3-diol))

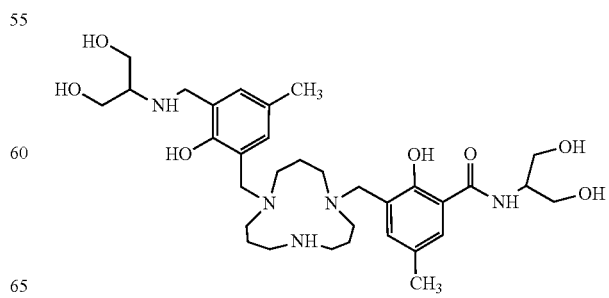

Compound 91 (3,3'-[1,5,9-triazacyclododecane-1,5-diylbis(methylene)]bis[N-(1,3-dihydroxypropan-2-yl)-2-hydroxy-5-methylbenzamide])

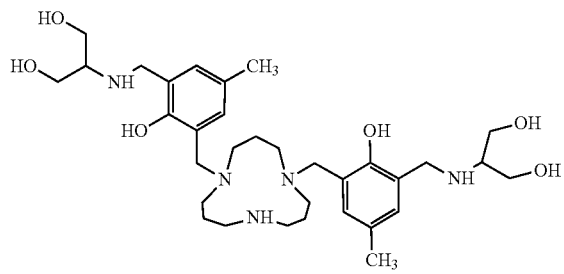 [SMILES: Cc1cc(CNC(CO)CO)c(O)c(CN2CCCNCCCN(Cc3cc(C)cc(CNC(CO)CO)c3O)CCC2)c1]

Compound 92 (2,2'-{1,5,9-triazacyclododecane-1,5-diylbis[methylene(2-hydroxy-5-methyl-3,1-phenylene)methyleneazanediyl]}di(propane-1,3-diol))

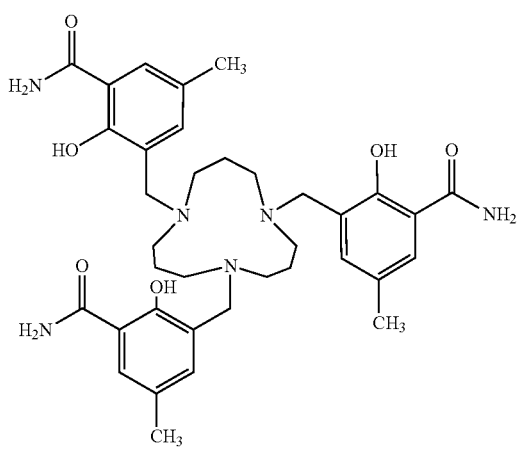 [SMILES: Cc1cc(CN2CCCN(Cc3cc(C)cc(C(N)=O)c3O)CCCN(Cc3cc(C)cc(C(N)=O)c3O)CCC2)c(O)c(C(N)=O)c1]

Compound 93 (3,3',3''-[1,5,9-triazacyclododecane-1,5,9-triyltris(methylene)]tris(2-hydroxy-5-methylbenzamide))

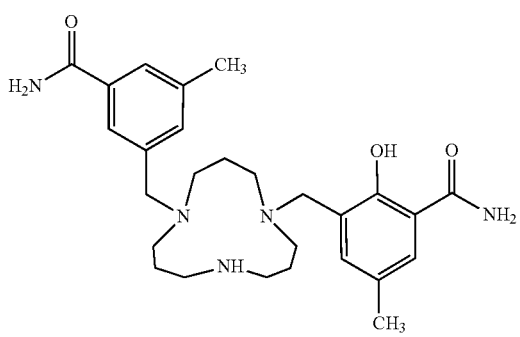 [SMILES: Cc1cc(CN2CCCNCCCN(Cc3cc(C)cc(C(N)=O)c3O)CCC2)cc(C(N)=O)c1]

Compound 94 (3,3'-[1,5,9-triazacyclododecane-1,5-diylbis(methylene)]bis(2-hydroxy-5-methylbenzamide))

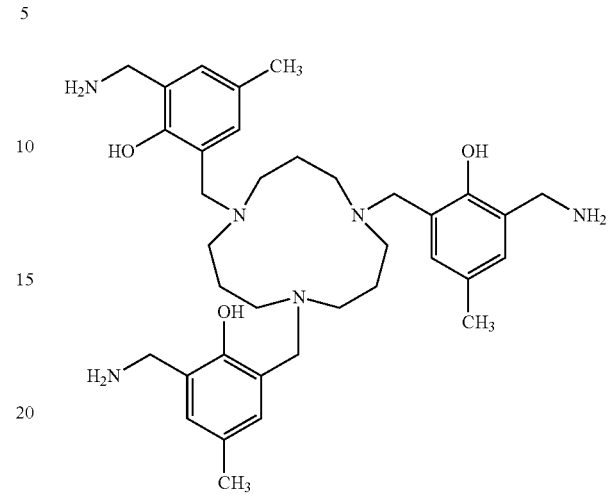

Compound 95 (2,2',2''-[1,5,9-triazacyclododecane-1,5,9-triyltris(methylene)]tris[6-(aminomethyl)-4-methylphenol])

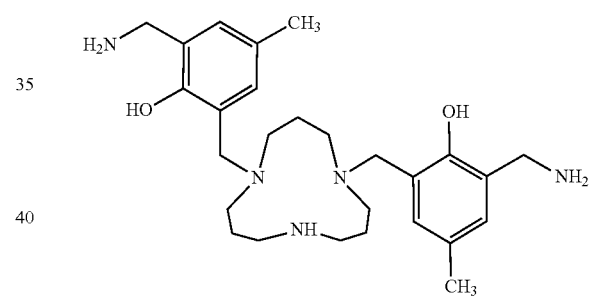

Compound 96 (2,2'-[1,5,9-triazacyclododecane-1,5-diylbis(methylene)]bis[6-(aminomethyl)-4-methylphenol])

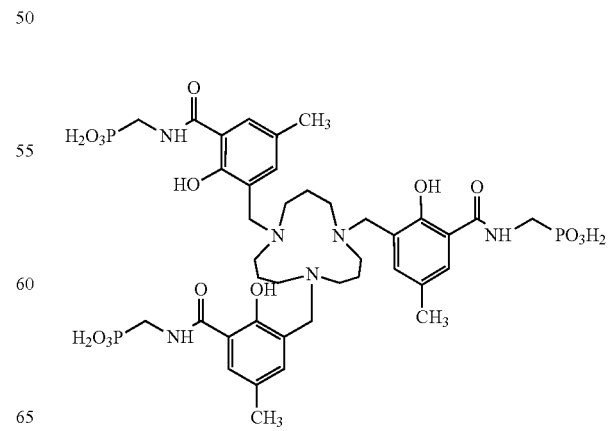

Compound 97 ({1,5,9-triazacyclododecane-1,5,9-triyltris[methylene(2-hydroxy-5-methyl-3,1-phenylene)carbonylazanediyimethylene]}tris(phosphonic acid))

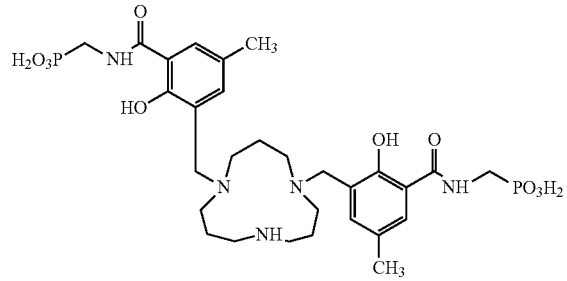

Compound 98 ({1,5,9-triazacyclododecane-1,5-diylbis[methylene(2-hydroxy-5-methyl-3,1-phenylene)carbonylazanediylmethylene]}bis(phosphonic acid))

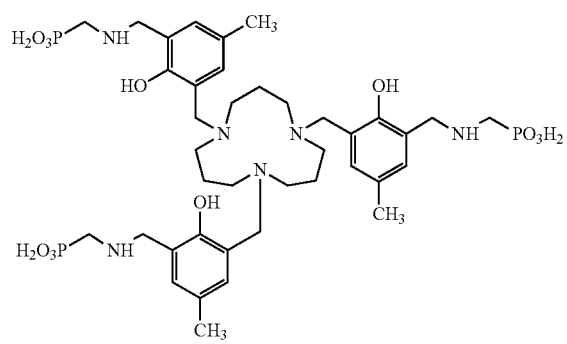

Compound 99 ({1,5,9-triazacyclododecane-1,5,9-triyltris[methylene(2-hydroxy-5-methyl-3,1-phenylene)methyleneazanediylmethylene]}tris(phosphonic acid))

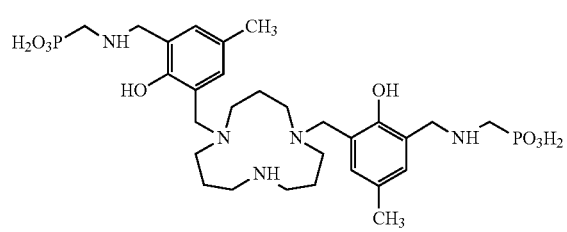

Compound 100 ({1,5,9-triazacyclododecane-1,5-diylbis[methylene(2-hydroxy-5-methyl-3,1-phenylene)methyleneazanediylmethylene]}bis(phosphonic acid))

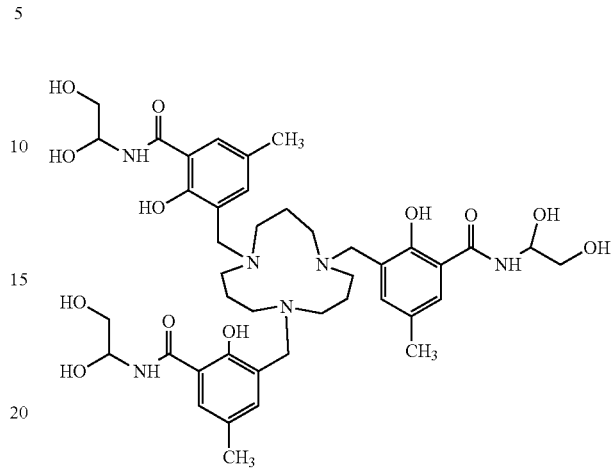

Compound 101 (3,3',3''-[1,5,9-triazacyclododecane-1,5,9-triyltris(methylene)]tris[N-(1,2-dihydroxyethyl)-2-hydroxy-5-methylbenzamide])

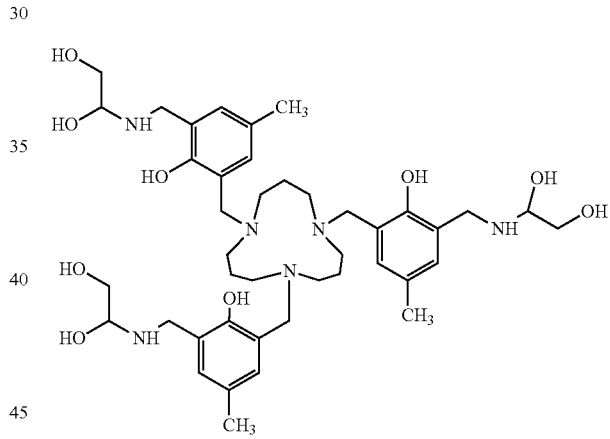

Compound 102 (1,1',1''-{1,5,9-triazacyclododecane-1,5,9-triyltris[methylene(2-hydroxy-5-methyl-3,1-phenylene)methyleneazanediyl]}tri(ethane-1,2-diol))

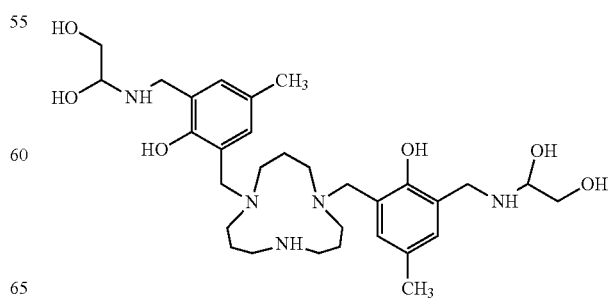

Compound 103 (3,3'-[1,5,9-triazacyclododecane-1,5-diylbis(methylene)]bis[N-(1,2-dihydroxyethyl)-2-hydroxy-5-methylbenzamide])

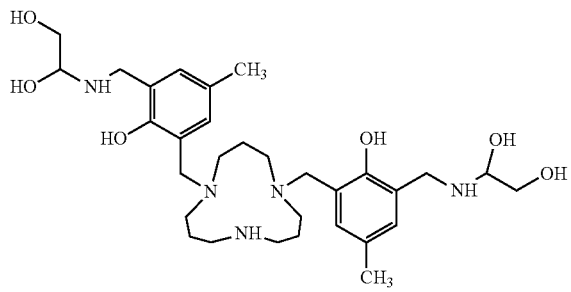 [SMILES: Cc1cc(CNC(O)CO)c(O)c(CN2CCCNCCCN(Cc3cc(C)cc(CNC(O)CO)c3O)CCC2)c1]

Compound 104 (1,1'-{1,5,9-triazacyclododecane-1,5-diylbis[methylene(2-hydroxy-5-methyl-3,1-phenylene)methyleneazanediyl]}di(ethane-1,2-diol))

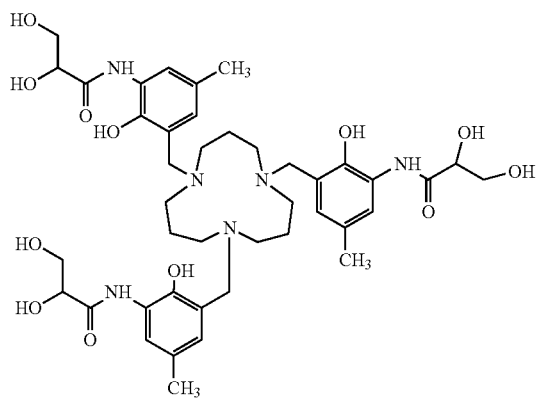 [SMILES: Cc1cc(CCN2CCCN(Cc3cc(C)cc(NC(=O)C(O)CO)c3O)CCCN(Cc3cc(C)cc(NC(=O)C(O)CO)c3O)CCC2)c(O)c(NC(=O)C(O)CO)c1]

Compound 105 (N,N',N''-{1,5,9-triazacyclododecane-1,5,9-triyltris[methylene(2-hydroxy-5-methyl-3,1-phenylene)]}tris(2,3-dihydroxypropanamide))

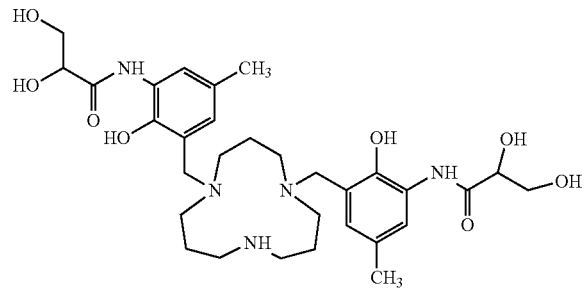 [SMILES: Cc1cc(CN2CCCNCCCN(Cc3cc(C)cc(NC(=O)C(O)CO)c3O)CCC2)c(O)c(NC(=O)C(O)CO)c1]

Compound 106 (N,N'-{1,5,9-triazacyclododecane-1,5-diylbis[methylene(2-hydroxy-5-methyl-3,1-phenylene)]}bis(2,3-dihydroxypropanamide))

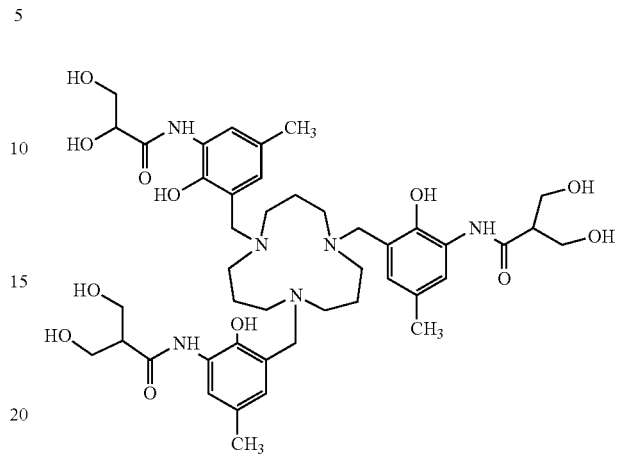

Compound 107 (N,N',N''-{1,5,9-triazacyclododecane-1,5,9-triyltris[methylene(2-hydroxy-5-methyl-3,1-phenylene)]}tris[3-hydroxy-2-(hydroxymethyl)propanamide])

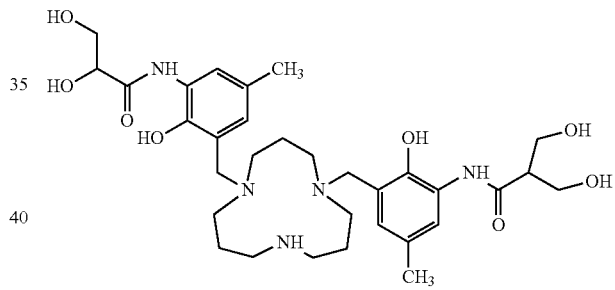

Compound 108 (N,N'-{1,5,9-triazacyclododecane-1,5-diylbis[methylene(2-hydroxy-5-methyl-3,1-phenylene)]}bis[3-hydroxy-2-(hydroxymethyl)propanamide])

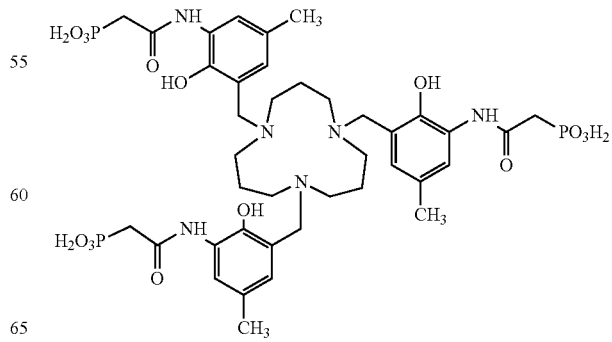

Compound 109 ({1,5,9-triazacyclododecane-1,5,9-triyltris[methylene(2-hydroxy-5-methyl-3,1-phenylene)azanediyl(2-oxoethane-2,1-diyl)]}tris(phosphonic acid))

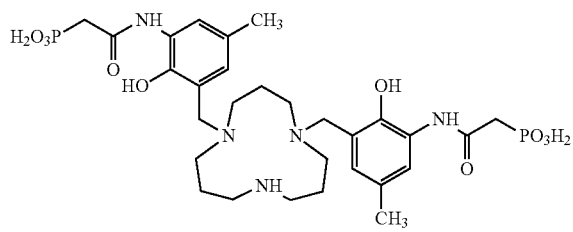

Compound 110 ({1,5,9-triazacyclododecane-1,5-diylbis[methylene(2-hydroxy-5-methyl-3,1-phenylene)azanediyl(2-oxoethane-2,1-diyl)]}bis(phosphonic acid))

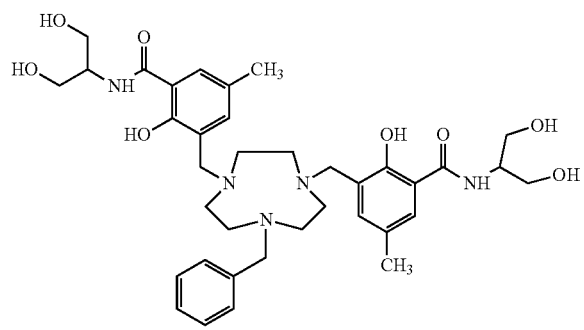 [SMILES: Cc1cc(CN2CCN(Cc3ccccc3)CCN(Cc3cc(C)cc(C(=O)NC(CO)CO)c3O)CC2)c(O)c(C(=O)NC(CO)CO)c1]

Compound 111 (3,3'-[(7-benzyl-1,4,7-triazonane-1,4-diyl)bis(methylene)]bis[N-(1,3-dihydroxypropan-2-yl)-2-hydroxy-5-methylbenzamide])

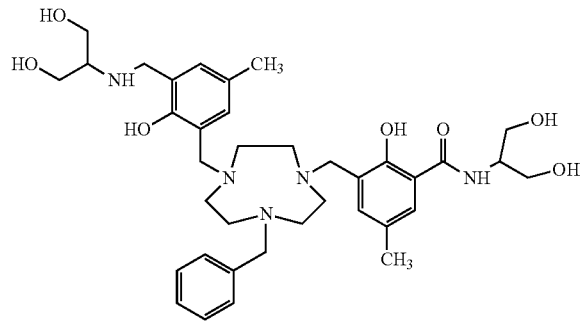 [SMILES: Cc1cc(CNC(CO)CO)c(O)c(CN2CCN(Cc3ccccc3)CCN(Cc3cc(C)cc(C(=O)NC(CO)CO)c3O)CC2)c1]

Compound 112 (2,2'-{(7-benzyl-1,4,7-triazonane-1,4-diyl)bis[methylene(2-hydroxy-5-methyl-3,1-phenylene)methyleneazanediyl]}di(propane-1,3-diol))

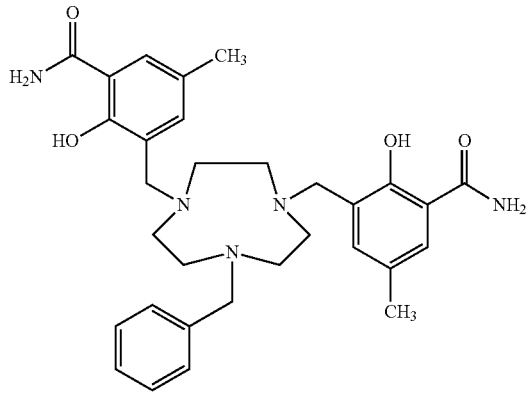 [SMILES: Cc1cc(CN2CCN(Cc3ccccc3)CCN(Cc3cc(C)cc(C(N)=O)c3O)CC2)c(O)c(C(N)=O)c1]

Compound 113 (3,3'-[(7-benzyl-1,4,7-triazonane-1,4-diyl)bis(methylene)]bis(2-hydroxy-5-methylbenzamide))

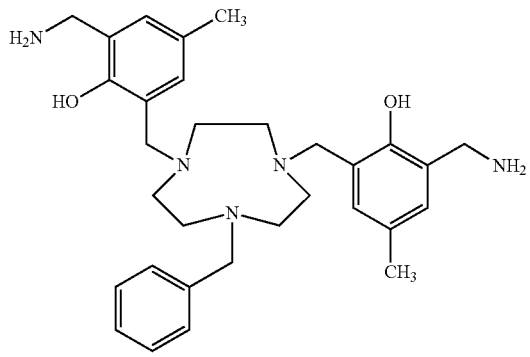 [SMILES: Cc1cc(CN)c(O)c(CN2CCN(Cc3ccccc3)CCN(Cc3cc(C)cc(CN)c3O)CC2)c1]

Compound 114 (2,2'-[(7-benzyl-1,4,7-triazonane-1,4-diyl)bis(methylene)]bis[6-(aminomethyl)-4-methylphenol])

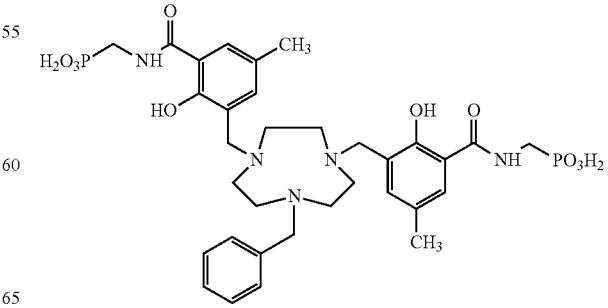

Compound 115 ({(7-benzyl-1,4,7-triazonane-1,4-diyl)bis[methylene(2-hydroxy-5-methyl-3,1-phenylene)carbonylazanediyimethylene]}bis(phosphonic acid))

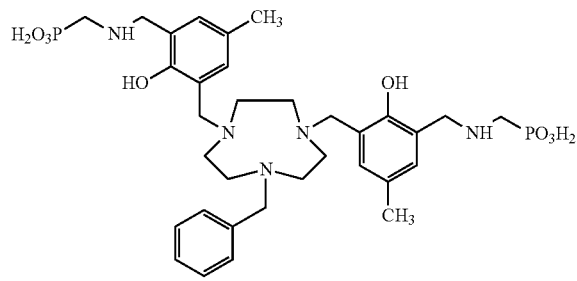

Compound 116 ({(7-benzyl-1,4,7-triazonane-1,4-diyl)bis[methylene(2-hydroxy-5-methyl-3,1-phenylene)methyleneazanediylmethylene]}bis(phosphonic acid))

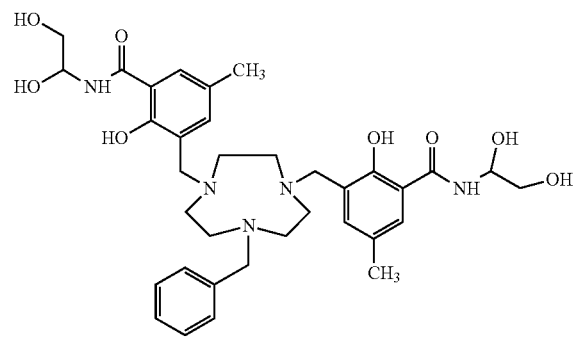 [SMILES: Cc1cc(CN2CCN(Cc3ccccc3)CCN(Cc3cc(C)cc(C(=O)NC(O)CO)c3O)CC2)c(O)c(C(=O)NC(O)CO)c1]

Compound 117 (3,3'-[(7-benzyl-1,4,7-triazonane-1,4-diyl)bis(methylene)]bis[N-(1,2-dihydroxyethyl)-2-hydroxy-5-methylbenzamide])

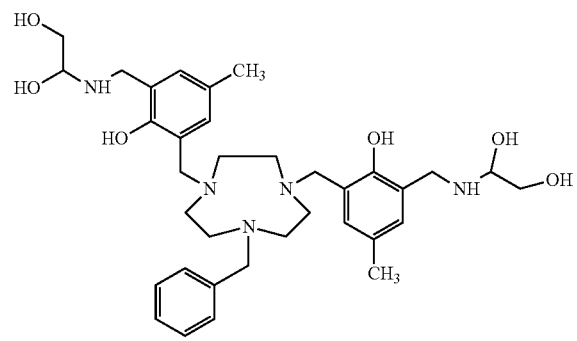 [SMILES: Cc1cc(CNC(O)CO)c(O)c(CN2CCN(Cc3ccccc3)CCN(Cc3cc(C)cc(CNC(O)CO)c3O)CC2)c1]

Compound 118 (1,1'-{(7-benzyl-1,4,7-triazonane-1,4-diyl)bis[methylene(2-hydroxy-5-methyl-3,1-phenylene)methyleneazanediyl]}di(ethane-1,2-diol))

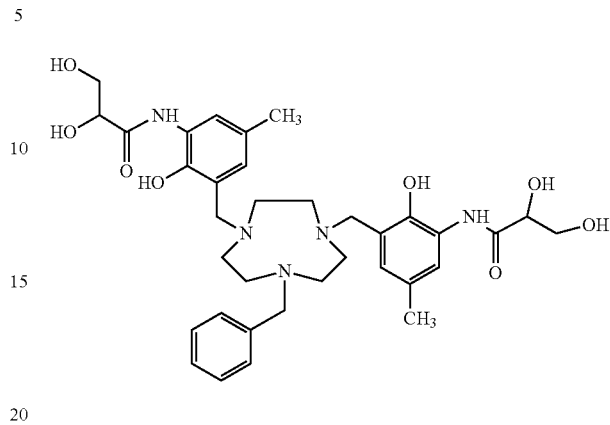

Compound 119 (N,N'-{(7-benzyl-1,4,7-triazonane-1,4-diyl)bis[methylene(2-hydroxy-5-methyl-3,1-phenylene)]}bis(2,3-dihydroxypropanamide))

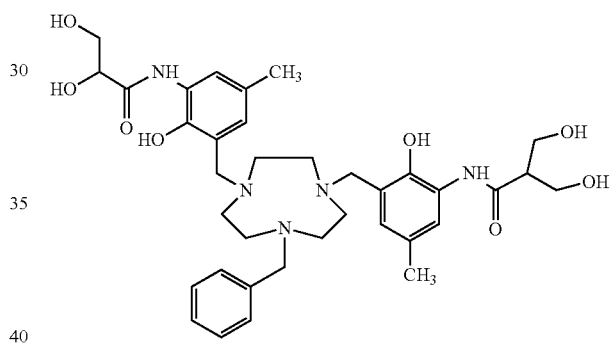

Compound 120 (N,N'-{(7-benzyl-1,4,7-triazonane-1,4-diyl)bis[methylene(2-hydroxy-5-methyl-3,1-phenylene)]}bis[3-hydroxy-2-(hydroxymethyl)propanamide])

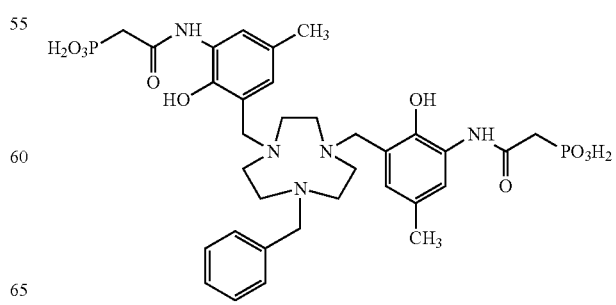

Compound 121 ({(7-benzyl-1,4,7-triazonane-1,4-diyl)bis[methylene(2-hydroxy-5-methyl-3,1-phenylene)azanediyl(2-oxoethane-2,1-diyl)]}bis(phosphonic acid))

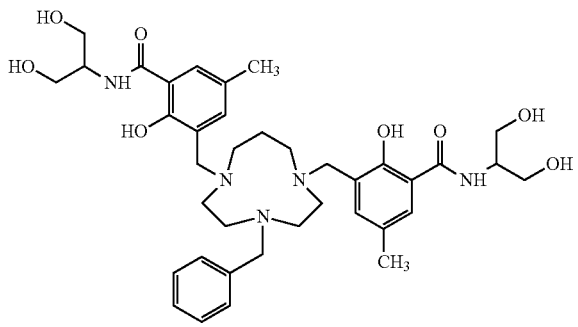 [SMILES: Cc1cc(CN2CCCN(Cc3cc(C)cc(C(=O)NC(CO)CO)c3O)CCN(Cc3ccccc3)CC2)c(O)c(C(=O)NC(CO)CO)c1]

Compound 122 (3,3'-[(4-benzyl-1,4,7-triazecane-1,7-diyl)bis(methylene)]bis[N-(1,3-dihydroxypropan-2-yl)-2-hydroxy-5-methylbenzamide])

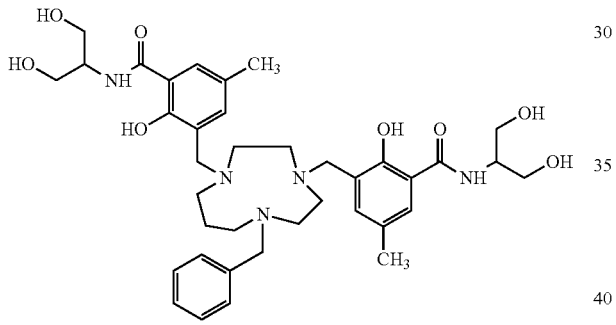

Compound 123 (3,3'-[(7-benzyl-1,4,7-triazecane-1,4-diyl)bis(methylene)]bis[N-(1,3-dihydroxypropan-2-yl)-2-hydroxy-5-methylbenzamide])

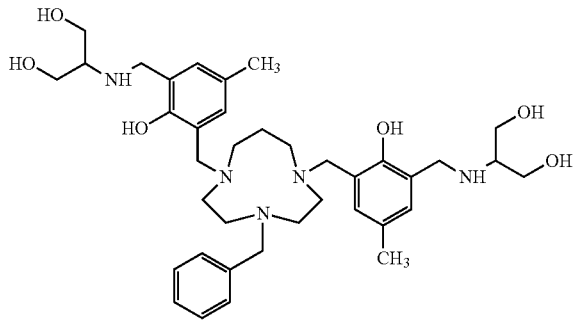 [SMILES: Cc1cc(CNC(CO)CO)c(O)c(CN2CCCN(Cc3cc(C)cc(CNC(CO)CO)c3O)CCN(Cc3ccccc3)CC2)c1]

Compound 124 (2,2'-{(4-benzyl-1,4,7-triazecane-1,7-diyl)bis[methylene(2-hydroxy-5-methyl-3,1-phenylene)methyleneazanediyl]}di(propane-1,3-diol))

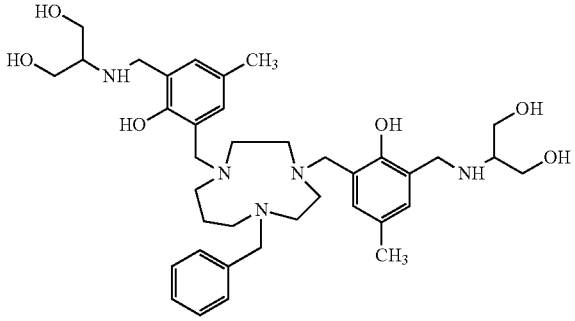 [SMILES: Cc1cc(CNC(CO)CO)c(O)c(CN2CCCN(Cc3ccccc3)CCN(Cc3cc(C)cc(CNC(CO)CO)c3O)CC2)c1]

Compound 125 (2,2'-{(7-benzyl-1,4,7-triazecane-1,4-diyl)bis[methylene(2-hydroxy-5-methyl-3,1-phenylene)methyleneazanediyl]}di(propane-1,3-diol))

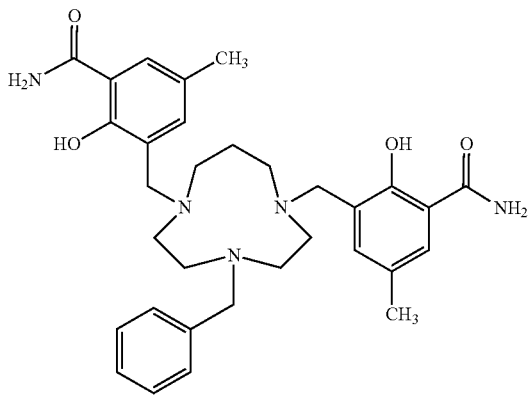

Compound 126 (3,3'-[(4-benzyl-1,4,7-triazecane-1,7-diyl)bis(methylene)]bis(2-hydroxy-5-methylbenzamide))

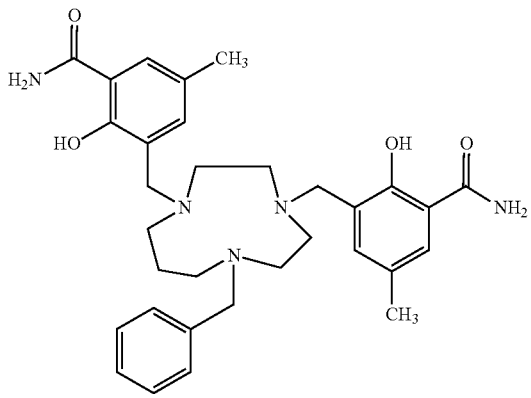 [SMILES: Cc1cc(CN2CCCN(Cc3ccccc3)CCN(Cc3cc(C)cc(C(N)=O)c3O)CC2)c(O)c(C(N)=O)c1]

Compound 127 (3,3'-[(7-benzyl-1,4,7-triazecane-1,4-diyl)bis(methylene)]bis(2-hydroxy-5-methylbenzamide))

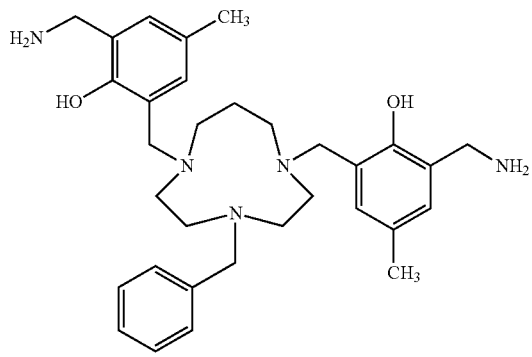 [SMILES: Cc1cc(CN)c(O)c(CN2CCCN(Cc3cc(C)cc(CN)c3O)CCN(Cc3ccccc3)CC2)c1]

Compound 128 (2,2'-[(4-benzyl-1,4,7-triazecane-1,7-diyl)bis(methylene)]bis[6-(aminomethyl)-4-methylphenol])

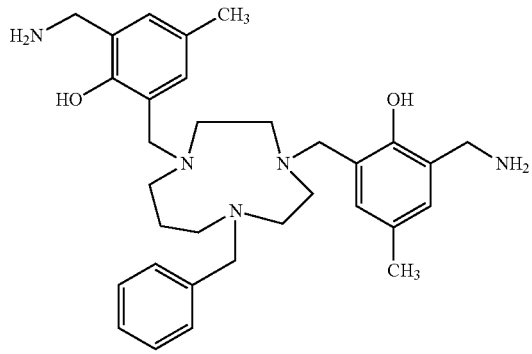 [SMILES: Cc1cc(CN)c(O)c(CN2CCCN(Cc3ccccc3)CCN(Cc3cc(C)cc(CN)c3O)CC2)c1]

Compound 129 (2,2'-[(7-benzyl-1,4,7-triazecane-1,4-diyl)bis(methylene)]bis[6-(aminomethyl)-4-methylphenol])

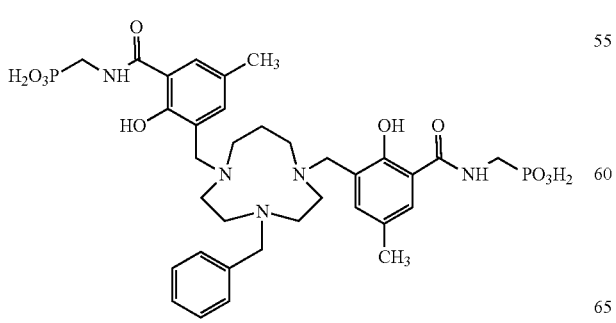

Compound 130 ({(4-benzyl-1,4,7-triazecane-1,7-diyl)bis[methylene(2-hydroxy-5-methyl-3,1-phenylene)carbonylazanediyimethylene]}bis(phosphonic acid))

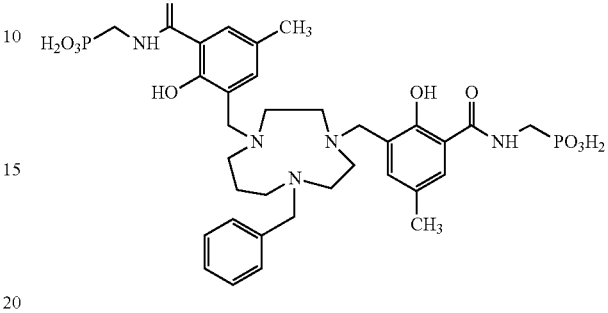

Compound 131 ({(7-benzyl-1,4,7-triazecane-1,4-diyl)bis[methylene(2-hydroxy-5-methyl-3,1-phenylene)carbonylazanediyimethylene]}bis(phosphonic acid))

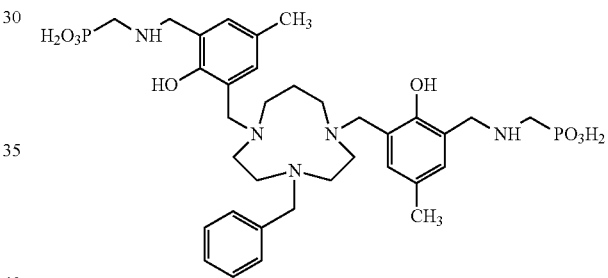

Compound 132 ({(4-benzyl-1,4,7-triazecane-1,7-diyl)bis[methylene(2-hydroxy-5-methyl-3,1-phenylene)methyleneazanediylmethylene]}bis(phosphonic acid))

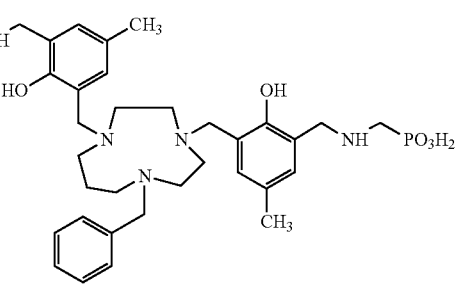

Compound 133 ({(7-benzyl-1,4,7-triazecane-1,4-diyl)bis[methylene(2-hydroxy-5-methyl-3,1-phenylene)methyleneazanediylmethylene]}bis(phosphonic acid))

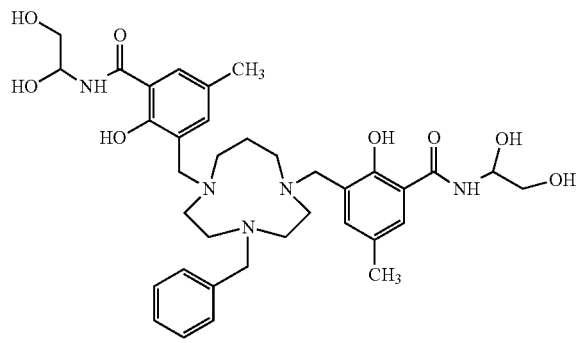 [SMILES: Cc1cc(CN2CCCN(Cc3cc(C)cc(C(=O)NC(O)CO)c3O)CCN(Cc3ccccc3)CC2)c(O)c(C(=O)NC(O)CO)c1]

Compound 134 (3,3'-[(4-benzyl-1,4,7-triazecane-1,7-diyl)bis(methylene)]bis[N-(1,2-dihydroxyethyl)-2-hydroxy-5-methylbenzamide])

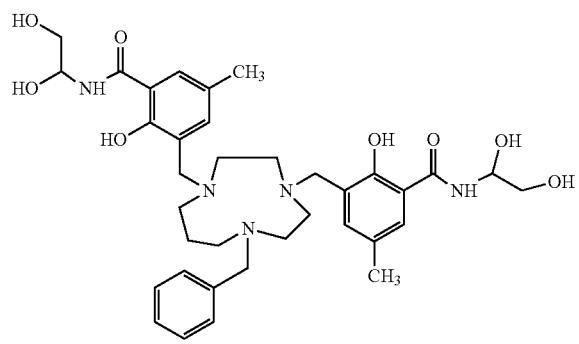 [SMILES: Cc1cc(CN2CCCN(Cc3ccccc3)CCN(Cc3cc(C)cc(C(=O)NC(O)CO)c3O)CC2)c(O)c(C(=O)NC(O)CO)c1]

Compound 135 (3,3'-[(7-benzyl-1,4,7-triazecane-1,4-diyl)bis(methylene)]bis[N-(1,2-dihydroxyethyl)-2-hydroxy-5-methylbenzamide])

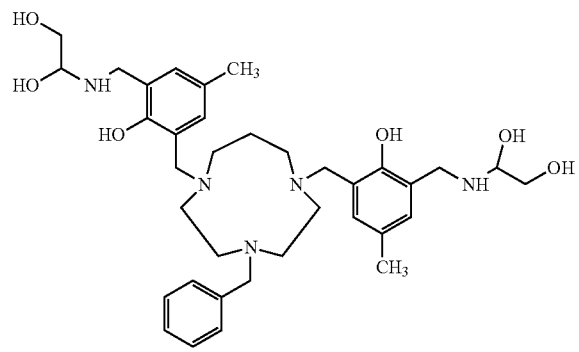 [SMILES: Cc1cc(CNC(O)CO)c(O)c(CN2CCCN(Cc3cc(C)cc(CNC(O)CO)c3O)CCN(Cc3ccccc3)CC2)c1]

Compound 136 (1,1'-{(4-benzyl-1,4,7-triazecane-1,7-diyl)bis[methylene(2-hydroxy-5-methyl-3,1-phenylene)methyleneazabediyl])}di(ethane-1,2-diol))

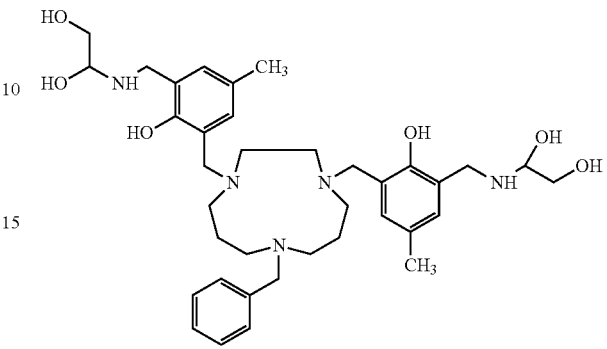

Compound 137 (1,1'-{(7-benzyl-1,4,7-triazecane-1,4-diyl)bis[methylene(2-hydroxy-5-methyl-3,1-phenylene)methyleneazanediyl]}di(ethane-1,2-diol))

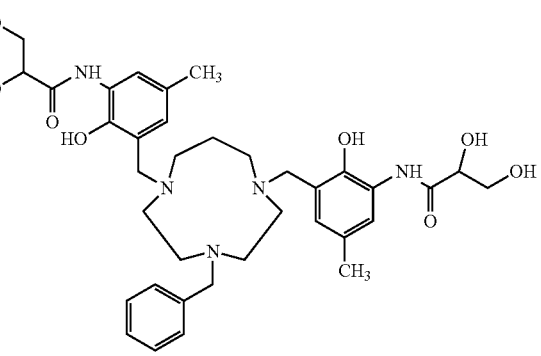

Compound 138 (N,N'-{(4-benzyl-1,4,7-triazecane-1,7-diyl)bis[methylene(2-hydroxy-5-methyl-3,1-phenylene)]}bis(2,3-dihydroxypropanamide))

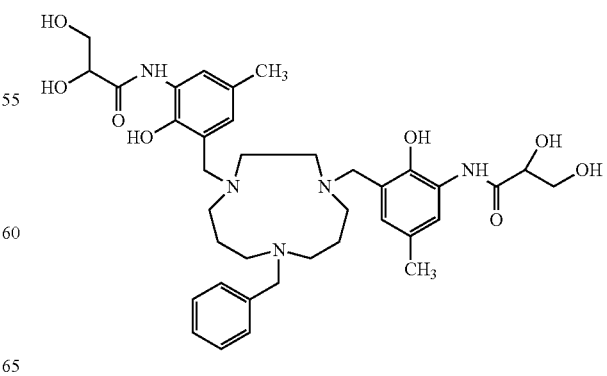

Compound 139 (N,N'-{(7-benzyl-1,4,7-triazecane-1,4-diyl)bis[methylene(2-hydroxy-5-methyl-3,1-phenylene)]}bis(2,3-dihydroxypropanamide))

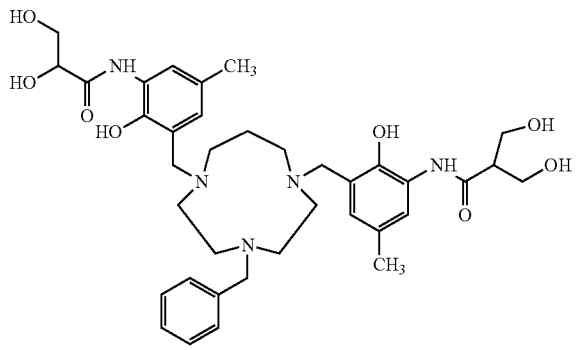 [SMILES: Cc1cc(CN2CCCN(Cc3cc(C)cc(NC(=O)C(CO)CO)c3O)CCN(Cc3ccccc3)CC2)c(O)c(NC(=O)C(O)CO)c1]

Compound 140 (N,N'-{(4-benzyl-1,4,7-triazecane-1,7-diyl)bis[methylene(2-hydroxy-5-methyl-3,1-phenylene)]}bis[3-hydroxy-2-(hydroxymethyl)propanamide])

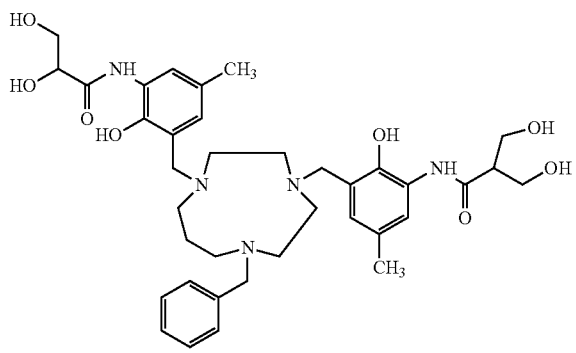

Compound 141 (N,N'-{(7-benzyl-1,4,7-triazecane-1,4-diyl)bis[methylene(2-hydroxy-5-methyl-3,1-phenylene)]}bis[3-hydroxy-2-(hydroxymethyl)propanamide])

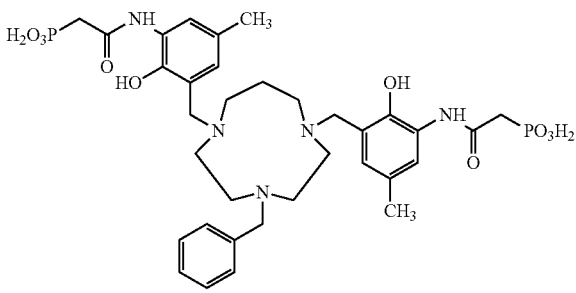

Compound 142 ({(4-benzyl-1,4,7-triazecane-1,7-diyl)bis[methylene(2-hydroxy-5-methyl-3,1-phenylene)azanediyl(2-oxoethane-2,1-diyl)]}bis(phosphonic acid))

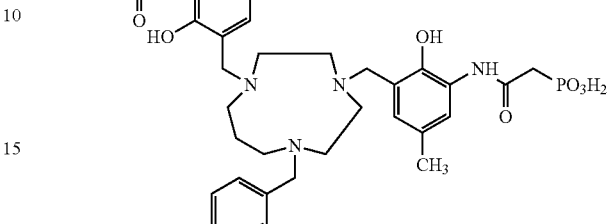

Compound 143 ({(7-benzyl-1,4,7-triazecane-1,4-diyl)bis[methylene(2-hydroxy-5-methyl-3,1-phenylene)azanediyl(2-oxoethane-2,1-diyl)]}bis(phosphonic acid))

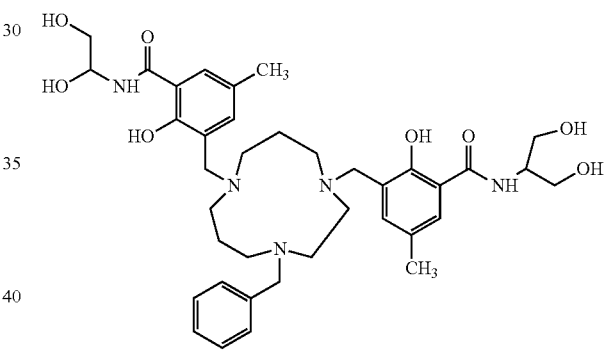

Compound 144 (3,3'-[(4-benzyl-1,4,8-triazacycloundecane-1,8-diyl)bis(methylene)]bis[N-(1,3-dihydroxypropan-2-yl)-2-hydroxy-5-methylbenzamide])

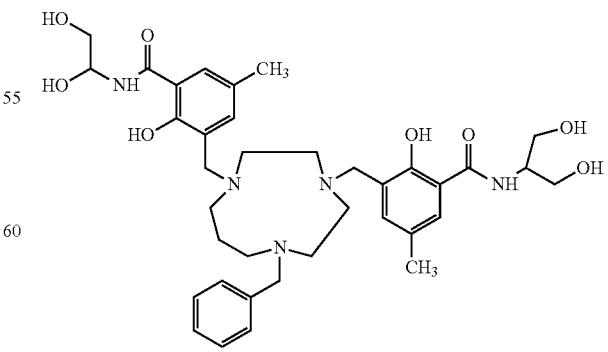

Compound 145 (3,3'-[(8-benzyl-1,4,8-triazacycloun-decane-1,4-diyl)bis(methylene)]bis[N-(1,3-dihy-droxypropan-2-yl)-2-hydroxy-5-methylbenzamide])

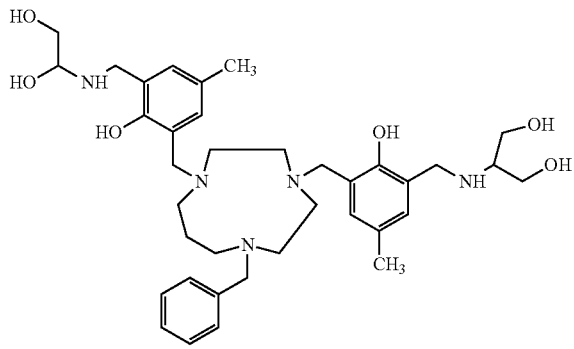

Compound 146 (2,2'-{(4-benzyl-1,4,8-triazacy-cloundecane-1,8-diyl)bis[methylene(2-hydroxy-5-methyl-3,1-phenylene)methyleneazanediyl]}di(pro-pane-1,3-diol))

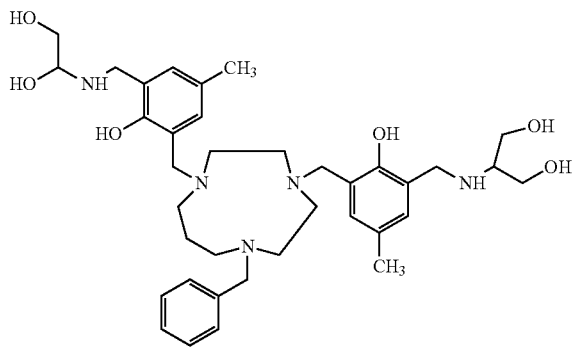

Compound 147 (2,2'-{(8-benzyl-1,4,8-triazacy-cloundecane-1,4-diyl)bis[methylene(2-hydroxy-5-methyl-3,1-phenylene)methyleneazanediyl]}di(pro-pane-1,3-diol))

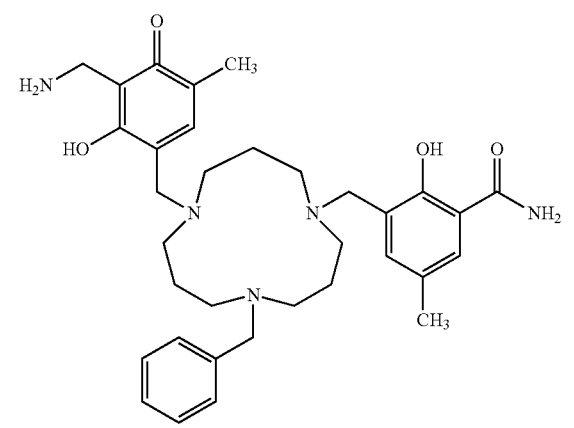

Compound 148 (3,3'-[(4-benzyl-1,4,8-triazacycloun-decane-1,8-diyl)bis(methylene)]bis(2-hydroxy-5-methylbenzamide))

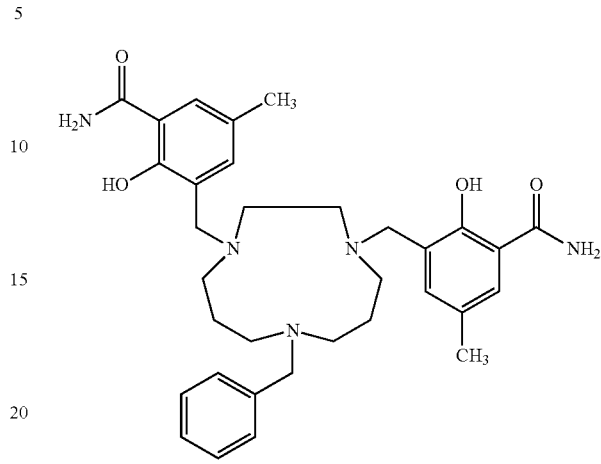

Compound 149 (3,3'-[(8-benzyl-1,4,8-triazacycloun-decane-1,4-diyl)bis(methylene)]bis(2-hydroxy-5-methylbenzamide))

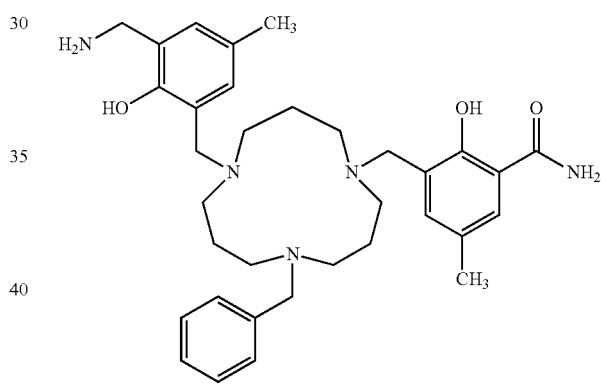

Compound 150 (2,2'-[(4-benzyl-1,4,8-triazacycloun-decane-1,8-diyl)bis(methylene)]bis[6-(aminom-ethyl)-4-methylphenol])

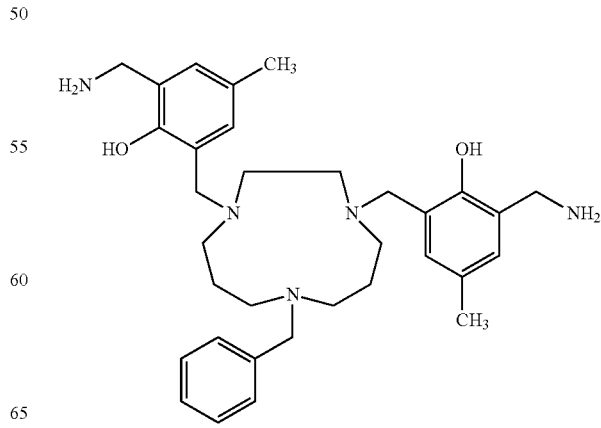

Compound 151 (2,2'-[(8-benzyl-1,4,8-triazacycloun-decane-1,4-diyl)bis(methylene)]bis[6-(aminomethyl)-4-methylphenol])

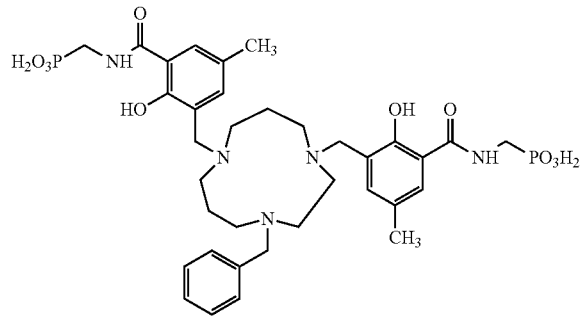

Compound 152 ({(4-benzyl-1,4,8-triazacycloundecane-1,8-diyl)bis[methylene(2-hydroxy-5-methyl-3,1-phenylene)carbonylazanediyimethylene]}bis(phosphonic acid))

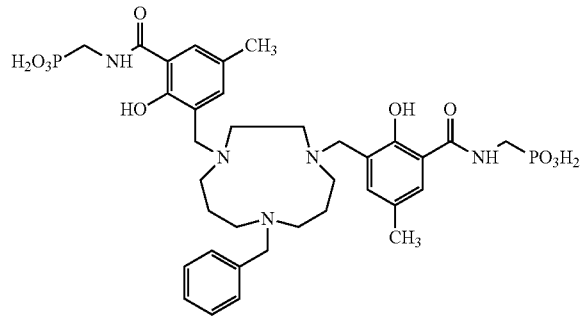

Compound 153 ({(8-benzyl-1,4,8-triazacycloundecane-1,4-diyl)bis[methylene(2-hydroxy-5-methyl-3,1-phenylene)carbonylazanediyimethylene]}bis(phosphonic acid))

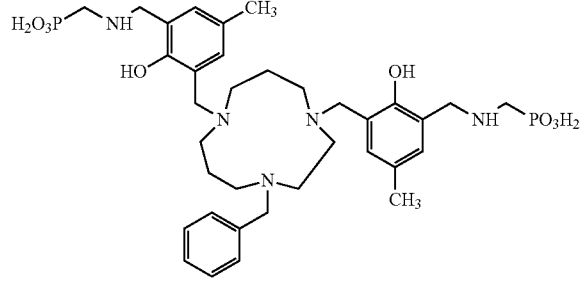

Compound 154 ({(4-benzyl-1,4,8-triazacycloundecane-1,8-diyl)bis[methylene(2-hydroxy-5-methyl-3,1-phenylene)methyleneazanediylmethylene]}bis(phosphonic acid))

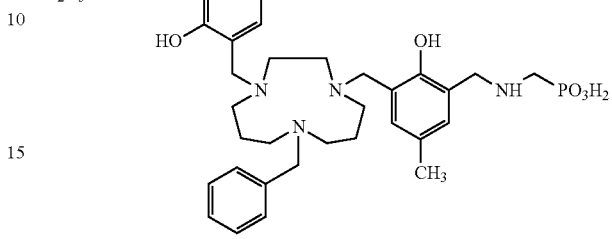

Compound 155 ({(8-benzyl-1,4,8-triazacycloundecane-1,4-diyl)bis[methylene(2-hydroxy-5-methyl-3,1-phenylene)methyleneazanediylmethylene]}bis(phosphonic acid))

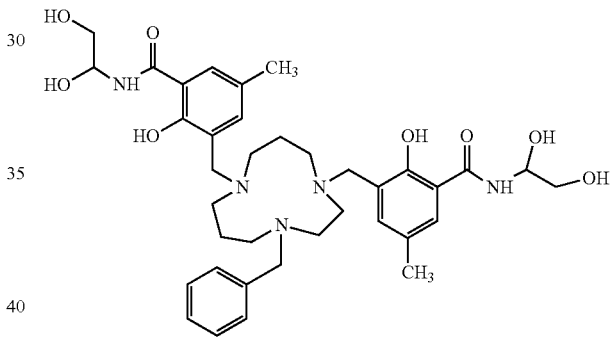

Compound 156 (3,3'-[(4-benzyl-1,4,8-triazacycloundecane-1,8-diyl)bis(methylene)]bis[N-(1,2-dihydroxyethyl)-2-hydroxy-5-methylbenzamide])

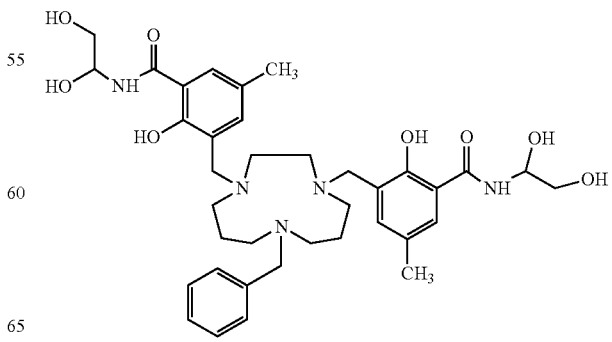

Compound 157 (3,3'-[(8-benzyl-1,4,8-triazacycloundecane-1,4-diyl)bis(methylene)]bis[N-(1,2-dihydroxyethyl)-2-hydroxy-5-methylbenzamide])

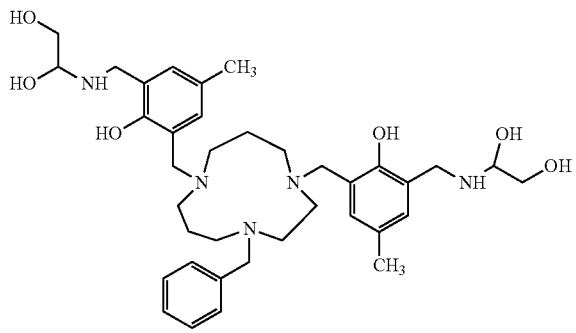 [SMILES: Cc1cc(CNC(O)CO)c(O)c(CN2CCCN(Cc3ccccc3)CCN(Cc3cc(C)cc(CNC(O)CO)c3O)CCC2)c1]

Compound 158 (1,1'-{(4-benzyl-1,4,8-triazacycloundecane-1,8-diyl)bis[methylene(2-hydroxy-5-methyl-3,1-phenylene)methyleneazanediyl]}di(ethane-1,2-diol))

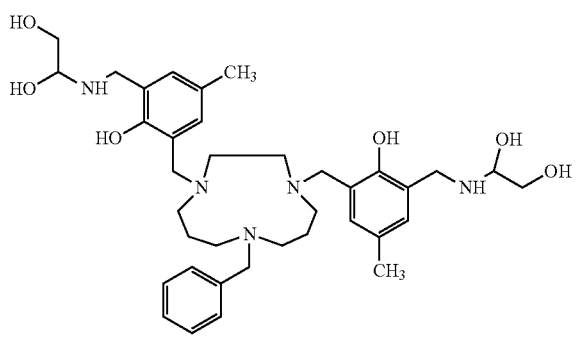 [SMILES: Cc1cc(CNC(O)CO)c(O)c(CN2CCCN(Cc3ccccc3)CCCN(Cc3cc(C)cc(CNC(O)CO)c3O)CC2)c1]

Compound 159 (1,1'-{(8-benzyl-1,4,8-triazacycloundecane-1,4-diyl)bis[methylene(2-hydroxy-5-methyl-3,1-phenylene)methyleneazanediyl]}di(ethane-1,2-diol))

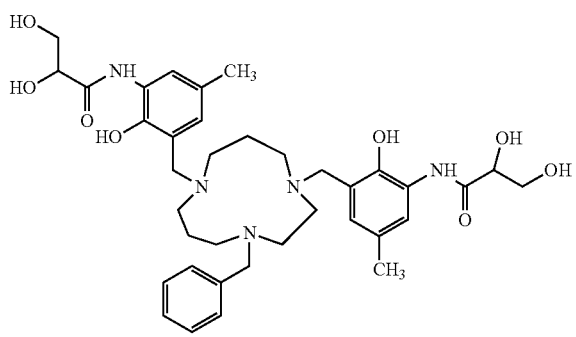 [SMILES: Cc1cc(CN2CCCN(Cc3ccccc3)CCN(Cc3cc(C)cc(NC(=O)C(O)CO)c3O)CCC2)c(O)c(NC(=O)C(O)CO)c1]

Compound 160 (N,N'-{(4-benzyl-1,4,8-triazacycloundecane-1,8-diyl)bis[methylene(2-hydroxy-5-methyl-3,1-phenylene)]}bis(2,3-dihydroxypropanamide))

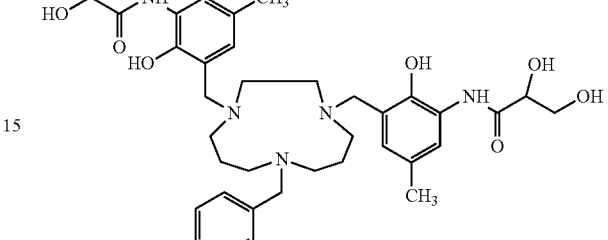

Compound 161 (N,N-{(8-benzyl-1,4,8-triazacycloundecane-1,4-diyl)bis[methylene(2-hydroxy-5-methyl-3,1-phenylene)]}bis(2,3-dihydroxypropanamide))

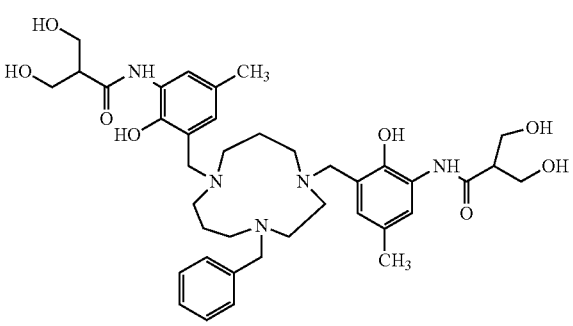 [SMILES: Cc1cc(CN2CCCN(Cc3ccccc3)CCN(Cc3cc(C)cc(NC(=O)C(CO)CO)c3O)CCC2)c(O)c(NC(=O)C(CO)CO)c1]

Compound 162 (N,N'-{(4-benzyl-1,4,8-triazacycloundecane-1,8-diyl)bis[methylene(2-hydroxy-5-methyl-3,1-phenylene)]}bis[3-hydroxy-2-(hydroxymethyl)propanamide])

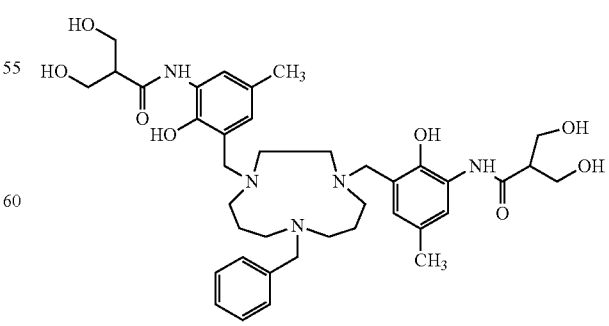

Compound 163 (N,N-{(8-benzyl-1,4,8-triazacycloundecane-1,4-diyl)bis[methylene(2-hydroxy-5-methyl-3,1-phenylene)]}bis[3-hydroxy-2-(hydroxymethyl)propanamide])

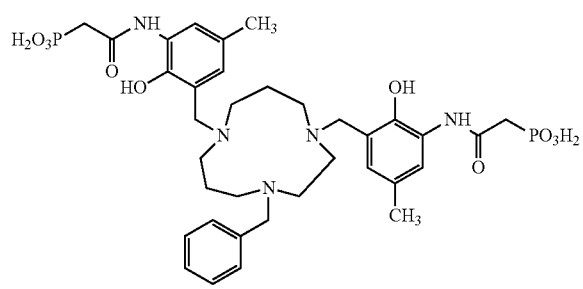

Compound 164 ({(4-benzyl-1,4,8-triazacycloundecane-1,8-diyl)bis[methylene(2-hydroxy-5-methyl-3,1-phenylene)azanediyl(2-oxoethane-2,1-diyl)]}bis(phosphonic acid))

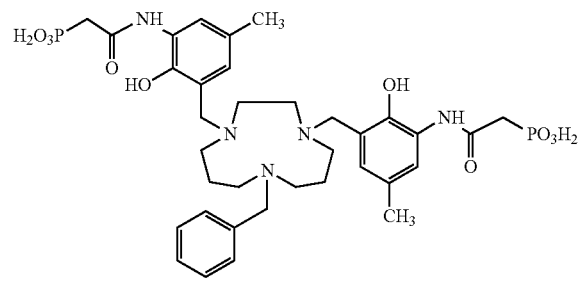

Compound 165 ({(8-benzyl-1,4,8-triazacycloundecane-1,4-diyl)bis[methylene(2-hydroxy-5-methyl-3,1-phenylene)azanediyl(2-oxoethane-2,1-diyl)]}bis(phosphonic acid))

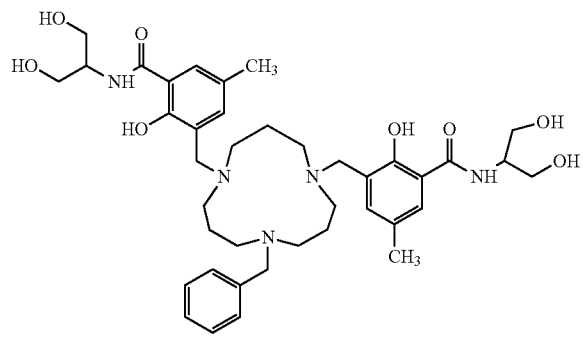

Compound 166 (3,3'-[(9-benzyl-1,5,9-triazacyclododecane-1,5-diyl)bis(methylene)]bis[N-(1,3-dihydroxypropan-2-yl)-2-hydroxy-5-methylbenzamide])

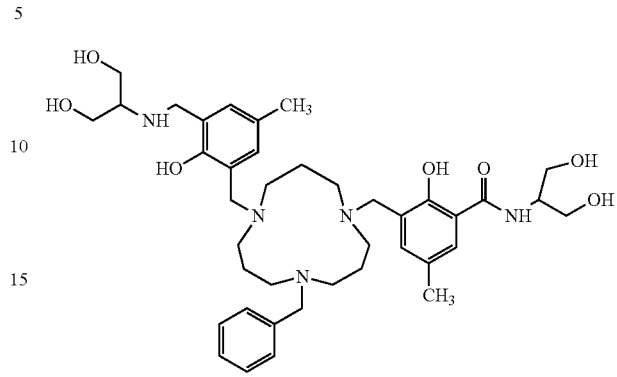

Compound 167 (2,2'-{(9-benzyl-1,5,9-triazacyclododecane-1,5-diyl)bis[methylene(2-hydroxy-5-methyl-3,1-phenylene)methyleneazanediyl]}di(propane-1,3-diol))

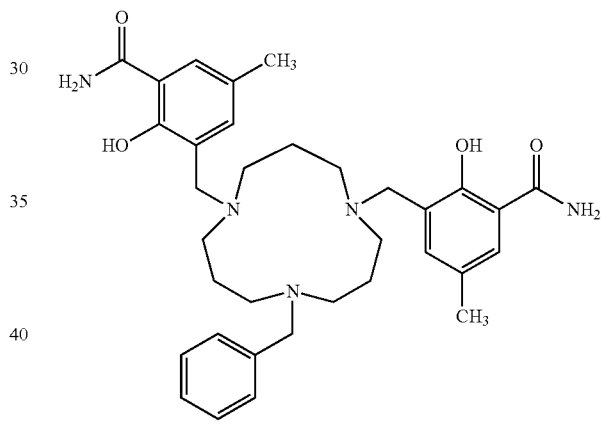

Compound 168 (3,3'-[(9-benzyl-1,5,9-triazacyclododecane-1,5-diyl)bis(methylene)]bis(2-hydroxy-5-methylbenzamide))

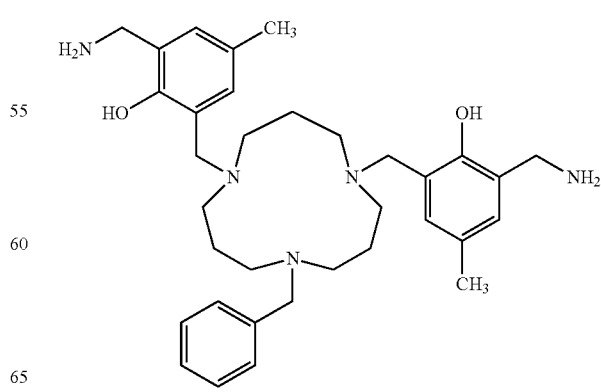

Compound 169 (2,2'-[(9-benzyl-1,5,9-triazacyclodo-decane-1,5-diyl)bis(methylene)]bis[6-(aminomethyl)-4-methylphenol])

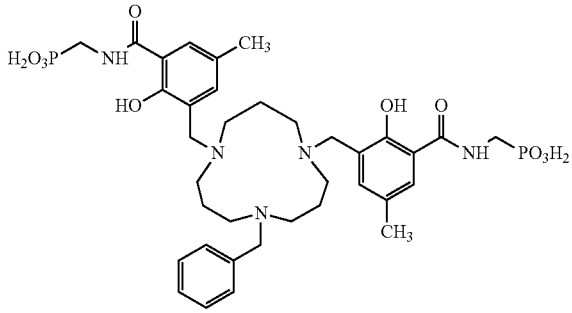

Compound 170 ({(9-benzyl-1,5,9-triazacyclododecane-1,5-diyl)bis[methylene(2-hydroxy-5-methyl-3,1-phenylene)carbonylazanediyimethylene]}bis(phosphonic acid))

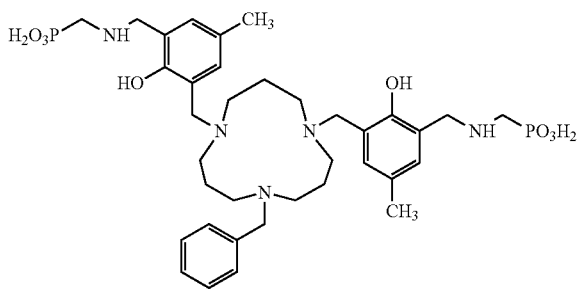

Compound 171 ({(9-benzyl-1,5,9-triazacyclododecane-1,5-diyl)bis[methylene(2-hydroxy-5-methyl-3,1-phenylene)methyleneazanediylmethylene]}bis(phosphonic acid))

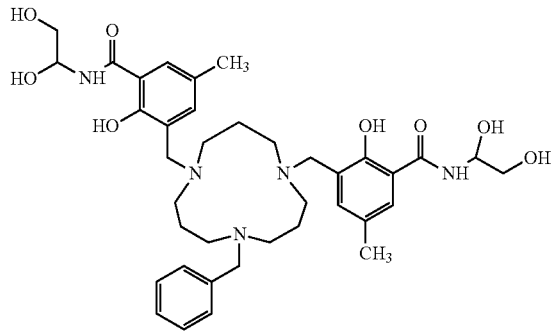

Compound 172 (3,3'-[(9-benzyl-1,5,9-triazacyclodo-decane-1,5-diyl)bis(methylene)]bis[N-(1,2-dihydroxyethyl)-2-hydroxy-5-methylbenzamide])

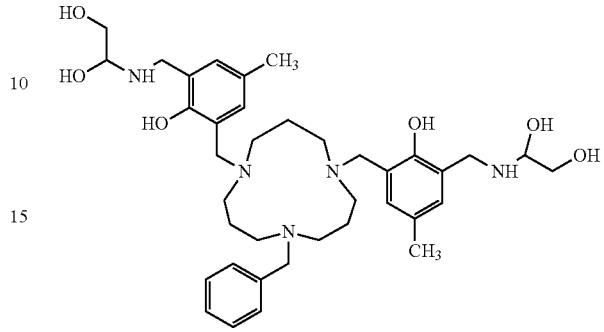

Compound 173 (1,1'-{(9-benzyl-1,5,9-triazacyclododecane-1,5-diyl)bis[methylene(2-hydroxy-5-methyl-3,1-phenylene)methyleneazanediyl]}di(ethane-1,2-diol))

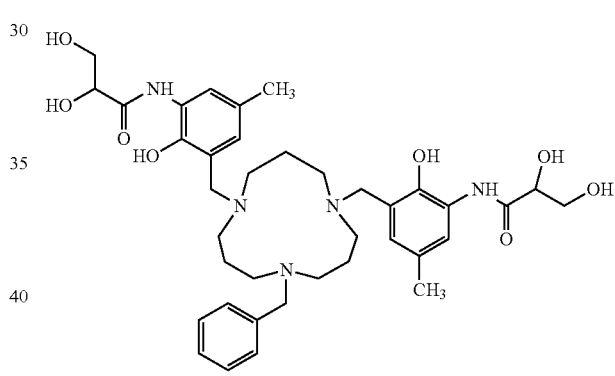

Compound 174 (N,N'-{(9-benzyl-1,5,9-triazacyclododecane-1,5-diyl)bis[methylene(2-hydroxy-5-methyl-3,1-phenylene)]}bis(2,3-dihydroxypropanamide))

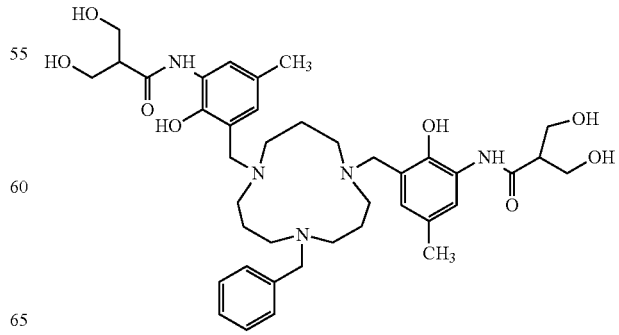

67
Compound 175 (N,N'-{(9-benzyl-1,5,9-triazacyclododecane-1,5-diyl)bis[methylene(2-hydroxy-5-methyl-3,1-phenylene)]}bis[3-hydroxy-2-(hydroxymethyl)propanamide])
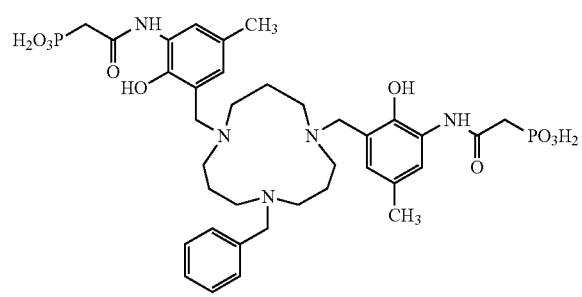
68
Compound 176 ({(9-benzyl-1,5,9-triazacyclododecane-1,5-diyl)bis[methylene(2-hydroxy-5-methyl-3,1-phenylene)azanediyl(2-oxoethane-2,1-diyl)]}bis(phosphonic acid)), and
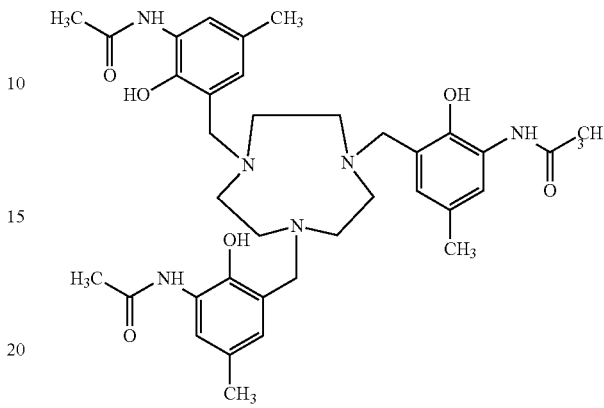
Compound 177 (N,N',N''-{1,4,7-triazonane-1,4,7-triyltris[methylene(2-hydroxy-5-methyl-3,1-phenylene)]}triacetamide)
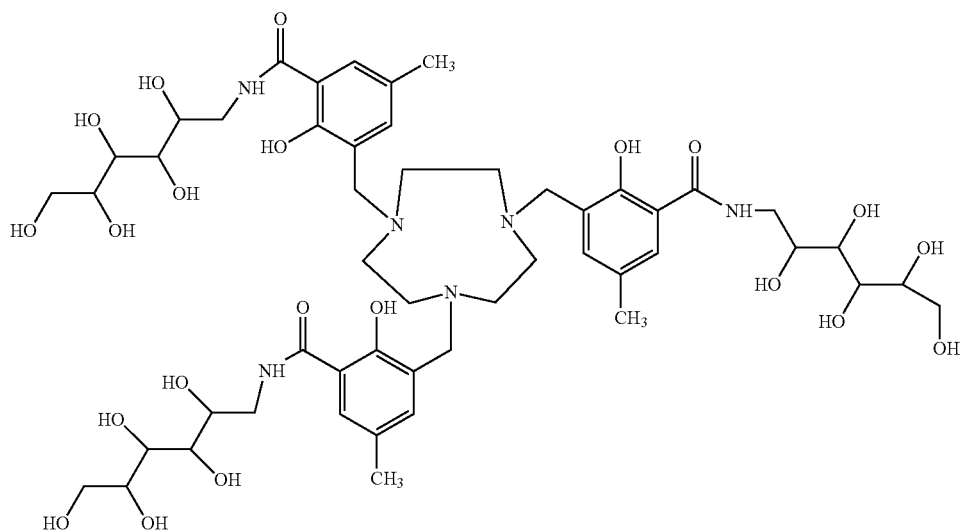 [SMILES: Cc1cc(CN2CCN(Cc3cc(C)cc(C(=O)NCC(O)C(O)C(O)C(O)CO)c3O)CCN(Cc3cc(C)cc(C(=O)NCC(O)C(O)C(O)C(O)CO)c3O)CC2)c(O)c(C(=O)NCC(O)C(O)C(O)C(O)CO)c1]

Compound 178 (3-{[4,7-bis({2-hydroxy-5-methyl-3-[(2,3,4,5,6-pentahydroxyhexyl)carbamoyl]phenyl}methyl)-1,4,7-triazonan-1-yl]methyl}-2-hydroxy-5-methyl-N-(2,3,4,5,6-pentahydroxyhexyl)benzamide)

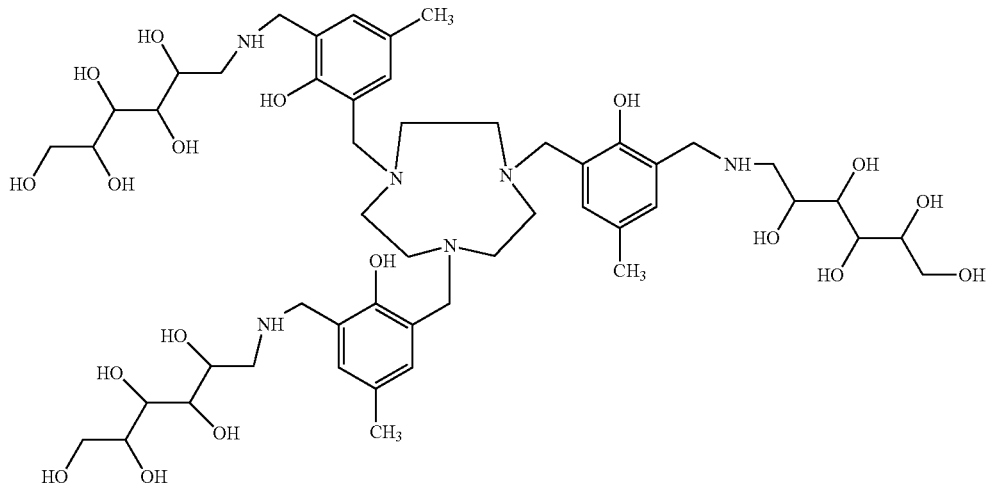 [SMILES: Cc1cc(CNCC(O)C(O)C(O)C(O)CO)c(O)c(CN2CCN(Cc3cc(C)cc(CNCC(O)C(O)C(O)C(O)CO)c3O)CCN(Cc3cc(C)cc(CNCC(O)C(O)C(O)C(O)CO)c3O)CC2)c1]

Compound 179 (6,6',6''-{1,4,7-triazonane-1,4,7-triyltris[methylene(2-hydroxy-5-methyl-3,1-phenylene)methyleneazanediyl]}tri(hexane-1,2,3,4,5-pentol))

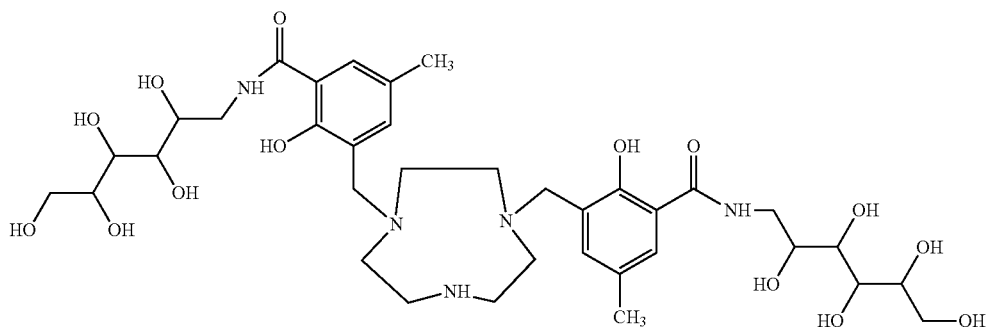 [SMILES: Cc1cc(CN2CCNCCN(Cc3cc(C)cc(C(=O)NCC(O)C(O)C(O)C(O)CO)c3O)CC2)c(O)c(C(=O)NCC(O)C(O)C(O)C(O)CO)c1]

Compound 180 (2-hydroxy-3-{[4-({2-hydroxy-5-methyl-3-[(2,3,4,5,6-pentahydroxyhexyl)carbamoyl]phenyl}methyl)-1,4,7-triazonan-1-yl]methyl}-5-methyl-N-(2,3,4,5,6-pentahydroxyhexyl)benzamide)

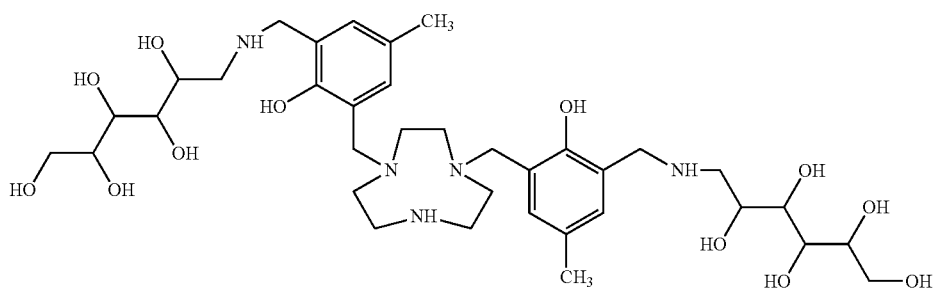 [SMILES: Cc1cc(CNCC(O)C(O)C(O)C(O)CO)c(O)c(CN2CCNCCN(Cc3cc(C)cc(CNCC(O)C(O)C(O)C(O)CO)c3O)CC2)c1]

Compound 181 (6,6'-{1,4,7-triazonane-1,4-diylbis
[methylene(2-hydroxy-5-methyl-3,1-phenylene)
methyleneazanediyl]}di(hexane-1,2,3,4,5-pentol))
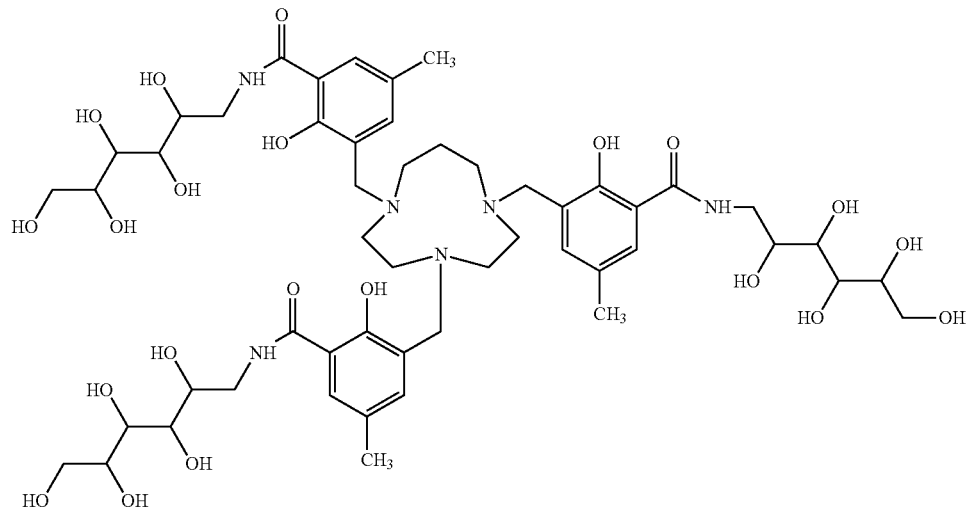 [SMILES: Cc1cc(CN2CCCN(Cc3cc(C)cc(C(=O)NCC(O)C(O)C(O)C(O)CO)c3O)CCN(Cc3cc(C)cc(C(=O)NCC(O)C(O)C(O)C(O)CO)c3O)CC2)c(O)c(C(=O)NCC(O)C(O)C(O)C(O)CO)c1]
Compound 182 (3-{[4,7-bis({2-hydroxy-5-methyl-
3-[(2,3,4,5,6-pentahydroxyhexyl)carbamoyl]
phenyl}methyl)-1,4,7-triazecan-1-yl]methyl}-2-hy-
droxy-5-methyl-N-(2,3,4,5,6-pentahydroxyhexyl)
benzamide)
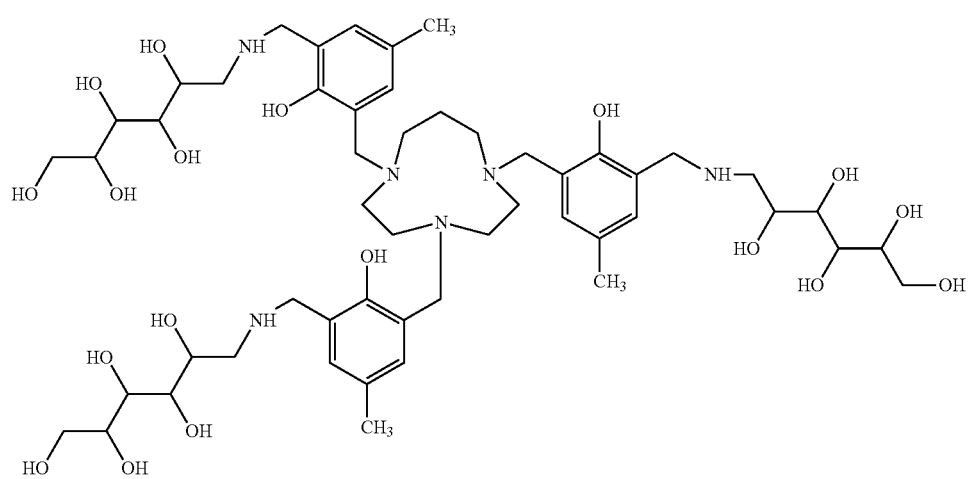 [SMILES: Cc1cc(CNCC(O)C(O)C(O)C(O)CO)c(O)c(CN2CCCN(Cc3cc(C)cc(CNCC(O)C(O)C(O)C(O)CO)c3O)CCN(Cc3cc(C)cc(CNCC(O)C(O)C(O)C(O)CO)c3O)CC2)c1]

Compound 183 (6,6',6''-{1,4,7-triazecane-1,4,7-triyltris[methylene(2-hydroxy-5-methyl-3,1-phenylene)methyleneazanediyl]}tri(hexane-1,2,3,4,5-pentol))

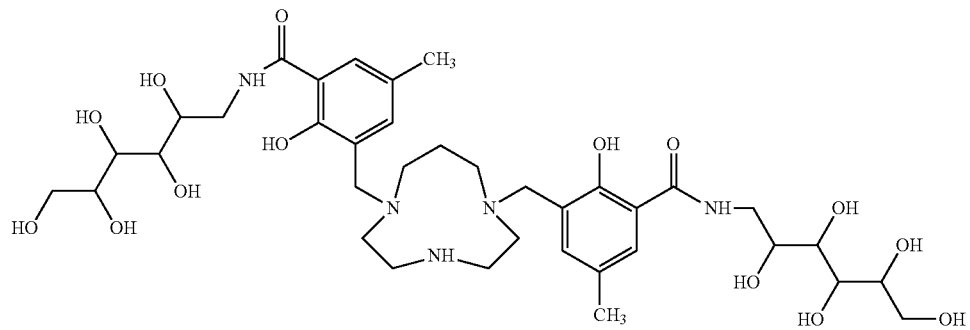 [SMILES: Cc1cc(CN2CCCN(Cc3cc(C)cc(C(=O)NCC(O)C(O)C(O)C(O)CO)c3O)CCNCC2)c(O)c(C(=O)NCC(O)C(O)C(O)C(O)CO)c1]

Compound 184 (2-hydroxy-3-{[7-({2-hydroxy-5-methyl-3-[(2,3,4,5,6-pentahydroxyhexyl)carbamoyl]phenyl}methyl)-1,4,7-triazecan-1-yl]methyl}-5-methyl-N-(2,3,4,5,6-pentahydroxyhexyl)benzamide)

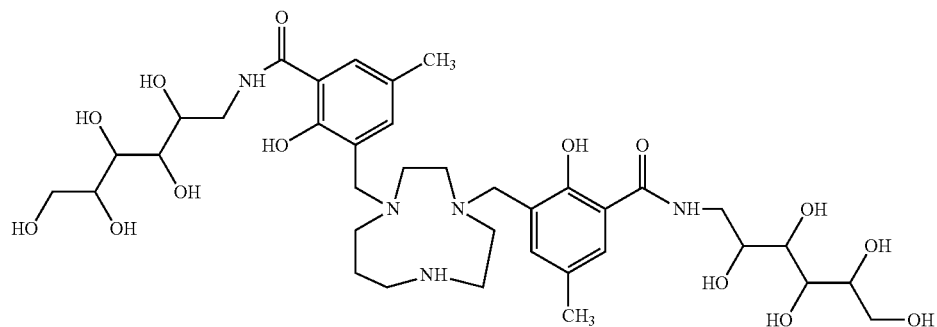 [SMILES: Cc1cc(CN2CCCNCCN(Cc3cc(C)cc(C(=O)NCC(O)C(O)C(O)C(O)CO)c3O)CC2)c(O)c(C(=O)NCC(O)C(O)C(O)C(O)CO)c1]

Compound 185 (2-hydroxy-3-{[4-({2-hydroxy-5-methyl-3-[(2,3,4,5,6-pentahydroxyhexyl)carbamoyl]phenyl}methyl)-1,4,7-triazecan-1-yl]methyl}-5-methyl-N-(2,3,4,5,6-pentahydroxyhexyl)benzamide)

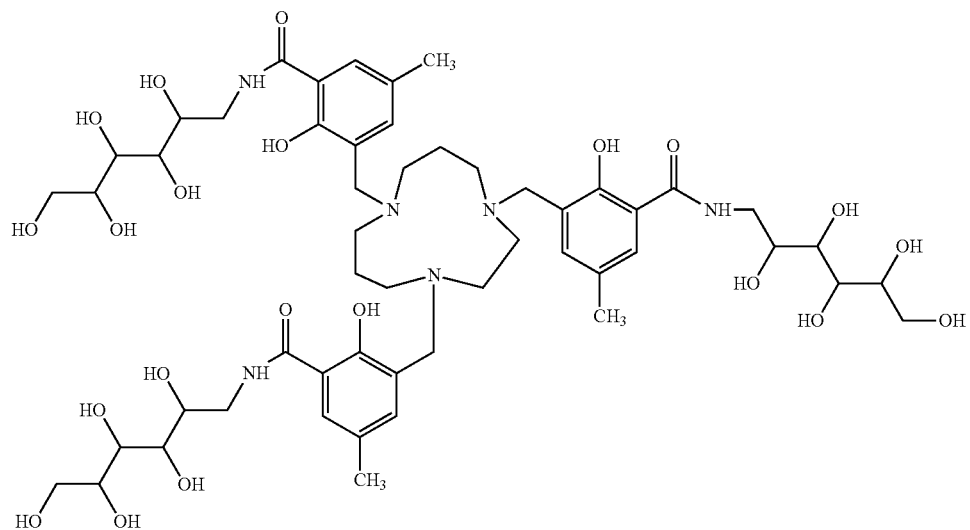 [SMILES: Cc1cc(CN2CCCN(Cc3cc(C)cc(C(=O)NCC(O)C(O)C(O)C(O)CO)c3O)CCN(Cc3cc(C)cc(C(=O)NCC(O)C(O)C(O)C(O)CO)c3O)CCC2)c(O)c(C(=O)NCC(O)C(O)C(O)C(O)CO)c1]

Compound 186 (3-{[1,4-bis({2-hydroxy-5-methyl-3-[(2,3,4,5,6-pentahydroxyhexyl)carbamoyl]phenyl}methyl)-1,4,8-triazacycloundecan-8-yl]methyl}-2-hydroxy-5-methyl-N-(2,3,4,5,6-pentahydroxyhexyl)benzamide)
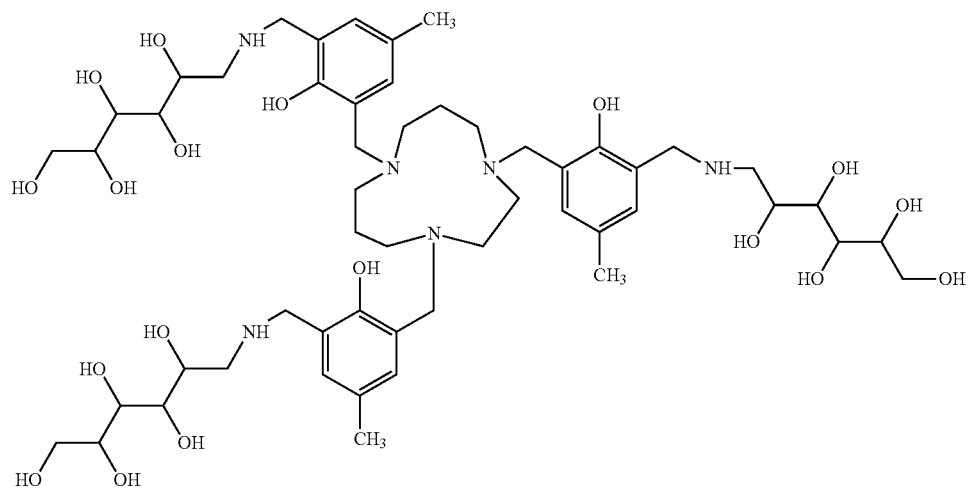 [SMILES: Cc1cc(CNCC(O)C(O)C(O)C(O)CO)c(O)c(CN2CCCN(Cc3cc(C)cc(CNCC(O)C(O)C(O)C(O)CO)c3O)CCN(Cc3cc(C)cc(CNCC(O)C(O)C(O)C(O)CO)c3O)CCC2)c1]
Compound 187 (6,6',6''-{1,4,8-triazacycloundecane-1,4,8-triyltris[methylene(2-hydroxy-5-methyl-3,1-phenylene)methyleneazanediyl]}tri(hexane-1,2,3,4,5-pentol))
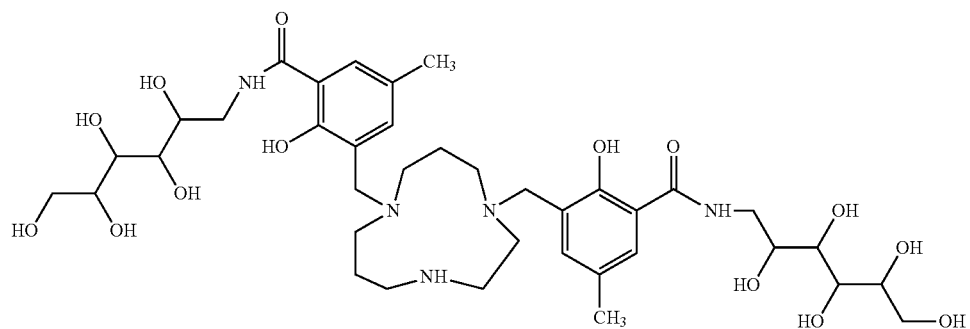 [SMILES: Cc1cc(CN2CCCNCCN(Cc3cc(C)cc(C(=O)NCC(O)C(O)C(O)C(O)CO)c3O)CCC2)c(O)c(C(=O)NCC(O)C(O)C(O)C(O)CO)c1]

Compound 188 (2-hydroxy-3-{[1-({2-hydroxy-5-methyl-3-[(2,3,4,5,6-pentahydroxyhexyl)carbamoyl]phenyl}methyl)-1,4,8-triazacycloundecan-8-yl]methyl}-5-methyl-N-(2,3,4,5,6-pentahydroxyhexyl)benzamide)

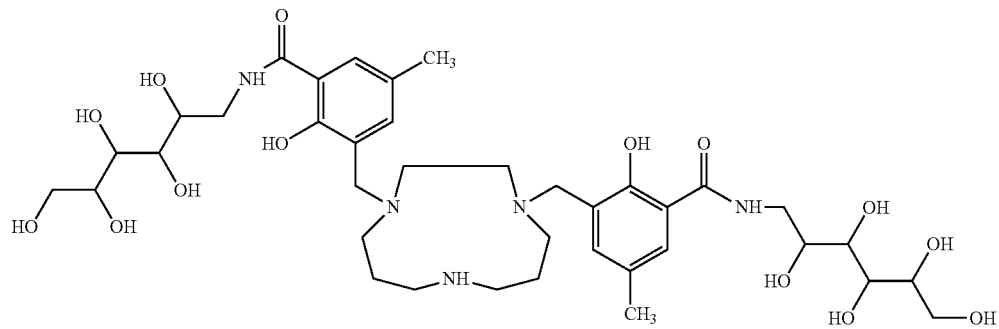 [SMILES: Cc1cc(CN2CCCNCCCN(Cc3cc(C)cc(C(=O)NCC(O)C(O)C(O)C(O)CO)c3O)CC2)c(O)c(C(=O)NCC(O)C(O)C(O)C(O)CO)c1]

Compound 189 (2-hydroxy-3-{[4-({2-hydroxy-5-methyl-3-[(2,3,4,5,6-pentahydroxyhexyl)carbamoyl]phenyl}methyl)-1,4,8-triazacycloundecan-1-yl]methyl}-5-methyl-N-(2,3,4,5,6-pentahydroxyhexyl)benzamide)

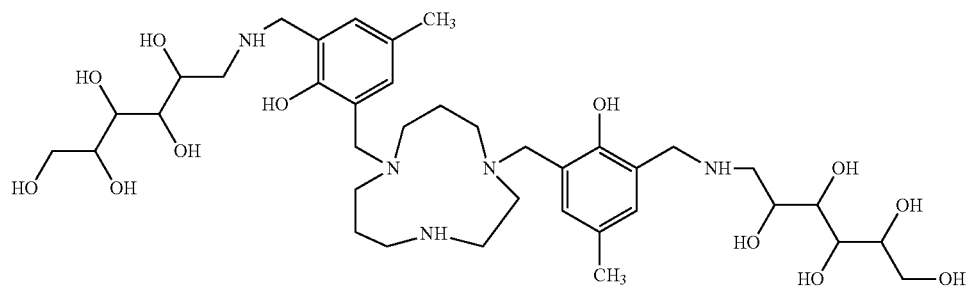 [SMILES: Cc1cc(CNCC(O)C(O)C(O)C(O)CO)c(O)c(CN2CCCNCCN(Cc3cc(C)cc(CNCC(O)C(O)C(O)C(O)CO)c3O)CCC2)c1]

Compound 190 (6,6'-{1,4,8-triazacycloundecane-1,8-diylbis[methylene(2-hydroxy-5-methyl-3,1-phenylene)methyleneazanediyl]}di(hexane-1,2,3,4,5-pentol))

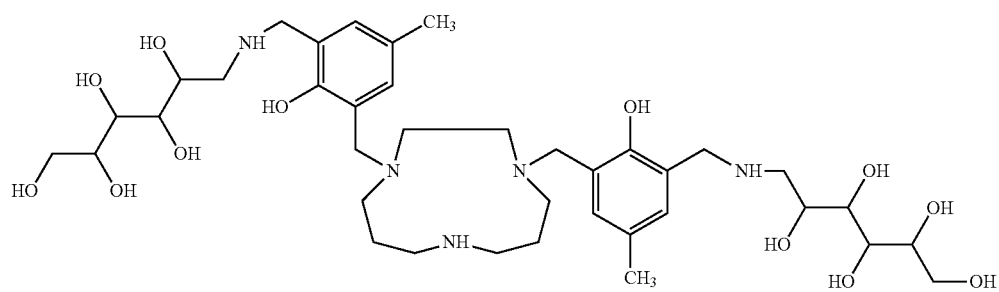 [SMILES: Cc1cc(CNCC(O)C(O)C(O)C(O)CO)c(O)c(CN2CCCNCCCN(Cc3cc(C)cc(CNCC(O)C(O)C(O)C(O)CO)c3O)CC2)c1]

Compound 191 (6,6'-{1,4,8-triazacycloundecane-1,
4-diylbis[methylene(2-hydroxy-5-methyl-3,1-phe-
nylene)methyleneazanediyl]}di(hexane-1,2,3,4,5-
pentol))
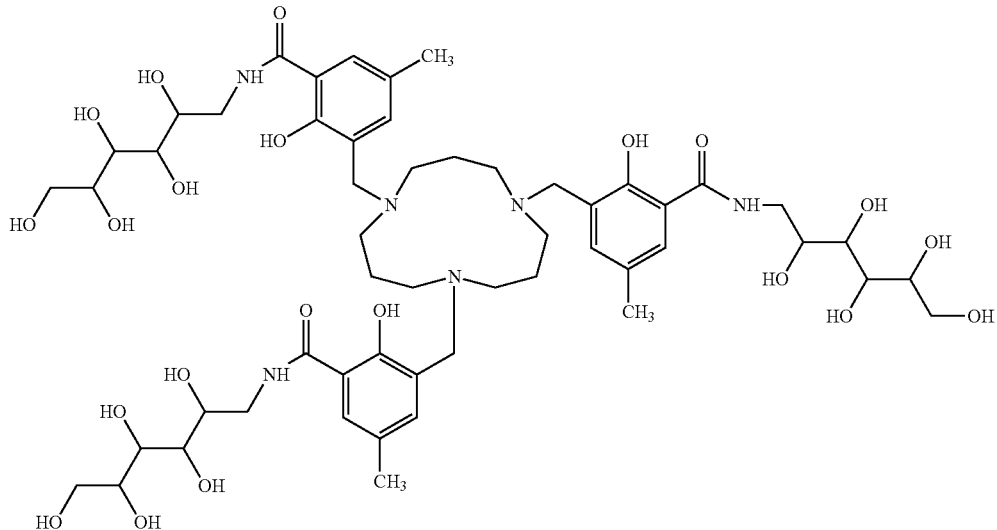 [SMILES: Cc1cc(CN2CCCN(Cc3cc(C)cc(C(=O)NCC(O)C(O)C(O)C(O)CO)c3O)CCCN(Cc3cc(C)cc(C(=O)NCC(O)C(O)C(O)C(O)CO)c3O)CCC2)c(O)c(C(=O)NCC(O)C(O)C(O)C(O)CO)c1]
Compound 192 (3-{[5,9-bis({2-hydroxy-5-methyl-
3-[(2,3,4,5,6-pentahydroxyhexyl)carbamoyl]
phenyl}methyl)-1,5,9-triazacyclododecan-1-yl]
methyl}-2-hydroxy-5-methyl-N-(2,3,4,5,6-
pentahydroxyhexyl)benzamide)
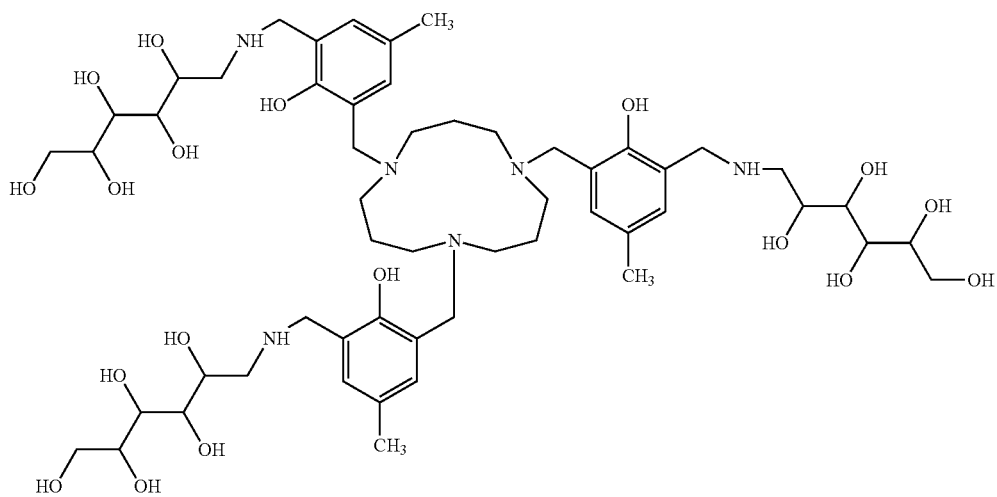 [SMILES: Cc1cc(CNCC(O)C(O)C(O)C(O)CO)c(O)c(CN2CCCN(Cc3cc(C)cc(CNCC(O)C(O)C(O)C(O)CO)c3O)CCCN(Cc3cc(C)cc(CNCC(O)C(O)C(O)C(O)CO)c3O)CCC2)c1]

Compound 193 (6,6',6''-{1,5,9-triazacyclododecane-1,5,9-triyltris[methylene(2-hydroxy-5-methyl-3,1-phenylene)methyleneazanediyl]}tri(hexane-1,2,3,4,5-pentol))

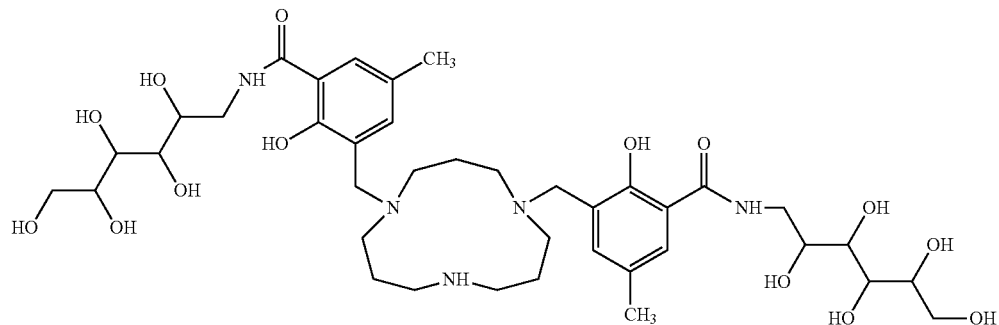 [SMILES: Cc1cc(CN2CCCNCCCN(Cc3cc(C)cc(C(=O)NCC(O)C(O)C(O)C(O)CO)c3O)CCC2)c(O)c(C(=O)NCC(O)C(O)C(O)C(O)CO)c1]

Compound 194 (2-hydroxy-3-{[5-({2-hydroxy-5-methyl-3-[(2,3,4,5,6-pentahydroxyhexyl)carbamoyl]phenyl}methyl)-1,5,9-triazacyclododecan-1-yl]methyl}-5-methyl-N-(2,3,4,5,6-pentahydroxyhexyl)benzamide)

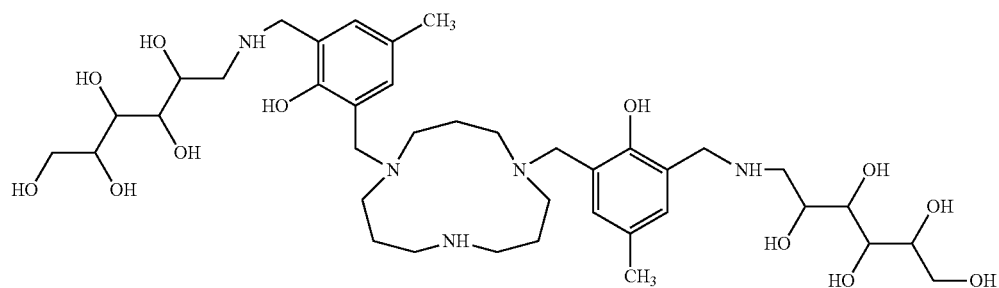 [SMILES: Cc1cc(CNCC(O)C(O)C(O)C(O)CO)c(O)c(CN2CCCNCCCN(Cc3cc(C)cc(CNCC(O)C(O)C(O)C(O)CO)c3O)CCC2)c1]

Compound 195 (6,6'-{1,5,9-triazacyclododecane-1,5-diylbis[methylene(2-hydroxy-5-methyl-3,1-phenylene)methyleneazanediyl]}di(hexane-1,2,3,4,5-pentol))

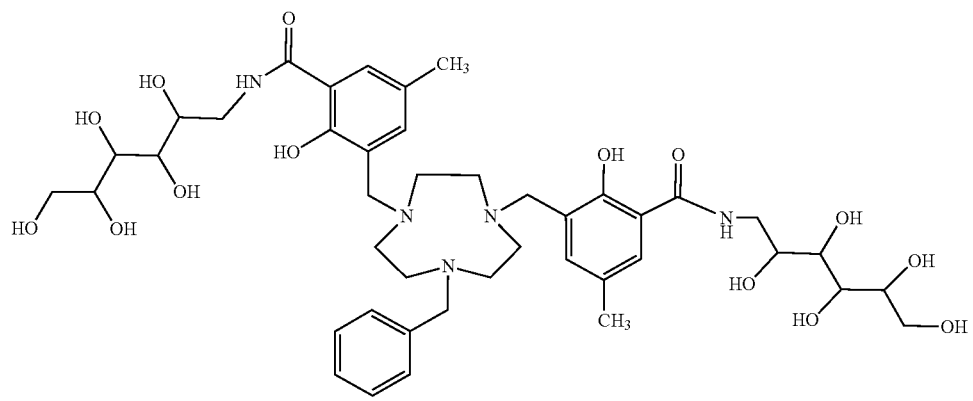 [SMILES: Cc1cc(CN2CCN(Cc3ccccc3)CCN(Cc3cc(C)cc(C(=O)NCC(O)C(O)C(O)C(O)CO)c3O)CC2)c(O)c(C(=O)NCC(O)C(O)C(O)C(O)CO)c1]

Compound 196 (3-{[4-benzyl-7-({2-hydroxy-5-methyl-3-[(2,3,4,5,6-pentahydroxyhexyl)carbamoyl]phenyl}methyl)-1,4,7-triazonan-1-yl]methyl}-2-hydroxy-5-methyl-N-(2,3,4,5,6-pentahydroxyhexyl)benzamide)
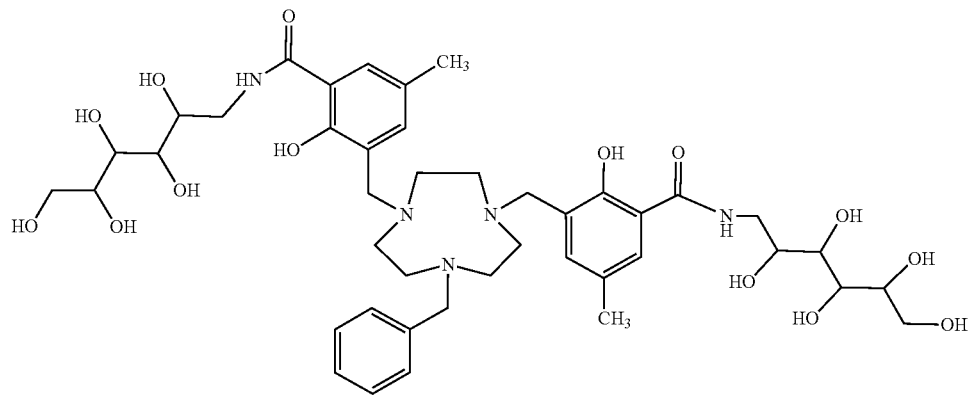 [SMILES: Cc1cc(CN2CCN(Cc3ccccc3)CCN(Cc3cc(C)cc(C(=O)NCC(O)C(O)C(O)C(O)CO)c3O)CC2)c(O)c(C(=O)NCC(O)C(O)C(O)C(O)CO)c1]
Compound 197 (6,6'-{(7-benzyl-1,4,7-triazonane-1,4-diyl)bis[methylene(2-hydroxy-5-methyl-3,1-phenylene)methyleneazanediyl]}di(hexane-1,2,3,4,5-pentol))
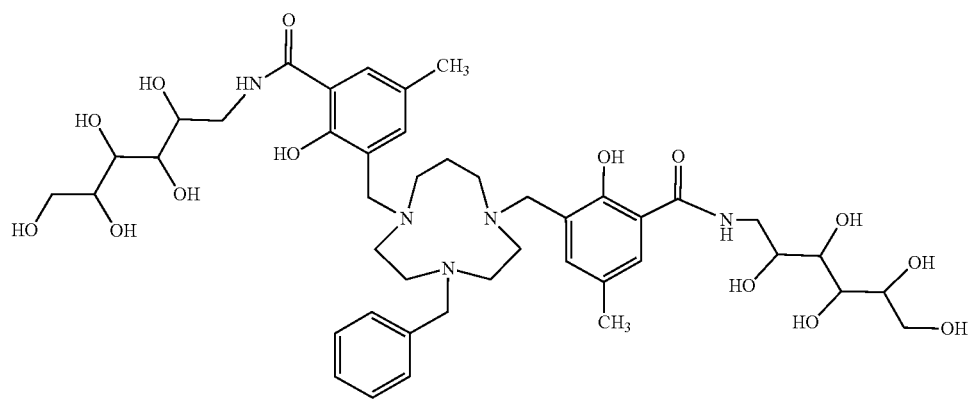 [SMILES: Cc1cc(CN2CCCN(Cc3cc(C)cc(C(=O)NCC(O)C(O)C(O)C(O)CO)c3O)CCN(Cc3ccccc3)CC2)c(O)c(C(=O)NCC(O)C(O)C(O)C(O)CO)c1]

Compound 198 (3-{[4-benzyl-7-({2-hydroxy-5-methyl-3-[(2,3,4,5,6-pentahydroxyhexyl)carbamoyl]phenyl}methyl)-1,4,7-triazecan-1-yl]methyl}-2-hydroxy-5-methyl-N-(2,3,4,5,6-pentahydroxyhexyl)benzamide)
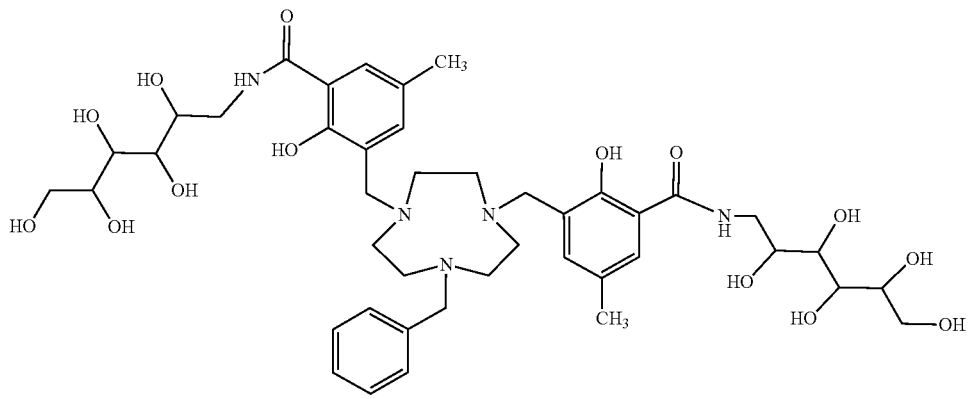 [SMILES: Cc1cc(CN2CCN(Cc3ccccc3)CCN(Cc3cc(C)cc(C(=O)NCC(O)C(O)C(O)C(O)CO)c3O)CC2)c(O)c(C(=O)NCC(O)C(O)C(O)C(O)CO)c1]
Compound 199 (3-{[7-benzyl-4-({2-hydroxy-5-methyl-3-[(2,3,4,5,6-pentahydroxyhexyl)carbamoyl]phenyl}methyl)-1,4,7-triazecan-1-yl]methyl}-2-hydroxy-5-methyl-N-(2,3,4,5,6-pentahydroxyhexyl)benzamide)
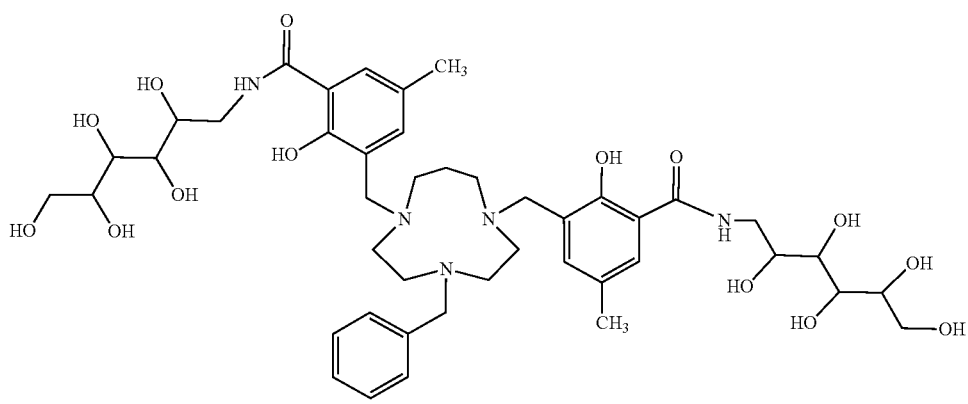 [SMILES: Cc1cc(CN2CCCN(Cc3cc(C)cc(C(=O)NCC(O)C(O)C(O)C(O)CO)c3O)CCN(Cc3ccccc3)CC2)c(O)c(C(=O)NCC(O)C(O)C(O)C(O)CO)c1]

Compound 200 (6,6'-{(4-benzyl-1,4,7-triazecane-1,7-diyl)bis[methylene(2-hydroxy-5-methyl-3,1-phenylene)methyleneazanediyl]}di(hexane-1,2,3,4,5-pentol))
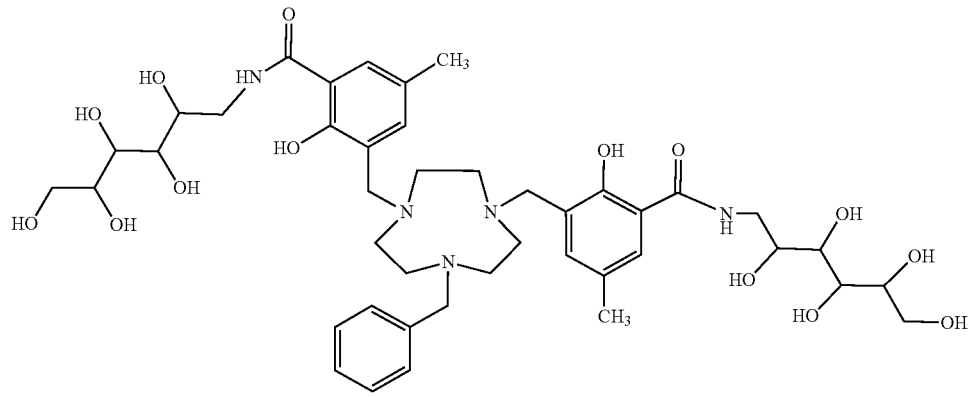 [SMILES: Cc1cc(CN2CCN(Cc3ccccc3)CCN(Cc3cc(C)cc(C(=O)NCC(O)C(O)C(O)C(O)CO)c3O)CC2)c(O)c(C(=O)NCC(O)C(O)C(O)C(O)CO)c1]
Compound 201 (6,6'-{(7-benzyl-1,4,7-triazecane-1,4-diyl)bis[methylene(2-hydroxy-5-methyl-3,1-phenylene)methyleneazanediyl]}di(hexane-1,2,3,4,5-pentol))
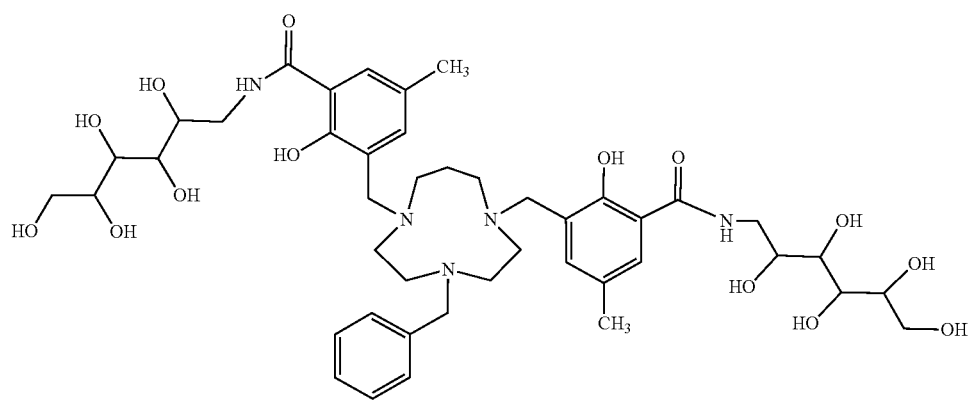 [SMILES: Cc1cc(CN2CCCN(Cc3cc(C)cc(C(=O)NCC(O)C(O)C(O)C(O)CO)c3O)CCN(Cc3ccccc3)CC2)c(O)c(C(=O)NCC(O)C(O)C(O)C(O)CO)c1]

Compound 202 (3-{[1-benzyl-4-({2-hydroxy-5-methyl-3-[(2,3,4,5,6-pentahydroxyhexyl)carbamoyl]phenyl}methyl)-1,4,8-triazacycloundecan-8-yl]methyl}-2-hydroxy-5-methyl-N-(2,3,4,5,6-pentahydroxyhexyl)benzamide)
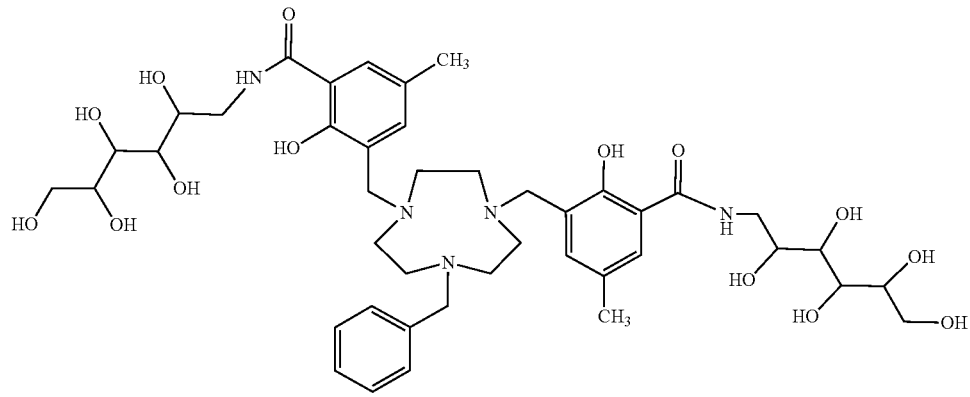 [SMILES: Cc1cc(CN2CCN(Cc3ccccc3)CCN(Cc3cc(C)cc(C(=O)NCC(O)C(O)C(O)C(O)CO)c3O)CC2)c(O)c(C(=O)NCC(O)C(O)C(O)C(O)CO)c1]
Compound 203 (3-{[8-benzyl-4-({2-hydroxy-5-methyl-3-[(2,3,4,5,6-pentahydroxyhexyl)carbamoyl]phenyl}methyl)-1,4,8-triazacycloundecan-1-yl]methyl}-2-hydroxy-5-methyl-N-(2,3,4,5,6-pentahydroxyhexyl)benzamide)
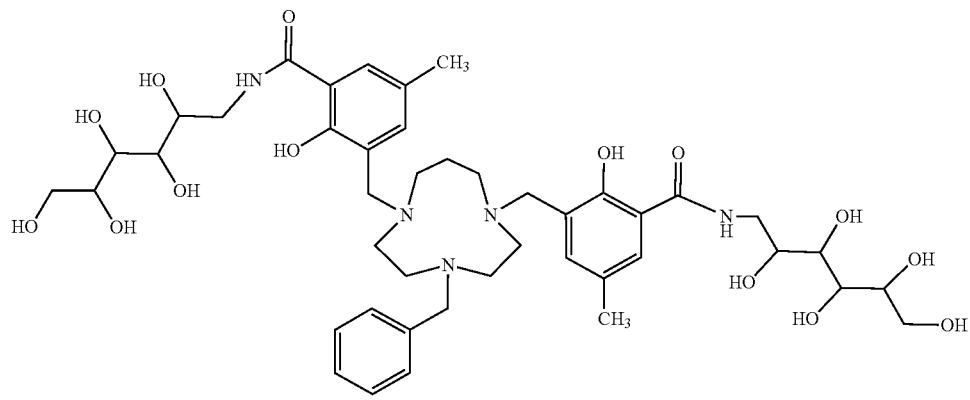 [SMILES: Cc1cc(CN2CCCN(Cc3cc(C)cc(C(=O)NCC(O)C(O)C(O)C(O)CO)c3O)CCN(Cc3ccccc3)CC2)c(O)c(C(=O)NCC(O)C(O)C(O)C(O)CO)c1]

Compound 204 (6,6'-{(4-benzyl-1,4,8-triazacycloundecane-1,8-diyl)bis[methylene(2-hydroxy-5-methyl-3,1-phenylene)methyleneazanediyl]}di(hexane-1,2,3,4,5-pentol))
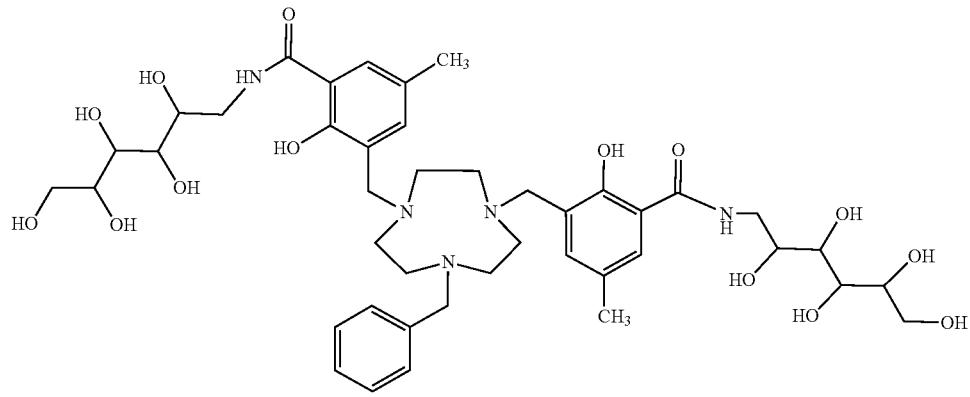 [SMILES: Cc1cc(CN2CCN(Cc3ccccc3)CCN(Cc3cc(C)cc(C(=O)NCC(O)C(O)C(O)C(O)CO)c3O)CC2)c(O)c(C(=O)NCC(O)C(O)C(O)C(O)CO)c1]
Compound 205 (6,6'-{(8-benzyl-1,4,8-triazacycloundecane-1,4-diyl)bis[methylene(2-hydroxy-5-methyl-3,1-phenylene)methyleneazanediyl]}di(hexane-1,2,3,4,5-pentol))
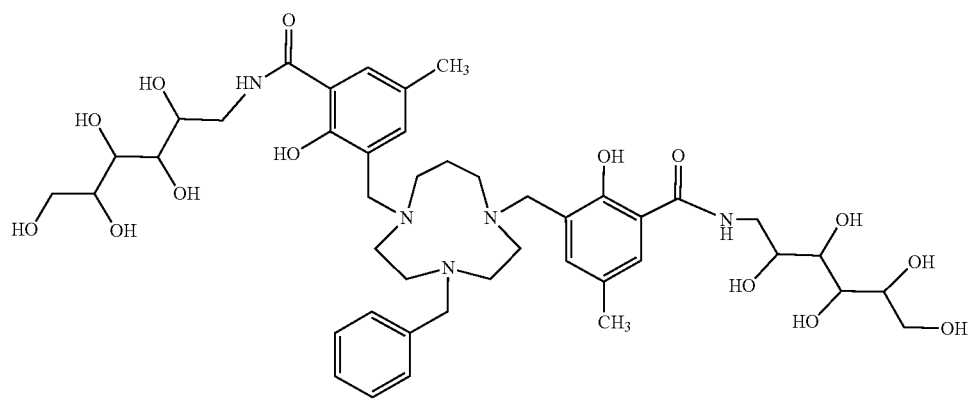 [SMILES: Cc1cc(CN2CCCN(Cc3cc(C)cc(C(=O)NCC(O)C(O)C(O)C(O)CO)c3O)CCN(Cc3ccccc3)CC2)c(O)c(C(=O)NCC(O)C(O)C(O)C(O)CO)c1]

Compound 206 (3-{[5-benzyl-9-({2-hydroxy-5-methyl-3-[(2,3,4,5,6-pentahydroxyhexyl)carbamoyl]phenyl}methyl)-1,5,9-triazacyclododecan-1-yl]methyl}-2-hydroxy-5-methyl-N-(2,3,4,5,6-pentahydroxyhexyl)benzamide)

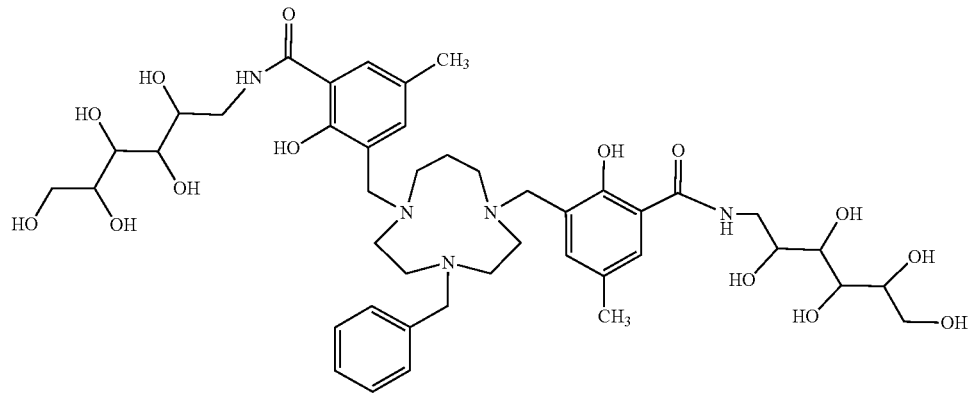 [SMILES: Cc1cc(CN2CCCN(Cc3cc(C)cc(C(=O)NCC(O)C(O)C(O)C(O)CO)c3O)CCN(Cc3ccccc3)CC2)c(O)c(C(=O)NCC(O)C(O)C(O)C(O)CO)c1]

Compound 207 (6,6'-{(9-benzyl-1,5,9-triazacyclododecane-1,5-diyl)bis[methylene(2-hydroxy-5-methyl-3,1-phenylene)methyleneazanediyl]}di(hexane-1,2,3,4,5-pentol))

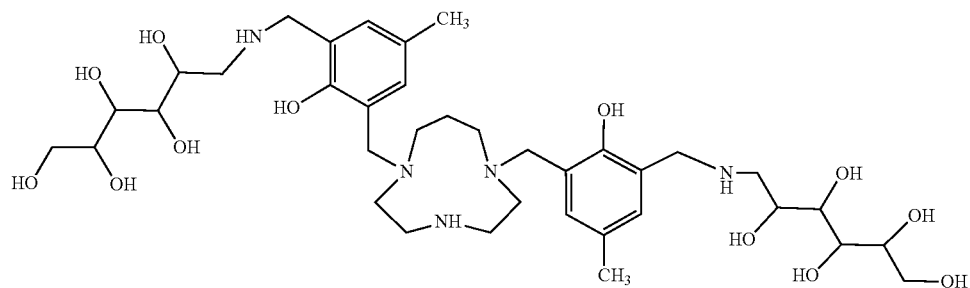 [SMILES: Cc1cc(CNCC(O)C(O)C(O)C(O)CO)c(O)c(CN2CCCN(Cc3cc(C)cc(CNCC(O)C(O)C(O)C(O)CO)c3O)CCNCC2)c1]

Compound 208 (6,6'-{1,4,7-triazecane-1,7-diylbis[methylene(2-hydroxy-5-methyl-3,1-phenylene)methyleneazanediyl]}di(hexane-1,2,3,4,5-pentol))

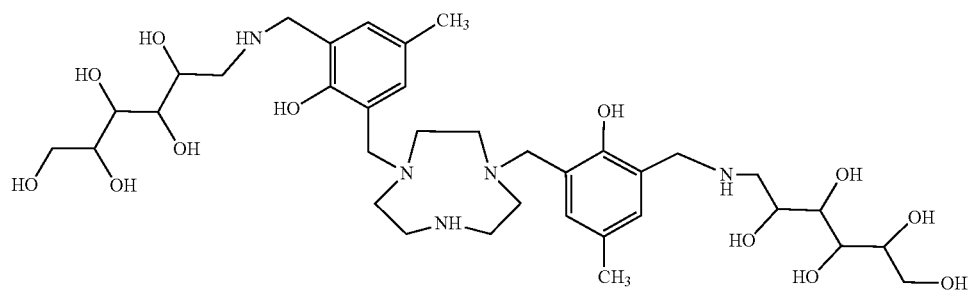 [SMILES: Cc1cc(CNCC(O)C(O)C(O)C(O)CO)c(O)c(CN2CCNCCN(Cc3cc(C)cc(CNCC(O)C(O)C(O)C(O)CO)c3O)CC2)c1]

Compound 209 (6,6'-{1,4,7-triazecane-1,4-diylbis[methylene(2-hydroxy-5-methyl-3,1-phenylene)methyleneazanediyl]}di(hexane-1,2,3,4,5-pentol))

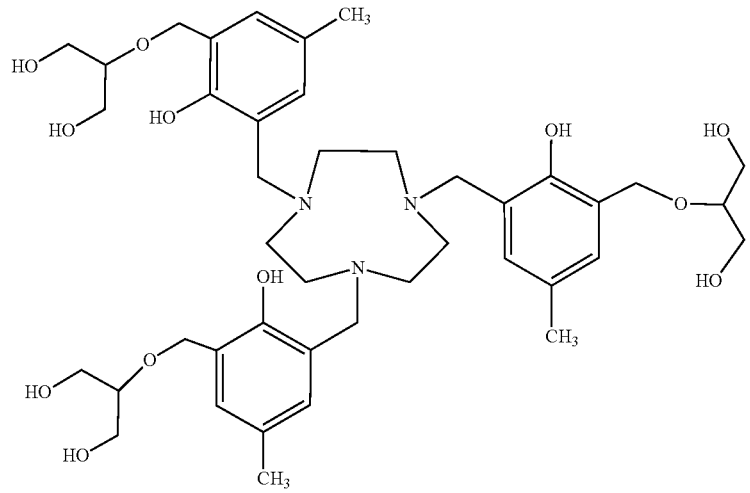 [SMILES: Cc1cc(COC(CO)CO)c(O)c(CN2CCN(Cc3cc(C)cc(COC(CO)CO)c3O)CCN(Cc3cc(C)cc(COC(CO)CO)c3O)CC2)c1]

Compound 210 (2,2',2''-{1,4,7-triazonane-1,4,7-triyltris[methylene(2-hydroxy-5-methyl-3,1-phenylene)methyleneoxy]}tri(propane-1,3-diol))

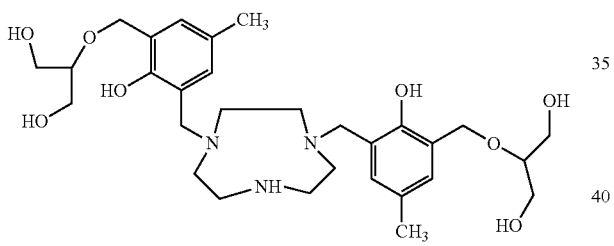

Compound 211 (2,2'-{1,4,7-triazonane-1,4-diylbis[methylene(2-hydroxy-5-methyl-3,1-phenylene)methyleneoxy]}di(propane-1,3-diol))

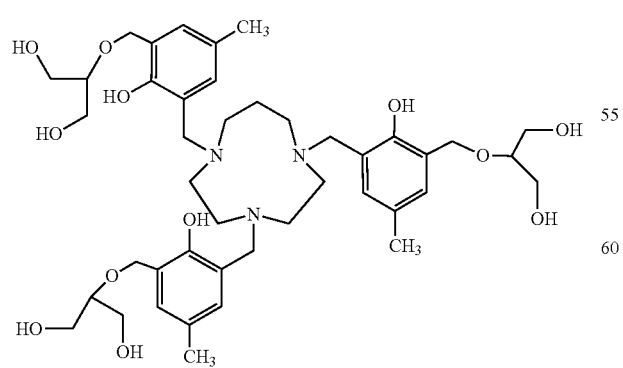

Compound 212 (2,2',2''-{1,4,7-triazecane-1,4,7-triyltris[methylene(2-hydroxy-5-methyl-3,1-phenylene)methyleneoxy]}tri(propane-1,3-diol))

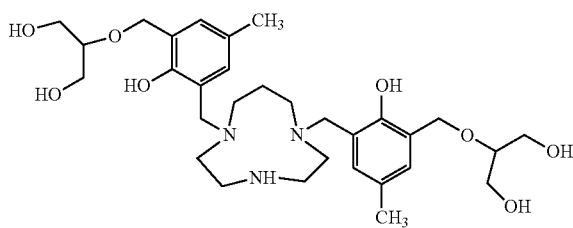 [SMILES: Cc1cc(COC(CO)CO)c(O)c(CN2CCCN(Cc3cc(C)cc(COC(CO)CO)c3O)CCNCC2)c1]

Compound 213 (2,2'-{1,4,7-triazecane-1,7-diylbis[methylene(2-hydroxy-5-methyl-3,1-phenylene)methyleneoxy]}di(propane-1,3-diol))

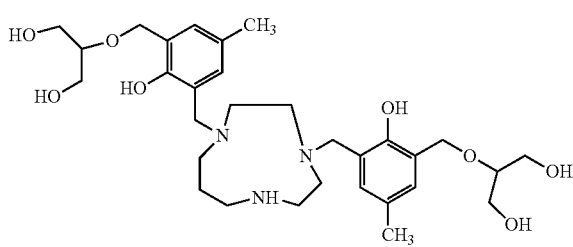 [SMILES: Cc1cc(COC(CO)CO)c(O)c(CN2CCCNCCN(Cc3cc(C)cc(COC(CO)CO)c3O)CC2)c1]

Compound 214 (2,2'-{1,4,7-triazecane-1,4-diylbis[methylene(2-hydroxy-5-methyl-3,1-phenylene)methyleneoxy]}di(propane-1,3-diol))

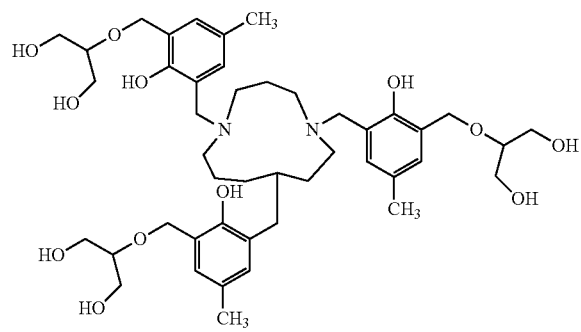 [SMILES: Cc1cc(COC(CO)CO)c(O)c(CC2CCCN(Cc3cc(C)cc(COC(CO)CO)c3O)CCCN(Cc3cc(C)cc(COC(CO)CO)c3O)CC2)c1]

Compound 215 (2,2',2''-{1,4,8-triazacycloundecane-1,4,8-triyltris[methylene(2-hydroxy-5-methyl-3,1-phenylene)methyleneoxy]}tri(propane-1,3-diol))

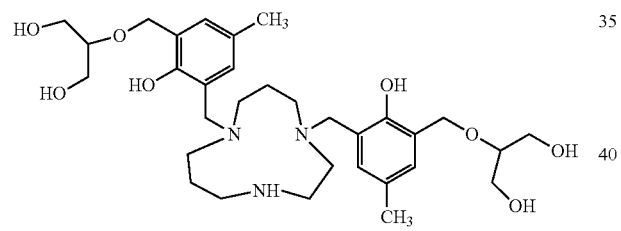

Compound 216 (2,2'-{1,4,8-triazacycloundecane-1,8-diylbis[methylene(2-hydroxy-5-methyl-3,1-phenylene)methyleneoxy]}di(propane-1,3-diol))

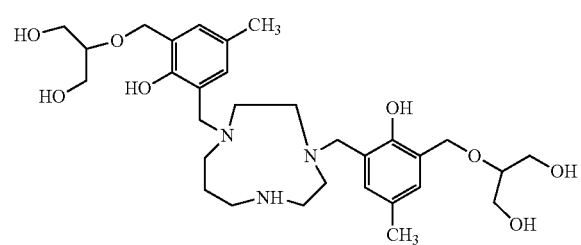 [SMILES: Cc1cc(COC(CO)CO)c(O)c(CN2CCCNCCN(Cc3cc(C)cc(COC(CO)CO)c3O)CC2)c1]

Compound 217 (2,2'-{1,4,8-triazacycloundecane-1,4-diylbis[methylene(2-hydroxy-5-methyl-3,1-phenylene)methyleneoxy]}di(propane-1,3-diol))

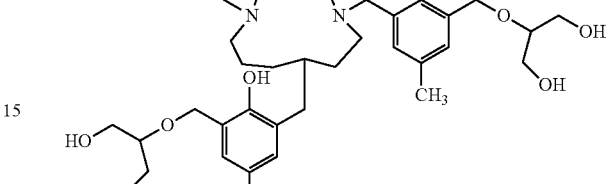

Compound 218 (2,2',2''-{1,5,9-triazacyclododecane-1,5,9-triyltris[methylene(2-hydroxy-5-methyl-3,1-phenylene)methyleneoxy]}tri(propane-1,3-diol))

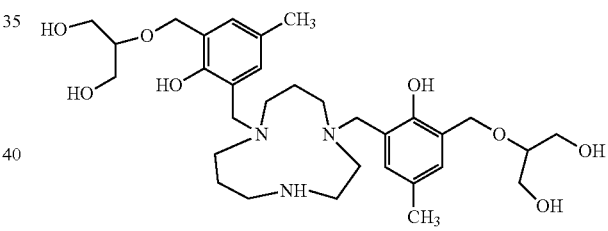

Compound 219 (2,2'-{1,5,9-triazacyclododecane-1,5-diylbis[methylene(2-hydroxy-5-methyl-3,1-phenylene)methyleneoxy]}di(propane-1,3-diol))

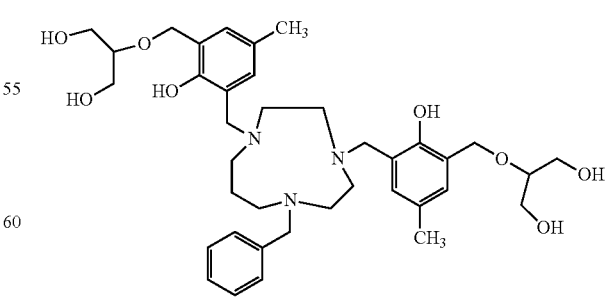

Compound 220 (2,2'-{(7-benzyl-1,4,7-triazonane-1,4-diyl)bis[methylene(2-hydroxy-5-methyl-3,1-phenylene)methyleneoxy]}di(propane-1,3-diol))

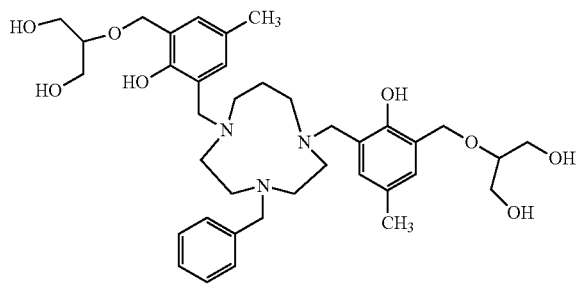 [SMILES: Cc1cc(COC(CO)CO)c(O)c(CN2CCCN(Cc3cc(C)cc(COC(CO)CO)c3O)CCN(Cc3ccccc3)CC2)c1]

Compound 221 (2,2'-{(4-benzyl-1,4,7-triazecane-1,7-diyl)bis[methylene(2-hydroxy-5-methyl-3,1-phenylene)methyleneoxy]}di(propane-1,3-diol))

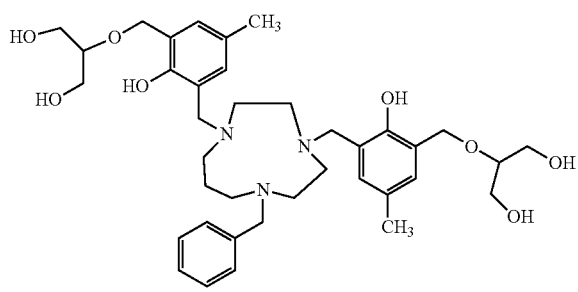 [SMILES: Cc1cc(COC(CO)CO)c(O)c(CN2CCCN(Cc3ccccc3)CCN(Cc3cc(C)cc(COC(CO)CO)c3O)CC2)c1]

Compound 222 (2,2'-{(7-benzyl-1,4,7-triazecane-1,4-diyl)bis[methylene(2-hydroxy-5-methyl-3,1-phenylene)methyleneoxy]}di(propane-1,3-diol))

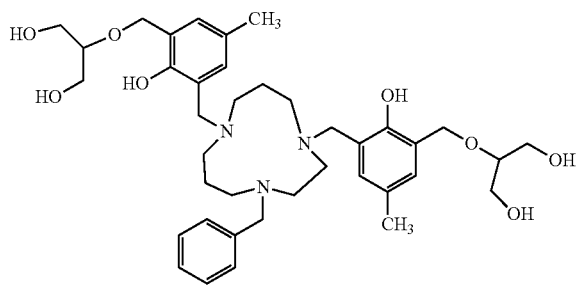 [SMILES: Cc1cc(COC(CO)CO)c(O)c(CN2CCCN(Cc3ccccc3)CCN(Cc3cc(C)cc(COC(CO)CO)c3O)CCC2)c1]

Compound 223 (2,2'-{(4-benzyl-1,4,8-triazacycloundecane-1,8-diyl)bis[methylene(2-hydroxy-5-methyl-3,1-phenylene)methyleneoxy]}di(propane-1,3-diol))

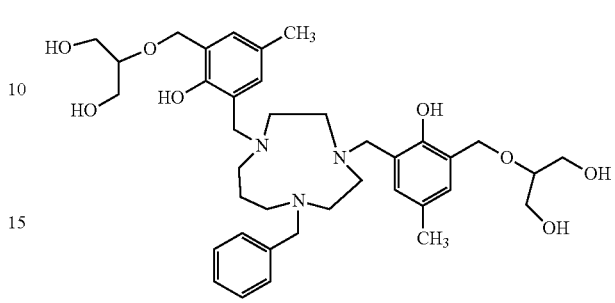

Compound 224 (2,2'-{(8-benzyl-1,4,8-triazacycloundecane-1,4-diyl)bis[methylene(2-hydroxy-5-methyl-3,1-phenylene)methyleneoxy]}di(propane-1,3-diol)), and

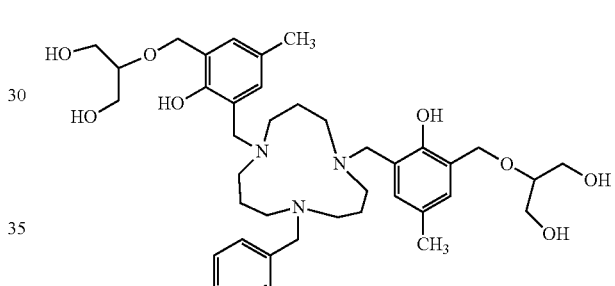

Compound 225 (2,2'-{(9-benzyl-1,5,9-triazacyclododecane-1,5-diyl)bis[methylene(2-hydroxy-5-methyl-3,1-phenylene)methyleneoxy]}di(propane-1,3-diol))

The chemical names provided for the Compounds of the invention listed above were generated through the software ACD/ChemSketch 2021.2.2 (ACD/Labs 2021.2.2 (File Version C35H41, Build 126536, 2 Mar. 2022)). These chemical names may slightly differ from standard IUPAC nomenclature. For the sake of clarity, in case of discrepancy between the chemical structures and the corresponding chemical names, the compound of the invention is identified univocally by its chemical structure.

According to a further aspect, the invention refers to a complex of a compound of formula (I) as above defined in any of its embodiments, hence encompassing compounds of formulae (II) to (V) as above defined, with $Fe^{3+}$, or a physiologically acceptable salt thereof. As demonstrated in the Experimental section, the complex of the invention possesses a balanced profile of high relaxivity, kinetic inertness, thermodynamic stability and stability to reduction, making it very suitable for its use in the diagnosis field, in particular as a contrast agent for magnetic resonance imaging (MRI).

According to another aspect, the invention refers to a complex as defined above or a physiologically acceptable salt thereof for use in a method of diagnosis preferably in vivo; more preferably, the complex or a physiologically acceptable salt thereof is for use in a method of diagnosis e.g. in vivo of a pathology by magnetic resonance imaging (MRI). The use of the complex as defined above or of a physiologically acceptable salt thereof for diagnostic methods e.g. in vivo, preferably for diagnosis e.g. in vivo of a pathology by magnetic resonance imaging (MRI), is also an aspect of the invention. A further aspect of the invention is the use of the complex of the invention as defined above, or of a salt thereof, as a contrast agent, preferably for MRI.

According to an additional aspect, the invention refers to the use of the complex as defined above or of a physiologically acceptable salt thereof for the manufacture of diagnostic agents, such as contrast agents, preferably of contrast agents for magnetic resonance imaging (MRI) e.g. for in vivo applications.

According to a further aspect, the invention refers to a method of imaging of a body tissue in a patient comprising the steps of administering to the patient an effective amount of a complex as defined above or of a physiologically acceptable salt thereof in a pharmaceutically acceptable carrier, and subjecting the patient to magnetic resonance imaging (MRI).

According to another aspect, the invention refers to a pharmaceutical composition comprising a complex as defined above or a physiologically acceptable salt thereof, and at least one pharmaceutically acceptable excipient.

A process for manufacturing a compound of the invention as above defined in any of its embodiment, hence encompassing compounds of formulae (I) to (V) as above defined, represents a further aspect of the present invention. This process can be generally carried out by coupling a macrocycle selected from the group consisting of triazacyclononane, triazacyclodecane, triazacycloundecane, and triazacyclododecane, possibly suitably protected with one or more protecting groups on one or more nitrogen atoms, with one or more suitable moieties to obtain the compound of the invention, or to obtain an intermediate thereof that can be then converted (e.g. by further coupling and/or reduction reactions) to the compound of the invention.

In an embodiment, the compound of the invention can be prepared according to the following general synthesis steps:

a) providing a phenol substituted at least in its orto positions (i) with a $C_1$-$C_5$-alkyl-bonded to a suitable leaving group, such as mesylate (MsO) or halo, e.g, thus providing a halo-$C_1$-$C_5$-alkyl, such as chloro-$C_1$-$C_5$-alkyl or bromo-$C_1$-$C_5$-alkyl; and (ii) with a L-Z group or a suitable substituent group that can be later converted to the L-Z groups, e.g. a substituent group selected from the group consisting of $C_1$-$C_4$-alkyl-aldehyde, $C_1$-$C_4$-alkyl-ester, and $C_1$-$C_4$-alkyl-carboxyl; for example, the phenol can be the compound of formula (VI)

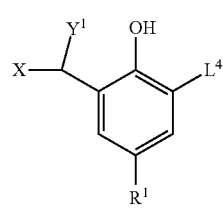

Formula (VI)

wherein $Y^1$ and $R_1$ have the same meaning provided for formula (I) or any embodiment thereof;
X is a leaving group, such as mesylate (MsO) or halogen, preferably Cl or Br, and
$L^4$ is a group selected from the group consisting of $C_1$-$C_4$-alkyl-aldehyde, $C_1$-$C_4$-alkyl-ester, and $C_1$-$C_4$-alkyl-carboxyl;

b) providing a macrocycle selected from the group consisting of triazacyclononane, triazacyclodecane, triazacycloundecane, and triazacyclododecane, optionally suitably protected with one or more protecting groups on one or more of the nitrogen atoms thereof, and/or optionally bearing on one of its nitrogen atoms a $C_1$-$C_4$ alkyl group optionally substituted by an aryl (such as a substituted or unsubstituted aryl);

c) reacting the phenol provided in step a), e.g. the compound of formula (VI), with the macrocycle provided in step b), to obtain the compound of the invention, or an intermediate of the compound of the invention, such as an intermediate bearing at least two suitable substituent groups that can be converted to the L-Z groups in the later steps. Such suitable substituent groups are e.g. at least two $L^4$ moieties, which can advantageously be converted in the subsequent step(s) to the groups $L^1$-$Z^1$, $L^2$-$Z^2$, and eventually $L^3$-$Z^3$ (if present). Such intermediate is for example the compound of formula (VII)

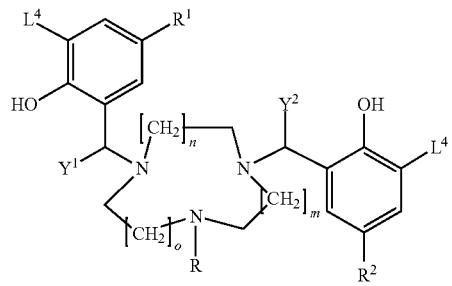

Formula (VII)

wherein $R_1$, $R_2$, $Y^1$, $Y^2$, m, n and o have the same meaning provided for formula (I) or any embodiment thereof,
$L^4$ is a group selected from the group consisting of $C_1$-$C_4$-alkyl-aldehyde, $C_1$-$C_4$-alkyl-ester, and $C_1$-$C_4$-alkyl-carboxyl; and
R" is selected from the group consisting of hydrogen, $C_1$-$C_4$ alkyl optionally substituted by an aryl (such as a substituted or unsubstituted aryl), and the moiety of Formula (VIIA):

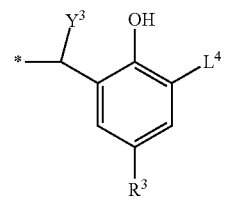

Formula (VIIA)

wherein: the asterisk (*) indicates the point of attachment of said moiety of formula (VIIA) to the nitrogen bearing the R' group;

$Y^3$ has the same meaning provided above for $Y^1$ and $Y^2$;

$R_3$ has the same meaning provided above for $R_1$ and $R_2$; and $L^4$ is a group selected from the group consisting of $C_1$-$C_4$-alkyl-aldehyde, $C_1$-$C_4$-alkyl-ester, and $C_1$-$C_4$-alkyl-carboxyl; and d) converting the intermediate of step c) to the compound of the invention, e.g. converting the $L^4$ moieties to the groups $L^1$-$Z^1$, $L^2$-$Z^2$, and $L^3$-$Z^3$ (if present), whereby the compound of the invention is obtained, e.g. by reacting the intermediate obtained in step c), such as the compound of formula (VII), with one or more suitable substrates, and optionally by reducing the so-obtained compound.

According to the present invention, the term "$C_1$-$C_4$-alkyl-aldehyde" refers to an alkyl group as above defined comprising from 1 to 4 carbons, one of which is an aldehyde group. Accordingly, the group $C_1$-$C_4$-alkyl-aldehyde comprises up to four carbons.

According to the present invention, the term "$C_1$-$C_4$-alkyl-ester" refers to an alkyl group as above defined comprising from 1 to 4 carbons, one of which is a carboxylate bound to an alkyl group (i.e. one of which is —C(O)O—$R^0$, wherein $R^0$ is an alkyl group, preferably a $C_1$-$C_2$-alkyl group). Accordingly, the group $C_1$-$C_4$-alkyl-ester comprises up to four carbons (not counting the alkyl group $R^0$ bound to the oxygen).

According to the present invention, the term "$C_1$-$C_4$-alkyl-carboxyl" refers to an alkyl group as above defined comprising from 1 to 4 carbons, one of which is a carboxyl (—COOH) group. Accordingly, the group $C_1$-$C_4$-alkyl-carboxyl comprises up to four carbons.

Step a) involves providing a phenol that is advantageously substituted in one of its orto positions with a leaving group-$C_1$-$C_6$-alkyl group, preferably a halomethyl group such as chloromethyl, or a MsO-methyl group. This group allows to couple the phenol to one or more, possibly two or three, of the nitrogen atoms of the macrocycle in step c). The phenol further comprises, in its orto position, a group that can be advantageously converted in the subsequent steps in the $L^1$-$Z^1$, $L^2$-$Z^2$, and eventually the $L^3$-$Z^3$ (if present) groups, such as a group selected from the group consisting of $C_1$-$C_4$-alkyl-aldehyde, $C_1$-$C_4$-alkyl-ester, and $C_1$-$C_4$-alkyl-carboxyl. Alternatively, in addition to the leaving group-$C_1$-$C_5$-alkyl group, such as the halo-$C_1$-$C_5$-alkyl group, the phenol may further comprise in its orto positions the L-Z group, e.g. $L^1$-$Z^1$ group, whereby the compound of the invention is directly obtained when the phenol is coupled to the macrocycle provided in step b). Advantageously, the phenol of step a), e.g. the compound of formula (VI), can be obtained by reacting the correspondent non-methylene-halogenated compound with paraformaldehyde in concentrated hydrohalic acids, preferably in hydrochloric or hydrobromic acid, at a temperature comprised in the range of 30 to 70° C., preferably of 40 to 60° C., more preferably at 50° C.

Step b) involves providing a macrocycle selected from the group consisting of triazacyclononane, triazacyclodecane, triazacycloundecane, and triazacyclododecane, optionally suitably protected with one or more protecting groups on one or more of the nitrogen atoms thereof, and/or optionally bearing on one of its nitrogen atoms a $C_1$-$C_4$ alkyl group optionally substituted by an aryl (such as a substituted or unsubstituted aryl). Such macrocycle will be coupled in step c) with the phenol of step a) in order to provide an intermediate of the compound of the invention (later to be converted to the compound of the invention), or to directly provide the compound of the invention.

According to an embodiment of step b), the macrocycle may be unprotected. In particular, when the compound of the invention to be obtained has all the three nitrogen atoms of the macrocycle bonded to the phenols bearing the L-Z groups (that is, when R is the group of formula (IA)), then the nitrogen atoms of the macrocycle may be unprotected. Indeed, in this way, the coupling reaction of step c) could involve all three unprotected nitrogen atoms of the macrocycle, whereby the compound of the invention, or an intermediate such as the one of formula (VII), with R" being the moiety of formula (VIIA), could be obtained; this intermediate can be later converted in the subsequent step(s) to a compound of the invention wherein R is the group of formula (IA). Moreover, the nitrogen atoms of the macrocycle may be unprotected also in case the compound to be obtained has only two nitrogen atoms of the macrocycle alkylated by the phenols bearing the L-Z groups, i.e. when the compound to be obtained has R or R' being hydrogen or $C_1$-$C_4$-alkyl optionally substituted by an aryl (such as a substituted or unsubstituted aryl) (or the preferred embodiments thereof disclosed above). Indeed, based on the reaction conditions of step c), such reaction conditions being selectable according to conventional and standard knowledge in the art, the reaction between the phenol and the macrocycle (step c)) could involve only two unprotected nitrogen atoms of the macrocycle instead of all three unprotected nitrogen atoms, whereby the product of such reaction is a macrocycle bonding only two (and not three) phenols bearing the L-Z groups, for example as set out in Example 6. For example, during step c), in particular for the macrocycles triazacyclodecane and triazacycloundecane, either all three or two out of three nitrogen atoms of the macrocycle can be de-protonated by suitably modulating the basicity of the reaction mixture of step c), whereby all three or only two out of three nitrogen atoms are alkylated during step c); e.g. when a base such as DIPEA is added to the reaction mixture of step c), all three nitrogen atoms of the macrocycle triazacycloundecane or triazacyclododecane are de-protonated, and thus a tri-alkylated macrocycle is obtained in step c); whereas if only carbonate is used in the reaction mixture, one nitrogen atom of the macrocycle triazacycloundecane or triazacyclododecane remains protonated and will not participate in the alkylation step c), thereby providing a di-alkylated macrocycle (see e.g. Example 6).

According to step b), the macrocycle can also possibly be suitably protected with one or more protecting groups on one or more of the nitrogen atoms thereof. In particular, when the compound of the invention to be obtained has R or R' being hydrogen or $C_1$-$C_4$-alkyl optionally substituted by an aryl (such as a substituted or unsubstituted aryl) (or the preferred embodiments thereof disclosed above), then one or more of the nitrogen atoms of the macrocycle may be suitably protected with one or more protecting groups. For example, Compound 4 (having R=hydrogen) can be synthesized preparing first the mono-Boc (tert-butyloxycarbonyl) protected macrocycle (e.g. as disclosed in S. J. Butler, B. K. McMahon, R. Pal, D. Parker, J. W. Walton, *Chem. Eur J.*, 2013, 19, 9511-9517), then by coupling it with the hydroxybenzaldehyde pendant, then by carrying out the reductive amination with serinol (2-amino-1,3-propanediol), and finally by deprotecting with TFA as illustrated in Scheme 1 below.

Scheme 1

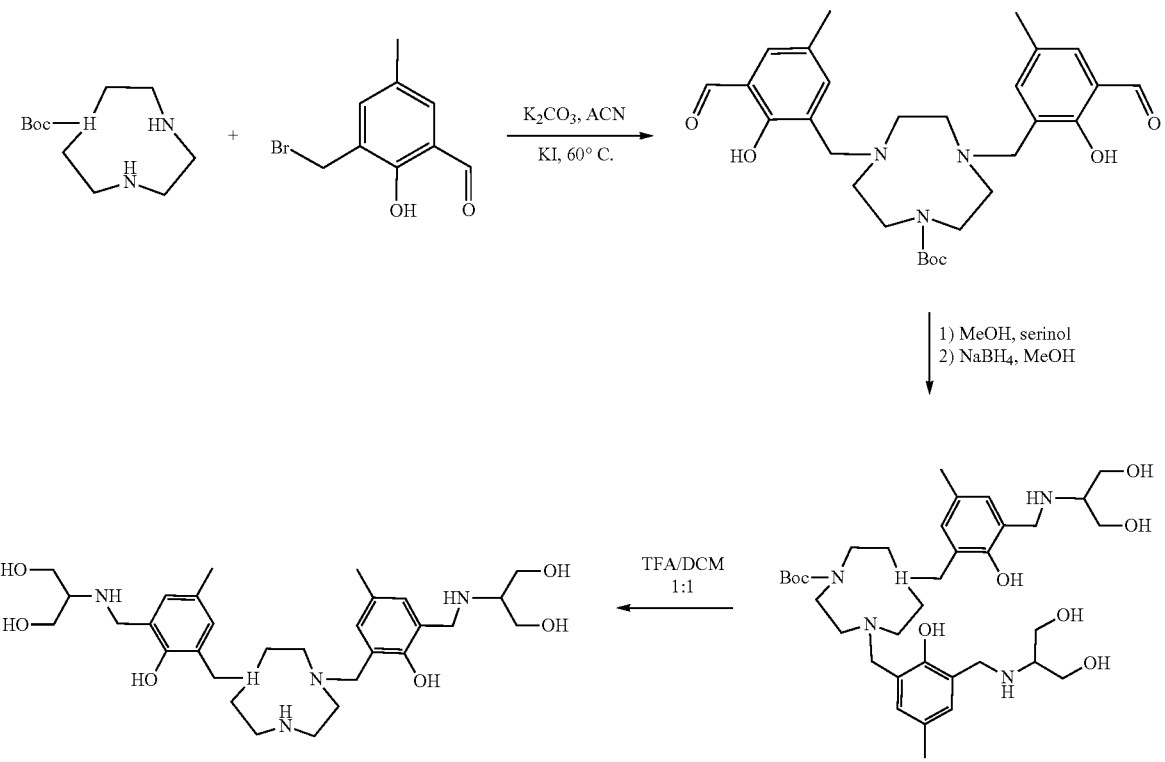

Moreover, thanks to (possibly selective) deprotection reaction(s), this embodiment of providing in step b) a macrocycle suitably protected with one or more protecting groups on one or more of the nitrogen atoms thereof, allows selecting which and how many nitrogen atoms of the macrocycle will react with the orto-substituted phenols in the coupling reaction of step c). In particular: any macrocycle described herein suitably protected with one or more protecting groups on one or more of the nitrogen atoms thereof can be synthesized for example starting from a suitable dialkylene triamine (e.g. diethylene triamine, dipropylene triamine, (2-aminoethyl)-1,3-propanediamine, etc.) that can be suitably protected (e.g. as disclosed in M. Devreux, C. Henoumont, F. Dioury, D. Stanicki, S. Boutry, L. Larbanoix, C. Ferroud, R. N. Muller, S. Laurent, *Eur. J. Inorg. Chem.* 2019, 3354-3365), in particular by protecting the primary amines of the dialkylene triamine with nosyl groups (Ns) and the secondary amine of the dialkylene triamine with Boc; the suitably protected macrocycle can then be obtained by carrying out Richman and Atkins cyclization on the protected dialkylene triamine using the appropriate ditosylated diol and appropriate reaction conditions, for example as illustrated in Scheme 2:

Scheme 2

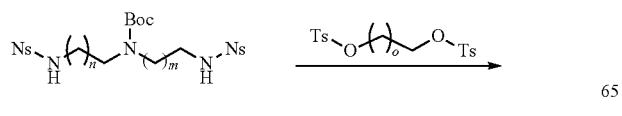

-continued

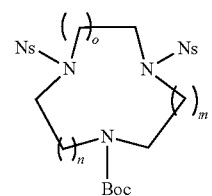

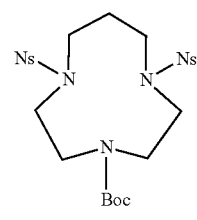

n, m = 1; o = 2

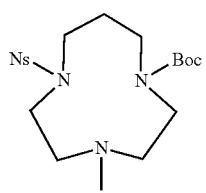

n, o = 1; m = 2

-continued

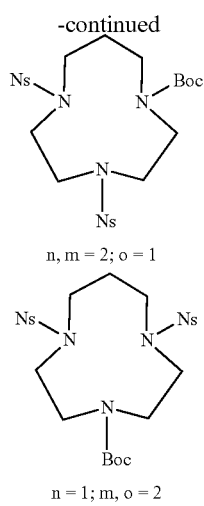

n, m = 2; o = 1 n = 1; m, o = 2

Once the suitably protected macrocycle has been obtained e.g. according to Scheme 2, the two nosyl groups (Ns) can be removed by using thiophenol in the presence of carbonate, whereby the two deprotected amines of the macrocycle can be alkylated with the suitable pendant arms e.g. as disclosed in step c), eventually by converting the groups on the pendant arms e.g. as disclosed in step d); Boc can finally be removed e.g. as disclosed in Scheme 1 above, thus obtaining the compound of the invention wherein R or R' is hydrogen, or by eventually further alkylating the deprotected nitrogen that once was bonded Boc.

The compound of the invention wherein R or R' is $C_1$-$C_4$ alkyl optionally substituted by an aryl (such as a substituted or unsubstituted aryl) can be obtained for example by operating as in Scheme 2 above, however instead of having the secondary amine of the dialkylene triamine protected with Boc, such secondary amine could be reacted with e.g. benzyl bromide (to insert the benzyl group) or e.g. with a $C_1$-$C_4$-alkyl-aldehyde, such as formaldehyde, and $NaBH_4$ (reductive amination) (to insert a $C_1$-$C_4$-alkyl group, such as the methyl group); this allows obtaining a macrocycle bearing two nosyl groups (Ns) and one $C_1$-$C_4$ alkyl optionally substituted by an aryl (such as a substituted or unsubstituted aryl). The remaining step(s) to obtain the compound of the invention can then be carried out as detailed above (i.e. removal of the Ns groups and alkylation according to step c)). The compound of the invention wherein R or R' is $C_1$-$C_4$ alkyl optionally substituted by an aryl (such as a substituted or unsubstituted aryl) can also be obtained starting from commercially available mono-alkylated macrocycles, for example as illustrated in Scheme 3 below for manufacturing Compound 112:

Scheme 3

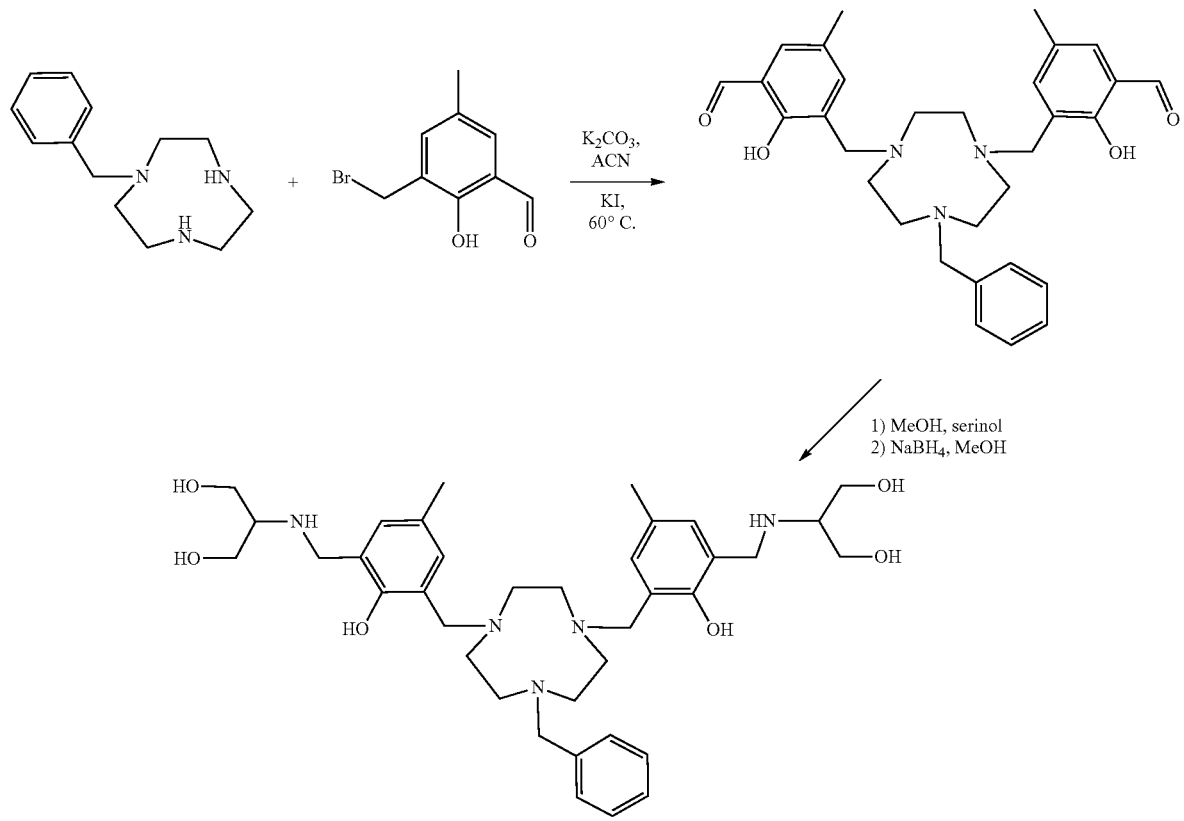

Step c) provides for reacting the phenols of step a) with the macrocycle of step b) to directly obtain the compound of the invention, or to obtain an intermediate of the compound of the invention, said intermediate being indeed reacted in the next step d) to obtain the final product.

Step c) can be carried out in an organic solvent, such as toluene or acetonitrile. Salts, such as potassium salts, for example KI, KOH, and $K_2CO_3$, can be comprised within such organic solvent, preferably in an amount of four times molar equivalents compared to the macrocycle provided in step b). KI might also be used in an amount of 0.05 to 0.4 molar equivalents, e.g. 0.1 to 0.2 molar equivalents, compared to the macrocycle provided in step b).

Step c) can be advantageously carried out without heating the reaction mixture. In particular, to reduce the risk of undesired polyalkylation reactions, step c) can be carried out at temperatures equal or lower than room temperature, that is, lower than 25° C.), for example for a temperature comprised in the range of 0° C. to 25° C.

Step d) is optional, and it may be optionally carried out when step c) provides an intermediate of the compound of the invention. Step d) involves converting the group groups of the intermediate, e.g. group $L^4$, to the $L^1$-$Z^1$, $L^2$-$Z^2$, and eventually $L^3$-$Z^3$ (if present), groups. This can be done e.g. by reacting the $L^4$ groups with one or more suitable substrates. For example, if $L^1$ is a $C_1$-$C_4$-alkylaminyl and $Z^1$ is a $C_1$-$C_6$ alkyl substituted by one or more hydroxyl groups, $L^4$ of formula (VII) and (VIIA) could be a $C_1$-$C_4$-alkyl-aldehyde, and the suitable substrate could be a $C_1$-$C_6$-alkyl-amine substituted by two or more hydroxyl groups, such as serinol or glucamine, whereby the coupling of the two provides an imide that is later reduced to obtain the intended $L^1$-$Z^1$ moiety (such as disclosed e.g. in Example 2 below). Alternatively, when $L^1$ is a $C_1$-$C_4$-alkylaminyl and $Z^1$ is a $C_1$-$C_6$ alkyl substituted by a phosphonate group, $L^4$ of formula (VII) and (VIIA) could be a $C_1$-$C_4$ alkyl-aldehyde, and the suitable substrate could be e.g. diethyl-2-aminomethylphosphonate, for example as illustrated in Scheme 4 below for obtaining Compound 11.

Scheme 4

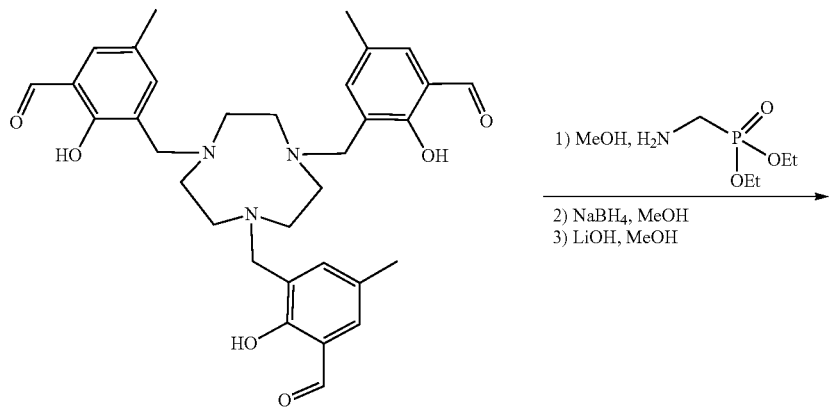

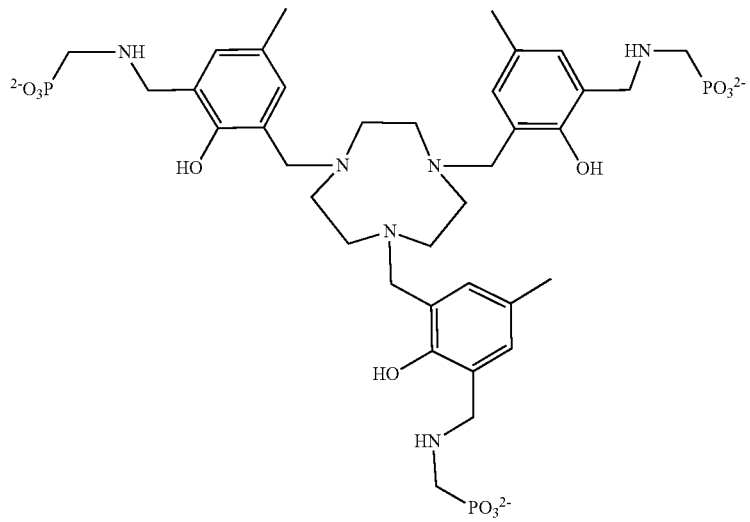

As a further illustrative example, when $L^1$ is a $C_1$-$C_4$-alkylamidyl and $Z^1$ hydrogen, $L^4$ of formula (VII) and (VIIA) could be a $C_1$-$C_4$ alkyl-ester, and the suitable substrate could be e.g. ammonia, for example as illustrated in Scheme 5 below for obtaining Compound 5.

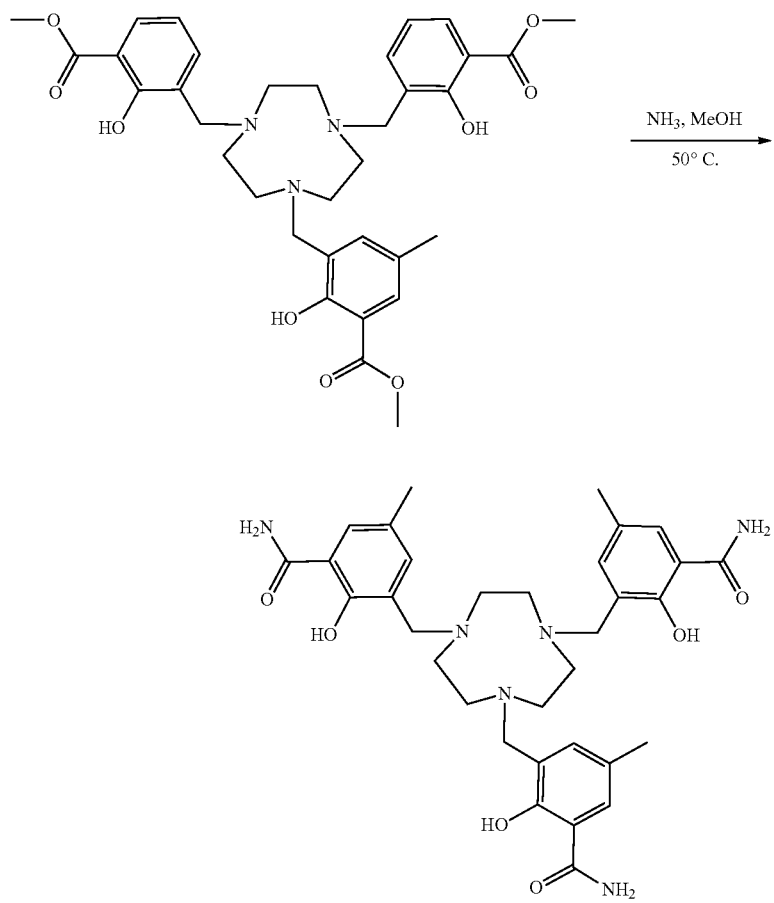

Scheme 5

As another illustrative example, when $L^1$ is a $C_1$-$C_4$-alkylether and $Z^1$ is a $C_1$-$C_6$-alkyl substituted by one or more hydroxyl groups, $L^4$ of formula (VII) and (VIIA) could be a $C_1$-$C_4$-alkyl-aldehyde, which can be reduced to obtain an hydroxyl group that can be in turn converted to an alkoxide; such alkoxide can take part in the well-known Williamson synthesis of ethers, whereby it is reacted with a suitable substrate such as e.g. an alkyl-hydroxyl-halide with its hydroxyl groups suitably protected, for example 2-chloro-1,3-propanediol or 2-bromo-1,3-propanediol with their hydroxyl groups suitably protected.

The compound of the invention might also be prepared by providing in step a) a phenol as defined above and bearing i.a. in its orto position the L-Z group. In this case, the compound of the invention can be directly obtained by reacting in step c) such orto-subtituted phenol with the macrocycle provided in step b). This embodiment can be illustrated for example according to the Scheme 6 below, which provides for obtaining a compound of the invention having as $L^1$ the following group *—NHC(O)—•, with the asterisk (*) representing the phenolic moiety and the middle dot (•) representing $Z^1$ group, and as $Z^1$ hydrogen (namely, Compound 177):

Scheme 6

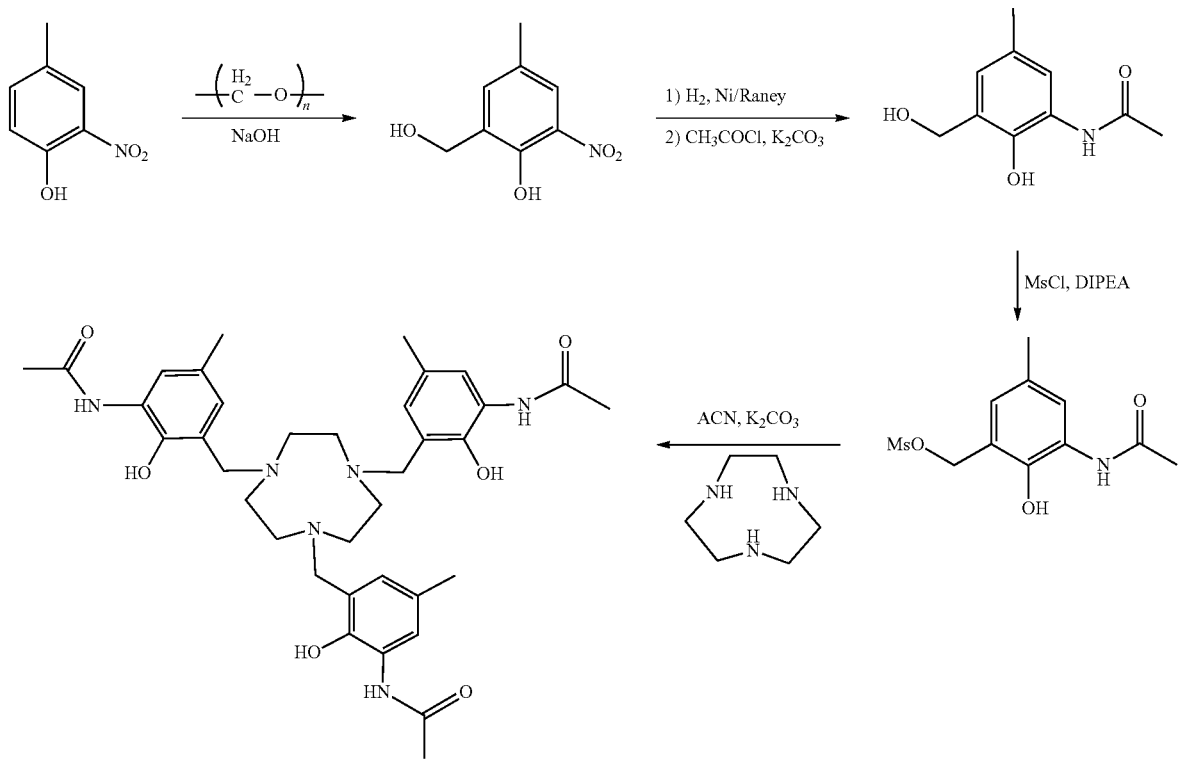

According to an embodiment, the compound of the invention can also be obtained by: providing a phenol according to step a) in any of its embodiment, and by:

b') providing an orthoamide derivative, i.e. a tricyclic trisaminomethane derivative, of a macrocycle selected from the group consisting of triazacyclononane, triazacyclodecane, triazacycloundecane, and triazacyclododecane, for example an orthoamide derivative of formula (VIII):

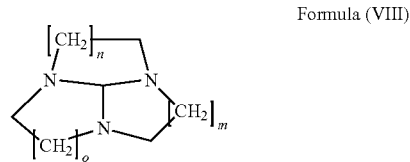

Formula (VIII)

wherein m, n, and o have the same meaning provided for formula (I) or any embodiment thereof;

c') reacting one or two phenols provided in step a), e.g. the compound of formula (VI), such as 2-hydroxy-3-bromometyl-5-methylbenzaldehyde, with the orthoamide derivative, e.g. the orthoamide derivative of formula (VIII), to obtain an orthoamide derivative coupled with one or two phenols provided in step a), e.g. with the compound of formula (VI), such as 2-hydroxy-3-bromometyl-5-methylbenzaldehyde;

d') hydrolysing the orthoamide derivative obtained in step c'), e.g. via acid hydrolysis, to obtain a macrocycle selected from the group consisting of triazacyclononane, triazacyclodecane, triazacycloundecane, and triazacyclododecane coupled with one or two phenols provided in step a), e.g. with the compound of formula (VI), such as 2-hydroxy-3-bromometyl-5-methylbenzaldehyde, and with a formyl (—C(O)H) group;

e') optionally reacting a further phenol provided in step a), e.g. the compound of formula (VI), such as 2-hydroxy-3-bromometyl-5-methylbenzaldehyde, with the macrocycle obtained in step d'), to obtain a macrocycle selected from the group consisting of triazacyclononane, triazacyclodecane, triazacycloundecane, and triazacyclododecane coupled with two phenols provided in step a), e.g. with the compound of formula (VI), such as 2-hydroxy-3-bromometyl-5-methylbenzaldehyde, and with a formyl (—C(O)H) group;

f') hydrolysing the macrocycle obtained in step d') or e'), and optionally convert the possible $C_1$-$C_4$-alkyl-aldehyde, $C_1$-$C_4$-alkyl-ester, or $C_1$-$C_4$-alkyl-carboxyl, wherein the hydrolysis and the optional conversion of this step f') are carried out in any order, to obtain a compound of the invention (wherein two nitrogen atoms of the macrocycle are bonded to the phenols bearing the L-Z groups, and one is bonded to a hydrogen); and g') optionally reacting a further phenol provided in step a), e.g. the compound of formula (VI), such as 2-hydroxy-3-bromometyl-5-methylbenzaldehyde, with the macrocycle obtained in step f'), and optionally convert the possible $C_1$-$C_4$-alkyl-aldehyde, $C_1$-$C_4$-alkyl-ester, or $C_1$-$C_4$-alkyl-carboxyl, to obtain a compound of the invention (wherein all three nitrogen atoms of the macrocycle are bonded to the phenols bearing the L-Z groups).

The following Scheme 7 illustrates a possible way to carry out the embodiment above, in particular when: step c') provides for reacting one phenol with the orthoamide derivative, step e') is carried out (and thus provides for reacting a further phenol with the macrocycle obtained in step d')), step f') provides for first carrying out the step of converting the possible $C_1$-$C_4$-alkyl-aldehyde and then to carry out the hydrolysis step to obtain the compound of the invention, and step g') is not carried out:

The hydrolyzation of step d') allows converting the orthoamide derivative to the macrocycle bonding a formyl group (as well as bonding the phenol(s) previously reacted in step c')). The formyl group seems to predominantly bond the nitrogen atom of the macrocycle that is less sterically hindered, such as e.g. one of the two nitrogen atoms in-between the ethylene and propylene moieties (and not the one in-between the two propylene moieties) of the macrocycle triazacycloundecane.

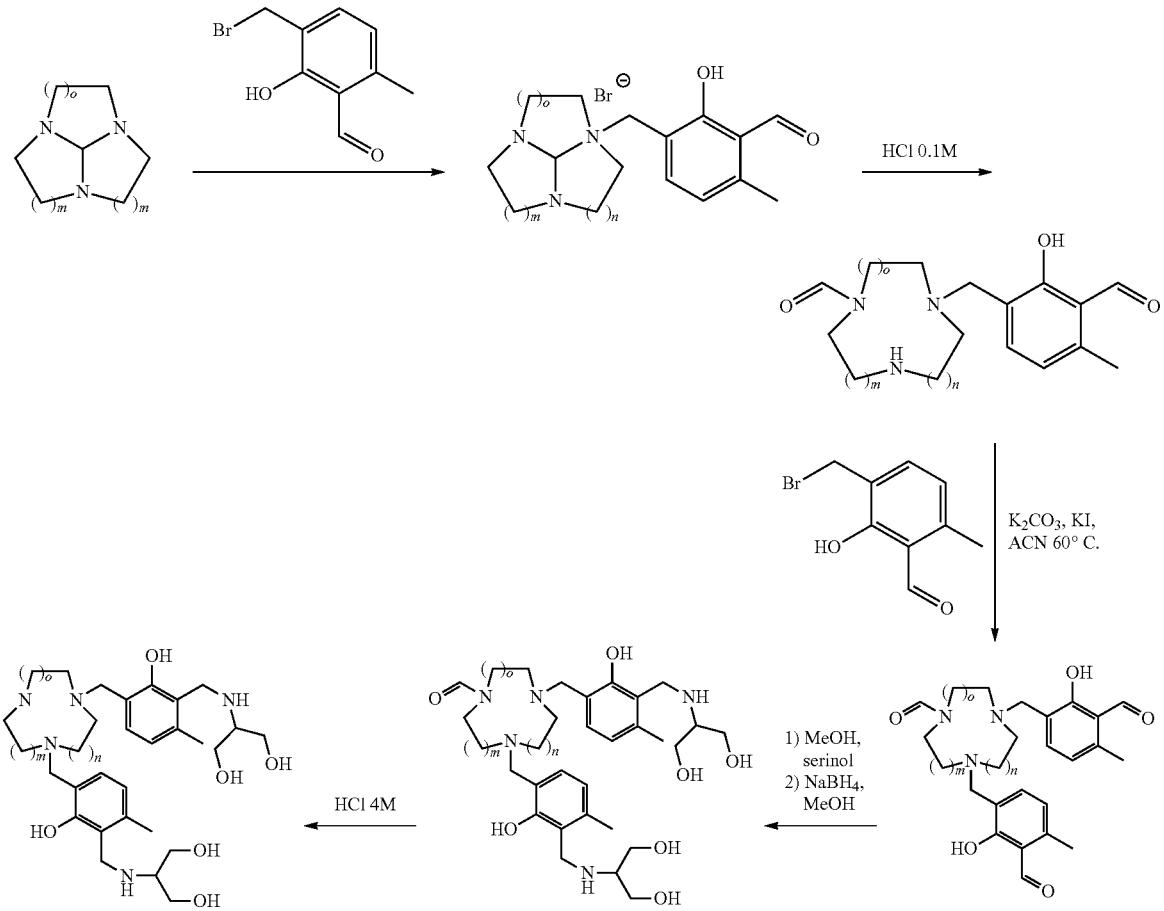

Scheme 7 m, n, o = 1: TACN; m, n = 1, o = 2, TACD; m = 1, n, o = 2, TACUD; m, n, o = 2, TADD

According to Scheme 7, compounds of the invention wherein two nitrogen atoms of the macrocycle are bonded to the phenols bearing the L-Z groups, and one is bonded to a hydrogen, can be synthesized. If the further step g') is carried out, compounds of the invention wherein three nitrogen atoms of the macrocycle are bonded to the phenols bearing the L-Z groups can be synthesized as well.

The orthoamide derivative provided in step b') can be obtained according to standard means in the art, e.g. by reacting a macrocycle selected from the group consisting of triazacyclononane, triazacyclodecane, triazacycloundecane, and triazacyclododecane, with formaldehyde dimethylacetal, or as reported in T. Atkins, J. Am. Chem. Soc. 1980, 102, 6364-6365; R. W. Alder et al. J. Chem. Soc. Chem. Commun. 1992, 507-508, e.g. starting from 1,4,6-triazabicyclo[3.3.0]oct-4-ene 1,5,7-triazabicyclo[4.4.0]dec-5-ene.

According to an embodiment, step d') can be carried out before step c'); in this case, step c') is carried out by reacting one or two phenols provided in step a) with the macrocycle obtained by the hydrolyzation step d'), i.e. with the macrocycle selected from the group consisting of triazacyclononane, triazacyclodecane, triazacycloundecane, and triazacyclododecane coupled with a formyl (—C(O)H) group.

In order to obtain a Fe(III) complex of a compound of the invention, which is also an aspect of the present invention, a step providing for complexing the compound of the invention with Fe(III) may be carried out, e.g. after step c) or step d), or after step f') or g'); said complexation step can be carried out for example according to the following step:

e) reacting the compound of the invention, for example as obtained in step c), step d), step f') or step g'), with a Fe(III) salt, such as with $FeCl_3$, $Fe(NO_3)_3$, $Fe(OH)_3$, and FeO(OH) to obtain the Fe(III) complex of the compound of the invention.

Step e) can be carried out in a non-aqueous polar solvent, such as a lower alcohol, e.g. methanol, ethanol, n-propanol, i-propanol, and mixtures thereof.

Non-limiting examples of the preparation of preferred compounds of the invention and intermediates for their preparation are reported in the following section, aimed to illustrate the invention in greater detail without limiting its scope.

Experimental Section

Material and Methods

Reactants and/or solvents employed in the following examples that are not specifically synthesized in the following Examples are known and readily available. If they are not commercially available per se, they may be prepared according to known methods in literature.

$^1$H and $^{13}$C NMR spectra were recorded on a Bruker Avance III spectrometer (Bruker, Milano, Italy) operating at 11.74 T and 298 K, corresponding to a protonic resonance frequency of 499.8 MHz. $^1$H and $^{13}$C NMR chemical shifts are reported relative to TMS and are referenced using the residual proton solvent resonances. Samples were prepared in 5 mm NMR tubes by dissolving the compounds in appropriate deuterated solvents.

Analytical and semi-preparative HPLC-MS runs were carried out on a Waters modular system equipped with Waters 1525 binary pump, Waters 2487 UV/Vis and Waters SQD 3100 (ESCI ionization mode) detectors (Waters Corporation, Milford, MA, USA). UPLC-MS analyses were performed using a UPLC Acquity H-Class coupled with QDa and TUV detectors (Waters Corporation, Milford, MA, USA). The ESI-MS were recorded on a Waters SQD 3100 (Waters Corporation, Milford, MA, USA).

Example 1—Synthesis of Compound 1

The synthesis of Compound 1 was carried out according to the following Scheme 8:

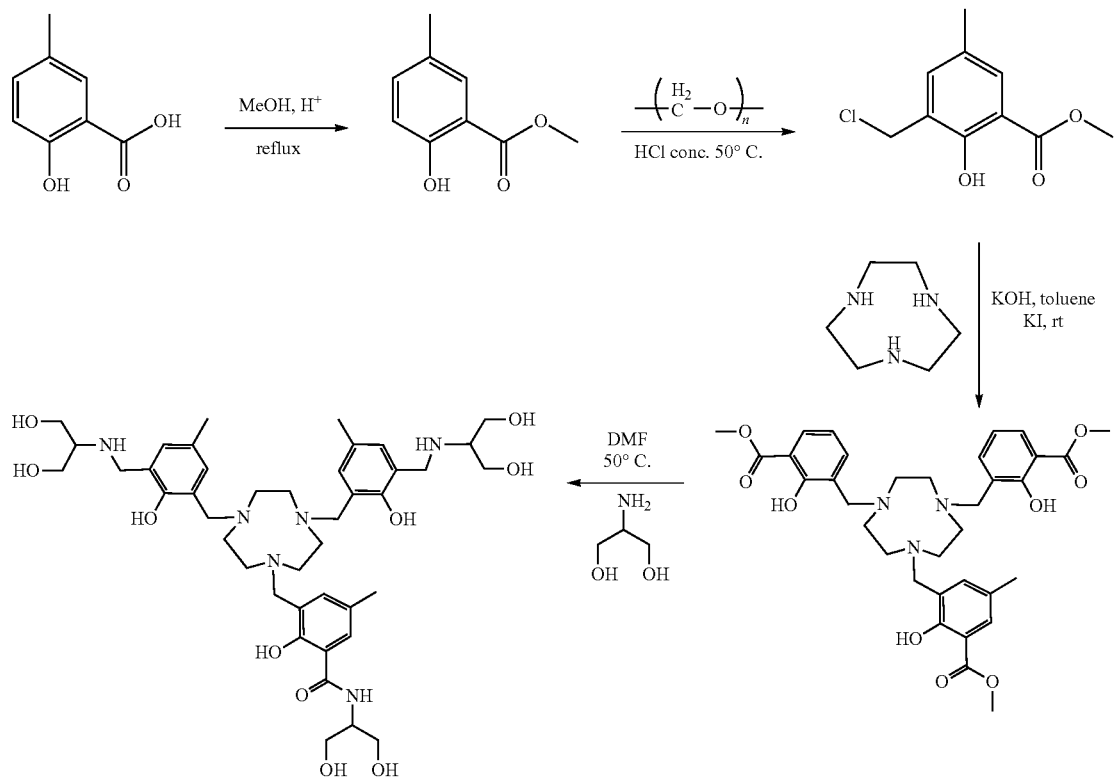

Scheme 8

Details of the synthesis of the present Example are provided in the following paragraphs.

A) Synthesis of (2-hydroxy-5-methyl)methyl benzoate 2-hydroxy-5-metylbenzoic acid (0.5 g, 3.28 mmol) was dissolved in 5 mL of MeOH and a few drops of HCl were added. The solution was stirred overnight at reflux temperature. The final product is used without further purification. Quantitative yield.

$^1$H NMR (CDCl$_3$, 500 MHZ): δ (ppm)=2.27 (s, —C—CH$_3$, 3H), 3.92 (s, —O—CH$_3$, 3H), 6.87 (d, —CH—CH—COH, 1H, J$_3$=8.5 Hz), 7.24 (dd, —CCH$_3$—CH—CH—, 1H, J$_3$=8.5 Hz, J$_4$=2.1 Hz), 7.62 (d, —C—CH—CCH$_3$, 1H, J$_4$=2.1 MHZ), 10.51 (bs, —OH). $^{13}$C NMR (CDCl$_3$, 125 MHZ): δ (ppm)=20.4 (—CH$_3$), 52.2 (—O—CH$_3$), 111.9 (—CH—C—CH—), 117.3 (—COH—CH—), 129.4 (—CH—C—COH—), 129.6 (—CH—CH—CCH$_3$), 136.6

(—C—CH—C—), 160.2 (—C—OH), 170.6 (—C=O—). ESI-MS (m/z): 167.2 (M+H⁺) (calculated for $C_9H_{10}O_3$: 166.2).

B) Synthesis of (2-hydroxy-5-methyl-3-metylchloro) carboxylic acid (2-hydroxy-5-methyl)methyl benzoate (0.5 g, 3.01 mmol) obtained in the previous step was dissolved in 4 mL of concentrated HCl and the temperature was raised to 50° C. Then, paraformaldehyde (0.181 g, 6.02 mmol) was added in portion and the reaction mixture was stirred at room temperature for 72 h. Then, the solution was washed with DCM (3×15 ml) and the organic layer with brine (2×15 ml). The organic phase was dried with $Na_2SO_4$, filtered and the solvent evaporated under reduced pressure. Yield: 72%.

$^1$H NMR (CDCl$_3$, 500 MHZ): δ (ppm)=2.29 (s, —CH$_3$, 3H), 3.94 (s, —O—CH$_3$, 3H), 4.67 (s, —CH$_2$—Cl, 2H), 7.37 (s, —C—CH—C—CH$_2$Cl, 1H), 7.63 (s, —C—CH—C—CH$_3$, 1H), 11.01 (bs, —OH). $^{13}$C NMR (CDCl$_3$, 125 MHZ): δ (ppm)=20.4 (—CH$_3$), 40.8 (—O—CH$_3$), 52.4 (—CH$_2$—Cl), 112.5 (—CH—C—CH$_3$), 125.5 (—C—CH$_2$Cl), 128.2 (—CH—C—COH), 130.4 (—CCH$_3$—CH—C—), 137.4 (—CCH$_3$—CH—CC=O—), 157.5 (—COH), 170.6 (—C=O—). ESI-MS (m/z): nd.

Synthesis of 1,4,7-tris-(3-carboxymethyl-2-hydroxy-5-methylbenzyl)-1,4,7-triazacyclononane Triazacyclononane·3HCl (0.095 g, 0.4 mmol, TACN) was dissolved in a small amount of toluene. KI (0.007 g, 0.04 mmol) and KOH (0.067 g, 1.2 mmol) were added and the solution was cooled to 0° C. (2-hydroxy-5-methyl-3-chlorometyl)methyl benzoate (0.258 g, 1.2 mmol) obtained in the previous step was dissolved in 2 ml of toluene and added dropwise in ca. 15 min to avoid as much as possible polyalkylation reactions. Then, the reaction mixture was stirred at room temperature for 2 h. An HPLC-MS analysis was carried out to characterize the product (XBridge Phenyl 3.5 µm (4.6×150 mm); A=H$_2$O/0.1% TFA; B=MeOH; flow=1 mL/min; 0-1 min=30% B; 1-15 min=from 30% to 100% B; 15-19 min=100% B; 19-20 min=from 100% to 30% B). Retention time: 13.79 minutes. Yield: 80%.

$^1$H NMR (CDCl$_3$, 500 MHZ): δ (ppm)=2.26 (s, —CH$_3$—, 3H), 2.86 (bs, macrocycle), 3.70 (bs, —CH$_2$—N—, 6H), 3.92 (—O—CH$_3$, 9H), 7.16 (s, —C—CH—CCH$_3$—, 1H), 7.23 (s, —CCH$_3$—CH—C—, 1H). $^{13}$C NMR (CDCl$_3$, 125 MHZ): δ (ppm)=20.5 (—CH$_3$), 52.2 (—O—CH$_3$), 35.5 (—N—CH$_2$—), 122.7 (—CH$_2$—C—CH—) 125.3 (—CCH$_3$—CH—C—), 128.3 (—CH—C—CH$_3$), 129.1 (—C—CH—CCH$_3$), 137.9 (—COH—C—CH—) 158.0 (—C—OH), 170.2 (C=O). ESI-MS (m/z): 636.7 (M+H⁺) (calculated for $C_{34}H_{41}N_3O_9$:635.7).

D) Synthesis of 3,3',3''-[1,4,7-triazonane-1,4,7-triyl-tris(methylene)]tris[N-(1,3-dihydroxypropan-2-yl)-2-hydroxy-5-methylbenzamide] (Compound 1)

Serinol (2-Amino-1,3-propanediol, 0.045 g, 0.5 mmol) was dissolved in DMF (1 mL) and added to a solution of 1,4,7-tris-(3-carboxymethyl-2-hydroxy-5-methylbenzyl)-1, 4,7-triazacyclononane (0.066 g, 0.1 mmol, obtained in the previous step) in DMF (2 mL). The reaction mixture was heated to 50° C. and stirred overnight. A HPLC-MS analysis was carried out to check the reaction (XBridge Phenyl 3.5 µm (4.6×150 mm); A=H$_2$O/0.1% TFA; B=MeOH; flow=1 mL/min; 0-1 min=30% B; 1-15 min=from 30% to 100% B; 15-19 min=100% B; 19-20 min=from 100% to 30% B). Retention time: 10.25 minutes. The solvent was then removed and the crude product was purified by semi-preparative HPLC-MS (XBridge Prep Phenyl OBD 5 µm (19×100 mm); A=H$_2$O/0.1% TFA; B=MeOH; flow=20 mL/min; 0-4 min=30% B; 4-12 min=from 30% to 57% B; 12-13 min=100% B; 13-14 min=100% B; 14-15 min=from 100% to 30% B; 15-17 min=30% B). Yield: 67%.

$^1$H NMR (D$_2$O, 500 MHZ): δ (ppm)=2.19 (s, —CH$_3$—, 9H), 3.26 (bs, macrocycle, 12H), 3.66-3.75 (m, —CH—CH$_2$—OH, 12H), 4.10 (s, —N—CH$_2$-Ph-, 6H), 4.18-4.28 (m, —NH—CH—CH$_2$—OH, 3H), 7.22 (s, —CH, 1H), 7.60 (s, —CH, 1H). $^{13}$C NMR (D$_2$O, 125 MHZ): δ (ppm)=19.4 (—CH$_3$—), 49.9 (—CH—CH$_2$—OH—), 53.1 (—N—CH$_2$-Ph-), 56.6 (—NH—CH—CH$_2$—OH), 60.6 (macrocycle), 115.2 (—CH$_2$—C—C—OH), 117.5 (—CH—C—CH$_3$), 128.8 (—CH$_2$—C—CH—) 129.6 (—C—CH—), 137.5 (—CH—C—CO), 156.1 (—C—OH), 170.6 (—C=O). ESI-MS (m/z): 841.4 (M+H⁺) (calculated for $C_{42}H_{60}N_6O_{12}$: 840.4).

Example 2—Synthesis of Compound 2

The synthesis of Compound 2 was carried out according to the following Scheme 9:

Scheme 9

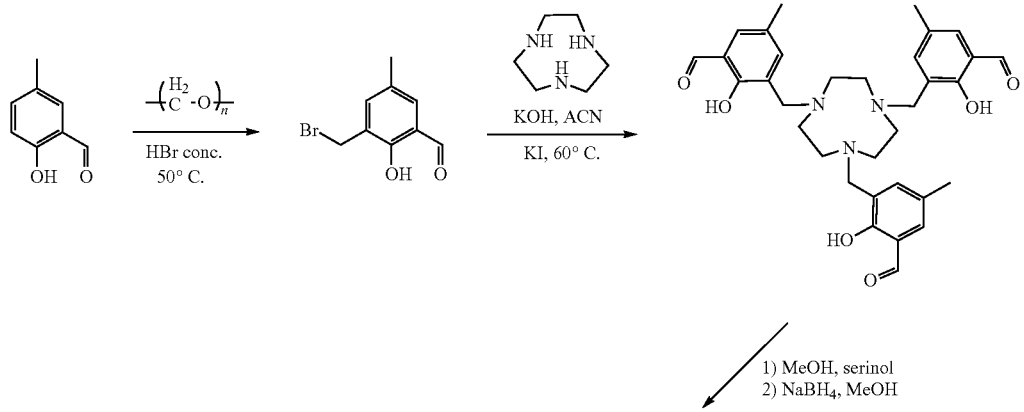

1) MeOH, serinol
2) NaBH$_4$, MeOH

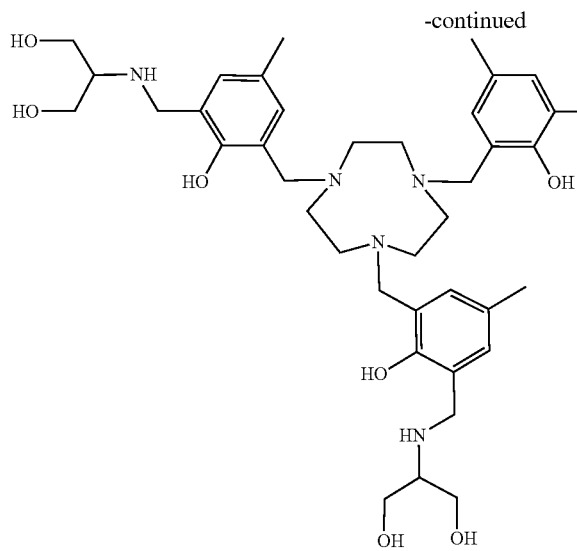

Details of the synthesis of the present Example are provided in the following paragraphs.

A) Synthesis of 2-hydroxy-3-bromometyl-5-methyl-benzaldehyde 2-hydroxy-5-methylbenzaldehyde (0.51 g, 3.7 mmol) was dissolved in 4 mL of 48% HBr and heated to 50° C. Then, paraformaldehyde (0.166 g, 5.55 mmol) was added and the reaction mixture stirred at room temperature for 72 h. Then, the solution was extracted with DCM (3×15 ml) and the organic layer was washed with brine (2×15 ml). The organic phase was dried with $Na_2SO_4$, filtered and the solvent evaporated under reduced pressure. Immediately after the DCM was removed, the product crystallizes. Yield: 69%.

$^1$H NMR (CDCl$_3$, 500 MHZ): δ (ppm)=2.34 (s, —CH$_3$, 3H), 4.55 (s, —CH$_2$—Br, 2H), 7.32 (s, —C—CH—CHO, 1H), 7.43 (s, —CCH$_3$—CH—CH$_2$Br, 1H), 9.85 (s, —CHO, 1H), 11.29 (s, —OH, 1H). $^{13}$C NMR (CDCl$_3$, 125 MHz): δ (ppm)=20.2 (—CH$_3$), 26.6 (—CH$_2$—Br), 126.3 (—C—CH$_3$), 129.3 (—CH—C—CH$_2$Br), 134.2 (—CCH$_3$—CH—C—, —CH—C—CHO), 138.9 (—CHO—CH—C—), 157.3 (—COH), 196.4 (—CHO).

B) Synthesis of 1,4,7-tris-(3-formyl-2-hydroxy-5-methylbenzyl)-1,4,7-triazacyclononane Triazacyclononane (0.042 g, 0.18 mmol, TACN) was dissolved in 3 ml of acetonitrile and KI (0.003 g, 0.018 mmol) and KOH (0.030 g, 0.54 mmol) were added. 2-hydroxy-3-chlorometyl-5-methylbenzaldehyde (0.21 g, 0.9 mmol) obtained in the previous step, dissolved in 1 ml of acetonitrile, was added dropwise to the solution. The reaction mixture was heated to 60° C. and stirred overnight. Then, the solution was filtered, and the crude product was precipitated in diethyl ether. Yield: 81%. A HPLC-MS analysis was carried out to check the reaction (XBridge Phenyl 3.5 μm (4.6×150 mm); A=H$_2$O/0.1% TFA; B=MeOH; flow=1 mL/min; 0-2 min=60% B; 2-12 min=from 60% to 100% B; 12-16 min=100% B; 16-17 min=from 100% to 60% B). Retention time: 5.60 minutes.

$^1$H NMR (CDCl$_3$, 500 MHZ): δ (ppm)=2.39 (s, —CH$_3$—, 3H), 2.46, 2.98 (bs, macrocycle), 3.93 (bs, —CH$_2$—N—, 6H), 7.40 (s, —C—CH—CCH$_3$—, 3H), 7.50 (s, —CCH$_3$—CH—C—, 3H), 9.89 (s, CHO, 3H). $^{13}$C NMR (CDCl$_3$, 125 MHZ): δ (ppm)=20.4 (—CH$_3$), 50.1-49.3 (—N—CH$_2$-macrocycle), 53.3 (—N—CH$_2$), 115.2 (—CH$_2$—C—CH—) 120.0 (—CCH$_3$—CH—C—), 131.0 (—CH—C—CH$_3$), 136.0 (—C—CH—CCH$_3$), 143.5 (—COH—C—CH—), 158.7 (—C—OH), 196.6 (C=O). ESI-MS (m/z): 574.7 (M+H$^+$) (calc. for C$_{33}$H$_{39}$N$_3$O$_6$:573.7).

C) Synthesis of 2,2',2"-{1,4,7-triazonane-1,4,7-triyltris[methylene(2-hydroxy-5-methyl-3,1-phenylene)methyleneazanediyl]}tri(propane-1,3-diol) (Compound 2)

1,4,7-tris-(3-formyl-2-hydroxy-5-methylbenzyl)-1,4,7-triazacyclononane (0.07 g, 0.12 mmol) obtained in the previous step was dissolved in 1 ml of MeOH and excess 2-Amino-1,3-propanediol (0.055 g, 0.61 mmol) was added. The solution was stirred at room temperature for 1 h. The imine intermediate was checked by MS spectrometry: ESI-MS (m/z): 794.0 (M+H$^+$) (calculated for C$_{42}$H$_{60}$N$_6$O$_9$: 793.0) and the mixture was used without purification. The solution was cooled to 0° C. and sodium borohydride (0.045 g, 1.8 mmol) was slowly added in portions. The reaction mixture was then left stirring for 3 hours. The reducing agent sodium borohydride was quenched by adding dropwise 2 ml of MeOH, waiting 15 minutes and, finally, the precipitate was removed by filtration. The final product was characterized by HPLC-MS (XBridge Phenyl 3.5 μm (4.6×150 mm); A=H$_2$O/0.1% TFA; B=MeOH; flow=1 mL/min; 0-1 min=30% B; 1-15 min=from 30% to 100% B; 15-19 min=100% B; 19-20 min=from 100% to 30% B). Retention time: 6.93 minutes.

The solvent was removed under reduced pressure and the crude product was purified by semi-preparative HPLC-MS (XBridge Prep Phenyl OBD 5 μm (19×100 mm); A=H$_2$O/ 0.1% TFA; B=MeOH; flow=20 mL/min; 0-4 min=20% B; 4-10 min=from 20% to 43% B; 10-11 min=100% B; 11-12 min=100% B; 12-13 min=from 100% to 20% B; 13-15 min=20% B). Yield: 80%.

$^1$H NMR (D$_2$O, 500 MHZ): δ (ppm)=2.17 (s, —CH$_3$, 9H), 3.27-3.29 (m, —NH—CH—CH$_2$—OH, 3H), 3.68-3.71 (m, —CH—CH$_2$—OH, 6H), 3.72-3.82 (m, —CH—CH'2—OH, 6H), 4.11 (bs, macrocycle, 12H), 4.27 (s, —N—CH$_2$-Ph-, 6H), 7.11 (s, —CH, 3H), 7.21 (s, —CH, 3H). $^{13}$C NMR (D$_2$O, 125 MHZ): δ (ppm)=19.5 (—CH$_3$—), 44.8 (—CH$_2$—NH—C), 49.5 (—N—CH$_2$Ph), 55.5 (—CH—CH$_2$—OH), 57.5 (macrocycle), 59.8 (—NH—CH—CH$_2$—OH), 115.2 (—CH$_2$—C—C—OH), 117.5 (—CH—C—CH$_3$), 128.8 (—CH$_2$—C—CH—), 129.6 (—C—CH—), 137.5 (—CH—C—CO), 156.1 (—C—OH). ESI-MS (m/z): 800.0 (M+H$^+$) (calc. for C$_{42}$H$_{60}$N$_6$O$_{12}$: 799.0).

Example 3—Synthesis of Compound 4

The synthesis of Compound 4 was carried out according to the following Scheme 10:

were added. 2-hydroxy-3-chlorometyl-5-methylbenzaldehyde (0.293 g, 1.59 mmol), dissolved in 1 ml of acetonitrile, was added dropwise to the solution. The reaction mixture was heated to 60° C. and stirred overnight. Then, the solution was filtered, and the crude product was purified with silica column (97:3 CH$_2$Cl$_2$/MeOH; TLC made in 95:5 CH$_2$Cl$_2$/MeOH conditions, Rf=0.2) to obtain 0.264 g of product (95% yield). The final product was characterized by HPLC-MS (XBridge Phenyl 3.5 μm (4.6×150 mm); A=H$_2$O/0.1% TFA; B=ACN; flow=1 mL/min; 0-1 min=50% B; 1-15 min=from 50% 100% B; 15-19 min=100% B; 19-20 min=from 100% to 50% B). Retention time: 5.60 minutes.

Scheme 10

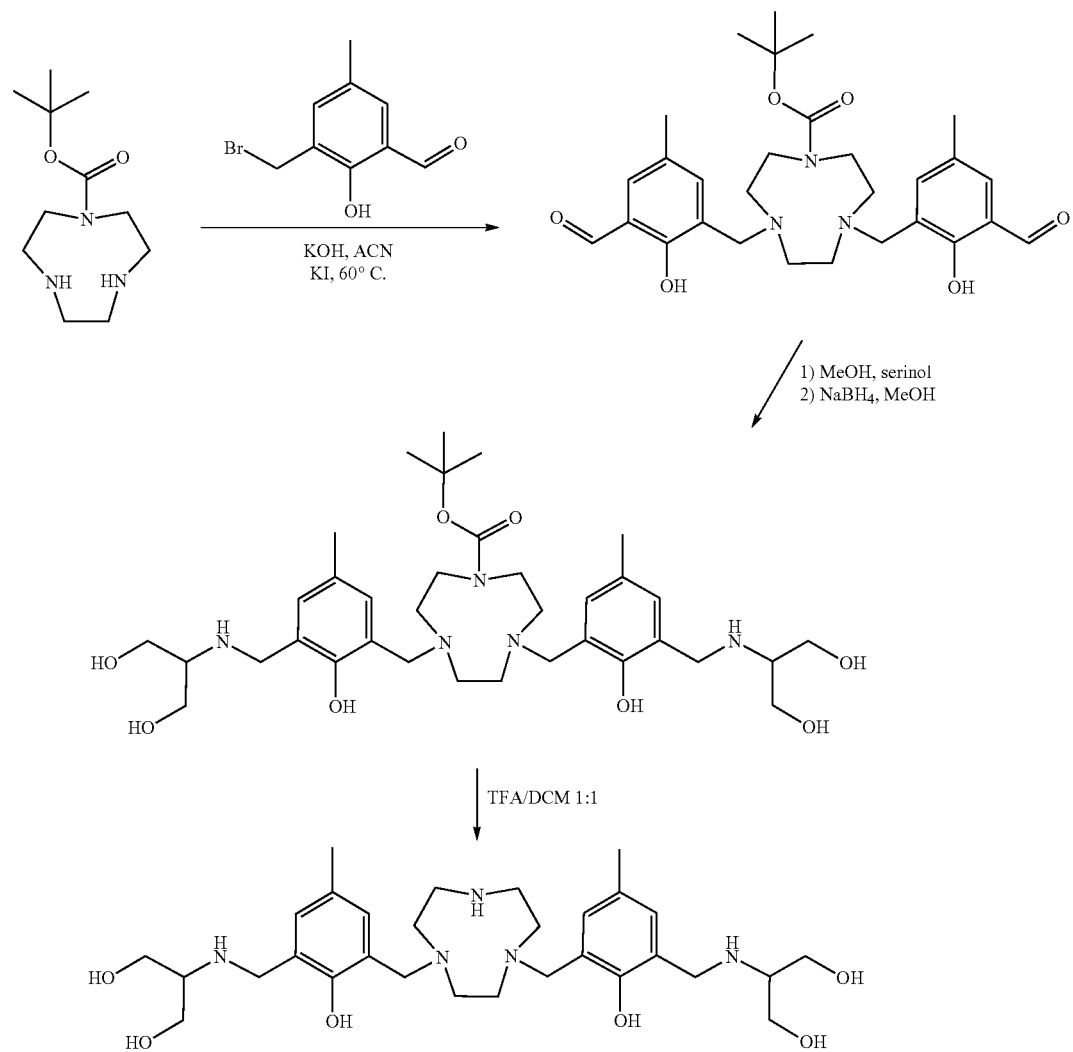

Details of the synthesis of the present Example are provided in the following paragraphs.

A) Synthesis of 1,4-bis-(3-formyl-2-hydroxy-5-methylbenzyl)-7-tert-butyloxycarbonyl-1,4,7-triazacyclononane 1-tert-butyloxycarbonyl-1,4,7-Triazacyclononane (0.122 g, 0.53 mmol) was dissolved in 3 ml of acetonitrile and KI (0.009 g, 0.053 mmol) and K$_2$CO$_3$ (0.207 g, 1.59 mmol)

$^1$H NMR (500 MHZ, CDCl$_3$): δ=1.44 (s, 9H, C—(CH$_3$)$_3$), 2.29/2.31 (s, 3H, CH$_3$Ph), 2.75-2.88 (m, 8H, CH$_2$—N), 3.25-3.30 (m, 4H, CH$_2$—N), 3.80/3.83 (s, 4H, N—CH$_2$Ph), 7.37/7.39 (s, 2H, ArH), 7.31/7.42 (s, 2H, ArH), 10.13/10.22 (s, 2H, CHO). $^{13}$C NMR (125 MHZ, CDCl$_3$): δ=20.4 (Ph-CH$_3$), 28.6 (C—(CH$_3$)$_3$), 52.1/52.6 (CH$_2$—N), 53.4 (CH$_2$—N), 55.1/55.5 (CH$_2$—N), 57.0/57.9 (N—CH$_2$Ph), 79.8 (O—C—(CH$_3$) 3), 121.6/121.9 (N—CH$_2$—C—CH), 125.4/125.8 (CH$_3$—C—CH—C), 128.5 (C—CHO), 129.4/130.2 (CH—C—CH), 137.6/138.1 (CH$_2$—C—CH—C—

CH$_3$), 155.3 (N—C=O), 158.8/159.2 (C—OH), 193.2/194.0 (C—CHO). ESI-MS (m/z): 526.3 (M+H$^+$) (calc. for C$_{29}$H$_{39}$N$_3$O$_6$:525.6).

B) Synthesis of 1,4-bis-{[3-(N-1,3-dihydroxypropan-2-yl)aminomethyl]-2-hydroxy-5-methylbenzyl}-7-tert-butyloxycarbonyl-1,4,7-triazacyclononane 1,4-bis-(3-formyl-2-hydroxy-5-methylbenzyl)-7-tert-butyloxycarbonyl-1,4,7-triazacyclononane (0.104 g, 0.20 mmol) was dissolved in 1 ml of MeOH and excess 2-Amino-1,3-propanediol (0.054 g, 0.60 mmol) was added. The solution was stirred at room temperature for 1 h. The imine intermediate was checked by MS spectrometry: ESI-MS (m/z): 672.4 (M+H$^+$) (calculated for C$_{35}$H$_{53}$N$_5$O$_8$:671.8) and the mixture was used without purification. The solution was cooled to 0° C. and sodium borohydride (0.030 g, 0.79 mmol) was slowly added in portions. The reaction mixture was then stirred for 3 hours at room temperature. The reducing agent was quenched by adding dropwise 2 ml of MeOH, waiting 15 minutes and, finally, the precipitate was removed by filtration. The final product was characterized by HPLC-MS (XBridge Phenyl 3.5 μm (4.6×150 mm); A=H$_2$O/0.1% TFA; B=ACN; flow=1 mL/min; 0-1 min=10% B; 1-15 min=from 10% to 100% B; 15-19 min=100% B; 19-20 min=from 100% to 10% B). Retention time: 8.50 minutes.

$^1$H NMR (500 MHZ, CDCl$_3$): δ=1.45 (s, 9H, C—(CH$_3$)$_3$), 2.21 (s, 6H, CH$_3$Ph), 2.56-2.93 (bs, 12H, CH$_2$—N), 2.93 (m, 2H, N—CH—CH$_2$—), 3.58 (m, 8H, N—CH—CH$_2$—), 3.65 (m, 4H, N—CH$_2$Ph), 3.72 (m, 4H, Ph-CH$_2$—N), 6.88-6.89 (bs, 4H, ArH). $^{13}$C NMR (125 MHZ, CDCl$_3$): δ=20.9 (Ph-CH$_3$), 27.6 (C—(CH$_3$)$_3$), 48.3 (CH$_2$—N), 54.1 (Ph-CH$_2$—N), 56.9 (CH$_2$—N), 61.0 (N—CH$_2$Ph), 63.3 (N—CH—CH$_2$—OH), 66.6 (N—CH—CH$_2$—OH), 79.8 (O—C—(CH$_3$)$_3$), 123.6 (N—CH$_2$—C—), 125.3 (C—CH$_2$—N), 127.1 (C—CH$_3$), 128.7 (—CH), 129.4 (—CH), 154.6 (—C=O), 155.6 (—C—OH). ESI-MS (m/z): 676.4 (M+H$^+$) (calc. for C$_{33}$H$_{57}$N$_5$O$_8$:675.8).

C) Synthesis of Compound 4 (2,2'-{1,4,7-triazonane-1,4-diylbis[methylene(2-hydroxy-5-methyl-3,1-phenylene)methyleneazanediyl]}di(propane-1,3-diol)

1,4-bis-{[3-(N-1,3-dihydroxypropan-2-yl)aminomethyl]-2-hydroxy-5-methylbenzyl}-7-tert-butyloxycarbonyl-1,4,7-triazacyclononane (0.92 g, 0.16 mmol) was dissolved in a 1:1 mixture of TFA and CH$_2$Cl$_2$ (4 mL) and the mixture was stirred at room temperature for 3 h. The solvent was evaporated under reduced pressure and the residue was dissolved in water and the solution filtrate with 0.2 μm filter to remove solid residues. The product was purified using semi-preparative HPLC-MS and obtained after lyophilization as a white monotrifluoroacetate salt (0.16 g, 53%). XBridge Prep Phenyl OBD 5 μm (19×100 mm); A=H$_2$O/0.1% TFA; B=ACN; flow=20 mL/min; 0-1 min=1% B; 1-6 min=from 1% to 100% B; 6-7 min=100% B; 7-9 min=100% B; 9-10 min=from 100% to 1% B; 10-12 min=1% B). The final product was characterized by HPLC-MS (XBridge Phenyl 3.5 μm (4.6×150 mm); A=H$_2$O/0.1% TFA; B=ACN; flow=1 mL/min; 0-1 min=1% B; 1-15 min=from 1% to 100% B; 15-19 min=100% B; 19-20 min=from 100% to 1% B). Retention time: 9.08 minutes.

$^1$H NMR (500 MHz, D$_2$O): δ=2.17 (s, 6H, C—CH$_3$), 2.93 (bs, 4H, CH$_2$—N), 3.26 (quint, 2H, J=,N—CH—CH$_2$), 3.33 (m, 4H, CH$_2$—N), 3.37 (m, 4H, CH$_2$—N), 3.67-3.80 (m, 8H, N—CH—CH$_2$), 3.99 (s, 4H, N—CH$_2$Ph), 4.26 (s, 4H, Ph-CH$_2$—N—CH), 7.07 (s, 2H, ArH), 7.19 (s, 2H, ArH). $^{13}$C NMR (125 MHZ, D$_2$O): δ=19.4 (Ph-CH$_3$), 42.6 (CH$_2$—N), 44.9 (Ph-CH$_2$—N), 49.1 (CH$_2$—N), 54.8 (N—CH$_2$Ph), 57.5 (N—CH—CH$_2$—OH), 59.7 (N—CH—CH$_2$—OH), 120.6 (N—CH$_2$—C—), 121.8 (C—CH$_2$—N), 132.5 (C—CH$_3$), 133.5 (—CH), 134.4 (—CH), 151.2 (—C—OH). ESI-MS (m/z): 576.4 (M+H$^+$) (calc. for C$_{30}$H$_{49}$N$_5$O$_6$: 575.7).

Example 4—Synthesis of Compound 57

The synthesis of Compound 57 was carried out according to the following Scheme 11:

Scheme 11

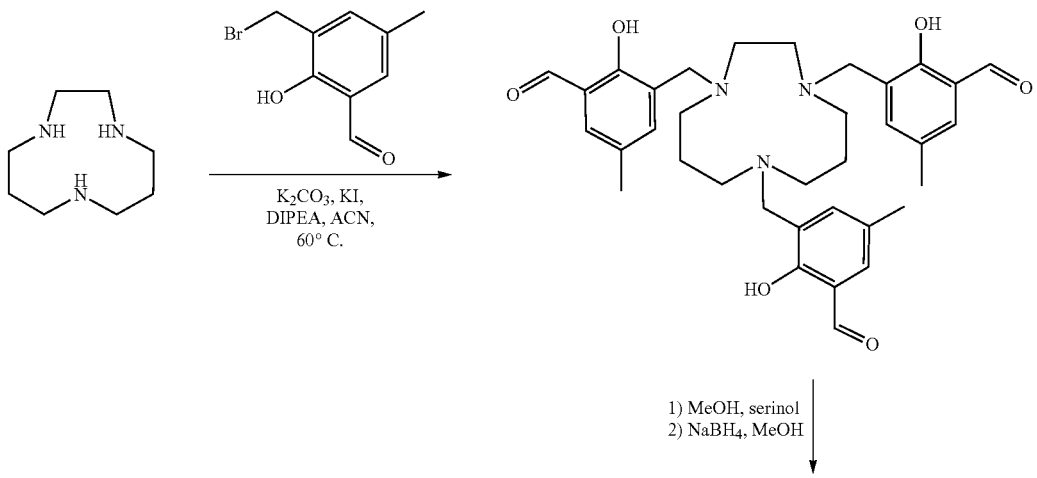

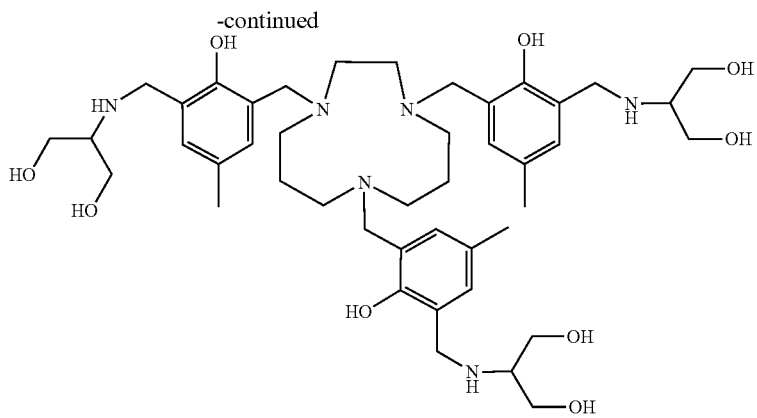

Synthesis of 2,2',2"-{1,4,8-triazonane-1,4,8-triyltris[methylene(2-hydroxy-5-methyl-3,1-phenylene)methyleneazanediyl]}tri(propane-1,3-diol) (Compound 57)

1,4,8-Triazacycloundecane (0.05 g, 0.32 mmol, TACUD) was dissolved in 1.5 ml of acetonitrile and KI (0.005 g, 0.032 mmol) and $K_2CO_3$ (0.176 g, 1.27 mmol) were added. 2-hydroxy-3-bromometyl-5-methylbenzaldehyde (0.291 g, 1.27 mmol), dissolved in 3 ml of an acetonitritrile/dichloromethane 1:1 solution, was added dropwise to the solution. The reaction mixture was heated to 60° C. and stirred for 4 h. Then, diisopropylethylamine (DIPEA 57 μL, 0.32 mmol) was added and the reaction mixture was stirred at 60° C. for 27 h. The solvent was removed under reduced pressure. Then, the product was dissolved in 20 ml of dichloromethane and washed with water (10 ml×2) and brine (10 ml×1); the organic phase was anhydrified with sodium sulphate, filtered and the solvent was evaporated. The product was characterized by UPLC-MS. (Acquity UPLC BEH C18 1.7 μm (2.1×50 mm); A=$H_2O$/0.1% TFA; B=ACN/0.1% TFA; flow=0.4 mL/min; 0-14 min=from 30% to 100% B; 14-15 min=100% B); retention time: 4.50 minutes. ESI-MS (m/z): 602.5 (M+H$^+$) (calculated for $C_{35}H_{43}N_3O_6$:601.7).

The product was used for the next step without further purification. Thus, the solid was dissolved in 20 ml of MeOH and excess 2-Amino-1,3-propanediol (0.118 g, 1.29 mmol), dissolved in 5 ml of methanol anhydrous, was added. The solution was stirred at room temperature overnight. The imine intermediate was checked by MS spectrometry: ESI-MS (m/z): 822.0 (M+H$^+$) (calculated for $C_{44}H_{64}N_6O_9$: 822.3). The solution was cooled to 0° C. and sodium borohydride (0.147 g, 3.87 mmol) was slowly added in portions. The reaction mixture was then stirred 48h at room temperature. The excess of reducing agent was then quenched by adding dropwise 1 ml of $H_2O$ and the solvent was removed under reduced pressure. The product was redissolved in 20 ml of ethanol the precipitate was removed by filtration. The solvent was removed under reduced pressure and the crude product was purified by semi-preparative HPLC-MS (XBridge Prep Phenyl OBD 5 μm (19×100 mm); A=$H_2O$/0.1% TFA; B=MeOH; flow=8 mL/min; 0-4 min=20% B; 4-10 min=from 20% to 40% B; 10-11 min=100% B; 11-14 min=100% B; 14-15 min=from 100% to 20% B). The final product (58 mg, 0.07 mmol, 22% yield) was characterized by UPLC-MS (Acquity UPLC BEH C18 1.7 μm (2.1×50 mm); A=$H_2O$/0.1% TFA; B=ACN/0.1% TFA; flow=0.4 mL/min; 0-14 min=from 2% to 100% B; 14-15 min=100% B); retention time: 3.47 minutes. ESI-MS (m/z): 828.3. (M+H$^+$) (calculated for $C_{44}H_{70}N_6O_9$: 827.1).

$^1$H NMR ($D_2O$, 500 MHz, pD=2): δ (ppm)=2.05 (br, $CH_2CH_2CH_2$, 4H), 2.20 (s, —$CH_3$, 9H), 3.01 (br, $NCH_2CH_2N$ macrocycle, 4H), 3.32 (m, —NH—CH—$CH_2$—OH, 3H), 3.65-3.70 (m, —CH—$CH_2$—OH, 6H), 3.72-3.82 (m, —CH—CH'$_2$—OH, 6H), 3.9 (br, $NCH_2CH_2CH_2$ macrocycle, 8H), 4.25, 4.30 (s, —N—$CH_2$-Ph-, 12H), 7.21 (s, —CH, 3H), 7.28 (s, —CH, 3H). $^{13}$C NMR ($D_2O$, 125 MHz): δ (ppm)=19.5 (—$CH_3$—), 20 (br, $CH_2CH_2CH_2$), 45.1 (—$CH_2$—NH-Ph), 54 (br, N—$CH_2$ macrocycle), 57.2 (—CH—$CH_2$—OH—), 59.8 (N—CH—$CH_2$—OH—), 118.2 ($C_{Ar}$), 120.5 ($C_{Ar}$), 132.8 (ArH), 135.6 (ArH), 137.5 ($C_{Ar}$), 154.1 (—$C_{Ar}$—OH).

Example 5—Synthesis of Compound 60

The synthesis of Compound 60 was carried out according to the following Scheme 12:

Scheme 12
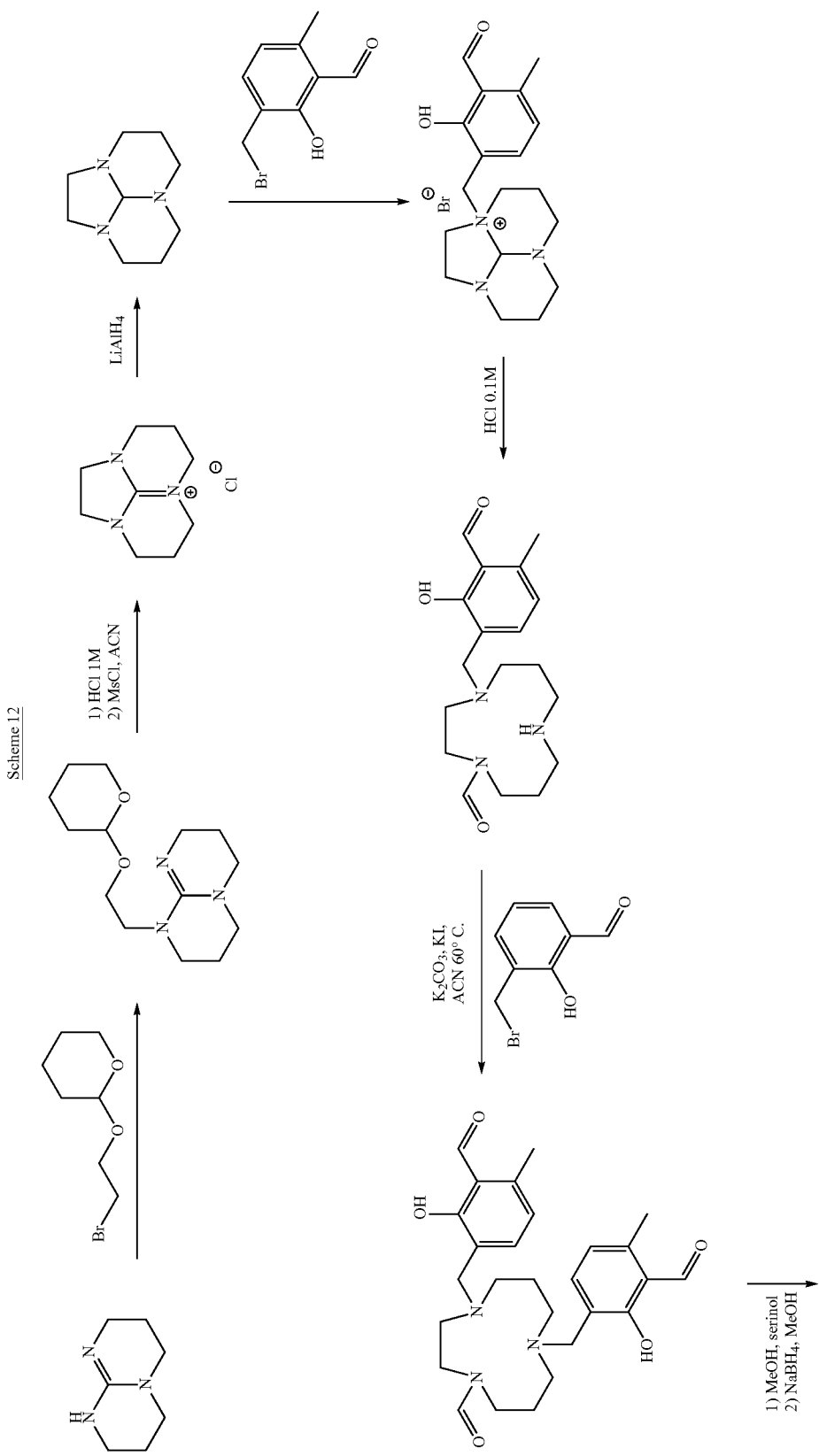

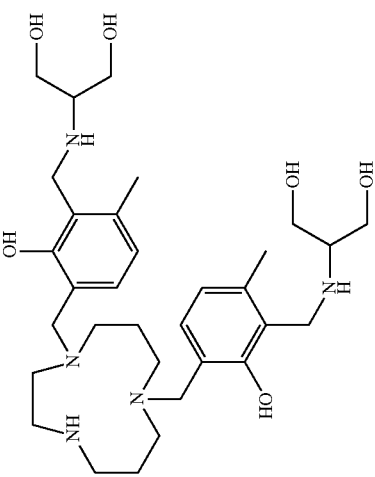
-continued
↑ HCl 4M
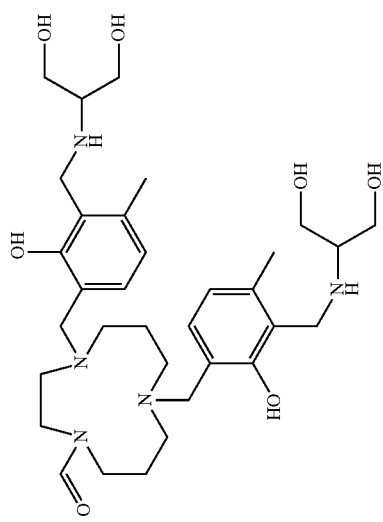

A) 1,5,7-Triazabicyclo[4.4.0]dec-5-ene (340 mg, 2.17 mmol) was dissolved in anhydrous THF (5.0 mL). The solution was put in an ice bath and NaH (221 mg, 1.7 eq) was added; the mixture was stirred under nitrogen atmosphere for 20 min. 2-(2-bromoethoxy)-tetrahydropyran (680 mg, 1.5 eq) dissolved in 5.0 ml of anhydrous THF was added, then the mixture was stirred for 48 h at room temperature under nitrogen atmosphere. The reaction was quenched with EtOH (2.0 mL), and stirred for further 1 h; finally, the mixture was filtered, and the solvent evaporated. The product was used without further purification. Crude product: 921 mg ESI$^+$ MS: m/z=268.4 [MH$^+$], (calculated for $C_{14}H_{25}N_3O_2$:267.4).

B) 7-(2-(2-tetrahydropiranoxy)ethyl)-1,5,7-triazabicyclo[4.4.0]dec-5-ene (921 mg) was dissolved in HCl 1M (15.0 mL), then the mixture was stirred at room temperature for 6 h. NaOH pellets were added to reach a pH value >11. The solvent was evaporated, and the product was redissolved in DCM, filtered and dried. This intermediate was used without further purification (663 mg, raw). The solid was dissolved in DCM anhydrous (15.0 mL) and put in an ice bath. Et$_3$N (0.626 mL, 2.5 eq) and mesyl chloride (0.541 mL, 1.2 eq) were added to the mixture, which was then stirred at room temperature under nitrogen atmosphere for 1 h. The reaction was quenched with deionized water, and stirred for further 10 min. The solvent was removed under reduced pressure and the product was used without further purification. ESI$^+$ MS: m/z=166.8 [M$^+$] (calculated for $C_9H_{16}N_3^+$: 166.2).

C) The product obtained in the previous step was dissolved in anhydrous THF (20.0 mL); the solution was cooled in an ice bath, and LiAlH$_4$ was added (3.25 ml of 1 M solution in THF, 1 eq). The mixture was stirred under nitrogen atmosphere for 1.5 h, then the reaction was quenched with MeOH (2.0 mL), and the stirring was maintained for about 15 min (until the end of effervescence). The solvent was removed under reduced pressure. The product was dissolved in DCM (35 mL) and washed with 1M Na$_2$CO$_3$ (3×10 mL); the organic phase was anhydrified with Na$_2$SO$_4$, filtered and the solvent was evaporated. Crude product: 350 mg. ESI$^+$ MS: m/z=168.2 [MH$^+$](calculated for $C_9H_{17}N_3$: 167.2).

D) The tricyclic orthoamide (350 mg, 2.09 mmol) was dissolved in ACN (30 mL), then 3-bromomethyl-5-methyl-2-hydroxybenzaldehyde (527 mg, 1.1 eq) was added. The mixture was stirred overnight at room temperature. The solvent was then removed under reduced pressure. The product was confirmed by HPLC-MS analysis (Waters XBridge Phenyl 3.5 μm 4.6×150 mm), A=H$_2$O; B=MeOH; flow=1 mL/min; 0-2 min=15% B; 2-16 min=from 15% to 100% B; 16-19 min=100% B; 19-20 min=from 100% to 15% B). Retention time: 14.8 minutes. ESI$^+$ MS: m/z=316.4 [M$^+$] (calculated for $C_{18}H_{26}N_3O_2+$: 316.2). The product was purified by flash chromatography (Sepachrom Purezza Phenyl 25μ 15 g), A=H$_2$O; B=MeOH; flow=15 mL/min; 1 column volume (CV) 40% B; 10 CV from 40 to 100% B; 2 CV 100% B. Retention time: 3.7 minutes. 11 mg of pure product were obtained.

E) The mono-alkylated product (11 mg, 0.028 mmol) was dissolved in HCl 0.1 M (3.0 mL) and the mixture was stirred at room temperature for 24 h. The acid was neutralized with NaOH 2 M (0.150 mL) and the solvent was removed under reduced pressure. The product was used without further purification. The product was confirmed by HPLC-MS analysis (Waters XBridge Phenyl 3.5 μm 4.6×150 mm), A=H$_2$O; B=MeOH; flow=1 mL/min; 0-2 min=10% B; 2-16 min=from 10% to 100% B; 16-19 min=100% B; 19-20 min=from 100% to 10% B). Retention time: 10.3 minutes. ESI$^+$ MS: m/z=334.5 [MH$^+$] (calculated for $C_{18}H_{27}N_3O_3$: 333.5).

F) The crude product (11 mg, 0.028 mmol) was dissolved in ACN (5.0 mL); then K$_2$CO$_3$ (12 mg, 3 eq) and 3-bromomethyl-5-methyl-2-hydroxybenzaldehyde (9 mg, 1.5 eq) were added. The mixture was stirred at room temperature for 6 h and then the solvent was evaporated under reduced pressure. The product (15 mg) was used for the next step without further purification. ESI$^+$ MS: m/z=482.6 [MH$^+$] (calculated for $C_{27}H_{35}N_3O_5$:481.6).

G) The previous intermediate (15 mg, 0.031 mmol) was dissolved in MeOH anhydrous (5.0 mL), then serinol (7 mg, 2.5 eq) was added. The mixture was stirred at room temperature overnight. NaBH$_4$ (6 mg, 5 eq) was added (0° C., iced bath) and stirred for 2 h. The reaction was quenched with deionized water (few drops), and stirred for further 30 min. The solvent was evaporated, the product was redissolved in EtOH, filtered and dried again under reduced pressure. The product (41 mg) was used without further purification. UPLC-MS (Acquity UPLC BEH C18 1.7 μm (2.1×50 mm); A=H$_2$O/0.1% TFA; B=ACN/0.1% TFA; flow=0.4 mL/min; 0-14 min=from 2% to 100% B; 14-15 min=100% B); retention time: 3.12 minutes. ESI$^+$ MS: m/z=632.8 [MH$^+$] (calculated for $C_{33}H_{53}N_5O_7$:631.8).

H) The previous intermediate was dissolved in HCl 4 M (1.0 mL) and stirred for 24 h at room temperature. The solvent was then removed under reduced pressure to obtain 39 mg of crude. UPLC-MS (Acquity UPLC BEH C18 1.7 μm (2.1×50 mm); A=H$_2$O/0.1% TFA; B=ACN/0.1% TFA; flow=0.4 mL/min; 0-14 min=from 2% to 100% B; 14-15 min=100% B); retention time: 3.34 minutes. ESI$^+$ MS: m/z=604.8 [MH$^+$] (calculated for $C_{32}H_{53}N_5O_6$:603.8).

$^1$H NMR (D$_2$O, 500 MHz): δ (ppm)=2.12, 2.19 (s, —CH$_3$, 6H), 2.0 (br, CH$_2$CH$_2$CH$_2$, 4H), 3.0-3.2 (br, NCH$_2$CH$_2$N macrocycle, 8H), 3.29 (m, —NH—CH—CH$_2$—OH, 2H), 3.6 (br, NCH$_2$CH$_2$CH$_2$ macrocycle, 4H), 3.71-3.74 (m, —CH—CH$_2$—OH, 4H), 3.81-3.85 (m, —CH—CH'$_2$—OH, 4H), 4.25, 4.29 (s, —N—CH$_2$-Ph-, 8H), 6.90 (s, —CH, 2H), 7.04 (s, —CH, 2H). $^{13}$C NMR (D$_2$O, 125 MHZ): δ (ppm)=19.4 (—CH$_3$—), 20 (br, CH$_2$CH$_2$CH$_2$), 45.6 (—CH—CH$_2$—OH—), 55, 56 (br, N—CH$_2$ macrocycle), 57.4 and 57.6 (—NH—CH—CH$_2$—OH), 59.5 (—CH$_2$—NH—C), 70.7 (—N—CH$_2$-Ph-), 119.4 ($C_{Ar}$), 128.2 ($C_{Ar}$), 130.2 (ArH), 131.8 (ArH), 132.3 ($C_{Ar}$), 149.9 (—$C_{Ar}$—OH).

Example 6—Synthesis of Compound 61

The synthesis of Compound 61 was carried out according to the following Scheme 13:

Scheme 13

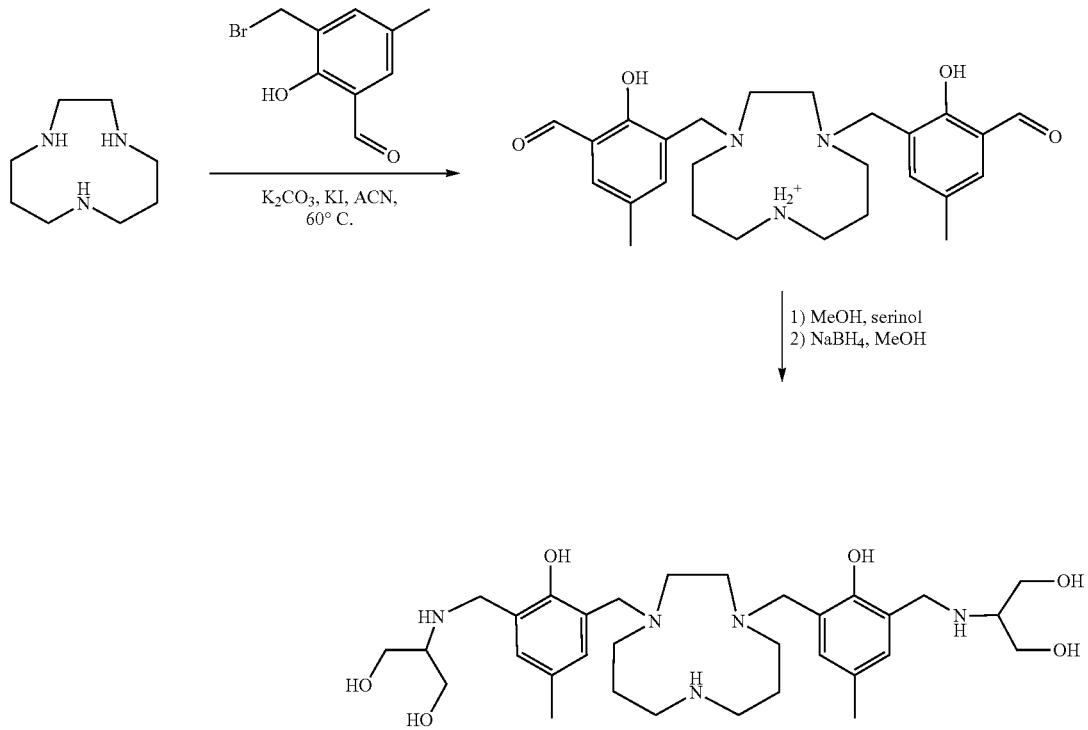

1,4,8-Triazacycloundecane (0.030 g, 0.192 mmol, TACUD) was dissolved in 1.5 ml of acetonitrile and KI (0.003 g, 0.019 mmol) and $K_2CO_3$ (0.066 g, 0.48 mmol) were added. 2-hydroxy-3-bromometyl-5-methylbenzaldehyde (0.11 g, 0.48 mmol), dissolved in 3 ml of an acetonitritrile/dichloromethane 1:1 solution, was added dropwise to the solution. The reaction mixture was heated to 60° C. and stirred for 24 h. Then, the solvent was removed under reduced pressure to obtain 0.16 g of crude product. The product was characterized by UPLC-MS. (Acquity UPLC BEH C18 1.7 μm (2.1×50 mm); A=$H_2O$/0.1% TFA; B=ACN/0.1% TFA; flow=0.4 mL/min; 0-14 min=from 30% to 100% B; 14-15 min=100% B); retention time: 1.44 minutes. ESI-MS (m/z): 454.5 (M+H$^+$) (calculated for $C_{26}H_{36}N_3O_4$:454.6). The product was used for the next step without further purification. Thus, the solid was dissolved in 15 ml of MeOH and excess 2-Amino-1,3-propanediol (0.096 g, 1.05 mmol), dissolved in 5 ml of methanol anhydrous, was added. The solution was stirred at room temperature for overnight. The imine intermediate was checked by MS spectrometry: ESI-MS (m/z): 600.4 (M+H$^+$) (calculated for $C_{32}H_{49}N_5O_6$:599.8). The solution was cooled to 0° C. and $NaBH_4$ (0.12 g, 3.2 mmol) was slowly added in portions. The reaction mixture was then stirred for 48 h at room temperature. The reducing agent was quenched by adding dropwise 1 ml of water and then the solvent was removed under reduced pressure. The product was redissolved in 20 ml of ethanol, the precipitate was removed by filtration and finally the solvent was removed under reduced pressure. The crude product was purified by semi-preparative HPLC-MS (XBridge Prep Phenyl OBD 5 μm (19×100 mm); A=$H_2O$/ 0.1% TFA; B=MeOH; flow=8 mL/min; 0-3 min=30% B; 3-6 min=from 30% to 60% B; 6-11 min=100% B; 11-14 min=100% B; 14-15 min=from 100% to 30% B;). The final product (72 mg, 0.12 mmol, 62% yield) was characterized by UPLC-MS (Acquity UPLC BEH C18 1.7 μm (2.1×50 mm); A=$H_2O$/0.1% TFA; B=ACN/0.1% TFA; flow=0.4 mL/min; 0-14 min=from 30% to 100% B; 14-15 min=100% B); retention time: 3.17 minutes. ESI-MS (m/z): 604.5 (M+H$^+$) (calculated for $C_{32}H_{53}N_5O_6$:603.8).

$^1$H NMR ($D_2O$, 500 MHZ): δ (ppm)=2.16 (s, —$CH_3$, 6H), 2.20 (br, $CH_2CH_2CH_2$, 4H), 3.20 (br, $NCH_2CH_2N$ macrocycle, 4H), 3.25 (m, —NH—CH—$CH_2$—OH, 2H), 3.69-3.74 (m, —CH—$CH_2$—OH, 4H), 3.79-3.84 (m, —CH—CH'$_2$—OH, 4H), 4.25, 4.30 (s, 8H, Ph-$CH_2$—N), 4.3 (br, $NCH_2CH_2CH_2$ macrocycle, 8H), 7.06 (s, —CH, 2H), 7.09 (s, —CH, 2H). $^{13}$C NMR ($D_2O$, 125 MHZ): δ (ppm)=19 (br, $CH_2CH_2CH_2$), 19.3 (—$CH_3$—), 45.3 (—N—$CH_2$-Ph-), 56 (br, N—$CH_2$ macrocycle), 57.4 and 57.6 (—NH—CH—$CH_2$—OH), 59.5 (—CH—$CH_2$—OH), 118.6 (CAP), 124.0 ($C_{Ar}$), 131.0 (ArH), 132.0 (ArH), 132.4 ($C_{Ar}$), 151.2 (—$C_{Ar}$—OH).

Example 7—Synthesis of Compound 112

The synthesis of Compound 112 was carried out according to the following Scheme 14:

Scheme 14

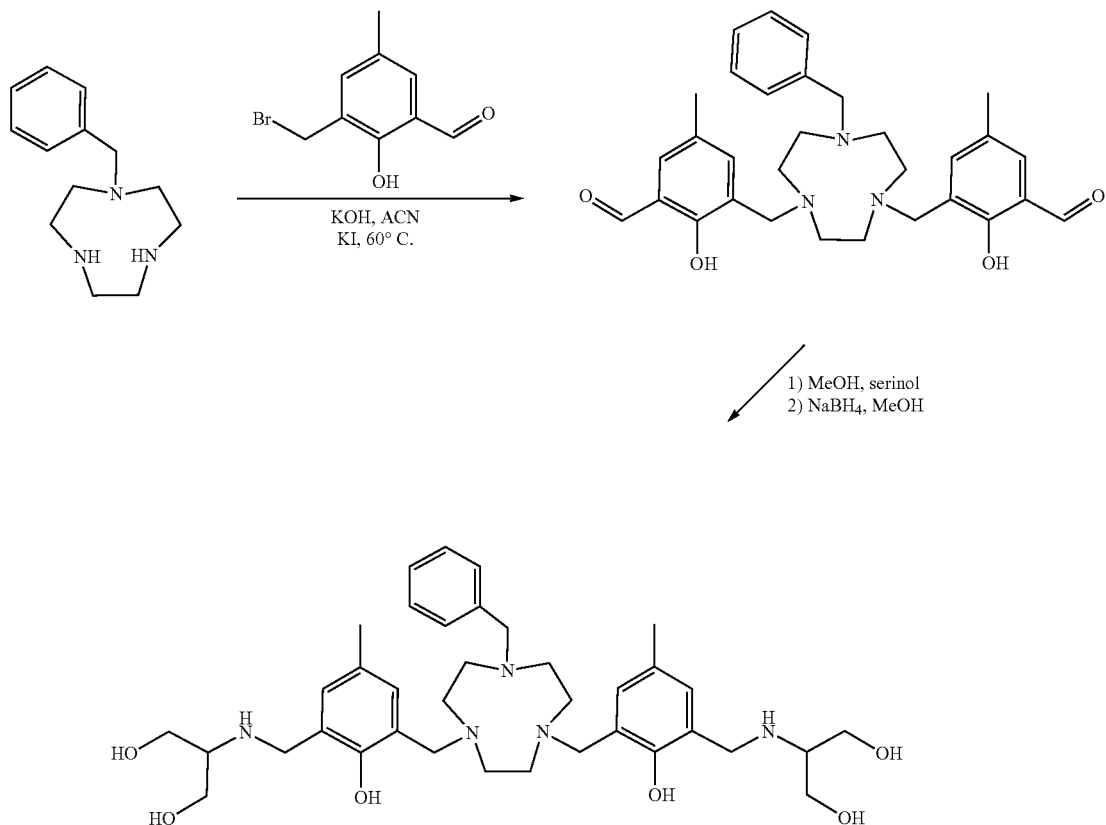

Details of the synthesis of the present Example are provided herein below.

1-benzyl-1,4,7-Triazacyclononane (0.08 g, 0.036 mmol) was dissolved in 3 ml of acetonitrile and KI (0.006 g, 0.036 mmol) and $K_2CO_3$ (0.151 g, 1.09 mmol) were added. 2-hydroxy-3-chlorometyl-5-methylbenzaldehyde (0.251 g, 1.09 mmol), dissolved in 1 ml of acetonitrile, was added dropwise to the solution. The reaction mixture was heated to 60° C. and stirred overnight. Then, the solution was filtered, and the crude product was precipitated in diethyl ether. The crude 1,4-bis-(3-formyl-2-hydroxy-5-methylbenzyl)-7-benzyl-1,4,7-triazacyclononane (0.19 g, 0.37 mmol) obtained in the previous step was then dissolved in 1 ml of MeOH and excess 2-Amino-1,3-propanediol (0.10 g, 1.12 mmol) was added. The solution was stirred at room temperature for 1 h. The imine intermediate was checked by MS spectrometry: ESI-MS (m/z): 662.4 (M+H$^+$) (calculated for $C_{37}H_{51}N_5O_6$: 661.8) and the mixture was used without purification. The solution was cooled to 0° C. and NaBH$_4$ (0.06 g, 1.5 mmol) was slowly added in portions. The reaction mixture was then left stirring for 3 hours. The reducing agent was quenched by adding dropwise 2 ml of MeOH, waiting 15 minutes and, finally, the precipitate was removed by filtration. The final product was characterized by HPLC-MS (XBridge Phenyl 3.5 μm (4.6×150 mm); A=H$_2$O/0.1% TFA; B=ACN; flow=1 mL/min; 0-2 min=10% B; 2-16 min=from 10% to 100% B; 16-19 min=100% B; 19-20 min=from 100% to 10% B). Retention time: 8.80 minutes.

The solvent was removed under reduced pressure and the crude product was purified by semi-preparative HPLC-MS (XBridge Prep Phenyl OBD 5 μm (19×100 mm); A=H$_2$O/0.1% TFA; B=ACN; flow=20 mL/min; 0-1 min=90% A; 1-9 min=from 10% to 54% B; 9-11 min=from 54% to 100% B; 11-13 min=100% B; 13-14 min=from 100% to 10% B; 14-16 min=10% B). Yield: 82%. $^1$H NMR (500 MHZ, CDCl$_3$): δ=2.34 (s, 6H, C—CH$_3$), 2.87 (bs, 8H, CH$_2$—N), 3.03 (m, 4H, CH$_2$—N), 3.81 (m, 2H, N—CH—CH$_2$), 3.87-3.88 (m, 8H, N—CH—CH$_2$), 4.05 (s, 2H, N—CH$_2$—Bz), 4.43 (s, 4H, N—CH$_2$Ph), 4.97 (s, 4H, Ph-CH$_2$—N—CH), 7.23 (s, 2H, ArH), 7.32 (s, 2H, ArH), 7.38 (s, 5H, ArH). $^{13}$C NMR (125 MHZ, CDCl$_3$): δ=19.1 (Ph-CH$_3$), 44.9 (Bz-CH$_2$—N), 49.3 (Ph-CH$_2$—N), 49.6 (CH$_2$—N), 49.9 (CH$_2$—N), 54.9 (N—CH$_2$Ph), 57.7 (N—CH—CH$_2$—OH), 60.2 (N—CH—CH$_2$—OH), 115.1 (Bz-C—CH$_2$—N), 117.4 (Bz-CH), 120.3 (Bz-CH), 122.9 (Bz-CH), 128.3 (C—CH$_3$), 128.7 (—CH), 129.8 (—CH), 131.1 (—CH$_2$—C—COH), 131.1 (—C—CH$_2$—N—), 152.4 (—C—OH). ESI-MS (m/z): 666.4 (M+H$^+$) (calc. for $C_{37}H_5N_5O_6$: 665.9).

Example 8—Synthesis of Compound 177

The synthesis of Compound 177 was carried out as stated in Scheme 15 below, and according to the details as follows:

Scheme 15

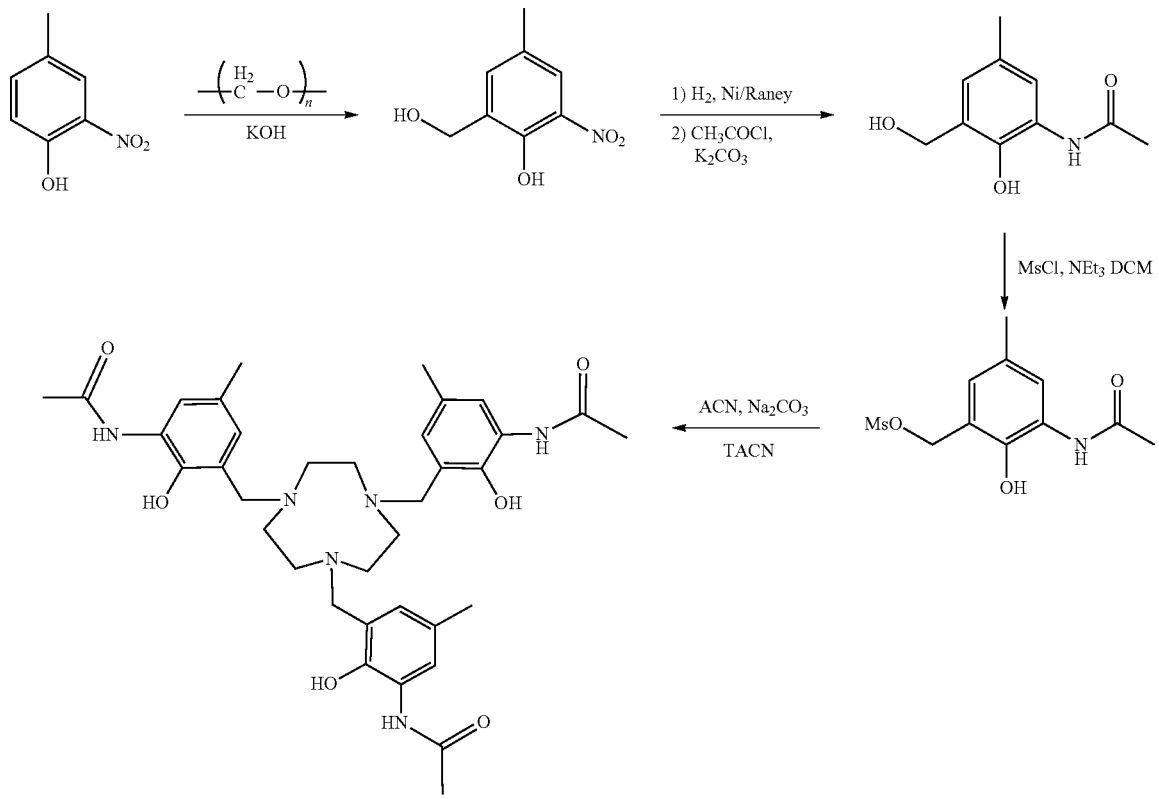

A) Synthesis of 2-hydroxymethyl-4-methyl-6-nitrophenol 4-methyl-2-nitrophenol (0.1 g, 0.65 mmol) was dissolved in 2 ml of KOH 4M and the temperature was settled at 80° C. When the temperature was reached, p-formaldehyde (0.029 g, 0.98 mmol) was added and the reaction mixture left under stirring for 48 h. The solution was neutralized with HCl and extracted with $H_2O$/DCM. Then, the organic phase was dried with $MgSO_4$, filtered and the solvent removed under reduced pressure to obtain a pale-yellow oil (0.106 g, 90% yield).

$^1$H NMR (500 MHZ, $CDCl_3$): δ=2.36 (s, 3H, —$CH_3$), 4.69 (s, 2H, —$CH_2$—), 7.54 (s, 1H, —CH), 7.90 (s, 1H, —CH), 10.86 (s, 1H, —COH). $^{13}$C NMR (125 MHZ, $CDCl_3$): δ=20.4 (Ph-$CH_3$), 60.4 (—$CH_2$), 124.9 (—CH), 128.6 (—$CCH_2$), 129.7 (—$CNO_2$), 134.2 (—$CCH_3$) 139.3 (—CH), 151.3 (—COH). MS calc. for $C_8H_9NO_4$: 183.05.

B) Synthesis of 3-hydroxymethyl-2-hydroxy-5-methylphenylacetamide 2-hydroxymethyl-4-methyl-6-nitrophenol (0.106 g, 0.58 mmol) was dissolved in 3 ml of acetonitrile and 20 w/w % Pd/C (0.014 g) was added and the suspension was stirred under $H_2$-atmosphere for 2 h at room temperature. The mixture was filtered with PTFE filter, in order to minimize the air-contact of the compound. Then, acetyl chloride was added (41 μl, 0.58 mmol) to the solution under $N_2$ atmosphere and the reaction mixture was stirred overnight. Finally, the solvent was removed under reduced pressure to obtain a pale yellow oil (34 mg, 30% yield).

$^1$H NMR (500 MHZ, $CDCl_3$): δ=2.13 (s, 3H, —$CH_3$), 2.14 (s, 3H, —$CH_3$), 4.65 (s, 2H, —$CH_2$—), 6.23 (s, 1H, —CH), 6.44 (s, 1H, —CH). MS calc. for $C_{10}H_{13}NO_3$: 195.2.

C) Synthesis of N,N',N''-{1,4,7-triazonane-1,4,7-triyltris[methylene(2-hydroxy-5-methyl-3,1-phenylene)]}triacetamide (Compound 177)

3-hydroxymethyl-2-hydroxy-5-methylphenylacetamide (0.017 g, 0.087 mmol) was dissolved in $CH_2Cl_2$ (2 mL) and triethylamine (159 μl, 0.013 g, 0.128 mmol) was added. Methansulphonyl chloride (89 μl, 0.015 g, 0.131 mmol) was added at 0° C. (ice bath) and the reaction mixture was stirred at room temperature for 1 h. The product was extracted washing the organic layer with 3x $H_2O$, and the organic phase dried with $MgSO_4$, filtered and the solvent removed under reduced pressure. This product was used without further purification. Thus, a solution of the mesylate in 1 ml of ACN was added dropwise to a solution of 1,4,7-triazacyclononane (1 mg, 0.01 mmol) and sodium carbonate (3 mg, 0.03 mmol) in ACN (1 mL). Then, the reaction mixture was stirred at room temperature overnight. The final compound was observed by ESI-MS (m/z): 661.4 (M+H$^+$) (calc. for $C_{29}H_{39}N_3O_6$:660.8).

Example 9—Fe(III) Complexation

Fe(III) chelates were prepared through complexation reaction, by dissolving the ligands obtained in Examples 1, 2, 7 and 8 in ethanol, and in Examples 3 to 6 in water, and then by adding $FeCl_3$ or $Fe(NO_3)_3$ with equimolar $Fe^{3+}$. The reaction was carried out at 298 K for 18 h. For the complexes obtained starting from Examples 1, 2, 7 and 8, the solvent was then removed, the product dissolved in water, and (for all the complexes) the pH of the solution was corrected to 8.5 with diluted NaOH in order to promote the precipitation of any excess of free $Fe^{3+}$.

Example 10—Relaxometric Analysis

The relaxivity values of some the complexes of the invention were evaluated by measuring them at 298 K at the magnetic fields that are relevant in clinical practice, namely at 1.5 and 3.0 T as follows. $^1$H NMRD profiles were measured in aqueous solution by using a variable field relaxometer equipped with an HTS-110 3T Metrology Cryogen-free Superconducting Magnet (Mede, Italy), operating in the overall range of proton Larmor frequencies of 20-120 MHZ (0.47-3.00 T). The measurements were performed using the standard inversion recovery sequence (20 experiments, 2 scans) with a typical 90° pulse width of 3.5 us and the reproducibility of the data was within ±0.5%. The temperature was controlled with a Stelar VTC-91 heater airflow. Additional points in the 0.01-10 MHZ frequency range were collected on a Fast-Field Cycling (FFC) Stelar SmarTracer Relaxometer. $T_1$ values at 500 MHz were collected with a Bruker NMR spectrometer operating at 11.7 T. Longitudinal and transversal relaxation rate values ($R_1$ and $R_2$) at 1.5 and 3.0 T in pure water and in reconstituted human serum (Seronorm matrix) were also measured at 298 and 310 K. All the experiments are repeated three times with a reproducibility of the data within ±0.5%. The concentration of $Fe^{3+}$ in the different solutions was determined by using bulk magnetic susceptibility (BMS) shift measurements performed at 11.7 T (D. F. Evans, J. Chem. Soc., 1959, 2003) and confirmed by ICP-MS analysis after mineralization of the samples with $HNO_3$ 65% at 408 K.

The relaxivity $r_1$ values of the Fe(III)-complexes of Compound 1 (concentration 0.40 mM), Compound 2 (concentration 0.60 mM), Compound 4 (concentration 0.65 mM), Compound 57 (concentration 0.50 mM), Compound 60 (concentration 0.47 mM), Compound 61 (concentration 0.60 mM), and Compound 112 (concentration 0.78 mM) at 1.5 and 3.0 T field strength, pH=7.4 and 310 K in 0.15 M NaCl, in 0.15 M NaCl and 25 mM $NaHCO_3$, and in Seronorm™ (lyophilized human serum) were determined as above described and are shown in Table 1.

TABLE 1

| | | $r_1$ [mM$^{-1}$ s$^{-1}$] | | |
|---|---|---|---|---|
| | | in NaCl 0.15M | in NaCl 0.15M ($HCO_3^-$ 25 mM) | in Seronorm ™ (+$HCO_3^-$ 25 mM) |
| Fe(III)-Cpd. 1 | 1.5 T | 1.50 | 1.52 | 1.50 |
| | 3.0 T | 1.56 | 1.65 | 1.55 |
| Fe(III)-Cpd. 2 | 1.5 T | 1.57 | 1.77 | 2.42 |
| | 3.0 T | 1.85 | 2.11 | 2.85 |
| Fe(III)-Cpd. 4 | 1.5 T | 2.92 | 2.94 | 3.17 |
| | 3.0 T | 3.43 | 3.46 | 3.82 |
| Fe(III)-Cpd. 57 | 1.5 T | 1.52 | 1.74 | 2.30 |
| | 3.0 T | 1.70 | 1.98 | 2.56 |
| Fe(III)-Cpd. 60 | 1.5 T | 1.46 | 1.49 | 1.87 |
| | 3.0 T | 1.55 | 1.58 | 1.98 |
| Fe(III)-Cpd. 61 | 1.5 T | 1.53 | 1.50 | 2.15 |
| | 3.0 T | 1.60 | 1.58 | 2.28 |
| Fe(III)-Cpd. 112 | 1.5 T | 2.45 | 2.63 | 2.90 |
| | 3.0 T | 3.04 | 3.20 | 3.47 |

In view of the data of Table 1, it can be seen that the complexes of the invention show high and suitable relaxivity $r_1$ values for MRI imaging, in particular at physiological conditions.

Moreover, it can be observed from Table 1 that the complexes of the invention do not substantially interact with proteins of the human serum, such as e.g. human serum albumin, because the relaxivity values in Seronorm™ (lyophilized human serum) are similar to the values obtained in the two other conditions, i.e. NaCl 0.15 M and NaCl 0.15 M ($HCO_3^-$ 25 mM).

For this reason, in vivo, the complexes of the invention could have a faster clearance and a homogeneous distribution into the organs and textiles, and thus could have a broader spectrum of MRI applications, compared to complexes interacting with proteins of the human serum.

Example 11—Thermodynamic Stability Analysis

To assess the thermodynamic stability of the Fe(III) complexes of the invention, as well as of comparative ones, the protonation constants of the respective ligands first, and then of the Fe(III) complexes, were determined by pH-potentiometry and/or by UV spectrophotometry. Finally, based on the protonation constants, the thermodynamic stability constant of the Fe(III) complexes of the invention were determined by observing the competition reaction between the Fe(III) complexes and the N,N'-bis(2-hydroxybenzyl)ethylenediamine-N,N'-diacetic acid (HBED) ligand using capillary zone electrophoresis (CZE) for Compound 2 and Vis spectrophotometry for Compound 4. A similar method to assess the thermodynamic stability of a different metallic complex was carried out in WO 2020/099398. HBED is the ligand with the following formula that forms a complex with Fe(III) having very low relaxivity ($r_1$ of 0.49 mM$^{-1}$·s$^{-1}$ at 60 MHZ, 40° C. in PBS buffer as mentioned in Bales et al., Contrast Media & Molecular Imaging, Volume 2019. Article ID 8356931)

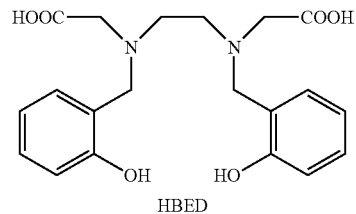 [SMILES: O=C(O)CN(CCN(CC(=O)O)Cc1ccccc1O)Cc1ccccc1O]

HBED

A) Determination of the Protonation Constants of the Ligands

Solid Fe(NO$_3$) 3 was dissolved in 0.1 M HNO$_3$ solution. The concentration of Fe(NO$_3$)$_3$ solution was determined by using standardized Na$_2$H$_2$EDTA in excess. The excess of the Na$_2$H$_2$EDTA was measured with a standardized ZnCl$_2$ solution and xylenol orange as indicator. The H$^+$ concentration of the Fe(NO$_3$)$_3$ solution was determined by pH potentiometric titration in the presence of Na$_2$H$_2$EDTA excess. The concentration of the ligands Compound 2, Compound 4, H$_3$NOTA (comparative-see formula below) and H$_4$HBED (comp.) was determined by pH-potentiometric titrations in the presence and absence of a 40-fold excess of Ca$^{2+}$. The pH-potentiometric titrations were made with standardized 0.2 M NaOH (concentration of the ligands was generally 0.002 M). For the pH measurements and titrations, Metrohm 888 Titrando titration workstation Metrohm-6.0234.110 combined electrode was used.

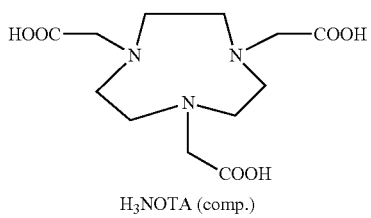 [SMILES: O=C(O)CN1CCN(CC(=O)O)CCN(CC(=O)O)CC1]

H₃NOTA (comp.)

The protonation constants ($K_i^H=[H_i\text{Ligand}]/([H_{i-1}\text{Ligand}]\times[H^+])$) of Compound 2, of NOTA (comparative) and of HBED (comparative) obtained by the pH potentiometric method above were later used for determining the protonation constants and the thermodynamic stabilities of the corresponding Fe(III) complexes.

The protonation constant of Compound 2 was confirmed by UV spectrophotometry analysis (with the instrument PerkinElmer Lambda 365 UV-Vis spectrophotometer) in the wavelength range of 210-390 nm ([Compound 2]=87 µM, 0.15 M NaClO₄, 25° C.). The deprotonation of the phenol-OH and isoserinol-NH₂⁺ groups of Compound 2 was investigated by spectrophotometry on the absorption band of the aromatic group of the ligand, following the absorbance values at 243 and 303 nm. The absorbance of the ligand is a combination of the absorption of each protonated species and expressed by the following equation (Beck, M. T. et al., Chemistry of Complex Equilibria, Akadémia Kiadó Budapest and Nostrand Reinhold Company Ltd. London, 1990):

$$A = \Sigma c_i \epsilon_i l$$

wherein A is the absorbance at a given wavelength, $c_i$, $\epsilon_i$ and l are the concentration, the molar absorptivity of the species and the path length of the cell, respectively. The absorbance values (A) have been fitted to the equation above (the concentration of the different protonated ligand has been expressed by the protonation constants $K_i^H$).

The protonation constants of Compound 4 have been determined by ¹H-NMR spectroscopy with Bruker Avance III (9.4 T) spectrometer, equipped with Bruker Variable Temperature Unit (BVT), Bruker Cooling Unit (BCU) and a BB inverse z gradient probe (5 mm) by recording the chemical shift variations of the non-labile protons as a function of pH at 25° C. in 0.15 M NaNO₃ solution. Since the protonation/deprotonation is fast on the NMR time scale, the chemical shifts of the observed signals represent a weighted average of the shifts of the different species with different protonation states and expressed by the following equation (Pagado, J. M.; Goldberg, D. E.; Fernelius, W. C.; J. Phys. Chem., 1961, 65, 1062.):

$$\delta_{H(obs)} = \Sigma c_i \delta_H^{HiL}$$

wherein $\delta_{H(obs)}$ is is the observed chemical shift of a given signal, $c_i$ and $\delta_H^{HiL}$ are the concentration and the chemical shift of the involved species, respectively. The observed chemical shift values ($\delta_{H(obs)}$) have been fitted to the equation above (the concentration of the different protonated ligand has been expressed by the protonation constants $K_i^H$).

B) Determination of the Protonation Constants of the Fe(III) Complexes

The protonation constants ($K_{MHiLigand}=[MH_i\text{Ligand}]/([MH_{i-1}\text{Ligand}]\times[H^+])$) of the Fe(III) complexes of Compound 2, of Compound 4, of NOTA (comparative), and of HBED (comparative) were determined by pH-potentiometric and/or by spectrophotometric studies.

In particular, the protonation constants of the Fe(NOTA) and Fe(HBED) complexes were determined using pH-potentiometry by titrating the pre-prepared complexes from pH=1.7 to pH=12.0 with 0.2 M NaOH([FeL]=0.002 M). For the pH measurements and titrations, Metrohm 888 Titrando titration workstation Metrohm-6.0234.110 combined electrode was used. Equilibrium measurements were carried out at a constant ionic strength (0.15 M NaNO₃ or NaClO₄) in 6 ml samples at 25° C. The solutions were stirred, and N₂ was bubbled through them. The titrations were made in the pH range of 1.7-12.0. KH-phthalate (pH=4.005) and borax (pH=9.177) buffers were used to calibrate the pH meter. For the calculation of [H⁺] from the measured pH values, the method disclosed in Irving et al. Anal. Chim. Acta, 1967, 38, 475-488 was used as follows: a 0.01M HNO₃ or HClO₄ solution was titrated with a standardized NaOH solution at 0.15 M NaNO₃ ionic strength. The differences (A) between the measured (pH$_{read}$) and calculated pH (−log [H⁺]) values were used to obtain the equilibrium H⁺ concentration from the pH values measured in the titration experiments (A=0.02 for 0.15 M NaNO₃, 0.01 for 0.15 M NaClO₄). For the equilibrium calculations, the stoichiometric water ionic product (pK$_w$) was also needed to calculate [OH⁻] values under basic conditions. The V$_{NaOH}$-pH$_{read}$ data pairs of the HNO₃—NaOH titration obtained in the pH range 10.5-12.0 were used to calculate the pK$_w$ value (pK$_w$=13.76).

The protonation constants of Fe(Compound 2) and Fe(Compound 4) complexes were determined by UV spectrophotometry analysis in the wavelength range of 210-700 nm ([Fe(Compound 2)]=43 µM, [Fe(Compound 4)]=100 µM, 0.15 M NaClO₄, 25° C.) according to the method disclosed in Example 11A above.

The protonation constants of the Fe(III) complexes of Compound 2, of Compound 4, of NOTA (comparative) and of HBED (comparative) were later used for determining the thermodynamic stability of the same Fe(III) complexes.

C) Determination of the Thermodynamic Stability of the Fe(III) Complexes

The thermodynamic stability constants ($K_{MLigand}=[ML\text{igand}]/([M]\times[\text{Ligand}])$) of the Fe(III) complexes were determined as follows.

The stability constant of the Fe(NOTA) complex was determined by spectrophotometry studies of the Fe³⁺-NOTA system at the absorption band of Fe$^{III}$ complexes at [H⁺]=0.01-3.0 M in the wavelength range of 350-800 nm. The concentrations of Fe³⁺ and NOTA were 0.002 M. The H⁺ concentration in the samples was adjusted with the addition of calculated amounts of a 6 M solution of HNO₃ (I=[Na⁺]+[H⁺]=0.15, [H⁺]≤0.15 M). The samples were kept at 25° C. for two weeks.

The absorbance values of the samples were determined at 11 wavelengths (370, 380, 390, 395, 400, 405, 410, 415, 420, 425 and 430 nm). For the calculations of the thermodynamic stability constant of the Fe(NOTA), the molar absorptivities of Fe³⁺ and Fe(NOTA) were determined by recording the spectra of 1.0×10⁻³, 1.5×10⁻³, 2.0×10⁻³ and 2.5×10⁻³ M solutions of Fe³⁺ and Fe(NOTA) solutions. The absorption spectra of the Fe(NOTA) solutions were recorded in the pH range of 1.7-7.5. All spectrophotometric measurements were performed at 25° C. in 0.15 M NaNO₃ solution. The pH was adjusted by stepwise addition of concentrated NaOH or HNO₃ solutions.

The stability constants of the Fe(HBED) complex was determined by following the competition reaction between HBED and NOTA ligands for Fe³⁺-ion with spectrophotometry at the absorption band of Fe(HBED) complex in the wavelength range of 400-700 nm. For Fe³⁺-HBED-NOTA systems, six samples were prepared with [Fe³⁺]=0.1 mM, [HBED]=0.2 mM and [NOTA]=0.0, 2.0, 4.0, 6.0, 8.0 and 10.0 mM in 0.15 M NaNO$_3$ solution. The pH values of the samples were adjusted to 5.0 by stepwise addition of the concentrated NaOH and HNO$_3$ solutions. The samples were kept for four weeks at 25° C. in order to attain equilibrium. The time needed to reach the equilibria was determined by spectrophotometry. The absorbance values of the samples were determined at the absorption band of the Fe(HBED) complex ([Fe(HBED)]-species predominates at pH=5.0). For the calculations of the thermodynamic stability constants of the Fe(HBED) complexes, the molar absorptivities of [Fe(HBED)]-species were determined by recording the spectra of 0.5, 0.1 and 0.2 mM solutions of [Fe(HBED)]$^-$ at pH=5 in the presence of 0.15 M NaNO$_3$. The spectrophotometric measurements were made with the use of Perki-nElmer Lambda 365 UV-Vis spectrophotometer, using 1.0 cm cells. The thermodynamic stability constants were calculated with the PSEQUAD program. (L. Zékány et al., Computational Method for Determination of Formation Constants, Ed. Legett D J, Plenum, New York, 1985, p. 291.)

The thermodynamic stability constants of the Fe(Compound 2) complex was determined by following the competition reaction between Compound 2 and HBED ligands for Fe$^{3+}$-ion with Capillary Zone Electrophoresis (CZE) at the signal of Fe(Compound 2) complex. CZE Separations were performed with Agilent 7100 Capillary Electrophoresis system using bare fused-silica capillaries of 64 cm×50 μm i.d. (Agilent). Before the first use of the capillary, the latter was washed with 1.0 M NaOH (15 min), with 0.1 M NaOH (30 min) and with the buffer electrolyte (30 min). Prior to CZE analysis, all buffers were filtered through a 0.45 μm syringe filter and stored in refrigerator at +4° C. In CZE, the sample solutions were introduced at the anodic end of the capillary in normal mode (50 mbar, 20 s). The effective length of the capillary was 56 cm. The capillary was preconditioned with the buffer electrolyte (150 mM sodium-bicarbonate, pH=8.2) for 3 minutes. The separation was performed at 37° C. with the application of 30 kV voltage. After analysis, the postconditioning (0.1 M NaOH (3 min) and buffer (3 min)) was applied to remove all possibly adsorbed materials from the capillary. In all measurements, 5 mM DMSO as internal standard was applied in order to correct the migration time of components on the electropherogram. The detection was carried out by on-column DAD measurement at 500 nm. The electropherograms were recorded and processed by ChemStation computer program of B.04.02 version (Agilent). For the equilibrium calculations, the molar integral values of the Fe(Compound 2) was used. The molar integral values of the Fe(Compound 2) were determined by recording the electropherograms of 22, 44 and 87 μM Fe(Compound 2) solutions at pH=6.0 and 25° C. in the presence of 0.15 M NaNO$_3$ ionic strength. The individual linear regression equation (response-concentration) for Fe(Compound 2) was determined according to three concentrations. The peak areas were found to be linear (R2>0.998) in a 22-87 μM concentration range with a precision better than 4%. The LOD, and molar integral values were found to be 2.7 μM and 133294 mAU$^{-1}$M$^{-1}$ (LOD=3σ/molar integral).

For Fe$^{3+}$—Compound 2—HBED systems, five samples were prepared with [Fe(Compound 2)]=87 μM, [HBED] =0.0, 4.0, 16.0, 30.0 and 50.0 mM in 0.15 M NaNO$_3$ solution. The pH values of the samples were adjusted to 11.0 by stepwise addition of the concentrated NaOH and HNO$_3$ solutions. The samples were kept for four weeks at 25° C. in order to attain equilibrium. The time needed to reach the equilibria was determined by CZE studies. The amount of the Fe(Compound 2) complex decreases according to the competition reaction between Compound 2 and HBED for Fe$^{3+}$-ion (Equation 1). No signals of the negatively charged Fe(HBED) and Compound 2 ligands appeared in the electropherograms.

$$K_{FeNB} = \frac{[Fe(HBED)][H_yCpd2]}{[Fe(H_zCpd2)][H_yCpd2]} = \frac{K_{Fe(HBED)}(1 + \alpha_H^{Cpd2})}{K_{Fe(Cpd2)}(1 + \alpha_{Fe(Cpd2)})(1 + \alpha_H^{HBED})}$$

Equation 1 where $\alpha_H = K_1^H[H^+] + K_1^H K_2^H[H^+]^2 + \ldots + K_1^H K_2^H \ldots K_n^H[H^+]^n$ and $K_1^H$, $K_2^H$, ... $K_n^H$ are the protonation constants of the free ligand determined in Example 11A, while $\alpha_{Fe(Cpd2)} = K_{FeHL}[H^+] + K_{FeHL}K_{FeH2L}[H^+]^2 + K_{FeHL}K_{FeH2L}K_{FeH3L}[H^+]^3$ are the protonation constants of the Fe(Compound 2) complex determined in Example 11B at 25° C. in 0.15 M NaNO$_3$ solution (Fe(HBED) species predominates at pH=11 and 25° C. in 0.15 M NaNO$_3$).

By taking into account the molar integral values of Fe(Compound 2) complex obtained by recording the electropherograms of 22, 44 and 87 μM Fe(Compound 2) solutions, and the total concentration of HBED ([HBED]$_{tot}$=[H$_x$HBED]+[Fe(HBED)]), Fe$^{3+}$ ion ([Fe$^{3+}$]$_{tot}$= [Fe(H$_z$Compound 2]+[Fe(HBED)] and Compound 2([Compound 2]$_{tot}$=[Fe(H$_z$Compound 2)]+[H$_y$Compound 2]) the K$_{FeNB}$ value was found to be (3.5±0.2)×10$^{-4}$. By taking into account the stability constant of Fe(HBED) (log K$_{Fe(HBED)}$ =40.2, 0.15 M NaNO$_3$, 25° C.), the protonation constants of Compound 2 and HBED ligand (Table 1, 25° C., 0.15 M NaNO$_3$) and the protonation constants of Fe(Compound 2) complex (Table 2, 25° C., 0.15 M NaNO$_3$), the thermodynamic stability constant of Fe(Compound 2) complex was found to be log K$_{Fe(Compound\ 2)}$=44.0 (3) at 25° C. in 0.15 M NaNO$_3$ solution.

The stability constant of the Fe(Compound 4) complex was determined by following the competition reaction between Compound 4 and HBED ligands for Fe$^{3+}$-ion with spectrophotometry at the absorption band of Fe(Compound 4) and Fe(HBED) complexes in the wavelength range of 400-700 nm. For Fe$^{3+}$—Compound 4—HBED systems, six samples were prepared with [Fe$^{3+}$]=0.1 mM, [Compound 4]=0.1 mM and [HBED]=0.0, 0.05, 0.1, 0.2, 0.4, 0.5, 1.0 and 2.0 mM in 0.15 M NaNO$_3$ solution. The pH values of the samples were adjusted to 12.0 by stepwise addition of the concentrated NaOH and HNO$_3$ solutions. The samples were kept for four weeks at 25° C. in order to attain equilibrium. The time needed to reach the equilibria was determined by spectrophotometry. The absorbance values of the samples were determined at the absorption band of the Fe(Compound 4) and Fe(HBED) complexes ([Fe(Compound 4)H$_{-1}$], [Fe (HBED)]$^-$ and [Fe(HBED)H$_{-1}$]$^{-2}$ species predominate at pH=12.0). For the calculations of the thermodynamic stability constants of the Fe(Compound 4) complexes, the molar absorptivities of [Fe(Compound 4)H$_{-1}$], [Fe (HBED)]$^-$ and [Fe(HBED)H$_{-1}$]$^{2-}$ species were determined by recording the spectra of 0.5, 0.1 and 0.2 mM solutions of [Fe(Compound 4)] and [Fe(HBED)]$^-$ in the pH range 7.0-12.5 in the presence of 0.15 M NaNO$_3$. The spectrophotometric measurements were made with the use of PerkinElmer Lambda 365 UV-Vis spectrophotometer, using 1.0 cm cells. The thermodynamic stability constants were calculated with the PSEQUAD program. (L. Zékány et al., Computational Method for Determination of Formation Constants, Ed. Legett D J, Plenum, New York, 1985, p. 291.)

D) Protonation Constants and Thermodynamic Stabilities of Fe(III) Complexes

The thermodynamic stability and protonation constants of Fe(III)-complexes of Compound 2 and Compound 4 as well as of comparative complexes NOTA, and HBED (determined according to the experiments above) are summarized in Table 2 below.

TABLE 2

| Fe(III)-Complex: | H$_3$NOTA (comp.) | H$_3$Cpd. 2[a] | H$_2$Cpd. 4[c] | H$_4$HBED[c] (ref.)[d] |
|---|---|---|---|---|
| Ionic strength | 0.15M NaNO$_3$ | 0.15M NaNO$_3$ | 0.15M NaNO$_3$ | 0.15M NaNO$_3$ |
| FeL | 27.53 (5) | 44.0 (3) | 37.1 (1) | 40.2 (1) |
| FeHL | — | 10.53 (4)[b] | 8.82 (1)[b] | 1.87 (4) |
| FeH$_2$L | — | 9.47 (1)[b] | 6.02 (1)[b] | — |
| FeH$_3$L | — | 7.82 (5)[b] | — | — |
| FeLH$_{-1}$ | 9.12 (4) | — | 10.12 (1)[b] | 12.3 (1) |
| pFe | 23.7 | 32.4 | 26.5 | 31.0 |

[a]Capillary Zone Electrophoreses (0.15M NaNO$_3$, 25° C.),
[b]Spectrophotometry (0.15M NaClO$_4$, 25° C.),
[c]Spectrophotometry (0.15M NaNO$_3$, 25° C.),
[d]Reference compound, used to determine the thermodynamic stability of Fe(III)-complex of Cpd. 2 and Cpd. 4

In order to compare the thermodynamic stabilities of the Fe(Compound 2), Fe(Compound 4), Fe(HBED) and Fe(NOTA) complexes, the pFe values (pFe=−log [Fe$^{3+}$]$_{free}$, [Fe$^{3+}$]$_{tot}$=1 µM, [L]$_{tot}$=10 µM, pH=7.4; S. Hajela et al., J. Am. Chem. Soc., 2000, 122, 11228-11229) characterizing the conditional stability of the Fe(III)-complexes have been calculated at pH=7.4 in the presence of 1 µM Fe$^{3+}$ and 10 µM ligand. Based on the pFe values, as it can be observed from the data of Table 2, Fe(Compound 2) has the highest thermodynamic stability, confirming the in vivo safety of the Fe(III) complex of the invention; such high thermodynamic stability is even higher than that of the comparative Fe(NOTA) complex. Moreover, based on the pFe value, also Fe(Compound 4) shows a very high thermodynamic stability, even higher than that of the comparative Fe(NOTA) complex.

Example 12—Kinetic Inertness Analysis

To obtain data relating to the kinetic inertness of Fe(Compound 2), Fe(Compound 4) and Fe(NOTA) (comparative), the transchelation reactions (schematized below) were investigated by VIS-spectrophotometry (for Fe(Compound 4) and Fe(NOTA), comparative) and by Capillary Zone Electrophoresis (CZE) (for Fe(Compound 2)) in the presence of a large excess of HBED as an exchanging ligand (Fe(Compound 2): [Fe(Compound 2)]=87 µM, [HBED]=0.1 and 0.2 M, 1.0 M NaClO$_4$, 25° C.; Fe(Compound 4): [Fe(Compound 4)]=100 µM, [HBED]=0.002 and 0.02 M, 0.15 M NaNO$_3$, 25° C. Fe(NOTA): [Fe(NOTA)]=0.2 mM, [HBED]=2.0 and 4.0 mM, 0.15 M NaNO$_3$, 25° C.) in order to guarantee the pseudo-first order kinetic conditions.

FeL+HBED ⇌ Fe(HBED)+L with L=Compound 2, Compound 4 or NOTA.

A) Determination of Kinetic Inertness of Fe(III) Complexes

The transchelation reactions of Fe(Compound 4) and Fe(NOTA) (comparative) were studied by spectrophotometry, following the formation of the resulting Fe(HBED) complex at 472 and 470 nm with PerkinElmer Lambda 365 UV-Vis spectrophotometer. The concentration of the Fe(Compound 4) and Fe(NOTA) complex was 0.1 and 0.2 mM, while the concentration of the HBED was 10-200 times higher, in order to guarantee pseudo-first-order conditions. The temperature was maintained at 25° C. and the ionic strength of the solutions was kept constant, 0.15 M for NaNO$_3$. The exchange rates were studied in the pH range about 9.5-14.0. Buffer was not used since the excess of HBED was able to maintain the constant pH values at pH<12. At pH>12, the OH$^-$ concentration in the samples was adjusted with the addition of calculated amounts of 19 M NaOH(I=[NaNO$_3$]+[NaOH]=0.15, [NaOH]≤0.15 M). The pseudo-first-order rate constants (k$_d$) were calculated by fitting of the absorbance—time data pairs to Equation 2.

$$A_t = (A_0 - A_p)e^{-k_d t} + A_p \qquad \text{Equation 2}$$

where A$_t$, A$_0$ and A$_p$ are the absorbance values at time t, the start of the reaction and at equilibrium, respectively.

The ligand exchange reactions in Fe(Compound 2)—HBED reacting systems have been studied by Capillary Zone Electrophoresis (CZE) in the pH range 9.5-11.5. The transchelation reactions of Fe(Compound 2) were studied by following the dissociation of the Fe(Compound 2) complex with Agilent 7100 Capillary Electrophoresis system (using the same conditions of the CZE experiments of Example 11). The concentration of the Fe(Compound 2) complex was 87 µM, while that of HBED was 0.1 and 0.2 M in order to guarantee pseudo-first-order conditions. The temperature was maintained at 25° C. and the ionic strength of the solutions was kept constant, 1.0 M for NaClO$_4$. The pseudo-first-order rate constants (k$_d$) were calculated by fitting the area-time data pairs to Equation 2 above, where A$_t$, A$_0$ and A$_p$ are the area values at time t, the start of the reaction and at equilibrium, respectively.

Calculation were performed with the Micromath Scientist computer program (version 2.0, Salt Lake City, UT, USA).

B) Kinetic Inertness of Fe(III) Complexes

The kinetic inertness results (in terms of dissociation rate constants. k$_d$, and of half-life, t$_{1/2}$) of Fe(III)-complexes of Compound 2, as well as of comparative complexes NOTA (determined according to the experiments above), EDTA, and CDTA (as disclosed in Baranyai Z. et al., Chem. Sci., 2021, 12, 11138-11145), are summarized in Table 3 below.

TABLE 3

| Fe(III)-complex: | Cpd. 2 | Cpd. 4 | NOTA (comp.) | EDTA (comp.) | CDTA (comp.) |
|---|---|---|---|---|---|
| Ionic strength | 1.0M NaClO$_4$ | 0.15M NaNO$_3$ | 0.15M NaNO$_3$ | 0.15M NaNO$_3$ | 0.15M NaNO$_3$ |
| k$_d$ (s$^{-1}$) at pH = 7.4 | 1.9 × 10$^{-9}$ | 3.4 × 10$^{-8}$ | 4.0 × 10$^{-9}$ | 2.9 × 10$^{-6}$ | 2.1 × 10$^{-9}$ |
| t$_{1/2}$ (h) at pH = 7.4 | 9.9 × 10$^4$ | 5.7 × 10$^3$ | 4.8 × 10$^4$ | 66 | 8.9 × 10$^4$ |

The dissociation rate constant ($k_d$) of Fe(III)-Compound 2 at pH=7.4, 25° C. (calculated by extrapolating the kinetic data obtained at pH>9.0) is approximately two times lower than that of Fe(NOTA), i.e. the complex of the invention is more inert than comparative Fe(NOTA). The dissociation half-life ($t_{1/2}=\ln(2)/k_d$) of the Fe(III)-Compound 2 and Fe(III)-Compound 4 complexes are about 11.3 and 0.65 years near to physiological condition (pH=7.4, 25° C.), which can be an indication of their safe in vivo applications.

Example 13—Transferrin Challenge Reactions

Transferrins are $Fe^{3+}$-binding transport proteins present in the body fluids. Human serum transferrin (sTf) is known to bind $Fe^{3+}$ with high affinity (log $K_{FeTf}$=21.44, log $K_{Fe2Tf}$=20.34) (W. R. Harris, Y. Chen, K. Wein, *Inorg. Chem.*, 1994, 33, 4991). Since serum transferrin is normally only 30% saturated with $Fe^{3+}$, it retains a relatively high capacity for binding $Fe^{3+}$ released by other Fe(III)-complexes, and even to promote the release of $Fe^{3+}$ from Fe(III)-complexes, thus promoting the dissociation of such Fe(III)-complexes. To investigate the possible role of transferrin in the dissociation of the Fe(III)-complexes of the invention, the reaction of 22.6% $Fe^{3+}$ saturated human serum transferrin (Sigma) with Fe(III)-Compound 2, Fe(III)-Compound 4, Fe(III)-Compound 57, Fe(III)-Compound 60 and Fe(IIII)-Compound 61 complexes were studied by following the possible formation of the $Fe^{3+}$ saturated human serum transferrin and the possible dissociation of the Fe(III)-Compound 2, Fe(III)-Compound 4, Fe(III)-Compound 57, Fe(III)-Compound 60 and Fe(III)-Compound 61 complexes. $Fe^{3+}$ saturation of the human serum transferrin was determined as disclosed in Z. Baranyai, F. Uggeri, A. Maiocchi, G. B. Giovenzana, C. Cavallotti, A. Takács, I. Tóth, I. Bányai, E. Brücher, S. Aime, *Eur. J. Inorg. Chem.* 2013, 147-162); as the $Fe^{3+}$ binding of sTf requires the concomitant binding of a synergistic anion, which in vivo is bicarbonate (G. W. Bates, M. R. Schlabach, *J. Biol. Chem.*, 1975, 250, 2177-2181), all measurements were performed in the presence of 25 mM $NaHCO_3$ at pH=7.4 and 25° C. Since the molar absorptivites of the Fe(III)-complexes and $Fe^{3+}$-human serum transferrin species are different, the possible metal-exchange reactions of Fe(III)-Compound 2, Fe(III)-Compound 4, Fe(III)-Compound 57, Fe(III)-Compound 60 and Fe(III)-Compound 61 complexes with 22.6% $Fe^{3+}$-saturated human serum transferrin were determined by following the eventual dissociation of Fe(III)-Compound 2, Fe(III)-Compound 4, Fe(III)-Compound 57, Fe(III)-Compound 60 and Fe(III)-Compound 61 complexes and the formation of the $Fe^{3+}$-saturated human serum transferrin by spectrophotometry with PerkinElmer Lambda 365 UV-Vis spectrophotometer in the presence of equimolar human transferrin in the wavelength range 400-700 nm. The concentration of the Fe(III)-Compound 2, Fe(III)-Compound 4, Fe(III)-Compound 57, Fe(III)-Compound 60 and Fe(III)-Compound 61 complexes and 22.6% $Fe^{3+}$ saturated human serum transferrin was 0.1 mM. The temperature was maintained at 25° C. and the ionic strength of the solutions was kept constant (0.15 M of NaCl). The pH of the sample was adjusted by stepwise addition of the concentrate NaOH and HCl solution. It was observed that the absorption spectra of the Fe(III)-Compound 2—human serum transferrin, Fe(III)-Compound 4—human serum transferrin, Fe(III)-Compound 57—human serum transferrin, Fe(III)-Compound 60—human serum transferrin and Fe(III)-Compound 61—human serum transferrin reacting systems within 1100 min reaction times remained unchanged, meaning that the Fe(III)-complexes formed with Compound 2, Compound 4, Compound 57, Compound 60 and Compound 61 have a very high kinetic inertness and/or higher conditional stability compared to the Fe(III)-complex of sTf. Indeed, the complexes of the invention were not dissociated even in the presence of 22.6% $Fe^{3+}$-saturated sTf (namely, close to physiological condition, the latter being pH=7.4, 25° C., 25 mM $NaHCO_3$, 0.15 M NaCl). This further demonstrate the high kinetic inertness and/or thermodynamic stability of the compounds of the invention when complexed with Fe(III), such as of Fe(III)-Compound 2, Fe(III)-Compound 4, Fe(III)-Compound 57, Fe(III)-Compound 60 and Fe(III)-Compound 61.

Example 14—Redox Stability Analysis

To characterize the redox stabilities of the Fe(III) complexes, the reaction of ascorbic acid with Fe(III)-Compound 2, Fe(III)-Compound 4, Fe(III)-Compound 57, Fe(III)-Compound 60 and Fe(III)-Compound 61 and Fe(III) (NOTA) (comparative) were studied by following the reduction of the Fe(III)-complexes by spectrophotometry in the presence of the large ascorbic acid excess ([Fe(III) (NOTA)]=2.0 mM, [Fe(III)-Compound 2]=25 µM, [Fe(III)-Compound 4]=100 µM, [Fe(III)-Compound 57]=25 µM, [Fe(III)-Compound 60]=100 µM, [Fe(III)-Compound 61]=100 µM [ascorbic acid]=20 mM, pH=7.4, [HEPES]=0.01 M, 0.15 M $NaNO_3$, 25° C.) as follows.
A) Determination of Redox Stability of Fe(III) Complexes The redox stability of the Fe(III) (NOTA), Fe(III)-Compound 2, Fe(III)-Compound 4, Fe(III)-Compound 57, Fe(III)-Compound 60 and Fe(III)-Compound 61 was characterized by assessing the rates of their reduction with ascorbic acid, observing the reduction reactions by spectrophotometry, following the formation of the Fe(II)-Ligand complexes at 375 nm for Fe(III) (NOTA), 480 nm for Fe(III)-Compound 2 and Fe(III)-Compound 57, 471 nm for Fe(III)-Compound 4 and 500 nm for Fe(III)-Compound 60 and Fe(III)-Compound 61 with PerkinElmer Lambda 365 UV-Vis spectrophotometer. The concentrations of the Fe(III) (NOTA), Fe(III)-Compound 2, Fe(III)-Compound 4, Fe(III)-Compound 57, Fe(III)-Compound 60 and Fe(III)-Compound 61 complexes were 2.0 mM, 25, 100, 25, 100, and 100 µM, respectively, while the ascorbic acid was used in high excess ([ascorbic acid]=20 mM), in order to guarantee the pseudo-first-order condition. For Fe(III) (NOTA) experiments, a four-fold excess of free NOTA ligand was added as a scavenger to complex possible $Fe^{2+}$ ions that can be released by Fe(II) NOTA following its possible reduction from Fe(III) (NOTA) (the stability of Fe(II) NOTA is low, whereby $Fe^{2+}$ ions can be released by such complex). The temperature was maintained at 25° C. and the ionic strength of the solutions was kept constant, 0.15 M for $NaNO_3$. The reduction rates were studied at pH=7.4. For keeping the pH values constant, HEPES buffer was used ([HEPES]=0.01 M). In the sample preparation, air was bubbled through all solutions in order to maintain oxygen free condition. The pseudo-first-order rate constants ($k_{obs}=k_d$) were calculated by fitting the absorbance—time data pairs to Equation 2 with the Micromath Scientist computer program (version 2.0, Salt Lake City, UT, USA).
B) Redox Stability Data of Fe(III) Complexes The absorption spectra of the experiments above show that, for Fe(III) (NOTA), the absorbance values decrease as a function of time due to the reduction of Fe(III) (NOTA) by ascorbic acid, and indeed the reduction half-life ($t_{1/2}=\ln2/k_{obs}$) characterizing the ascorbic acid mediated reduction of Fe(III) (NOTA) was found to be $t_{1/2}$=2.7 min (with the excess of ascorbic acid mentioned in section A) above). By taking into account in vivo concentration of the ascorbic acid ([ascorbic acid]=43 µM, P. M. May, D. R. Williams, P. W. Linder, *J. Chem. Soc. Dalton Trans.,* 1977, 588-595) and considering that the reduction rate of the Fe(III)-complex is directly proportional to the concentration of the ascorbic acid (Baranyai, Z.; Carniato, F.; Nucera, A.; Horváth, D.; Tei, L.; Platas-Iglesias, C.; Botta, *M. Chem. Sci.* 2021, 12, 11138-11145), the ascorbic acid mediated reduction of Fe(III) (NOTA) was found to be $t_{1/2}$=19.5 h at physiological condition ([ascorbic acid]=43 µM, pH=7.4, 0.01 M HEPES, 0.15 M $NaNO_3$ 25° C.).

It was further observed that the absorbance values of Fe(III)-Compound 4—ascorbic acid, Fe(III)-Compound 60—ascorbic acid and Fe(III)-Compound 61—ascorbic acid reacting systems slowly decreases as a function of time, namely, respectively, a 12, 35 and 40% decrease of the absorbance values within 1 day, even in the presence of 200 fold ascorbic acid excess. Based on such spectral changes, reduction of the Fe(III)-Compound 4, Fe(III)-Compound 60 and Fe(III)-Compound 61 to Fe(II)-Compound 4, Fe(II)-Compound 60 and Fe(II)-Compound 61 seems to take place very slowly in the Fe(III)-Compound 4—ascorbic acid, Fe(III)-Compound 60—ascorbic acid and Fe(III)-Compound 61-ascorbic acid reacting systems. By taking into account in vivo concentration of the ascorbic acid ([ascorbic acid]=43 µM) and considering that the reduction rate of the Fe(III)-complex is directly proportional to the concentration of the ascorbic acid, the ascorbic acid mediated reduction of Fe(III)-Compound 4, Fe(III)-Compound 60 and Fe(III)-Compound 61 was found to be $t_{1/2}$=3.5×10$^3$, 1.6×10$^3$ and 3.0×10$^3$ h at physiological condition, respectively ([ascorbic acid]=43 µM, pH=7.4, 0.01 M HEPES, 0.15 M $NaNO_3$ 25° C.). These $t_{1/2}$ values can be an indication of their safe and effective in vivo applications.

Furthermore, it was observed that the absorption spectra of the Fe(III)-Compound 2—ascorbic acid and Fe(III)-Compound 57—ascorbic acid reacting systems within 1 day reaction time remains unchanged, which can be explained by the high selectivity of the Compound 2 and Compound 57 for Fe(III)-ion over Fe(II)-ion (ΔpFe>16); in other words, iron prefers to remain in +3 oxidation state, without being reduced to +2, even in the presence of large ascorbic acid (reducing agent) excess when complexed to Compound 2 and Compound 57. Again, this can be an indication of the safe and effective in vivo applications of the Fe(III)-complexes of the invention.

The invention claimed is:

1. A compound of Formula (I):

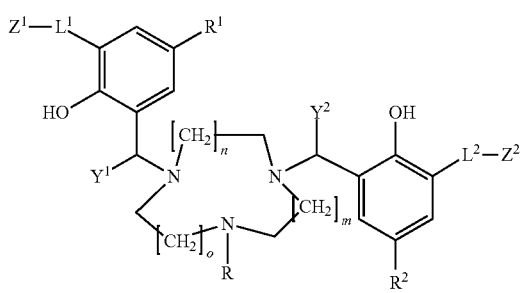

Formula (I)

wherein: n, m, and o are integer numbers independently selected between 1 and 2;

$Y^1$ and $Y^2$ are independently selected from the group consisting of hydrogen and $C_1$-$C_4$-alkyl;

$R^1$ and $R^2$ are independently selected from the group consisting of hydrogen and $C_1$-$C_4$-alkyl;

$L^1$ and $L^2$ are independently selected from the group consisting of $C_1$-$C_4$-alkylaminyl, $C_1$-$C_4$-alkylamidyl, and $C_1$-$C_4$-alkylether;

$Z^1$ and $Z^2$ are independently selected from the group consisting of hydrogen and a $C_1$-$C_6$-alkyl, said $C_1$-$C_6$-alkyl being optionally substituted by one or more groups selected from the group consisting of hydroxyl (—OH), carboxyl (—COOH), and phosphonate (—$PO_3H_2$);

R is selected from the group consisting of hydrogen, $C_1$-$C_4$ alkyl optionally substituted by an aryl, and the moiety of Formula (IA):

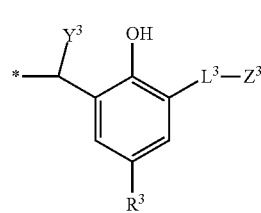

Formula (IA)

wherein: the asterisk (*) indicates the point of attachment of said moiety of Formula (IA) to the nitrogen bearing the R group;

$Y^3$ has the same meaning provided above for $Y^1$ and $Y^2$;

$R^3$ has the same meaning provided above for $R^1$ and $R^2$;

$L^3$ has the same meaning provided above for $L^1$ and $L^2$; and $Z^3$ has the same meaning provided above for $Z^1$ and $Z^2$;

or an ion, or a stereoisomer, or a tautomer, or a hydrate, or a solvate, or a pharmaceutically acceptable salt thereof, or a mixture of the same.

2. The compound according to claim 1, wherein $Y^1$ and $Y^2$, and $Y^3$ if present, are independently selected from the group consisting of hydrogen and a $C_1$-$C_3$-alkyl.

3. The compound according to claim 2, wherein $Y^1$ and $Y^2$, and $Y^3$ if present, are independently selected from the group consisting of hydrogen and a $C_1$-$C_2$-alkyl.

4. The compound according to claim 3, wherein $Y^1$ and $Y^2$, and $Y^3$ if present, are independently selected from the group consisting of hydrogen and a $C_1$-alkyl.

5. The compound according to claim 4, wherein $Y^1$ and $Y^2$, and $Y^3$ if present, are hydrogen.

6. The compound according to claim 1, wherein $R^1$, $R^2$, and $R^3$ if present, are independently selected from the group consisting of hydrogen and $C_1$-$C_3$-alkyl.

7. The compound according to claim 6, wherein $R^1$, $R^2$, and $R^3$ if present, are independently selected from the group consisting of hydrogen and $C_1$-$C_2$-alkyl.

8. The compound according to claim 7, wherein $R^1$, $R^2$, and $R^3$ if present, are independently selected from the group consisting of hydrogen and $C_1$-alkyl.

9. The compound according to claim 8, wherein $R^1$, $R^2$, and $R^3$ if present, are methyl (—$CH_3$).

10. The compound according to claim 1, wherein $L^1$, $L^2$, and $L^3$ if present, are independently selected from the group consisting of $C_1$-$C_3$-alkylaminyl, $C_1$-$C_3$-alkylamidyl, and $C_1$-$C_3$-alkylether.

11. The compound according to claim 10, wherein $L^1$, $L^2$, and $L^3$ if present, are independently selected from the group consisting of $C_1$-$C_2$-alkylaminyl, $C_1$-$C_2$-alkylamidyl, and $C_1$-$C_2$-alkylether.

12. The compound according to claim 11, wherein $L^1$, $L^2$, and $L^3$ if present, are independently selected from the group consisting of $C_1$-alkylaminyl, $C_1$-alkylamidyl, and $C_1$-alkylether.

13. The compound according to claim 12, wherein $L^1$, $L^2$, and $L^3$ if present, are independently selected from the group consisting of *—CH$_2$—NH—•, *—C(O)—NH—•, *—NHC(O)—•, and *—CH$_2$—O—•, with the asterisk (*) representing the phenolic moiety and the middle dot (•) representing the $Z^1$, $Z^2$, or $Z^3$ group if present.

14. The compound according to claim 13, wherein $L^1$, $L^2$, and $L^3$ if present, are independently selected from the group consisting of *—CH$_2$—NH—•, *—C(O)—NH—•, and *—CH$_2$—O—•; with the asterisk (*) representing the phenolic moiety and the middle dot (•) representing the $Z^1$, $Z^2$, or $Z^3$ group if present.

15. The compound according to claim 1, wherein $Z^1$, $Z^2$, and $Z^3$ if present, are independently selected from the group consisting of hydrogen, $C_4$-$C_6$-alkyl substituted by two or more hydroxyl (—OH) groups, and $C_1$-$C_3$-alkyl substituted by at least one group selected from the group consisting of hydroxyl (—OH), carboxyl (—COOH), and phosphonate (—PO$_3$H$_2$).

16. The compound according to claim 15, wherein $Z^1$, $Z^2$, and $Z^3$ if present, are independently selected from the group consisting of hydrogen, $C_6$-alkyl substituted by two to five hydroxyl (—OH) groups, $C_1$-$C_3$-alkyl substituted by at least one hydroxyl (—OH) group, and $C_1$-alkyl substituted by carboxyl (—COOH) or phosphonate (—PO$_3$H$_2$).

17. The compound according to claim 1, wherein $Z^1$ and $Z^2$, and $Z^3$ if present, are independently selected from the group consisting of hydrogen and a $C_1$-$C_4$-alkyl, said $C_1$-$C_4$-alkyl being optionally substituted by one or more groups selected from the group consisting of hydroxyl (—OH), carboxyl (—COOH), and phosphonate (—PO$_3$H$_2$).

18. The compound according to claim 1, wherein R is a $C_1$-$C_3$-alkyl or a $C_1$-$C_3$-alkyl substituted by an aryl.

19. The compound according to claim 18, wherein R is a $C_1$-$C_2$-alkyl or a $C_1$-$C_2$-alkyl substituted by an aryl.

20. The compound according to claim 19, wherein R is a $C_1$-alkyl or a $C_1$-alkyl substituted by an aryl.

21. The compound according to claim 1, wherein R is selected from the group consisting of hydrogen, $C_1$-alkyl, $C_1$-alkyl substituted by an aryl, and the moiety of Formula (IA),

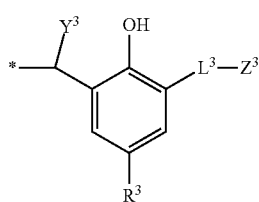

Formula (IA)

wherein $Y^3$, $R^3$, $L^3$, and $Z^3$ have the same meanings provided above for, respectively, $Y^1$, $R^1$, $L^1$, and $Z^1$.

22. The compound according to claim 1, wherein n, m, and o are 1, whereby the compound has the following formula (II)

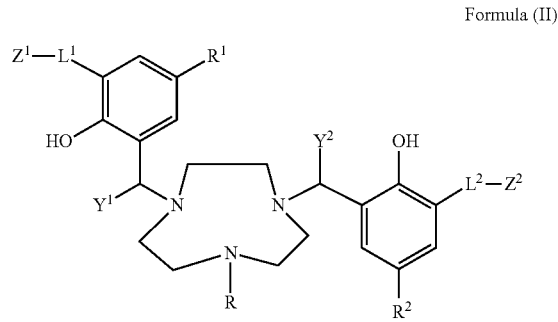

Formula (II)

wherein R, $R^1$, $R^2$, $Y^1$, $Y^2$, $L^1$, $L^2$, $Z^1$, and $Z^2$ are as above defined.

23. The compound according to claim 1, wherein only one between n, m, and o is 2, and the other two are 1, whereby the compound has one of the formulae (IIIA), (IIIB) or (IIIC)

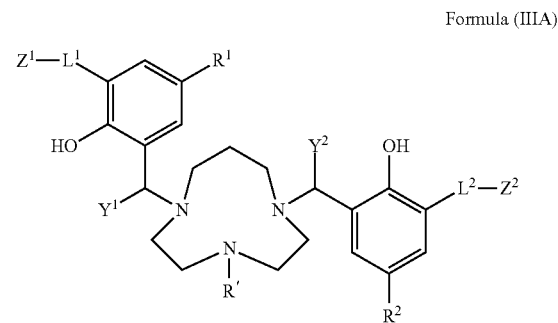

Formula (IIIA)

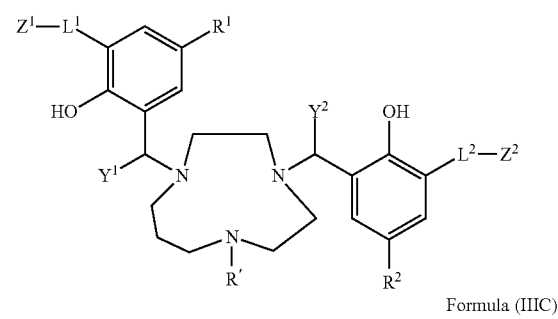

Formtula (IIIB)

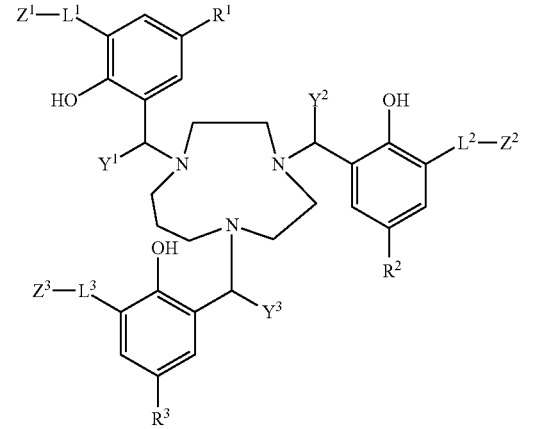

Formula (IIIC)

wherein, for formulae (IIIA), (IIIB), and (IIIC), R¹, R², R³, Y¹, Y², Y³, L¹, L², L³, Z¹, Z², and Z³ are as above defined, and R' is hydrogen or $C_1$-$C_4$-alkyl optionally substituted by an aryl.

24. The compound according to claim 23, wherein R' is hydrogen or $C_1$-$C_3$-alkyl optionally substituted by an aryl.

25. The compound according to claim 24, wherein R' is hydrogen or $C_1$-$C_2$-alkyl optionally substituted by an aryl.

26. The compound according to claim 25, wherein R' is hydrogen or $C_1$-alkyl optionally substituted by an aryl.

27. The compound according to claim 1, wherein only one between n, m, and o is 1, and the other two are 2, whereby the compound has one of the formulae (IVA), (IVB), or (IVC)

Formula (IVA)

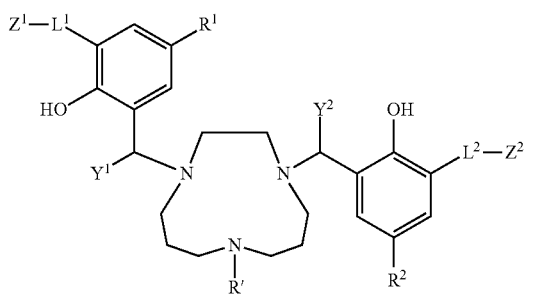

Formula (IVB)

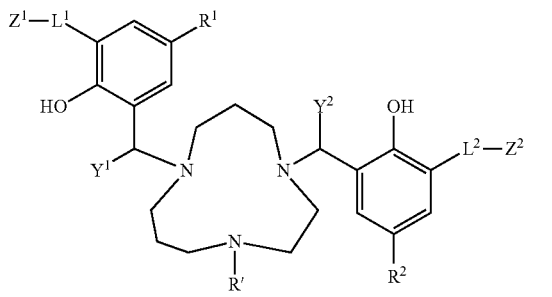

Formula (IVC)

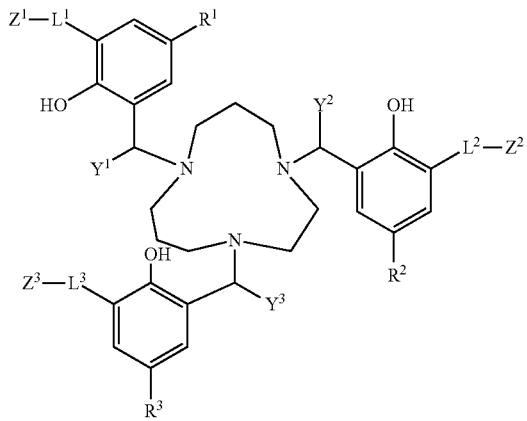

wherein, for formulae (IVA), (IVB), and (IVC), R¹, R², R³, Y¹, Y², Y³, L¹, L², L³, Z¹, Z², and Z³ are as above defined, and R' is hydrogen or $C_1$-$C_4$-alkyl optionally substituted by an aryl.

28. The compound according to claim 27, wherein R' is hydrogen or $C_1$-$C_3$-alkyl optionally substituted by an aryl.

29. The compound according to claim 28, wherein R' is hydrogen or $C_1$-$C_2$-alkyl optionally substituted by an aryl.

30. The compound according to claim 29, wherein R' is hydrogen or $C_1$-alkyl optionally substituted by an aryl.

31. The compound according to claim 1, wherein n, m, and o are 2, whereby the compound has the following formula (V)

Formula (V)

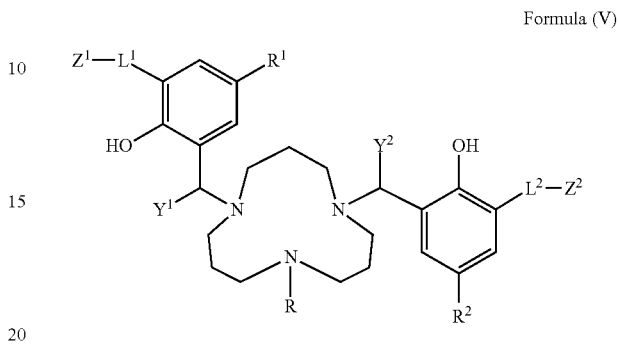

wherein R, R¹, R², Y¹, Y², L¹, L², Z¹, and Z² are as above defined.

32. The compound according to claim 1, wherein the compound is selected from the group consisting of: 3,3',3''-[1,4,7-triazonane-1,4,7-triyltris(methylene)]tris[N-(1,3-dihydroxypropan-2-yl)-2-hydroxy-5-methylbenzamide]; 2,2',2''-{1,4,7-triazonane-1,4,7-triyltris[methylene (2-hydroxy-5-methyl-3,1-phenylene)methyleneazanediyl]}tri(propane-1,3-diol); 3,3'-[1,4,7-triazonane-1,4-diylbis(methylene)]bis[N-(1,3-dihydroxypropan-2-yl)-2-hydroxy-5-methylbenzamide]; 2,2'-{1,4,7-triazonane-1,4-diylbis[methylene (2-hydroxy-5-methyl-3,1-phenylene)methyleneazanediyl]}di(propane-1,3-diol); 3,3',3''-[1,4,7-triazonane-1,4,7-triyltris(methylene)]tris(2-hydroxy-5-methylbenzamide); 3,3'-[1,4,7-triazonane-1,4-diylbis(methylene)]bis(2-hydroxy-5-methylbenzamide); 2,2',2''-[1,4,7-triazonane-1,4,7-triyltris(methylene)]tris[6-(aminomethyl)-4-methylphenol]; 2,2'-[1,4,7-triazonane-1,4-diylbis(methylene)]bis[6-(aminomethyl)-4-methylphenol]; {1,4,7-triazonane-1,4,7-triyltris[methylene(2-hydroxy-5-methyl-3,1-phenylene)carbonylazanediylmethylene]}tris(phosphonic acid); {1,4,7-triazonane-1,4-diylbis[methylene(2-hydroxy-5-methyl-3,1-phenylene)carbonylazanediylmethylene]}bis(phosphonic acid); {1,4,7-triazonane-1,4,7-triyltris[methylene(2-hydroxy-5-methyl-3,1-phenylene)methyleneazanediylmethylene]}tris(phosphonic acid); {1,4,7-triazonane-1,4-diylbis[methylene(2-hydroxy-5-methyl-3,1-phenylene)methyleneazanediylmethylene]}bis(phosphonic acid); 3,3',3''-[1,4,7-triazonane-1,4,7-triyltris(methylene)]tris[N-(1,2-dihydroxyethyl)-2-hydroxy-5-methylbenzamide]; 1,1',1''-{1,4,7-triazonane-1,4,7-triyltris[methylene(2-hydroxy-5-methyl-3,1-phenylene)methyleneazanediyl]}tri(ethane-1,2-diol); 3,3'-[1,4,7-triazonane-1,4-diylbis(methylene)]bis[N-(1,2-dihydroxyethyl)-2-hydroxy-5-methylbenzamide]; 1,1'-{1,4,7-triazonane-1,4-diylbis[methylene(2-hydroxy-5-methyl-3,1-phenylene)methyleneazanediyl]}di(ethane-1,2-diol); N,N°,N''-{1,4,7-triazonane-1,4,7-triyltris[methylene (2-hydroxy-5-methyl-3,1-phenylene)]}tris(2,3-dihydroxypropanamide); N,N-{1,4,7-triazonane-1,4-diylbis[methylene(2-hydroxy-5-methyl-3,1-phenylene)]}bis(2,3-dihydroxypropanamide); N,N°,N''-{1,4,7-triazonane-1,4,7-triyltris[methylene(2-hydroxy-5-methyl-3,1-phenylene)]}tris[3-hydroxy-2-(hydroxymethyl) propanamide]; N,N-{1,4,7-triazonane-1,4-diylbis[methylene(2-hydroxy-5-methyl-3,1-phenylene)]}bis[3-hydroxy-2-(hydroxymethyl)

propanamide]; {1,4,7-triazonane-1,4, 7-triyltris[methylene (2-hydroxy-5-methyl-3,1-phenylene)azanediyl(2-oxoethane-2,1-diyl)]}tris(phosphonic acid); {1,4,7-triazonane-1,4-diylbis[methylene(2-hydroxy-5-methyl-3,1-phenylene) azanediyl(2-oxoethane-2,1-diyl)]}bis (phosphonic acid); 3,3',3''-[1,4,7-triazecane-1,4,7-triyltris (methylene)]tris[N-(1,3-dihydroxypropan-2-yl)-2-hydroxy-5-methylbenzamide]; 2,2',2''-{1,4,7-triazecane-1,4,7-triyltris[methylene(2-hydroxy-5-methyl-3,1-phenylene) methyleneazanediyl]}tri(propane-1,3-diol); 3,3'-[1,4,7-triazecane-1,7-diylbis(methylene)]bis[N-(1,3-dihydroxypropan-2-yl)-2-hydroxy-5-methylbenzamide]; 3,3'-[1,4,7-triazecane-1,4-diylbis(methylene)]bis[N-(1,3-dihydroxypropan-2-yl)-2-hydroxy-5-methylbenzamide]; 2,2'-{1,4,7-triazecane-1,7-diylbis[methylene(2-hydroxy-5-methyl-3,1-phenylene)methyleneazanediyl]}di(propane-1,3-diol); 2,2'-{1,4,7-triazecane-1,4-diylbis[methylene(2-hydroxy-5-methyl-3,1-phenylene)methyleneazanediyl]}di (propane-1,3-diol); 3,3',3''-[1,4,7-triazecane-1,4,7-triyltris (methylene)]tris(2-hydroxy-5-methylbenzamide); 3,3'-[1,4,7-triazecane-1, 7-diylbis(methylene)]bis(2-hydroxy-5-methylbenzamide); 3,3'-[1,4,7-triazecane-1,4-diylbis (methylene)]bis(2-hydroxy-5-methylbenzamide); 2,2',2''-[1,4,7-triazecane-1,4,7-triyltris(methylene)]tris[6-(aminomethyl)-4-methylphenol]; 2,2'-[1,4,7-triazecane-1,7-diylbis(methylene)]bis[6-(aminomethyl)-4-methylphenol]; 2,2'-[1,4,7-triazecane-1,4-diylbis(methylene)]bis[6-(aminomethyl)-4-methylphenol]; {1,4,7-triazecane-1,4,7-triyltris[methylene(2-hydroxy-5-methyl-3,1-phenylene)carbonylazanediylmethylene]}tris(phosphonic acid); {1,4,7-triazecane-1,7-diylbis[methylene(2-hydroxy-5-methyl-3,1-phenylene)carbonylazanediylmethylene]}bis(phosphonic acid); {1,4,7-triazecane-1,4-diylbis[methylene(2-hydroxy-5-methyl-3,1-phenylene)carbonylazanediylmethylene]}bis (phosphonic acid); {1,4,7-triazecane-1,4,7-triyltris[methylene(2-hydroxy-5-methyl-3,1-phenylene) methyleneazanediylmethylene]}tris(phosphonic acid); {1,4,7-triazecane-1,7-diylbis[methylene(2-hydroxy-5-methyl-3,1-phenylene)methyleneazanediylmethylene]}bis (phosphonic acid); {1,4,7-triazecane-1,4-diylbis[methylene (2-hydroxy-5-methyl-3,1-phenylene) methyleneazanediylmethylene]}bis(phosphonic acid); 3,3',3''-[1,4,7-triazecane-1,4,7-triyltris(methylene)]tris[N-(1,2-dihydroxyethyl)-2-hydroxy-5-methylbenzamide]; 1,1',1''-{1,4,7-triazecane-1,4,7-triyltris[methylene(2-hydroxy-5-methyl-3,1-phenylene)methyleneazanediyl]}tri(ethane-1,2-diol); 3,3'-[1,4,7-triazecane-1,7-diylbis(methylene)]bis[N-(1,2-dihydroxyethyl)-2-hydroxy-5-methylbenzamide]; 3,3'-[1,4,7-triazecane-1,4-diylbis(methylene)]bis[N-(1,2-dihydroxyethyl)-2-hydroxy-5-methylbenzamide]; 1,1'-{1,4,7-triazecane-1,7-diylbis[methylene(2-hydroxy-5-methyl-3,1-phenylene)methyleneazanediyl]}di(ethane-1,2-diol); 1,1'-{1,4,7-triazecane-1,4-diylbis[methylene(2-hydroxy-5-methyl-3,1-phenylene)methyleneazanediyl]}di(ethane-1,2-diol); N,N°,N''-{1,4,7-triazecane-1,4,7-triyltris[methylene (2-hydroxy-5-methyl-3,1-phenylene)]}tris(2,3-dihydroxypropanamide); N,N-{1,4,7-triazecane-1,7-diylbis [methylene(2-hydroxy-5-methyl-3,1-phenylene)]}bis(2,3-dihydroxypropanamide); N,N-{1,4,7-triazecane-1,4-diylbis [methylene(2-hydroxy-5-methyl-3,1-phenylene)]}bis(2,3-dihydroxypropanamide); N,N,N''-{1,4,7-triazecane-1,4,7-triyltris[methylene(2-hydroxy-5-methyl-3,1-phenylene)]}tris[3-hydroxy-2-(hydroxymethyl) propanamide]; N,N-{1,4,7-triazecane-1,7-diylbis[methylene(2-hydroxy-5-methyl-3,1-phenylene)]}bis[3-hydroxy-2-(hydroxymethyl) propanamide]; N,N-{1,4,7-triazecane-1,4-diylbis [methylene(2-hydroxy-5-methyl-3,1-phenylene)]}bis[3-hydroxy-2-(hydroxymethyl)propanamide]; {1,4,7-triazecane-1,4,7-triyltris[methylene (2-hydroxy-5-methyl-3,1-phenylene)azanediyl(2-oxoethane-2,1-diyl)]}tris (phosphonic acid); {1,4,7-triazecane-1,7-diylbis[methylene (2-hydroxy-5-methyl-3, 1-phenylene)azanediyl(2-oxoethane-2,1-diyl)]}bis(phosphonic acid); {1,4,7-triazecane-1,4-diylbis[methylene(2-hydroxy-5-methyl-3,1-phenylene)azanediyl(2-oxoethane-2,1-diyl)]}bis (phosphonic acid); 3,3',3''-[1,4,8-triazacycloundecane-1,4,8-triyltris(methylene)]tris[N-(1,3-dihydroxypropan-2-yl)-2-hydroxy-5-methylbenzamide]; 2,2',2''-{1,4,8-triazacycloundecane-1,4,8-triyltris[methylene(2-hydroxy-5-methyl-3,1-phenylene)methyleneazanediyl]}tri(propane-1,3-diol); 3,3'-[1,4,8-triazacycloundecane-1,8-diylbis (methylene)]bis[N-(1,3-dihydroxypropan-2-yl)-2-hydroxy-5-methylbenzamide]; 3,3'-[1,4,8-triazacycloundecane-1,4-diylbis(methylene)]bis[N-(1,3-dihydroxypropan-2-yl)-2-hydroxy-5-methylbenzamide]; 2,2'-{1,4,8-triazacycloundecane-1,8-diylbis[methylene(2-hydroxy-5-methyl-3,1-phenylene)methyleneazanediyl]}di(propane-1,3-diol); 2,2'-{1,4,8-triazacycloundecane-1,4-diylbis [methylene 2-hydroxy-5-methyl-3,1-phenylene) methyleneazanediyl]}di(propane-1,3-diol); 3,3',3''-[1,4,8-triazacycloundecane-1,4,8-triyltris(methylene)]tris(2-hydroxy-5-methylbenzamide); 3,3'-[1,4,8-triazacycloundecane-1,8-diylbis(methylene)]bis(2-hydroxy-5-methylbenzamide); 3,3'-[1,4,8-triazacycloundecane-1,4-diylbis(methylene)]bis(2-hydroxy-5-methylbenzamide); 2,2',2''-[1,4,8-triazacycloundecane-1,4,8-triyltris(methylene)]tris[6-(aminomethyl)-4-methylphenol]; 2,2'-[1,4,8-triazacycloundecane-1,8-diylbis(methylene)]bis[6-(aminomethyl)-4-methylphenol]; 2,2'-[1,4,8-triazacycloundecane-1,4-diylbis(methylene)]bis[6-(aminomethyl)-4-methylphenol]; {1,4,8-triazacycloundecane-1,4,8-triyltris [methylene(2-hydroxy-5-methyl-3,1-phenylene) carbonylazanediylmethylene]}tris(phosphonic acid); {1,4,8-triazacycloundecane-1,8-diylbis[methylene (2-hydroxy-5-methyl-3,1-phenylene)carbonylazanediylmethylene]}bis (phosphonic acid); {1,4,8-triazacycloundecane-1,4-diylbis [methylene(2-hydroxy-5-methyl-3,1-phenylene) carbonylazanediylmethylene]}bis(phosphonic acid); {1,4,8-triazacycloundecane-1,4,8-triyltris[methylene(2-hydroxy-5-methyl-3,1-phenylene)methyleneazanediylmethylene]}tris (phosphonic acid); {1,4,8-triazacycloundecane-1,8-diylbis [methylene(2-hydroxy-5-methyl-3,1-phenylene) methyleneazanediylmethylene]}bis(phosphonic acid); {1,4,8-triazacycloundecane-1,4-diylbis[methylene(2-hydroxy-5-methyl-3,1-phenylene)methyleneazanediylmethylene]}bis (phosphonic acid); (3,3',3''-[1,4,8-triazacycloundecane-1,4,8-triyltris(methylene)]tris[N-(1,2-dihydroxyethyl)-2-hydroxy-5-methylbenzamide]; 1,1',1''-{1,4,8-triazacycloundecane-1,4,8-triyltris[methylene(2-hydroxy-5-methyl-3,1-phenylene)methyleneazanediyl]}tri(ethane-1,2-diol); (3,3'-[1,4,8-triazacycloundecane-1,8-diylbis (methylene)]bis[N-(1,2-dihydroxyethyl)-2-hydroxy-5-methylbenzamide]; 3,3'-[1,4,8-triazacycloundecane-1,4-diylbis(methylene)]bis[N-(1,2-dihydroxyethyl)-2-hydroxy-5-methylbenzamide]; 1,1'-{1,4,8-triazacycloundecane-1,8-diylbis[methylene(2-hydroxy-5-methyl-3,1-phenylene) methyleneazanediyl]}di(ethane-1,2-diol); 1,1'-{1,4,8-triazacycloundecane-1,4-diylbi[methylene(2-hydroxy-5-methyl-3,1-phenylene)methyleneazanediyl]}di(ethane-1,2-diol); N,N',N''-{1,4,8-triazacycloundecane-1,4,8-triyltris [methylene(2-hydroxy-5-methyl-3,1-phenylene)]}tris(2,3-dihydroxypropanamide); N,N-{1,4,8-triazacycloundecane-1,8-diylbis[methylene(2-hydroxy-5-methyl-3,1-phenylene)]}bis(2,3-dihydroxypropanamide); N,N-{1,4,8- triazacycloundecane-1,4-diylbis[methylene(2-hydroxy-5-methyl-3,1-phenylene)]}bis(2,3-dihydroxypropanamide); N,N°,N"-{1,4,8-triazacycloundecane-1,4,8-triyltris[methylene(2-hydroxy-5-methyl-3,1-phenylene)]}tris[3-hydroxy-2-(hydroxymethyl)propanamide]; N,N'-{1,4,8-triazacycloundecane-1,8-diylbis[methylene(2-hydroxy-5-methyl-3,1-phenylene)]}bis[3-hydroxy-2-(hydroxymethyl)propanamide]; N,N-{1,4,8-triazacycloundecane-1,4-diylbis[methylene(2-hydroxy-5-methyl-3,1-phenylene)]}bis[3-hydroxy-2-(hydroxymethyl)propanamide]; {1,4,8-triazacycloundecane-1,4,8-triyltris[methylene(2-hydroxy-5-methyl-3,1-phenylene)azanediyl(2-oxoethane-2,1-diyl)]}tris(phosphonic acid); {1,4,8-triazacycloundecane-1,8-diylbis[methylene(2-hydroxy-5-methyl-3,1-phenylene)azanediyl(2-oxoethane-2,1-diyl)]}bis(phosphonic acid); {1,4,8-triazacycloundecane-1,4-diylbis[methylene(2-hydroxy-5-methyl-3,1-phenylene)azanediyl(2-oxoethane-2,1-diyl)]}bis(phosphonic acid); 3,3',3"-[1,5,9-triazacyclododecane-1,5,9-triyltris(methylene)]tris[N-(1,3-dihydroxypropan-2-yl)-2-hydroxy-5-methylbenzamide]; 2,2',2"-{1,5,9-triazacyclododecane-1,5,9-triyltris[methylene(2-hydroxy-5-methyl-3,1-phenylene)methyleneazanediyl]}tri(propane-1,3-diol); 3,3'-[1,5,9-triazacyclododecane-1,5-diylbis(methylene)]bis[N-(1,3-dihydroxypropan-2-yl)-2-hydroxy-5-methylbenzamide]; 2,2'-{1,5,9-triazacyclododecane-1,5-diylbis[methylene(2-hydroxy-5-methyl-3,1-phenylene)methyleneazanediyl]}di(propane-1,3-diol); 3,3',3"-[1,5,9-triazacyclododecane-1,5,9-triyltris(methylene)]tris(2-hydroxy-5-methylbenzamide); 3,3'-[1,5,9-triazacyclododecane-1,5-diylbis(methylene)]bis(2-hydroxy-5-methylbenzamide); 2,2',2"-[1,5,9-triazacyclododecane-1,5,9-triyltris(methylene)]tris[6-(aminomethyl)-4-methylphenol]; 2,2'-[1,5,9-triazacyclododecane-1,5-diylbis(methylene)]bis[6-(aminomethyl)-4-methylphenol]; {1,5,9-triazacyclododecane-1,5,9-triyltris[methylene(2-hydroxy-5-methyl-3,1-phenylene)carbonylazanediylmethylene]}tris(phosphonic acid); {1,5,9-triazacyclododecane-1,5-diylbis[methylene(2-hydroxy-5-methyl-3,1-phenylene)carbonylazanediylmethylene]}bis(phosphonic acid); {1,5,9-triazacyclododecane-1,5,9-triyltris[methylene(2-hydroxy-5-methyl-3,1-phenylene)methyleneazanediylmethylene]}tris(phosphonic acid); {1,5,9-triazacyclododecane-1,5-diylbis[methylene(2-hydroxy-5-methyl-3,1-phenylene)methyleneazanediylmethylene]}bis(phosphonic acid); 3,3',3"-[1,5,9-triazacyclododecane-1,5,9-triyltris(methylene)]tris[N-(1,2-dihydroxyethyl)-2-hydroxy-5-methylbenzamide]; 1,1',1"-{1,5,9-triazacyclododecane-1,5,9-triyltris[methylene(2-hydroxy-5-methyl-3,1-phenylene)methyleneazanediyl]}tri(ethane-1,2-diol); 3,3'-[1,5,9-triazacyclododecane-1,5-diylbis(methylene)]bis[N-(1,2-dihydroxyethyl)-2-hydroxy-5-methylbenzamide]; 1,1'-{1,5,9-triazacyclododecane-1,5-diylbis[methylene(2-hydroxy-5-methyl-3,1-phenylene)methyleneazanediyl]}di(ethane-1,2-diol); N,N',N"-{1,5,9-triazacyclododecane-1,5,9-triyltris[methylene(2-hydroxy-5-methyl-3,1-phenylene)]}tris(2,3-dihydroxypropanamide); N,N-{1,5,9-triazacyclododecane-1,5-diylbis[methylene(2-hydroxy-5-methyl-3,1-phenylene)]}bis(2,3-dihydroxypropanamide); N,N',N"-{1,5,9-trizacyclododecane-1,5,9-triyltris[methylene(2-hydroxy-5-methyl-3,1-phenylene)]}tris[3-hydroxy-2-(hydroxymethyl)propanamide]; N,N-{1,5,9-triazacyclododecane-1,5-diylbis[methylene(2-hydroxy-5-methyl-3,1-phenylene)]}bis[3-hydroxy-2-(hydroxymethyl)propanamide]; {1,5,9-triazacyclododecane-1,5,9-triyltris[methylene(2-hydroxy-5-methyl-3,1-phenylene)azanediyl(2-oxoethane-2,1-diyl)]}tris(phosphonic acid); {1,5,9-triazacyclododecane-1,5-diylbis[methylene(2-hydroxy-5-methyl-3,1-phenylene)azanediyl(2-oxoethane-2,1-diyl)]}bis(phosphonic acid); 3,3'-[(7-benzyl-1,4,7-triazonane-1,4-diyl)bis(methylene)]bis[N-(1,3-dihydroxypropan-2-yl)-2-hydroxy-5-methylbenzamide]; 2,2'-{(7-benzyl-1,4,7-triazonane-1,4-diyl)bis[methylene(2-hydroxy-5-methyl-3,1-phenylene)methyleneazanediyl]}di(propane-1,3-diol); 3,3'-[(7-benzyl-1,4,7-triazonane-1,4-diyl)bis(methylene)]bis(2-hydroxy-5-methylbenzamide); 2,2'-[(7-benzyl-1,4,7-triazonane-1,4-diyl)bis(methylene)]bis[6-(aminomethyl)-4-methylphenol]; {(7-benzyl-1,4,7-triazonane-1,4-diyl)bis[methylene(2-hydroxy-5-methyl-3,1-phenylene)carbonylazanediylmethylene]}bis(phosphonic acid); {(7-benzyl-1,4,7-triazonane-1,4-diyl)bis[methylene(2-hydroxy-5-methyl-3,1-phenylene)methyleneazanediylmethylene]}bis(phosphonic acid); 3,3'-[(7-benzyl-1,4,7-triazonane-1,4-diyl)bis(methylene)]bis[N-(1,2-dihydroxyethyl)-2-hydroxy-5-methylbenzamide]; 1,1'-{(7-benzyl-1,4,7-triazonane-1,4-diyl)bis[methylene(2-hydroxy-5-methyl-3,1-phenylene)methyleneazanediyl]}di(ethane-1,2-diol); N,N'-{(7-benzyl-1,4,7-triazonane-1,4-diyl)bis[methylene(2-hydroxy-5-methyl-3,1-phenylene)]}bis(2,3-dihydroxypropanamide); N,N-{(7-benzyl-1,4,7-triazonane-1,4-diyl)bis[methylene(2-hydroxy-5-methyl-3,1-phenylene)]}bis[3-hydroxy-2-(hydroxymethyl)propanamide]; {(7-benzyl-1,4,7-triazonane-1,4-diyl)bis[methylene (2-hydroxy-5-methyl-3,1-phenylene)azanediyl(2-oxoethane-2,1-diyl)]}bis(phosphonic acid); 3,3'-[(4-benzyl-1,4,7-triazecane-1,7-diyl)bis(methylene)]bis[N-(1,3-dihydroxypropan-2-yl)-2-hydroxy-5-methylbenzamide]; 3,3'-[(7-benzyl-1,4,7-triazecane-1,4-diyl)bis(methylene)]bis[N-(1,3-dihydroxypropan-2-yl)-2-hydroxy-5-methylbenzamide]; 2,2'-{(4-benzyl-1,4,7-triazecane-1,7-diyl)bis[methylene(2-hydroxy-5-methyl-3,1-phenylene)methyleneazanediyl]}di(propane-1,3-diol); 2,2'-{(7-benzyl-1,4,7-triazecane-1,4-diyl)bis[methylene(2-hydroxy-5-methyl-3,1-phenylene)methyleneazanediyl]}di(propane-1,3-diol); 3,3'-[(4-benzyl-1,4,7-triazecane-1,7-diyl)bis(methylene)]bis(2-hydroxy-5-methylbenzamide); 3,3'-[(7-benzyl-1,4,7-triazecane-1,4-diyl)bis(methylene)]bis(2-hydroxy-5-methylbenzamide); 2,2'-[(4-benzyl-1,4,7-triazecane-1,7-diyl)bis(methylene)]bis[6-(aminomethyl)-4-methylphenol]; 2,2'-[(7-benzyl-1,4,7-triazecane-1,4-diyl)bis(methylene)]bis[6-(aminomethyl)-4-methylphenol]; {(4-benzyl-1,4,7-triazecane-1,7-diyl)bis[methylene(2-hydroxy-5-methyl-3,1-phenylene)carbonylazanediylmethylene]}bis(phosphonic acid); {(7-benzyl-1,4,7-triazecane-1,4-diyl)bis[methylene(2-hydroxy-5-methyl-3,1-phenylene)carbonylazanediylmethylene]}bis(phosphonic acid); {(4-benzyl-1,4,7-triazecane-1,7-diyl)bis[methylene(2-hydroxy-5-methyl-3,1-phenylene)methyleneazanediylmethylene]}bis(phosphonic acid); {(7-benzyl-1,4,7-triazecane-1,4-diyl)bis[methylene(2-hydroxy-5-methyl-3,1-phenylene)methyleneazanediylmethylene]}bis(phosphonic acid); 3,3'-[(4-benzyl-1,4,7-triazecane-1,7-diyl)bis(methylene)]bis[N-(1,2-dihydroxyethyl)-2-hydroxy-5-methylbenzamide]; 3,3'-[(7-benzyl-1,4,7-triazecane-1,4-diyl)bis(methylene)]bis[N-(1,2-dihydroxyethyl)-2-hydroxy-5-methylbenzamide]; 1,1'-{(4-benzyl-1,4,7-triazecane-1,7-diylbis[methylene(2-hydroxy-5-methyl-3,1-phenylene)methyleneazanediyl]}di(ethane-1,2-diol); 1,1'-{(7-benzyl-1,4,7-triazecane-1,4-diyl)bis[methylene(2-hydroxy-5-methyl-3,1-phenylene)methyleneazanediyl]}di(ethane-1,2-diol); N,N-{(4-benzyl-1,4,7-triazecane-1,7-diylbis[methylene(2-hydroxy-5-methyl-3,1-phenylene)]}bis(2,3-dihydroxypropanamide); N,N'-{(7-benzyl-1,4,7-triazecane-1,4-diyl)bis[methylene (2-hydroxy-5-methyl-3,1-phenylene)]}bis(2,3-dihydroxypropanamide); N,N-{(4-benzyl-1,4,7-triazecane-1,7-diyl)

bis[methylene(2-hydroxy-5-methyl-3,1-phenylene)]}bis[3-hydroxy-2-(hydroxymethyl)propanamide]; N,N'-{(7-benzyl-1,4,7-triazecane-1,4-diyl)bis[methylene(2-hydroxy-5-methyl-3, 1-phenylene)]}bis[3-hydroxy-2-(hydroxymethyl) propanamide]; {(4-benzyl-1,4,7-triazecane-1,7-diyl)bis[methylene(2-hydroxy-5-methyl-3,1-phenylene)azanediyl(2-oxoethane-2,1-diyl)]}bis(phosphonic acid); {(7-benzyl-1,4,7-triazecane-1,4-diyl)bis[methylene(2-hydroxy-5-methyl-3,1-phenylene) azanediyl (2-oxoethane-2,1-diyl)]}bis(phosphonic acid); 3,3'-[(4-benzyl-1,4,8-triazacycloundecane-1,8-diyl)bis(methylene)]bis[N-(1,3-dihydroxypropan-2-yl)-2-hydroxy-5-methylbenzamide]; 3,3'-[(8-benzyl-1,4,8-triazacycloundecane-1,4-diyl)bis(methylene)]bis[N-(1,3-dihydroxypropan-2-yl)-2-hydroxy-5-methylbenzamide]; 2,2'-{(4-benzyl-1,4,8-triazacycloundecane-1,8-diyl)bis[methylene(2-hydroxy-5-methyl-3,1-phenylene)methyleneazanediyl]}di(propane-1,3-diol); 2,2'-{(8-benzyl-1,4,8-triazacycloundecane-1,4-diyl)bis[methylene(2-hydroxy-5-methyl-3,1-phenylene)methyleneazanediyl]}di(propane-1, 3-diol); 3,3'-[(4-benzyl-1,4,8-triazacycloundecane-1,8-diyl) bis(methylene)]bis[2-hydroxy-5-methylbenzamide]; 3,3'-[(8-benzyl-1,4,8-triazacycloundecane-1,4-diyl)bis (methylene)]bis[2-hydroxy-5-methylbenzamide]; 2,2'-[(4-benzyl-1,4,8-triazacycloundecane-1,8-diyl)bis(methylene)] bis[6-(aminomethyl)-4-methylphenol]; 2,2'-[(8-benzyl-1,4, 8-triazacycloundecane-1,4-diyl)bis(methylene)]bis[6-(aminomethyl)-4-methylphenol]; {(4-benzyl-1,4,8-triazacycloundecane-1,8-diyl)bis[methylene(2-hydroxy-5-methyl-3,1-phenylene)carbonylazanediylmethylene]}bis(phosphonic acid); {(8-benzyl-1,4,8-triazacycloundecane-1, 4-diyl)bis[methylene(2-hydroxy-5-methyl-3,1-phenylene) carbonylazanediylmethylene]}bis(phosphonic acid); {(4-benzyl-1,4,8-triazacycloundecane-1,8-diyl)bis[methylene (2-hydroxy-5-methyl-3,1-phenylene) methyleneazanediylmethylene]}bis(phosphonic acid); {(8-benzyl-1,4,8-triazacycloundecane-1,4-diyl)bis[methylene (2-hydroxy-5-methyl-3,1-phenylene) methyleneazanediylmethylene]}bis(phosphonic acid); 3,3'-[(4-benzyl-1,4,8-triazacycloundecane-1,8-diyl)bis (methylene)]bis[N-(1,2-dihydroxyethyl)-2-hydroxy-5-methylbenzamide]; 3,3'-[(8-benzyl-1,4,8-triazacycloundecane-1,4-diyl)bis(methylene)]bis[N-(1,2-dihydroxyethyl)-2-hydroxy-5-methylbenzamide]; 1,1'-{(4-benzyl-1,4,8-triazacycloundecane-1,8-diyl)bis[methylene (2-hydroxy-5-methyl-3,1-phenylene)methyleneazanediyl] }di(ethane-1,2-diol); 1,1'-{(8-benzyl-1,4,8-triazacycloundecane-1,4-diyl)bis[methylene(2-hydroxy-5-methyl-3,1-phenylene)methyleneazanediyl]}di(ethane-1,2-diol); N,N-{(4-benzyl-1,4,8-triazacycloundecane-1,8-diyl) bis[methylene(2-hydroxy-5-methyl-3,1-phenylene)]}bis(2, 3-dihydroxypropanamide); N,N-{(8-benzyl-1,4,8-triazacycloundecane-1,4-diyl)bis[methylene(2-hydroxy-5-methyl-3,1-phenylene)]}bis(2,3-dihydroxypropanamide); N,N-{(4-benzyl-1,4,8-triazacycloundecane-1,8-diyl)bis [methylene(2-hydroxy-5-methyl-3,1-phenylene)]}bis[3-hydroxy-2-(hydroxymethyl)propanamide]; N,N-{(8-benzyl-1, 4,8-triazacycloundecane-1,4-diyl)bis[methylene(2-hydroxy-5-methyl-3,1-phenylene)]}bis[3-hydroxy-2-(hydroxymethyl)propanamide]; {(4-benzyl-1,4,8-triazacycloundecane-1,8-diyl)bis[methylene(2-hydroxy-5-methyl-3,1-phenylene)azanediyl(2-oxoethane-2,1-diyl)] }bis(phosphonic acid); {(8-benzyl-1,4,8-triazacycloundecane-1,4-diyl)bis[methylene(2-hydroxy-5-methyl-3,1-phenylene)azanediyl(2-oxoethane-2,1-diyl)] }bis(phosphonic acid); 3,3'-[(9-benzyl-1,5,9-triazacyclododecane-1,5-diyl)bis(methylene)]bis[N-(1,3-dihydroxypropan-2-yl)-2-hydroxy-5-methylbenzamide]; 2,2'-{(9-benzyl-1,5,9-triazacyclododecane-1,5-diyl)bis [methylene(2-hydroxy-5-methyl-3,1-phenylene)methyleneazanediyl]}di(propane-1,3-diol); 3,3'-[(9-benzyl-1,5,9-triazacyclododecane-1,5-diyl)bis(methylene)]bis(2-hydroxy-5-methylbenzamide); 2,2'-[(9-benzyl-1,5,9-triazacyclododecane-1,5-diyl)bis(methylene)]bis[6-(aminomethyl)-4-methylphenol]; {(9-benzyl-1,5,9-triazacyclododecane-1,5-diyl)bis[methylene(2-hydroxy-5-methyl-3,1-phenylene)carbonylazanediylmethylene]}bis(phosphonic acid); {(9-benzyl-1,5,9-triazacyclododecane-1, 5-diyl)bis[methylene(2-hydroxy-5-methyl-3,1-phenylene) methyleneazanediylmethylene]}bis(phosphonic acid); 3,3'-[(9-benzyl-1,5,9-triazacyclododecane-1,5-diyl)bis (methylene)]bis[N-(1,2-dihydroxyethyl)-2-hydroxy-5-methylbenzamide]; 1,1'-{(9-benzyl-1,5,9-triazacyclododecane-1,5-diyl)bis[methylene(2-hydroxy-5-methyl-3,1-phenylene)methyleneazanediyl]}di(ethane-1,2-diol); N,N-{(9-benzyl-1,5,9-triazacyclododecane-1,5-diyl) bis[methylene(2-hydroxy-5-methyl-3,1-phenylene)]}bis(2, 3-dihydroxypropanamide); N,N-{(9-benzyl-1,5,9-triazacyclododecane-1,5-diyl)bis[methylene(2-hydroxy-5-methyl-3,1-phenylene)]}bis[3-hydroxy-2-(hydroxymethyl) propanamide]; {(9-benzyl-1,5,9-triazacyclododecane-1,5-diyl)bis[methylene(2-hydroxy-5-methyl-3,1-phenylene) azanediyl(2-oxoethane-2,1-diyl)]}bis(phosphonic acid); N,N',N"-{1,4,7-triazonane-1,4,7-triyltris[methylene(2-hydroxy-5-methyl-3,1-phenylene)]}triacetamide); 3-{[4,7-bis ({2-hydroxy-5-methyl-3-[(2,3,4,5,6-pentahydroxyhexyl) carbamoyl]phenyl}methyl)-1,4,7-triazonan-1-yl]methyl}-2-hydroxy-5-methyl-N-(2,3,4,5,6-pentahydroxyhexyl) benzamide; 6,6',6"-{1,4, 7-triazonane-1,4,7-triyltris [methylene(2-hydroxy-5-methyl-3,1-phenylene) methyleneazanediyl]}tris(hexane-1,2,3,4,5-pentol); 2-hydroxy-3-{[4-({2-hydroxy-5-methyl-3-[(2,3,4,5,6-pentahydroxyhexyl)carbamoyl]phenyl}methyl)-1,4,7-triazonan-1-yl]methyl}-5-methyl-N-(2,3,4,5,6-pentahydroxy-hexyl)benzamide; 6,6'-{1,4,7-triazonane-1,4-diylbis [methylene(2-hydroxy-5-methyl-3,1-phenylene) methyleneazanediyl]}di(hexane-1,2,3,4,5-pentol); 3-{[4,7-bis({2-hydroxy-5-methyl-3-[(2,3,4,5,6-pentahydroxyhexyl) carbamoyl]phenyl}methyl)-1,4,7-triazecan-1-yl]methyl}-2-hydroxy-5-methyl-N-(2,3,4,5,6-pentahydroxyhexyl) benzamide; 6,6',6"-{1,4,7-triazecane-1,4, 7-triyltris [methylene(2-hydroxy-5-methyl-3,1-phenylene) methyleneazanediyl]}tri(hexane-1,2,3,4,5-pentol); 2-hydroxy-3-{[7-({2-hydroxy-5-methyl-3-[(2,3,4,5,6-pentahydroxyhexyl)carbamoyl]phenyl}methyl)-1,4,7-triazecan-1-yl]methyl}-5-methyl-N-(2,3,4,5,6-pentahydroxy-hexyl)benzamide; 2-hydroxy-3-{[4-({2-hydroxy-5-methyl-3-[(2,3,4,5,6-pentahydroxyhexyl)carbamoyl] phenyl}methyl)-1,4,7-triazecan-1-yl]methyl}-5-methyl-N-(2,3,4,5,6-pentahydroxyhexyl)benzamide; 3-{[1,4-bis({2-hydroxy-5-methyl-3-[(2,3,4,5,6-pentahydroxyhexyl) carbamoyl]phenyl}methyl)-1,4,8-triazacycloundecan-8-yl] methyl}-2-hydroxy-5-methyl-N-(2,3,4,5,6-pentahydroxyhexyl)benzamide; 6,6',6"-{1,4,8-triazacycloundecane-1,4,8-triyltris[methylene(2-hydroxy-5-methyl-3,1-phenylene)methyleneazanediyl]}tri(hexane-1,2, 3,4,5-pentol); 2-hydroxy-3-{[1-({2-hydroxy-5-methyl-3-[(2,3,4,5,6-pentahydroxyhexyl)carbamoyl]phenyl}methyl)-1,4,8-triazacycloundecan-8-yl]methyl}-5-methyl-N-(2,3,4, 5,6-pentahydroxyhexyl)benzamide; 2-hydroxy-3-{[4-({2-hydroxy-5-methyl-3-[(2,3,4,5,6-pentahydroxyhexyl) carbamoyl]phenyl}methyl)-1,4,8-triazacycloundecan-1-yl] methyl}-5-methyl-N-(2,3,4,5,6-pentahydroxyhexyl) benzamide; 6,6'-{1,4,8-triazacycloundecane-1,8-diylbis

[methylene(2-hydroxy-5-methyl-3,1-phenylene)methyleneazanediyl]}di(hexane-1,2,3,4,5-pentol); 6,6'-{1,4,8-triazacycloundecane-1,4-diylbis[methylene(2-hydroxy-5-methyl-3,1-phenylene)methyleneazanediyl]}di(hexane-1,2,3,4,5-pentol); 3-{[5,9-bis({2-hydroxy-5-methyl-3-[(2,3,4,5,6-pentahydroxyhexyl)carbamoyl]phenyl}methyl)-1,5,9-triazacyclododecan-1-yl]methyl}-2-hydroxy-5-methyl-N-(2,3,4,5,6-pentahydroxyhexyl)benzamide; 6,6',6"-{1,5,9-triazacyclododecane-1,5,9-triyltris[methylene(2-hydroxy-5-methyl-3,1-phenylene)methyleneazanediyl]}tri(hexane-1,2,3,4,5-pentol); 2-hydroxy-3-{[5-({2-hydroxy-5-methyl-3-[(2,3,4,5,6-pentahydroxyhexyl)carbamoyl]phenyl}methyl)-1,5,9-triazacyclododecan-1-yl]methyl}-5-methyl-N-(2,3,4,5,6-pentahydroxyhexyl)benzamide; 6,6'-{1,5,9-triazacyclododecane-1,5-diylbis[methylene(2-hydroxy-5-methyl-3,1-phenylene)methyleneazanediyl]}di(hexane-1,2,3,4,5-pentol); 3-{[4-benzyl-7-({2-hydroxy-5-methyl-3-[(2,3,4,5,6-pentahydroxyhexyl)carbamoyl]phenyl}methyl)-1,4,7-triazonan-1-yl]methyl}-2-hydroxy-5-methyl-N-(2,3,4,5,6-pentahydroxyhexyl)benzamide; 6,6'-{(7-benzyl-1,4,7-triazonane-1,4-diyl)bis[methylene(2-hydroxy-5-methyl-3,1-phenylene)methyleneazanediyl]}di(hexane-1,2,3,4,5-pentol); 3-{[4-benzyl-7-({2-hydroxy-5-methyl-3-[(2,3,4,5,6-pentahydroxyhexyl)carbamoyl]phenyl}methyl)-1,4,7-triazecan-1-yl]methyl}-2-hydroxy-5-methyl-N-(2,3,4,5,6-pentahydroxyhexyl)benzamide; 3-{[7-benzyl-4-({2-hydroxy-5-methyl-3-[(2,3,4,5,6-pentahydroxyhexyl)carbamoyl]phenyl}methyl)-1,4,7-triazecan-1-yl]methyl}-2-hydroxy-5-methyl-N-(2,3,4,5,6-pentahydroxyhexyl)benzamide; 6,6'-{(4-benzyl-1,4,7-triazecane-1,7-diyl)bis[methylene(2-hydroxy-5-methyl-3,1-phenylene)methyleneazanediyl]}di(hexane-1,2,3,4,5-pentol); 6,6'-{(7-benzyl-1,4,7-triazecane-1,4-diyl)bis[methylene(2-hydroxy-5-methyl-3,1-phenylene)methyleneazanediyl]}di(hexane-1,2,3,4,5-pentol); 3-{[1-benzyl-4-({2-hydroxy-5-methyl-3-[(2,3,4,5,6-pentahydroxyhexyl) carbamoyl]phenyl}methyl)-1,4,8-triazacycloundecan-8-yl]methyl}-2-hydroxy-5-methyl-N-(2,3,4,5,6-pentahydroxyhexyl)benzamide; 3-{[8-benzyl-4-({2-hydroxy-5-methyl-3-[(2,3,4,5,6-pentahydroxyhexyl)carbamoyl]phenyl}methyl)-1,4,8-triazacycloundecan-1-yl]methyl}-2-hydroxy-5-methyl-N-(2,3,4,5,6-pentahydroxyhexyl)benzamide; 6,6'-{(4-benzyl-1,4,8-triazacycloundecane-1,8-diyl)bis[methylene(2-hydroxy-5-methyl-3,1-phenylene)methyleneazanediyl]}di(hexane-1,2,3,4,5-pentol); 6,6'-{(8-benzyl-1,4,8-triazacycloundecane-1,4-diyl)bis[methylene(2-hydroxy-5-methyl-3,1-phenylene)methyleneazanediyl]}di(hexane-1,2,3,4,5-pentol); 3-{[5-benzyl-9-({2-hydroxy-5-methyl-3-[(2,3,4,5,6-pentahydroxyhexyl)carbamoyl]phenyl}methyl)-1,5,9-triazacyclododecan-1-yl]methyl}-2-hydroxy-5-methyl-N-(2,3,4,5,6-pentahydroxyhexyl)benzamide; 6,6'-{(9-benzyl-1,5,9-triazacyclododecane-1,5-diyl)bis[methylene(2-hydroxy-5-methyl-3,1-phenylene)methyleneazanediyl]}di(hexane-1,2,3,4,5-pentol); 6,6'-{1,4,7-triazecane-1,7-diylbis[methylene(2-hydroxy-5-methyl-3,1-phenylene)methyleneazanediyl]}di(hexane-1,2,3,4,5-pentol); 6,6'-{1,4,7-triazacane-1,4-diylbis[methylene(2-hydroxy-5-methyl-3,1-phenylene)methyleneazanediyl]}di(hexane-1,2,3,4,5-pentol); 2,2',2"-{1,4, 7-triazonane-1,4, 7-triyltris[methylene(2-hydroxy-5-methyl-3,1-phenylene)methyleneoxy]}tri(propane-1,3-diol); 2,2'-{1,4,7-triazonane-1,4-diylbis[methylene(2-hydroxy-5-methyl-3,1-phenylene)methyleneoxy]}di(propane-1,3-diol); 2,2',2"-{1,4,7-triazecane-1,4,7-triyltris[methylene(2-hydroxy-5-methyl-3,1-phenylene)methyleneoxy]}tri(propane-1,3-diol); 2,2'-{1,4,7-triazecane-1,7-diylbis[methylene(2-hydroxy-5-methyl-3,1-phenylene)methyleneoxy]}di(propane-1,3-diol); 2,2'-{1,4,7-triazecane-1,4-diylbis[methylene(2-hydroxy-5-methyl-3,1-phenylene)methyleneoxy]}di(propane-1,3-diol); 2,2',2"-{1,4,8-triazacycloundecane-1,4,8-triyltris[methylene(2-hydroxy-5-methyl-3,1-phenylene)methyleneoxy]}tri(propane-1,3-diol); 2,2'-{1,4,8-triazacycloundecane-1,8-diylbis[methylene(2-hydroxy-5-methyl-3,1-phenylene)methyleneoxy]}di(propane-1,3-diol); 2,2'-{1,4,8-triazacycloundecane-1,4-diylbis[methylene(2-hydroxy-5-methyl-3,1-phenylene)methyleneoxy]}di(propane-1,3-diol); 2,2',2"-{1,5,9-triazacyclododecane-1,5,9-triyltris[methylene(2-hydroxy-5-methyl-3,1-phenylene)methyleneoxy]}tri(propane-1,3-diol); 2,2'-{1,5,9-triazacyclododecane-1,5-diylbis[methylene(2-hydroxy-5-methyl-3,1-phenylene)methyleneoxy]}di(propane-1,3-diol); 2,2'-{(7-benzyl-1,4,7-triazonane-1,4-diyl)bis[methylene(2-hydroxy-5-methyl-3,1-phenylene)methyleneoxy]}di(propane-1,3-diol); 2,2'-{(4-benzyl-1,4,7-triazecane-1,7-diyl)bis[methylene(2-hydroxy-5-methyl-3,1-phenylene)methyleneoxy]}di(propane-1,3-diol); 2,2'-{(7-benzyl-1,4,7-triazecane-1,4-diyl)bis[methylene(2-hydroxy-5-methyl-3,1-phenylene)methyleneoxy]}di(propane-1,3-diol); 2,2'-{(4-benzyl-1,4,8-triazacycloundecane-1,8-diyl)bis[methylene(2-hydroxy-5-methyl-3,1-phenylene)methyleneoxy]}di(propane-1,3-diol); 2,2'-{(8-benzyl-1,4,8-triazacycloundecane-1,4-diyl)bis[methylene(2-hydroxy-5-methyl-3,1-phenylene)methyleneoxy]}di(propane-1,3-diol); and 2,2'-{(9-benzyl-1,5,9-triazacyclododecane-1,5-diyl)bis[methylene(2-hydroxy-5-methyl-3,1-phenylene)methyleneoxy]}di(propane-1,3-diol).

33. A complex of a compound according to claim 1 with $Fe^{3+}$, or a physiologically acceptable salt of said complex.

34. Method of imaging of a body tissue in a patient comprising the steps of administering to the patient an effective amount of a complex according to claim 33 in a pharmaceutically acceptable carrier, and subjecting the patient to magnetic resonance imaging (MRI).

35. A pharmaceutical composition comprising a complex as defined in claim 33 and at least one pharmaceutically acceptable excipient.

36. Process for preparing the compound as defined in claim 1 comprising the following steps:
   a) providing a phenol substituted at least in its orto positions (i) with a $C_1$-$C_6$-alkyl-bonded to a leaving group; and (ii) with a L-Z group, or a substituent group selected from the group consisting of $C_1$-$C_4$-alkyl-aldehyde, $C_1$-$C_4$-alkyl-ester, and $C_1$-$C_4$-alkyl-carboxyl;
   b) providing a macrocycle selected from the group consisting of triazacyclononane, triazacyclodecane, triazacycloundecane, and triazacyclododecane, optionally suitably protected with one or more protecting groups on one or more of the nitrogen atoms thereof, and/or optionally bearing on one of its nitrogen atoms a $C_1$-$C_4$ alkyl group optionally substituted by an aryl;
   c) reacting the phenol provided in step a) with the macrocycle provided in step b), to obtain the compound, or an intermediate thereof; and
   d) converting the intermediate of step c) to the compound.

37. The process according to claim 36, wherein:
   the phenol provided in step a) has the following formula (VI):

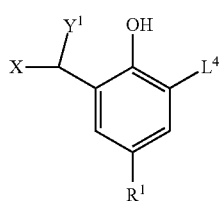

Formula (VI)

wherein Y¹ is independently selected from the group consisting of hydrogen and $C_1$-$C_4$-alkyl; and R¹ is independently selected from the group consisting of hydrogen and $C_1$-$C_4$-alkyl;

X is a leaving group, and $L^4$ is a group selected from the group consisting of $C_1$-$C_4$-alkyl-aldehyde, $C_1$-$C_4$-alkyl-ester, and $C_1$-$C_4$-alkyl-carboxyl;

the intermediate obtained in step c) has the following formula (VII):

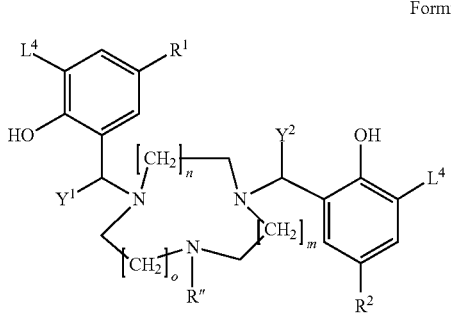

Formula (VII)

wherein R¹ and Y¹ have the same meaning provided above, R² is independently selected from the group consisting of hydrogen and $C_1$-$C_4$-alkyl, Y² is independently selected from the group consisting of hydrogen and $C_1$-$C_4$-alkyl, m, n and o are integer numbers independently selected between 1 and 2, $L^4$ is a group selected from the group consisting of $C_1$-$C_4$-alkyl-aldehyde, $C_1$-$C_4$-alkyl-ester, and $C_1$-$C_4$-alkyl-carboxyl; and R" is selected from the group consisting of hydrogen, $C_1$-$C_4$ alkyl optionally substituted by an aryl, and the moiety of Formula (VIIA):

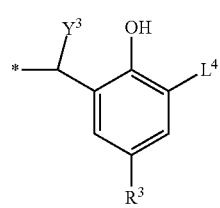

Formula (VIIA)

wherein: the asterisk (*) indicates the point of attachment of said moiety of formula (VIIA) to the nitrogen bearing the R" group;

Y³ has the same meaning provided above for Y¹ and Y²;

R³ has the same meaning provided above for R¹ and R²; and

L4 is a group selected from the group consisting of $C_1$-$C_4$-alkyl-aldehyde, $C_1$-$C_4$-alkyl-ester, and $C_1$-$C_4$-alkyl-carboxyl; and step d) provides for converting the $L^4$ moieties to the groups $L^1$-$Z^1$, $L^2$-$Z^2$, and $L^3$-$Z^3$ (if present).

38. Process for preparing the compound as defined in claim 1 comprising the following steps:

a) providing a phenol substituted at least in its orto positions (i) with a $C_1$-$C_5$-alkyl-bonded to a leaving group; and (ii) with a L-Z group, or a substituent group selected from the group consisting of $C_1$-$C_4$-alkyl-aldehyde, $C_1$-$C_4$-alkyl-ester, and $C_1$-$C_4$-alkyl-carboxyl;

b') providing an orthoamide derivative of a macrocycle selected from the group consisting of triazacyclononane, triazacyclodecane, triazacycloundecane, and triazacyclododecane;

c') reacting one or two phenols provided in step a) with the orthoamide derivative, to obtain an orthoamide derivative coupled with one or two phenols provided in step a);

d') hydrolysing the orthoamide derivative obtained in step c') to obtain a macrocycle selected from the group consisting of triazacyclononane, triazacyclodecane, triazacycloundecane, and triazacyclododecane coupled with one or two phenols provided in step a) and with a formyl (—C(O)H) group;

e') optionally reacting a further phenol provided in step a) with the macrocycle obtained in step d'), to obtain a macrocycle selected from the group consisting of triazacyclononane, triazacyclodecane, triazacycloundecane, and triazacyclododecane coupled with two phenols provided in step a) and with a formyl (—C(O)H) group;

f) hydrolysing the macrocycle obtained in step d') or e') and optionally converting the possible $C_1$-$C_4$-alkyl-aldehyde, $C_1$-$C_4$-alkyl-ester, or $C_1$-$C_4$-alkyl-carboxyl, wherein the hydrolysis and the optional conversion of this step f) are carried out in any order, to obtain the compound; and g') optionally reacting a further phenol provided in step a) with the macrocycle obtained in step f'), and optionally converting the possible $C_1$-$C_4$-alkyl-aldehyde, $C_1$-$C_4$-alkyl-ester, or $C_1$-$C_4$-alkyl-carboxyl, to obtain the compound.

39. The process according to claim 38, wherein the orthoamide derivative provided in step b') has the following formula (VIII):

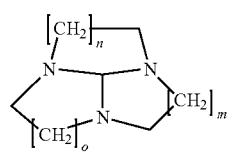

Formula (VIII)

wherein m, n, and o are integer numbers independently selected between 1 and 2.

40. Process for preparing a complex, comprising carrying out the following step:

e) reacting the compound obtained in step c) or step d) as defined in claim 36 with a Fe(III) salt, to obtain the Fe(III) complex.

* * * * *